(12) United States Patent
Sugimoto et al.

(10) Patent No.: US 8,299,035 B2
(45) Date of Patent: Oct. 30, 2012

(54) 10A-AZALIDE COMPOUND HAVING 4-MEMBERED RING STRUCTURE

(75) Inventors: Tomohiro Sugimoto, Saitama (JP); Kanako Yamamoto, Saitama (JP); Jun Kurosaka, Saitama (JP); Naoki Sasamoto, Saitama (JP); Masato Kashimura, Saitama (JP); Tomoaki Miura, Kanagawa (JP); Kenichi Kanemoto, Kanagawa (JP); Satoshi Yoshida, Kanagawa (JP); Kou Kumura, Tokyo (JP); Keiichi Ajito, Kanagawa (JP)

(73) Assignees: Taisho Pharmaceutucal Co., Ltd., Tokyo (JP); Meiji Seika Pharma Co., Ltd., Tokyo (JP)

( * ) Notice: Subject to any disclaimer, the term of this patent is extended or adjusted under 35 U.S.C. 154(b) by 0 days.

(21) Appl. No.: 12/992,335

(22) PCT Filed: May 15, 2009

(86) PCT No.: PCT/JP2009/002135
§ 371 (c)(1),
(2), (4) Date: Mar. 14, 2011

(87) PCT Pub. No.: WO2009/139181
PCT Pub. Date: Nov. 19, 2009

(65) Prior Publication Data
US 2011/0152239 A1    Jun. 23, 2011

(30) Foreign Application Priority Data

May 15, 2008    (JP) .................................. 2008-127832
Feb. 5, 2009    (JP) .................................. 2009-024457

(51) Int. Cl.
*A61K 31/70*    (2006.01)
*C07H 17/08*    (2006.01)
(52) U.S. Cl. .......................................... 514/29; 536/7.4
(58) Field of Classification Search .................... 536/7.4
See application file for complete search history.

(56) References Cited

U.S. PATENT DOCUMENTS

| | | | |
|---|---|---|---|
| 4,474,768 A | 10/1984 | Bright | |
| 4,517,359 A | 5/1985 | Kobrehel et al. | |
| 5,635,485 A | 6/1997 | Agouridas et al. | |
| 6,100,404 A | 8/2000 | Agouridas et al. | |
| 6,329,345 B1 | 12/2001 | Rafka et al. | |
| 2007/0042974 A1 | 2/2007 | Miura et al. | |
| 2009/0281292 A1 | 11/2009 | Sugimoto et al. | |

FOREIGN PATENT DOCUMENTS

| | | |
|---|---|---|
| EP | 0508726 | 10/1992 |
| EP | 0680967 | 5/1995 |
| JP | 6-056871 | 1/1994 |
| JP | 2002-530422 A | 9/2002 |
| WO | 98/09978 | 3/1998 |
| WO | 02/32919 | 4/2002 |
| WO | 2003/014136 | 2/2003 |
| WO | 2005/019238 | 3/2005 |
| WO | 2007/091393 A1 | 8/2007 |
| WO | 2009/019868 | 2/2009 |

OTHER PUBLICATIONS

U.S. Appl. No. 12/671,813 to Tomohiro Sugimoto et al., which was filed Feb. 2, 2010.
International Search Report that issued with respect to PCT/JP2009/002135, mailed Jul. 7, 2009.
International Preliminary Report on Patentability that issued with respect to PCT/JP2009/002135, mailed Nov. 25, 2010.

*Primary Examiner* — Elli Peselev
(74) *Attorney, Agent, or Firm* — Greenblum & Bernstein, P.L.C.

(57) ABSTRACT

A 10*a*-azalide compound having a 4-membered ring structure crosslinked at the 10*a*- and 12-positions, which is represented by the formula (I), and is effective on even *Haemophilus influenzae*, or erythromycin resistant bacteria (e.g., resistant pneunococci and streptococci).

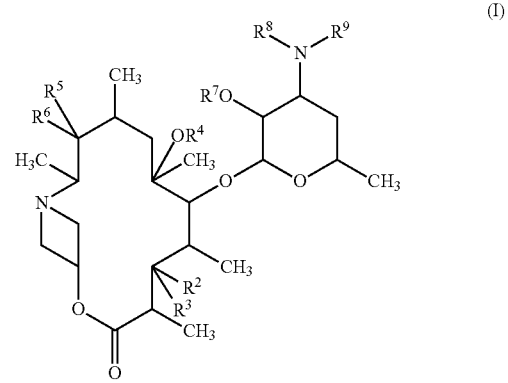

30 Claims, No Drawings

10A-AZALIDE COMPOUND HAVING 4-MEMBERED RING STRUCTURE

TECHNICAL FIELD

The present invention relates to a novel antibiotic having an erythromycin-like structure. More specifically, the present invention relates to a novel 10a-azalide compound having a 4-membered ring structure crosslinked at the 10a- and 12-positions.

BACKGROUND ART

Erythromycin A is an antibiotic which has been widely used as a therapeutic agent for infectious diseases caused by Gram-positive bacteria, mycoplasmas, and the like. However, due to decomposition by gastric acid, erythromycin has a drawback of inconstant pharmacokinetics. Therefore, derivatives of erythromycin having increased stability to acids were researched. As a result, macrolides having stable pharmacokinetics such as clarithromycin, azithromycin (Patent documents 1 and 2) and roxithromycin have been developed. These macrolide agents have been applied in a therapeutic field of respiratory infectious diseases of ambulatory patients, and therefore, they are required to have a potent antibacterial activity especially against pneumococci, streptococci, and *Haemophilus influenzae* which are frequently isolated clinically. Furthermore, since macrolide-resistant pneumococci have been highly frequently isolated from community acquired pneumonia patients, it has been considered important that they are effective against the resistant pneumococci.

As a result of various researches in recent years, Agouridas et al. found HMR3647 (telithromycin, Patent document 3) in 1995, and successively Or et al. found ABT-773 (cethromycin, Patent document 4) in 1998 as macrolides that are effective both against erythromycin resistant pneumococci and erythromycin resistant streptococci. Then, 2-fluoroketolide (Patent document 5) of which efficacy was further enhanced was reported.

From a structural viewpoint, marketed macrolides are mainly classified into 14-membered or 15-membered ring type macrolides which are erythromycin derivatives, and 16-membered ring type macrolides which are leucomycin derivatives. Among the erythromycin derivatives, the 15-membered ring macrolides include azithromycin mentioned above. Azithromycin, unlike the other 14-membered ring macrolides, possesses a structural feature of having a nitrogen atom in the lactone ring, and therefore the macrolide is called azalide. Nomenclature of azalides is based on the position number of a carbon atom substituted with a nitrogen atom when the carbonyl group of the lactone is assumed to be in the 1-position. In the case of azithromycin mentioned above, since the nitrogen atom is introduced in the position of the ninth carbon atom from the carbonyl group, the compound is called 9a-azalide.

In addition to the 9a-azalides, 8a-azalides (Patent document 6) and 11a-azalides (Patent document 7) are known as examples of reported azalides obtainable by chemical conversion of 14-membered ring macrolides.

As for 10a-azalides, those derived from 16-membered ring macrolides which are leucomycin derivatives (Patent document 8) and those derived from 14-membered ring macrolides (Patent document 9) have recently been reported. However, no 10a-azalides having a 4-membered ring structure crosslinked at the 10a- and 12-positions have been reported.

Patent document 1: U.S. Pat. No. 4,474,768
Patent document 2: U.S. Pat. No. 4,517,359
Patent document 3: EP680967
Patent document 4: WO98/09978
Patent document 5: WO02/32919
Patent document 6: EP508726
Patent document 7: WO2003/014136
Patent document 8: WO2005/019238
Patent document 9: WO2007/091393

DISCLOSURE OF THE INVENTION

Object to be Achieved by the Invention

An object of the present invention is to provide a compound having a novel structure which is effective against *Haemophilus influenzae* and erythromycin resistant bacteria (for example, resistant pneumococci and streptococci) as well as against conventional erythromycin sensitive bacteria.

Means for Achieving the Object

The inventors of the present invention conducted various researches on azalide compounds, and as a result, succeeded in synthesis of novel azalides derived from 14-membered ring macrolides.

More specifically, the inventors of the present invention used 14-membered ring macrolides as starting materials, and oxidized 11-oxo compounds, which were obtained by oxidative cleavage of the diol moieties in the 11- and 12-positions, to derive into carboxyl compounds. Then, they performed rearrangement reactions by using the carboxyl compounds as starting materials to synthesize compounds having 10-amino group. Further, by performing partial structural conversion, then macrocyclization, and followed by intramolecular cyclization of the resultant compounds, or by successively forming two rings in the inverse order, they succeeded in providing 10a-azalide compounds having a 4-membered ring structure crosslinked at the 10a- and 12-positions, which constitutes a novel skeleton. Further, as a result of evaluation of antibacterial activity of these compounds, the inventors found that the 10a-azalide compounds having a 4-membered ring structure crosslinked at the 10a- and 12-positions had activities superior to those of the erythromycin derivatives as the starting materials, and accomplished the present invention.

The present invention provides a 10a-azalide compound represented by the following formula (I):

[Formula 1]

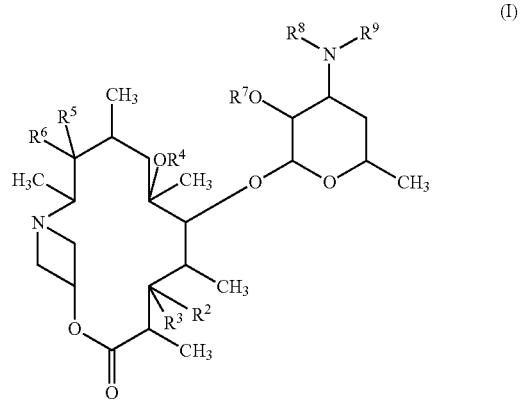

wherein, in the formula, $R^2$ and $R^3$ combine together to represent oxo group, or one of them is hydrogen atom, and the other is:
hydroxyl group,
a protected hydroxyl group,
a group represented by the formula —$X^{O31}$—$R^{O31}$, or a group represented by the formula (II):

[Formula 2]

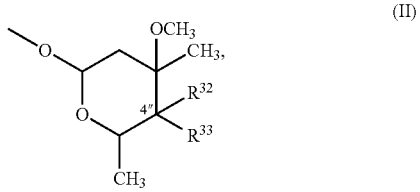

wherein $X^{O31}$ is:
a group represented by the formula —O—,
a group represented by the formula —OCO—, or
a group represented by the formula —OCON($R^{20}$)—,
$R^{O31}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A,
the group A is a group consisting of hydroxyl group, a halogen atom, amino group, carboxyl group, cyano group, a $C_{1-6}$ alkyl group (this $C_{1-6}$ alkyl group may be substituted with amino group, or a $C_{1-6}$ alkylamino group), a $C_{1-6}$ alkylamino group, a $C_{1-6}$ haloalkyl group, a $C_{1-6}$ alkoxy group, a $C_{1-6}$ alkylthio group, a $C_{2-7}$ alkoxycarbonyl group, nitro group, a saturated heterocyclic group, a $C_{7-12}$ aralkyloxy group, and a $C_{1-11}$ acyl group,
one of $R^{32}$ and $R^{33}$ is hydrogen atom, and the other is:
hydrogen atom,
hydroxyl group,
a protected hydroxyl group,
amino group,
a protected amino group,
a group represented by the formula —$X^{331}$—$R^{331}$,
a group represented by the formula —$X^{331}$-$A^{331}$-$X^{332}$—$R^{331}$,
a group represented by the formula —$X^{331}$-$A^{331}$-$X^{332}$-$A^{332}$-$X^{333}$—$R^{331}$, or
a group represented by the formula —$X^{331}$-$A^{331}$-$X^{332}$-$A^{332}$-$X^{333}$-$A^{333}$-$X^{334}$—$R^{331}$, wherein $X^{331}$ is:
a group represented by the formula —O—,
a group represented by the formula —OCO—,
a group represented by the formula —OCON($R^{20}$)—,
a group represented by the formula —N($R^{20}$)—,
a group represented by the formula —N($R^{20}$)CO—, or
a group represented by the formula —OCSN($R^{20}$)—, and
$R^{331}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or
one of $R^{32}$ and $R^{33}$ is hydroxyl group, and the other is:
a group represented by the formula —$X^{335}$—$R^{332}$,
a group represented by the formula —$X^{335}$-$A^{334}$-$X^{336}$—$R^{332}$, or
a group represented by the formula —$X^{335}$-$A^{334}$-$X^{336}$-$A^{335}$-$X^{337}$—$R^{332}$,
wherein $X^{335}$ is:
a single bond,
a group represented by the formula —$CH_2$N($R^{20}$)—,
a group represented by the formula —$CH_2$N($R^{20}$)CO—,
a group represented by the formula —$CH_2$N($R^{20}$)$CO_2$—,
a group represented by the formula —$CH_2$N($R^{20}$)CON($R^{21}$)—,
a group represented by the formula —$CH_2$-$A^{336}$
a group represented by the formula —$CH_2$O—, or
a group represented by the formula —$CH_2$S(O)$_p$—,
$A^{336}$ is:
a divalent nitrogen-containing heterocyclic group which may be substituted with hydroxyl group or a $C_{1-6}$ alkoxy group,
$R^{332}$ is
a $C_{1-6}$ alkyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, and
p is an integer of 0 to 2, or
$R^{32}$ and $R^{33}$ combine together to represent oxo group,
oxime group,
a protected oxime group,
a group represented by the formula:

[Formula 3]

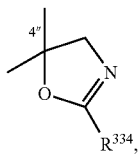

a group represented by the formula:

[Formula 4]

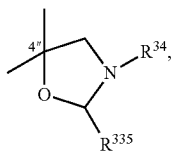

or
a group represented by the formula:

[Formula 5]

wherein $R^{334}$ is:
a group represented by the formula —OH or by the formula —SH,
$R^{335}$ is hydrogen atom, or a $C_{1-6}$ alkyl group,
$R^{34}$ is:
a group represented by the formula —$R^{336}$,
a group represented by the formula -$A^{337}$-$X^{338}$—$R^{336}$, or
a group represented by the formula -$A^{337}$-$X^{338}$-$A^{338}$-$X^{339}$—$R^{336}$, and
$R^{336}$ is
a $C_{1-6}$ alkyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A,
$R^4$ is:
hydrogen atom,
a group represented by the formula —$R^{041}$,
a group represented by the formula —$CH_2$—$CH(OH)$—$CH_2$—$NHR^{041}$, or
a group represented by the formula —$CH_2$—$CH(OH)$—$CH_2$—$NH$-$A^{041}$-$X^{042}$—$R^{041}$,
wherein $A^{041}$ is:
a divalent $C_{1-10}$ aliphatic hydrocarbon group, or
a divalent heterocyclic group, and
$R^{041}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or
$R^4$ may combine with $R^6$ to form a cyclic carbonate [—CON($R^{22}$)—],
one of $R^5$ and $R^6$ is hydrogen atom, and the other is:
hydrogen atom,
hydroxyl group,
a protected hydroxyl group,
amino group,
a protected amino group,
a group represented by the formula —$X^{051}$—$R^{051}$, or
a group represented by the formula —$X^{051}$-$A^{051}$-$X^{052}$—$R^{051}$,
wherein $X^{051}$ is:
a group represented by the formula —O—,
a group represented by the formula —$OCON(R^{22})$—,
a group represented by the formula —$N(R^{22})$—, or
a group represented by the formula —$N(R^{22})CO$—, and
$R^{051}$ is
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, or $R^5$ and $R^6$ combine together to represent oxo group, oxime group, a protected oxime group, a group represented by the formula $=N-X^{053}-R^{052}$, or a group represented by the formula $=N-X^{053}-A^{052}-X^{054}-R^{052}$, wherein $X^{053}$ is:

a group represented by the formula —O—, or a group represented by the formula —CO—, and $R^{052}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, $R^7$ is hydrogen atom, or a protective group of hydroxyl group, $R^8$ and $R^9$, which are the same or different, represent hydrogen atom, a $C_{1-6}$ alkyl group, or a protective group of amino group, $X^{332}, X^{333}, X^{334}, X^{336}, X^{337}, X^{338}, X^{339}, X^{042}, X^{052}$ and $X^{054}$ mentioned above, which are the same or different, represent a single bond, a group represented by the formula —O—, a group represented by the formula —OCO—, a group represented by the formula —OCO$_2$—, a group represented by the formula —OCON($R^{25}$)—, a group represented by the formula —S(O)$_r$—, a group represented by the formula —SO$_2$N($R^{25}$)—, a group represented by the formula —OCS—, a group represented by the formula —CO—, a group represented by the formula —CO$_2$—, a group represented by the formula —CON($R^{25}$)—, a group represented by the formula —CH=N—, a group represented by the formula —CH=N—O—, a group represented by the formula —C($R^{25}$)=N—, a group represented by the formula —C($R^{25}$)=N—O—, a group represented by the formula —C($R^{25}$)=N—N($R^{26}$)—, a group represented by the formula —CH=N—N($R^{25}$)—, a group represented by the formula —CS—, a group represented by the formula —C(S)O—, a group represented by the formula —CSN($R^{25}$)—, a group represented by the formula —O—N=C($R^{25}$)—, a group represented by the formula —N=CH—, a group represented by the formula —N($R^{25}$)—, a group represented by the formula —N($R^{25}$)CO—, a group represented by the formula —N($R^{25}$)CS—, a group represented by the formula —N($R^{25}$)SO$_2$—, a group represented by the formula —N($R^{25}$)CO$_2$—, or a group represented by the formula —N($R^{25}$)CON($R^{26}$)—, r is an integer of 0 to 2, $A^{331}, A^{332}, A^{333}, A^{334}, A^{335}, A^{337}, A^{338}, A^{051}$, and $A^{052}$ mentioned above, which are the same or different, represent a divalent $C_{1-16}$ aliphatic hydrocarbon group which may be substituted with hydroxyl group, a $C_{1-6}$ alkoxy group, amino group, a $C_{1-6}$ alkylamino group or a heterocyclic group, an arylene group which may be substituted with hydroxyl group or a $C_{1-6}$ alkoxy group, or a divalent heterocyclic group which may be substituted with hydroxyl group or a $C_{1-6}$ alkoxy group, and $R^{20}, R^{21}, R^{22}, R^{25}$, and $R^{26}$ mentioned above, which are the same or different, represent hydrogen atom, or a $C_{1-6}$ alkyl group which may be substituted with 1 to 3 groups selected from the group A, or a salt thereof, or a hydrate or a solvate thereof.

According to preferred embodiments of the aforementioned invention, there are provided:

(1) The 10a-azalide compound or a salt thereof, or a hydrate or a solvate thereof, wherein $R^2$ and $R^3$ combine together to represent oxo group, or one of them is hydrogen atom, and the other is:

hydroxyl group, a protected hydroxyl group, a group represented by the formula —$X^{031}$—$R^{031}$, or a group represented by the formula (II)

[Formula 6]

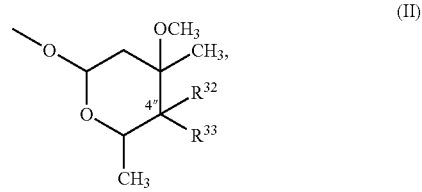

(II)

wherein $X^{031}$ is:

a group represented by the formula —O—, a group represented by the formula —OCO—, or a group represented by the formula —OCON($R^{20}$)—, $R^{031}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, the group B is a group consisting of hydroxyl group, a halogen atom, amino group, carboxyl group, cyano group, a $C_{1-6}$ alkyl group, a $C_{1-6}$ alkylamino group, a $C_{1-6}$ haloalkyl group, a $C_{1-6}$ alkoxy group, a $C_{2-7}$ alkoxycarbonyl group, nitro group, a saturated heterocyclic group, and a $C_{1-11}$ acyl group, one of $R^{32}$ and $R^{33}$ is hydrogen atom, and the other is:

hydrogen atom, hydroxyl group, a protected hydroxyl group, amino group, a protected amino group, a group represented by the formula —$X^{331}$—$R^{331}$, a group represented by the formula —$X^{331}$-$A^{331}$-$X^{332}$—$R^{331}$, a group represented by the formula —$X^{331}$-$A^{331}$-$X^{332}$-$A^{332}$-$X^{333}$—$R^{331}$, or a group represented by the formula —$X^{331}$-$A^{331}$-$X^{332}$-$A^{332}$-$X^{333}$-$A^{333}$-$X^{334}$—$R^{331}$, wherein $X^{331}$ is:

a group represented by the formula —O—, a group represented by the formula —OCO—, a group represented by the formula —OCON($R^{20}$)—, a group represented by the formula —N($R^{20}$)—, a group represented by the formula —N($R^{20}$)CO—, or a group represented by the formula —OCSN($R^{20}$)—, and $R^{331}$ is a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, or one of $R^{32}$ and $R^{33}$ is hydroxyl group, and the other is:

a group represented by the formula —$X^{335}$—$R^{332}$, a group represented by the formula —$X^{335}$-$A^{334}$-$X^{336}$—$R^{332}$, or a group represented by the formula —$X^{335}$-$A^{334}$-$X^{336}$-$A^{335}$-$X^{337}$—$R^{332}$, wherein $X^{335}$ is:

a single bond, a group represented by the formula —$CH_2N(R^{20})$—, a group represented by the formula —$CH_2N(R^{20})CO$—, a group represented by the formula —$CH_2N(R^{20})CO_2$—, a group represented by the formula —$CH_2N(R^{20})CON(R^{21})$—, a group represented by the formula —$CH_2O$—, or a group represented by the formula —$CH_2S(O)_p$—, $R^{332}$ is a $C_{1-6}$ alkyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, and p is an integer of 0 to 2, or $R^{32}$ and $R^{33}$ combine together to represent oxo group, oxime group, a protected oxime group, a group represented by the formula:

[Formula 7]

or a group represented by the formula:

[Formula 8]

wherein $R^{334}$ is:

a group represented by the formula —OH, or by the formula —SH, $R^4$ is:

hydrogen atom, a group represented by the formula —$R^{041}$, a group represented by the formula —$CH_2$—CH(OH)—$CH_2$—$NHR^{041}$, or a group represented by the formula —$CH_2$—CH(OH)—$CH_2$—NH-$A^{041}$-$X^{042}$—$R^{041}$, wherein $A^{041}$ is:

a divalent $C_{1-10}$ aliphatic hydrocarbon group, or a divalent heterocyclic group, and $R^{041}$ is a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, or $R^4$ may combine with $R^6$ to form a cyclic carbonate [—CON($R^{22}$)—], one of $R^5$ and $R^6$ is hydrogen atom, and the other is:

hydrogen atom, hydroxyl group, a protected hydroxyl group, amino group, a protected amino group, a group represented by the formula —$X^{051}$—$R^{051}$, or a group represented by the formula —$X^{051}$-$A^{051}$-$X^{052}$—$R^{051}$, wherein $X^{051}$ is:

a group represented by the formula —O—, a group represented by the formula —OCON($R^{22}$)—, a group represented by the formula —N($R^{22}$)—, or a group represented by the formula —N($R^{22}$)CO—, and $R^{051}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, or $R^5$ and $R^6$ combine together to represent oxo group, oxime group, a protected oxime group, a group represented by the formula =N—$X^{053}$—$R^{052}$, or a group represented by the formula =N—$X^{053}$-$A^{052}$-$X^{054}$—$R^{052}$, wherein $X^{O53}$ is:

a group represented by the formula —O—, or a group represented by the formula —CO—, and $R^{052}$ is a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, $X^{332}$, $X^{333}$, $X^{334}$, $X^{336}$, $X^{337}$, $X^{042}$, $X^{052}$, and $X^{054}$ mentioned above, which are the same or different, represent a single bond, a group represented by the formula —O—, a group represented by the formula —OCO—, a group represented by the formula —$OCO_2$—, a group represented by the formula —OCON($R^{25}$)—, a group represented by the formula —$S(O)_r$—, a group represented by the formula —$SO_2$N($R^{25}$)—, a group represented by the formula —OCS—, a group represented by the formula —CO—, a group represented by the formula —$CO_2$—, a group represented by the formula —CON($R^{25}$)—, a group represented by the formula —CH=N—, a group represented by the formula —CH=N—O—, a group represented by the formula —C($R^{25}$)=N—, a group represented by the formula —C($R^{25}$)=N—O—, a group represented by the formula —C($R^{25}$)=N—N($R^{26}$)—, a group represented by the formula —CH=N—N($R^{25}$)—, a group represented by the formula —CS—, a group represented by the formula —C(S)O—, a group represented by the formula —CSN($R^{25}$)—, a group represented by the formula —O—N=C($R^{25}$)—, a group represented by the formula —N=CH—, a group represented by the formula —N($R^{25}$)—, a group represented by the formula —N($R^{25}$)CO—, a group represented by the formula —N($R^{25}$)CS—, a group represented by the formula —N($R^{25}$)$SO_2$—, a group represented by the formula —N($R^{25}$)$CO_2$—, or a group represented by the formula —N($R^{25}$)CON($R^{26}$)—, and r is an integer of 0 to 2, $A^{331}$, $A^{332}$, $A^{333}$, $A^{334}$, $A^{335}$, $A^{051}$, and $A^{052}$ mentioned above, which are the same or different, represent a divalent $C_{1-10}$ aliphatic hydrocarbon group which may be substituted with hydroxyl group, a $C_{1-6}$ alkoxy group, or a heterocyclic group, an arylene group which may be substituted with hydroxyl group, or a $C_{1-6}$ alkoxy group, or a divalent heterocyclic group which may be substituted with hydroxyl group, or a $C_{1-6}$ alkoxy group, and $R^{20}$, $R^{21}$, $R^{22}$, $R^{25}$, and $R^{26}$ mentioned above, which are the same or different, represent hydrogen atom or a $C_{1-6}$ alkyl group which may be substituted with 1 to 3 groups selected from the group B.

(2) The 10a-azalide compound or a salt thereof, or a hydrate or a solvate thereof, wherein one of $R^2$ and $R^3$ is hydrogen atom, and the other is:

a group represented by the formula (II), $R^4$ is hydrogen atom, or methyl group one of $R^5$ and $R^6$ is hydrogen atom, and the other is hydroxyl group, or amino group, or $R^5$ and $R^6$ combine together to represent oxo group, or oxime group, $R^7$ is hydrogen atom, and $R^8$ and $R^9$ are methyl groups.

(3) The 10a-azalide compound or a salt thereof, or a hydrate or a solvate thereof, wherein one of $R^{32}$ and $R^{33}$ is hydroxyl group, and the other is:

a group represented by the formula —$CH_2N(R^{20})$—$R^{332}$, a group represented by the formula —$CH_2N(R^{20})$-$A^{334}$-$X^{336}$—$R^{332}$, or a group represented by the formula —$CH_2N(R^2)$-$A^{334}$-$X^{336}$-$A^{335}$*$X^{337}$—$R^{332}$.

(4) The 10a-azalide compound or a salt thereof, or a hydrate or a solvate thereof, wherein one of $R^{32}$ and $R^{33}$ is hydroxyl group, and the other is:

a group represented by the formula —$CH_2N(R^{20})$-$A^{334}$-$X^{336}$—$R^{332}$.

(5) The 10a-azalide compound or a salt thereof, or a hydrate or a solvate thereof, wherein $A^{334}$ is a $C_{2-6}$ alkylene group, and $X^{336}$ is:

a group represented by the formula —N($R^{25}$)—.

(6) The 10a-azalide compound or a salt thereof, or a hydrate or a solvate thereof, wherein one of $R^{32}$ and $R^{33}$ is hydrogen atom, and the other is:

a group represented by the formula —OCON($R^{20}$)—$R^{331}$, a group represented by the formula —OCON($R^{20}$)-$A^{331}$-$X^{332}$—$R^{331}$, or a group represented by the formula —OCON($R^2$)-$A^{331}$-$X^{332}$-$A^{332}$-$X^{333}$—$R^{331}$.

(7) The 10a-azalide compound or a salt thereof, or a hydrate or a solvate thereof, wherein one of $R^{32}$ and $R^{33}$ is hydrogen atom, and the other is:

a group represented by the formula —OCON($R^{20}$)-$A^{331}$-$X^{332}$—$R^{331}$.

(8) The 10a-azalide compound or a salt thereof, or a hydrate or a solvate thereof, wherein $A^{331}$ is a $C_{2-6}$ alkylene group, and $X^{332}$ is:

a group represented by the formula —N($R^{25}$)—.

As another aspect of the present invention, there is provided a macrolide antibiotic comprising a substance selected from the group consisting of a 10a-azalide compound represented by the aforementioned formula (I), a physiologically acceptable salt thereof, a hydrate thereof, and a solvate thereof. The present invention also provides a medicament, preferably a medicament for prophylactic and/or therapeutic treatment of an infectious disease, comprising a substance selected from the group consisting of a 10a-azalide compound represented by the aforementioned formula (I), a physiologically acceptable salt thereof, a hydrate thereof, and a solvate thereof as an active ingredient.

The present invention further provides an antimicrobial agent comprising a substance selected from the group consisting of a 10a-azalide compound represented by the aforementioned formula (I), a physiologically acceptable salt thereof, a hydrate thereof, and a solvate thereof as an active ingredient, and a prophylactic and/or therapeutic agent for an infectious disease, which comprises a substance selected from the group consisting of a 10a-azalide compound represented by the aforementioned formula (I), a physiologically acceptable salt thereof, a hydrate thereof, and a solvate thereof as an active ingredient.

In addition to these, the present invention also provides use of a substance selected from the group consisting of a 10a-azalide compound represented by the aforementioned formula (I), a physiologically acceptable salt thereof, a hydrate thereof, and a solvate thereof for manufacture of the aforementioned medicament, and a method for prophylactic and/or therapeutic treatment of an infectious disease, which comprises the step of administering an effective amount of a substance selected from the group consisting of a 10a-azalide compound represented by the aforementioned formula (I), a physiologically acceptable salt thereof, a hydrate thereof, and a solvate thereof to a mammal including human.

Effect of the Invention

The 10a-azalide compounds of the present invention, salts thereof, hydrates thereof, and solvates thereof have an antibacterial activity against a wide variety of microorganisms, preferably aerobic or anaerobic bacteria such as Gram-positive or Gram-negative bacteria, mycoplasmas, chlamydiae, and the like, and they are characterized in, in particular, that they have superior antibacterial activity also against *Haemophilus influenzae*, erythromycin resistant pneumococci, and the like, against which sufficient antibacterial activity cannot be obtained with conventional macrolide antibiotics.

BEST MODE FOR CARRYING OUT THE INVENTION

In the present invention, the symbol "$C_{x-y}$" means that the group mentioned after that has x to y of carbon atoms.

The "halogen atom" is fluorine, chlorine, bromine, or iodine.

The "alkyl group" is a linear or branched alkyl group, and examples include, for example, methyl group, ethyl group, n-propyl group, isopropyl group, n-butyl group, 2-butyl group, t-butyl group, n-pentyl group, isopentyl group, 1,1-dimethylpropyl group, n-hexyl group, 1,1,3,3-tetramethylbutyl group, n-nonyl group, n-decyl group, and the like.

The "alkenyl group" is a linear or branched alkenyl group corresponding to the aforementioned "alkyl group" having one or more double bonds at arbitrary positions, and examples include, for example, vinyl group, 1-propenyl group, 2-propenyl group, 1-butenyl group, 1,3-butadienyl group, 2-pentenyl group, 3-pentenyl group, 2-hexenyl group, and the like.

The "alkynyl group" means a linear or branched alkynyl group corresponding to the aforementioned "alkyl group"

having one or more triple bonds at arbitrary positions, and examples include, for example, ethynyl group, 1-propynyl group, 2-propynyl group, and the like.

The "alkoxy group" is a linear or branched alkoxy group, and examples include, for example, methoxy group, ethoxy group, 1-propoxy group, isopropoxy group, 1-butoxy group, 1-methyl-1-propoxy group, t-butoxy group, 1-pentyloxy group, 1,1,3,3-tetramethylbutoxy group, n-decyloxy group, and the like.

The "alkoxycarbonyl group" means a group formed by bonding the aforementioned "alkoxy group" and carbonyl group, and examples include, for example, methoxycarbonyl group, ethoxycarbonyl group, t-butoxycarbonyl group, and the like.

The "haloalkyl group" is an alkyl group corresponding to the aforementioned "alkyl group" of which one or two or more hydrogen atoms are substituted with one or two or more halogen atoms, and examples of include, for example, fluoromethyl group, difluoromethyl group, trifluoromethyl group, 2,2,2-trifluoroethyl group, 2,2,2-trichloroethyl group, pentafluoroethyl group, 3,3,3-trifluoropropyl group, perfluoropropyl group, 4-fluorobutyl group, 4-chlorobutyl group, 4-bromobutyl group, perfluorohexyl group, and the like.

The "alkylamino group" is a group formed by bonding one or two of the aforementioned "alkyl groups" and amino group, and examples include, for example, methylamino group, dimethylamino group, diethylamino group, N-ethyl-N-methylamino group, and the like.

The "alkylthio group" is a linear or branched alkylthio group, and examples include, for example, methylthio group, ethylthio group, 1-propylthio group, isopropylthio group, 1-butylthio group, 1-methyl-1-propylthio group, t-butylthio group, 1-pentylthio group, and the like.

The "aryl group" is a monocyclic to tetracyclic aromatic carbon ring group having 6 to 18 carbon atoms, this aromatic carbon ring group may condense with a cycloalkyl ring, and this cycloalkyl ring may be substituted with oxo group. Examples of the aromatic carbon ring group include, for example, phenyl group, naphthyl group, anthryl group, phenanthrenyl group, tetracenyl group, pyrenyl group, and the like. Examples of the aromatic carbon ring group condensed with a cycloalkyl ring include fluorenyl group, oxofluorenyl group, indanyl group, oxoindanyl group, tetrahydronaphthyl group, oxotetrahydronaphthyl group, and the like.

The "aralkyloxy group" is a group corresponding to the aforementioned "alkoxy group" of which one hydrogen atom is replaced with an aromatic carbon ring group, and examples include, for example, benzyloxy group, phenethyloxy group, and the like.

The "heterocyclic group" is a monocyclic heterocyclic group, or a condensed ring type heterocyclic group containing 1 to 5 of atoms arbitrarily selected from nitrogen atom, oxygen atom and sulfur atom as ring constituting atoms, and includes a saturated heterocyclic group, an aromatic heterocyclic group, a partially saturated monocyclic aromatic heterocyclic group and a condensed ring type heterocyclic group comprising an aromatic heterocyclic group having a single partially saturated ring. The condensed ring type heterocyclic group having a single partially saturated ring may be substituted with oxo group. When the hetero atom is sulfur atom, dioxide compounds also fall within the scope of the present invention.

As the heterocyclic group, a heterocyclic group having 1 to 10 carbon atoms in the ring system is preferred.

In this specification, an "aromatic heterocyclic group" is also referred to as "heteroaryl group" for convenience, and the aromatic heterocyclic group and the heteroaryl group have the same meaning.

Examples of the saturated heterocyclic group include, for example, aziridinyl group, azetidinyl group, pyrrolidinyl group, imidazolidinyl group, pyrazolidinyl group, oxolanyl group, thiolanyl group, piperidinyl group, piperazinyl group, morpholinyl group, and the like.

Examples of the aromatic heterocyclic group include, for example, pyridyl group, pyridazinyl group, pyrimidinyl group, pyrazinyl group, quinolyl group (e.g., 2-quinolyl, 3-quinolyl group, 4-quinolyl group, 5-quinolyl group), isoquinolyl group, thienyl group (e.g., 2-thienyl group, 3-thienyl group), pyrrolyl group (e.g., 1-pyrrolyl group, 2-pyrrolyl group, 3-pyrrolyl group), thiazolyl group (e.g., 2-thiazolyl group, 4-thiazolyl group, 5-thiazolyl group), isothiazolyl group (e.g., 3-isothiazolyl group, 4-isothiazolyl group, 5-isothiazolyl group), pyrazolyl group (e.g., 1-pyrazolyl group, 3-pyrazolyl group, 4-pyrazolyl group), imidazolyl group (e.g., 1-imidazolyl group, 2-imidazolyl group, 3-imidazolyl group), furyl group (e.g., 2-furyl group, 3-furyl group), oxazolyl group (e.g., 2-oxazolyl group, 4-oxazolyl group, 5-oxazolyl group), isoxazolyl group (e.g., 3-isoxazolyl group, 4-isoxazolyl group, 5-isoxazolyl group), oxadiazolyl group (e.g., 1,2,3-oxadiazolyl group, 1,3,4-oxadiazolyl group), thiadiazolyl group (e.g., 1,2,3-thiadiazolyl group, 1,3,4-thiadiazolyl group), triazolyl group (e.g., 1,2,4-triazolyl group), tetrazolyl group, benzofuranyl group (e.g., 2-benzofuranyl group, 3-benzofuranyl group, 4-benzofuranyl group, 5-benzofuranyl group), benzothienyl group (e.g., 2-benzothienyl group, 3-benzothienyl group, 4-benzothienyl group, 5-benzothienyl group), indolyl group (e.g., 2-indolyl group, 3-indolyl group, 4-indolyl group, 5-indolyl group), benzoxazolyl group (e.g., 2-benzoxazolyl group, 4-benzoxazolyl group, 5-benzoxazolyl group, 6-benzoxazolyl group), benzisoxazolyl group (e.g., 3-benzo[c]isoxazolyl group, 4-benzo[c]isoxazolyl group, 5-benzo[c]isoxazolyl group, 6-benzo[c]isoxazolyl group, 3-benzo[d]isoxazolyl group, 4-benzo[d]isoxazolyl group, 5-benzo[d]isoxazolyl group, 6-benzo[d]isoxazolyl group), indazolyl group (e.g., 3-indazolyl group, 4-indazolyl group, 5-indazolyl group, 6-indazolyl group), benzimidazolyl group (e.g., 2-benzimidazolyl group, 4-benzimidazolyl group, 5-benzimidazolyl group, 6-benzimidazolyl group), benzooxadiazolyl group (e.g. 4-benzo[1,2,5]oxadiazolyl group, 5-benzo[1,2,5]oxadiazolyl group, 4-benzo[1,2,3]oxadiazolyl group, 5-benzo[1,2,3]oxadiazolyl group), benzothiadiazolyl group (e.g., 4-benzo[1,2,5]thiadiazolyl group, 5-benzo[1,2,5]thiadiazolyl group, 4-benzo[1,2,3] thiadiazolyl group, 5-benzo[1,2,3]thiadiazolyl group), indolidinyl group (e.g., 1-indolidinyl group, 2-indolidinyl group, 3-indolidinyl group, 5-indolidinyl group), thienopyridyl group (e.g., 2-thieno[2,3-b]pyridyl group, 3-thieno[2,3-b]pyridyl group, 5-thieno[2,3-b]pyridyl group, 6-thieno[2,3-b]pyridyl group, 2-thieno[3,2-b]pyridyl group, 3-thieno[3,2-b]pyridyl group, 5-thieno[3,2-b]pyridyl group, 6-thieno[3,2-b]pyridyl group), pyrazolopyridyl group (e.g., 2-pyrazolopyridyl group, 3-pyrazolopyridyl group, 5-pyrazolopyridyl group, 6-pyrazolopyridyl group), imidazopyridyl group (e.g., 1-imidazo[1,5-a]pyridyl group, 3-imidazo[1,5-a]pyridyl group, 5-imidazo[1,5-a]pyridyl group, 7-imidazo[1,5-a]pyridyl group, 2-imidazo[1,2-a]pyridyl group, 3-imidazo[1,2-a]pyridyl group, 5-imidazo[1,2-a]pyridyl group, 7-imidazo[1,2-a]pyridyl group), imidazopyrazyl group (e.g., 1-imidazo[1,5-a]pyrazyl group, 3-imidazo[1,5-a]pyrazyl group, 5-imidazo[1,5-a]pyrazyl group, 8-imidazo[1,5-a]pyrazyl group, 2-imidazo[1,2-a]pyrazyl group, 3-imidazo[1, 2-a]pyrazyl group, 5-imidazo[1,2-a]pyrazyl group, 8-imidazo[1,2-a]pyrazyl group), pyrazolopyrimidyl group (e.g., 2-pyrazolo[1,5-a]pyrimidyl group, 3-pyrazolo[1,5-a]pyrimidyl group, 5-pyrazolo[1,5-a]pyrimidyl group, 6-pyrazolo[1,5-a]pyrimidyl group, 2-pyrazolo[1,5-c]pyrimidyl group, 3-pyrazolo[1,5-c]pyrimidyl group, 4-pyrazolo[1,5-c]pyrimidyl group, 5-pyrazolo[1,5-c]pyrimidyl group), triazolopyrimidyl group (e.g., 3-[1,2,3]triazolo[1,5-a]pyrimidyl group, 5-[1,2,3]triazolo[1,5-a]pyrimidyl group, 6-[1,2,3]triazolo[1,5-a]pyrimidyl group, 3-[1,2,3]triazolo[1,5-c]pyrimidyl group, 4-[1,2,3]triazolo[1,5-c]pyrimidyl group, 5-[1,2,3]triazolo[1,5-c]pyrimidyl group, 2-[1,2,4]triazolo[1,5-a]pyrimidyl group, 5-[1,2,4]triazolo[1,5-a]pyrimidyl group, 6-[1,2,4]triazolo[1,5-a]pyrimidyl group, 7-[1,2,4]triazolo[1,5-a]pyrimidyl group, 2-[1,2,4]triazolo[1,5-c]pyrimidyl group, 5-[1,2,4]triazolo[1,5-c]pyrimidyl group, 7-[1,2,4]triazolo[1,5-c]pyrimidyl group, 8-[1,2,4]triazolo[1,5-c]pyrimidyl group), thienothienyl group (e.g., 2-thieno[2,3-b]thienyl group, 3-thieno[2,3-b]thienyl group, 2-thieno[3,2-b]thienyl group, 3-thieno[3,2-b]thienyl group), imidazothiazolyl group (e.g., 2-imidazo[2,1-b]thiazolyl group, 3-imidazo[2,1-b]thiazolyl group, 5-imidazo[2,1-b]thiazolyl group, 2-imidazo[5,1-b]thiazolyl group, 3-imidazo[5,1-b]thiazolyl group, 5-imidazo[5,1-b]thiazolyl group), and the like.

Examples of the partially saturated monocyclic aromatic heterocyclic group and condensed ring type heterocyclic group comprising an aromatic heterocyclic group having a single partially saturated ring include, for example, maleimido group, tetrahydrobenzofuranyl group, tetrahydrobenzothienyl group, tetrahydrobenzopyrrolyl group, tetrahydroisoquinolyl group, 2,3-dihydro-1H-benzofuranyl group, 2,3-dihydro-1H-benzothienyl group, 2,3-dihydro-1H-indolyl group, 2,3-dihydro-1H-indazolyl group, 2,3-dihydro-1H-benzotriazolyl group, 2,3-dihydro-1H-benzoxazolyl group, 2,3-dihydro-1H-benzothiazolyl group, benzo[1,3]oxathioly group, benzo[1,3]dioxolyl group, 2H-chromenyl group, chromanyl group, indolinyl group, isoindolinyl group, and the like.

Examples of the condensed ring type heterocyclic group having a single partially saturated ring and substituted with oxo group include, for example, 2-oxo-1,3-dihydro-1H-indolyl ring, 3-oxo-1,2-dihydro-1H-indazolyl ring, 2-oxo-3H-benzoxazolyl ring, 2-oxo-3H-benzothiazolyl ring, 2-oxobenzo[1,3]oxathiolyl ring, 2-oxo-benzo[1,3]dioxolyl ring, 2-oxo-chromenyl ring, and the like.

The "biaryl group" is a group formed by bonding two groups selected from the aforementioned aryl groups and/or the heteroaryl groups, and examples include, for example, biphenyl group, pyridylphenyl group (e.g., 4-(pyridin-3-yl) phenyl group), furylphenyl group (e.g., 3-(furan-2-yl)phenyl group, 4-(furan-3-yl)phenyl group), imidazolylphenyl group (e.g., imidazol-1-ylphenyl group), pyridylimidazole group (e.g., 4-(pyridin-3-yl)imidazole group), phenylthiazole group (e.g., 2-phenylthiazole group), and the like.

The "acyl group" is a group formed by eliminating hydroxyl group from a carboxylic acid, and examples include, for example, acetyl group, propionyl group, butyryl group, isobutyryl group, pivaloyl group, cyclopentylcarbonyl group, benzoyl group, nicotinoyl group, and the like.

The "divalent aliphatic hydrocarbon group" means an alkylene group, an alkenylene group, an alkynylene group, a cycloalkylene group, or a cycloalkenylene group.

The "alkylene group" is a linear or branched alkylene group, and examples include, for example, —$CH_2$—, —$(CH_2)_2$—, —$(CH_2)_3$—, —$CH(CH_3)$—, —$(CH_2)_3$—, —$CH(CH_3)CH_2$—, —$(CH(CH_3))_2$—, —$(CH_2)_2$—$CH(CH_3)$—, —$(CH_2)_3$—$CH(CH_3)$—, —$CH(CH(CH_3)_2)$—$CH_2$—, —$(CH_2)_2$—$CH(C_2H_5)$—, —$(CH_2)_6$—, —$(CH_2)_2$—$C(C_2H_5)_2$—, —$(CH_2)_3C(CH_3)_2CH_2$—, —$(CH_2)_8$—, —$(CH_2)_3C(CH_3)_2(CH_2)_3$—, —$(CH_2)_{10}$—, and the like.

The "alkenylene group" is a linear or branched alkenylene group having one or two or more double bonds in the chain, and examples include, for example, a divalent group having a double bond formed by eliminating 2 to 6 hydrogen atoms on adjacent carbon atoms of the aforementioned alkylene group.

The "alkynylene group" is a linear or branched alkynylene group having one or two or more triple bonds in the chain, and examples include, for example, a divalent group having a triple bond formed by further eliminating hydrogen atoms from carbon atoms at the double bond moiety of the aforementioned alkenylene group.

Further, the "divalent aliphatic hydrocarbon group" may contain a double bond and triple bond.

The "cycloalkylene group" is a divalent group formed by eliminating arbitrary 2 of hydrogen atoms from a cycloalkane, and examples include, for example, 1,1-cyclopropylene group, 1,2-cyclopentylene group, 1,2-cyclohexylene group, 1,3-cyclohexylene group, 1,4-cyclohexylene group, 1,3-cycloheptylene group, and the like.

The "cycloalkenylene group" is a divalent group formed by eliminating arbitrary 2 of hydrogen atoms from a cycloalkene, and examples include, for example, 3-cyclohexen-1,2-ylene group, 2,5-cyclohexadien-1,4-ylene group, and the like.

The "arylene group" is a divalent group formed by eliminating arbitrary 2 of hydrogen atoms from a mono- to tetracyclic aromatic hydrocarbon having 6 to 18 carbon atoms, and examples include, for example, divalent groups formed by eliminating arbitrary 2 of hydrogen atoms from benzene, naphthalene, azulene, fluorene, phenanthrene, anthracene, pyrene, and the like.

The "divalent heterocyclic group" is a divalent group formed by further eliminating arbitrary 1 of hydrogen atom from the aforementioned "heterocyclic group", and examples include, for example, divalent groups formed by eliminating arbitrary 1 of hydrogen atom from pyrazolidinyl group, oxolanyl group, thiolanyl group, azetidinyl group, piperidinyl group, piperazinyl group, morpholinyl group, pyridyl group, pyridazinyl group, pyrimidinyl group, pyrazinyl group, quinolyl group, isoquinolyl group, thienyl group, pyrrolyl group, thiazolyl group, isothiazolyl group, pyrazolyl group, imidazolyl group, furyl group, oxazolyl group, isoxazolyl group, oxadiazolyl group, thiadiazolyl group, triazolyl group, benzofuranyl group, benzothienyl group, indolyl group, benzoxazolyl group, benzisoxazolyl group, indazolyl group, benzimidazolyl group, benzoxadiazolyl group, benzothiadiazolyl group, indolidinyl group, or thienopyridyl group, and the like.

The "divalent nitrogen-containing heterocyclic group" is the aforementioned "divalent heterocyclic group" which contains a nitrogen atom in the ring, and it is preferably a monocyclic group.

The "protected hydroxyl group" means hydroxyl group protected with "a protective group of hydroxyl group".

The "protected amino group" means amino group protected with "a protective group of amino group".

The "protected oxime group" means oxime group protected with "a protective group of oxime group".

Examples of the "protective group of hydroxyl group", "protective group of amino group" and "protective group of oxime group" include a silyl type protective group such as trimethylsilyl group, triethylsilyl group and tert-butyldimethylsilyl group, an acyl type protective group such as acetyl group and benzoyl group, an ether type protective group such as benzyl group, p-methoxybenzyl group and 2-chlorobenzyl group, an acetal type protective group such as tetrahydropyranyl group, tetrahydrofuranyl group and 1-ethoxyethyl group, protective groups such as benzyloxycarbonyl group, t-butyloxycarbonyl group and ((9-9H-fluorenyl)methoxy) carbonyl group, and the like.

In the aforementioned formula (I), the preferred examples of $R^2$ to $R^9$ are as follows. The compounds one of which $R^2$ to $R^9$ corresponds to any one of the preferred examples of $R^2$ to $R^9$ explained below are preferred compounds, and the compounds having two or more of the preferred examples of $R^2$ to $R^9$ are more preferred compounds. However, the scope of the present invention is not limited to the following preferred examples.

It is preferred that $R^2$ is hydrogen atom, and it is preferred that $R^3$ is a group represented by the formula (II) at the same time.

When $R^2$ is hydrogen atom, and $R^3$ is a group represented by the formula (II), it is preferred that $R^{32}$ is hydrogen atom, and $R^{33}$ is a group represented by the formula —OCON($R^{20}$)-$A^{331}$-$X^{332}$—$R^{331}$. It is also preferred that $R^{32}$ is hydroxyl group, and $R^{33}$ is a group represented by the formula —CH$_2$N ($R^{20}$)-$A^{334}$-$X^{336}$—$R^{332}$.

In this case, it is preferred that $A^{331}$ is a $C_{2-6}$ alkylene group, $X^{332}$ is a group represented by the formula —N($R^{25}$)—, $A^{334}$ is a $C_{2-6}$ alkylene group, and $X^{336}$ is a group represented by the formula —N($R^{25}$)—. It is also preferred that $R^{331}$ is a $C_{1-6}$ alkyl group substituted with one group selected from "an aryl group, and a heterocyclic group (the aryl group, and the heterocyclic group may be substituted with one group selected from the group A)", an aryl group which may be substituted with one group selected from the group A, or a heterocyclic group which may be substituted with one group selected from the group A, and $R^{332}$ is a $C_{1-6}$ alkyl group which may be substituted with one group selected from "an aryl group, and a heterocyclic group (the aryl group, and the heterocyclic group may be substituted with one group selected from the group A)", an aryl group which may be substituted with one group selected from the group A, or a heterocyclic group which may be substituted with one group selected from the group A.

It is preferred that $R^4$ is hydrogen atom, or methyl group, and it is more preferred that $R^4$ is methyl group.

It is preferred that $R^5$ is hydrogen atom, and it is preferred that $R^6$ is hydroxyl group at the same time.

It is also preferred that $R^5$ and $R^6$ combine to form oxo group, or oxime group.

It is preferred that $R^7$ is hydrogen atom.

It is preferred that both $R^8$ and $R^9$ are methyl groups.

The salt of the 10a-azalide compound represented by the aforementioned formula (I) may be an acid addition salt or a base addition salt. Examples of the acid addition salt include, for example, salts with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid, laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer, and examples of the base addition salt include salts with an inorganic base such as sodium salts, potassium salts and calcium salts, salts with an organic amine such as morpholine and piperidine, and salts with an amino acid, but the salt is not limited to these. Among them, physiologically acceptable salts are preferred.

The 10a-azalide compounds of the present invention represented by the aforementioned formula (I) and salts thereof may exist as hydrates or arbitrary solvates, and these hydrates and solvates also fall within the scope of the present invention. Further, the 10a-azalide compounds of the present invention represented by the aforementioned formula (I) have two or more asymmetric carbons, and these asymmetric carbons may be in arbitrary configurations. Stereoisomers such as optical isomers and diastereoisomers in pure forms based on these asymmetric carbons, arbitrary mixtures of stereoisomers, racemates, and the like are all encompassed within the scope of the present invention. Moreover, the 10a-azalide compounds of the present invention represented by the aforementioned formula (I) may have one or more double bonds, and geometrical isomers thereof originating in a double bond or a ring structure may also exist. It should be understood that any geometrical isomers of pure forms or arbitrary mixtures of geometrical isomers fall within the scope of the present invention. One class of the preferred stereoisomers is shown below. However, the compounds of the present invention are not limited to the following specific type of stereoisomers. The configurations shown in the following structural formulas are absolute configurations, and represented with usual indications.

[Formula 9]

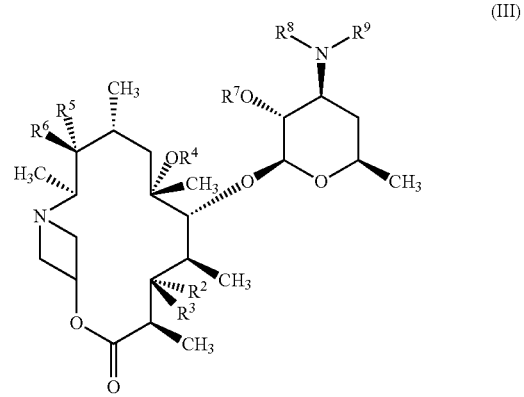

(III)

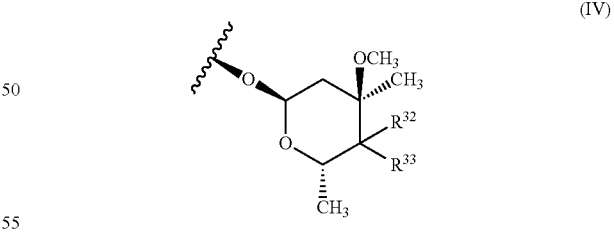

(IV)

The compounds of the present invention can be synthesized by, for example, the following methods. However, the preparation methods of the compounds of the present invention are not limited to these methods.

Although all of the compounds of the present invention are novel compounds not having been described in literatures, they can be prepared by known methods described in literatures, or similar methods. Examples of such literatures include S. R. Sandler et al., Organic Functional Group Preparations, Academic Press Inc., New York and London, 1968; S. R. Wagner et al., Synthetic Organic Chemistry, John Wiley, 1961; R. C. Larock, Comprehensive Organic Transformations, 1989; L. A. Paquette et al., Encyclopedia of Reagents for Organic Synthesis, 1995; Compendium of Organic Synthetic Methods, and the like.

In the text of the specification, the term base means, unless specifically indicated, for example, an organic base (e.g., an amine such as triethylamine, diisopropylethylamine, pyridine and 4-dimethylaminopyridine, a metal alkoxide such as sodium methoxide, and the like), or an inorganic base (e.g., an alkali metal carbonate such as sodium carbonate and potassium carbonate, an alkaline earth metal carbonate such as calcium carbonate, a metal hydroxide such as sodium hydroxide and potassium hydroxide, and the like), but the base is not limited to these.

The term solvent means, unless specifically indicated, for example, a polar solvent (e.g., water, an alcohol type solvent such as methanol, and the like), an inert solvent (e.g., a halogenated hydrocarbon type solvent such as chloroform and methylene chloride, an ether type solvent such as diethyl ether, tetrahydrofuran and 1,4-dioxane, an aprotic solvent such as dimethylformamide, dimethyl sulfoxide and acetonitrile, an aromatic hydrocarbon type solvent such as toluene, a hydrocarbon such as cyclohexane, and the like), or a mixed solvent thereof, but the solvent is not limited to these.

The condensing agent means, unless specifically indicated, for example, a chloroformic acid ester (e.g., isobutyl chloroformate, ethyl chloroformate, methyl chloroformate and the like), an acid chloride (e.g., pivaloyl chloride, oxalyl chloride, 2,4,6-trichlorobenzoyl chloride and the like), a dehydration condensing agent (e.g., a carbodiimide reagent such as 1-ethyl-3-[3-(dimethylamino)propyl]carbodiimide hydrochloride and dicyclohexylcarbodiimide, carbonyldiimidazole, 2-chloro-1-methylpyridinium iodide salt, and the like), and the like, but the condensing agent is not limited to these.

<Scheme 1>

[Formula 10]

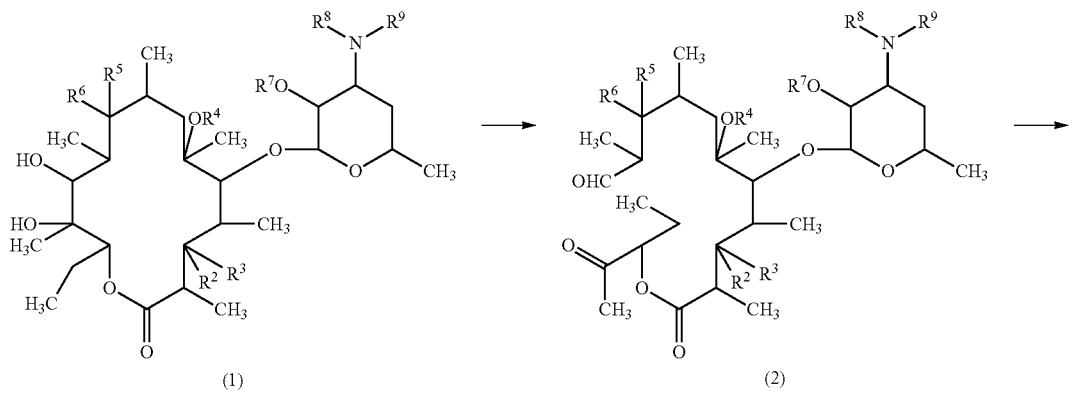

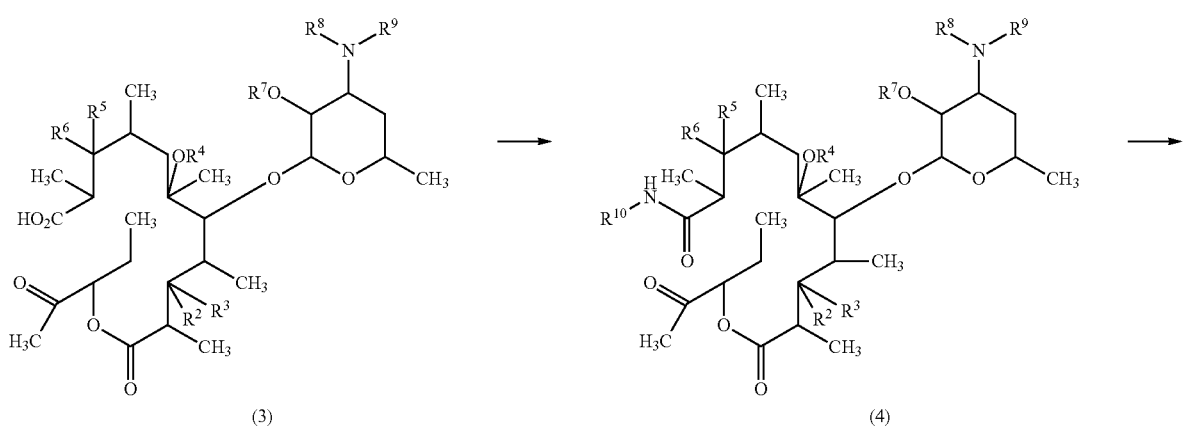

-continued

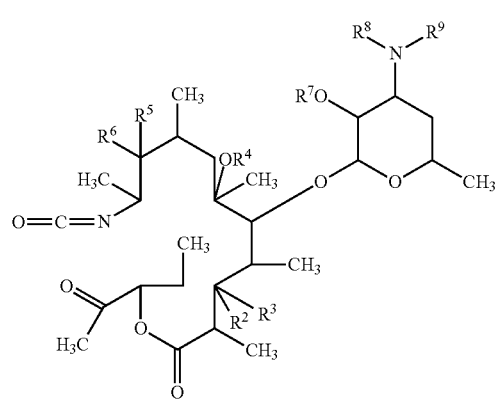

(5)

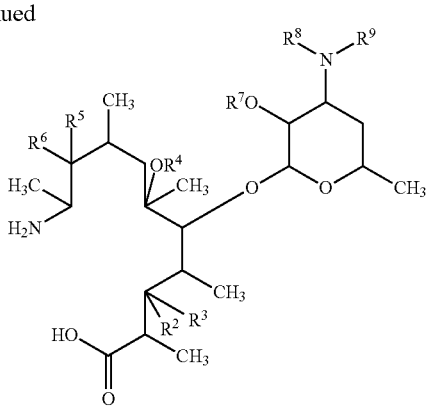

(6)

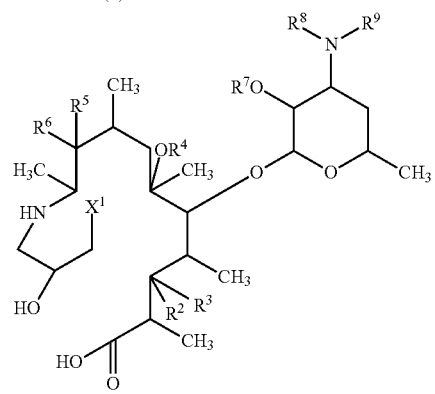

(7)

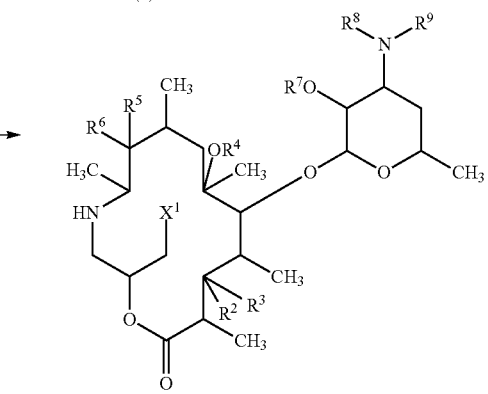

(8)

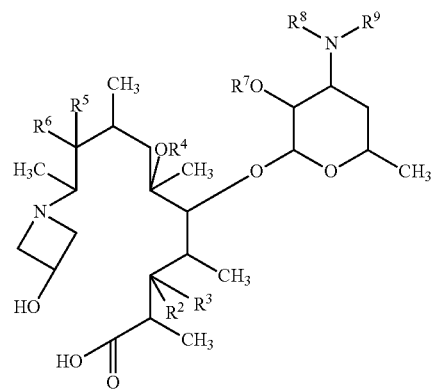

(10)

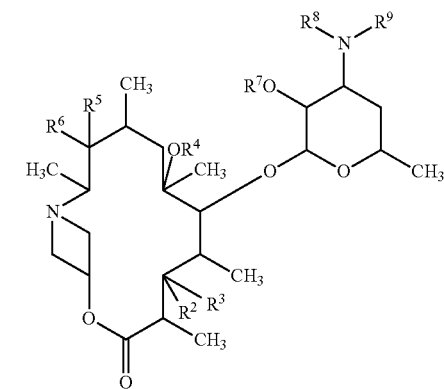

(9)

(In the formula, $R^{10}$ represents hydrogen atom, or hydroxyl group, and the other symbols have the same meanings as those defined above.)

The erythromycin analogue compounds represented by the formula (1) can be synthesized by, for example, the methods described in the publications (e.g., WO99/28332, WO02/096922, U.S. Pat. No. 6,420,535, WO01/077134, WO00/069875, WO05/030786, WO04/078770, and the like), or obtained by reducing any of the compounds wherein $R^5$ and $R^6$ combine together to form oxo group with a hydride reducing agent (for example, sodium borohydride, and lithium triethylborohydride are preferred) or the like, and then converting hydroxyl groups into other substituents defined as $R^5$ and $R^6$ according to a generally used functional group conversion method.

The compounds represented by the formula (2) can be prepared according to the methods described in the publications (e.g., WO03/014136 and the like) by using a compound represented by the formula (1) (a compound wherein $R^6$ is a protected hydroxyl group, and $R^6$ is hydrogen atom is preferred) as a starting material, specifically, by stirring a compound represented by the formula (1) with an oxidizing agent (examples include, for example, lead tetraacetate, periodic acid salts and the like, and among them, lead tetraacetate is preferred) in a solvent (e.g., chloroform is preferred). The reaction temperature is chosen from the range of, for example, from -20° C. to the boiling temperature of the solvent, and within that range, a temperature of from 0° C. to room temperature is preferred. The compounds represented by the formula (2) can be used in the following reaction without isolation from the reaction system.

The compounds represented by the formula (3) can be obtained by stirring a compound represented by the formula (2) with an oxidizing agent (examples include, for example, sodium chlorite, sodium perchlorate, potassium permanganate, and the like, and among them, sodium chlorite is preferred) in a solvent (for example, a mixed solvent of chloroform, tetrahydrofuran, or tert-butyl alcohol and water is preferred). The reaction temperature is selected from the range of, for example, −20° C. to the boiling temperature of the solvent, and a temperature of from 0° C. to room temperature is especially preferred.

The compounds represented by the formula (4) can be obtained by stirring a compound represented by the formula (3) with a condensing agent (for example, a chloroformic acid ester is preferred) in a solvent (for example, chloroform is preferred) in the presence or absence of an organic base (for example, an amine such as triethylamine is preferred), adding ammonia when $R^{10}$ is hydrogen atom, or adding hydroxylamine when $R^{10}$ is hydroxyl group, and then stirring the mixture. Although ammonia is preferably added as ammonia gas, ammonia may also be added as a solution in a solvent (for example, water, alcohol, dioxane and the like). Hydroxylamine can be used in a state of a solution in a solvent (examples of the solvent include, for example, water, alcohol, dioxane and the like, and water is especially preferred). The reaction temperature is selected from the range of, for example, −20° C. to room temperature, and a temperature of from −5° C. to 5° C. is especially preferred.

The compounds represented by the formula (5) can be obtained by stirring a compound represented by the formula (4) wherein $R^{10}$ is hydrogen atom in a solvent (e.g., ethyl acetate and the like) in the presence of iodobenzene diacetate, iodobenzene bistrifluoroacetate or the like. Further, the compounds represented by the formula (5) can also be obtained by stirring a compound represented by the formula (4) wherein $R^{10}$ is hydroxyl group in a solvent (for example, tetrahydrofuran is especially preferred) in the presence of a sulfonyl chloride (examples include, for example, p-toluenesulfonyl chloride, methanesulfonyl chloride and the like, and among them, p-toluenesulfonyl chloride is especially preferred). The reaction temperature is chosen from the range of, for example, from −20° C. to the boiling temperature of the solvent, and within that range, a temperature of from 0° C. to room temperature is preferred. The compounds of the formula (5) can be used for the following reaction without isolation from the reaction system.

The compounds represented by the formula (6) can be obtained by stirring a compound represented by the formula (5) in an aqueous solution of a metal hydroxide (examples include, for example, lithium hydroxide, sodium hydroxide and the like, and among them, lithium hydroxide is preferred), or in a mixed solvent of such an aqueous solution and an alcohol solvent such as methanol and ethanol, tetrahydrofuran, or the like. The reaction temperature is selected from the range of, for example, from 0° C. to the boiling temperature of the solvent, and a temperature of from 0° C. to room temperature is especially preferred.

The compounds represented by the formula (7) can be obtained by reacting a compound represented by the formula (6) with an epoxide represented by the following formula (11) in an inert solvent (examples include, for example, tetrahydrofuran, toluene, ethyl acetate, 1,4-dioxane, chloroform, and the like, and among them, tetrahydrofuran is preferred) in the presence or absence of a Lewis acid (for example, ytterbium triflate and the like) and in the presence or absence of a base (examples include, for example, an amine such as triethylamine, diisopropylethylamine, and pyridine, and among them, triethylamine is preferred) with heating. The reaction temperature of the aforementioned reaction is chosen from the range of, for example, from room temperature to 120° C., and a temperature of from 50 to 100° C. is preferred. This reaction may be carried out under ordinary pressure, or in a sealed tube.

The epoxide represented by the formula (11) is a compound represented as:

[Formula 11]

(11)

(In the formula, $X^1$ represents a leaving group (e.g., chloro group, bromo group, iodo group, methanesulfonyloxy group, p-toluenesulfonyloxy group, and the like, and among them, chloro group is preferred)).

The compounds represented by the formula (8) can be obtained by using a compound represented by is the formula (7) as a starting material, and reacting the compound with a Mitsunobu reagent (examples include, for example, an azodicarboxylate reagent such as diethyl azodicarboxylate, diisopropyl azodicarboxylate, and di-t-butyl azodicarboxylate, and among them, di-t-butyl azodicarboxylate or diisopropyl azodicarboxylate is preferred) in an inert solvent (examples include, for example, toluene, tetrahydrofuran, chloroform, and the like, and among them, toluene is preferred) in the presence of a phosphine reagent (for example, triphenylphosphine, and the like). The reaction temperature of the aforementioned reaction is chosen from the range of, for example, from −20° C. to the boiling temperature of the solvent, and the temperature is preferably in the range of from 0° C. to room temperature.

The compounds represented by the formula (9) can be obtained by using a compound represented by the formula (8) as a starting material, and reacting the compound in an inert solvent (for example, dimethylformamide is preferred) in the presence of a base (for example, diisopropylethylamine is preferred) and in the presence or absence of an inorganic salt (for example, potassium iodide is preferred). The reaction temperature of the aforementioned reaction is chosen from the range of, for example, from room temperature to 150° C., and the temperature is preferably in the range of from 50° C. to 120° C. This reaction may be carried out under ordinary pressure, or in a sealed tube.

The compounds represented by the formula (10) can be obtained by using a compound represented by the formula (7) as a starting material, and reacting the compound in an inert solvent (for example, tetrahydrofuran is preferred) with heating in the presence or absence of a Lewis acid (for example, ytterbium triflate) and in the presence or absence of a base (examples include, for example, amines such as triethylamine, diisopropylethylamine and pyridine). The reaction temperature of the aforementioned reaction is chosen from the range of, for example, from room temperature to 120° C., and the temperature is preferably in the range of from 50° C. to 100° C. This reaction may be carried out under ordinary pressure, or in a sealed tube.

The compounds represented by the formula (9) can also be obtained by a method of reacting a compound represented by the formula (10) with a condensing agent (for example, 2,4,6-trichlorobenzoyl chloride is preferred) in a solvent (for example, tetrahydrofuran is preferred) in the presence of an organic base (an amine such as triethylamine is preferred), and performing a reaction using the resulting reaction solution and a solution of a base (for example, 4-dimethylaminopyridine is preferred) in an inert solvent (for example, toluene or acetonitrile is preferred), or a method of reacting a compound represented by the formula (10) with a solution of an acid anhydride (for example, 2-methyl-6-nitrobenzoic anhydride is preferred) and a base (for example, 4-dimethylaminopyridine is preferred) in an inert solvent (examples include, for example, dichloromethane, chloroform, toluene, acetonitrile, and the like, and among them, dichloromethane or chloroform is preferred). The reaction temperature of the aforementioned reaction is preferably a temperature in the range of from room temperature to the boiling temperature of the solvent.

(In the formula, $R^{3'}$ is a group represented by the formula $—X^{031}—R^{031}$, $X^{031}$, and $R^{031}$ have the same meanings as those defined above, and the other symbols used in the formulas have the same meanings as those defined above.)

The compounds represented by the formula (13) can be obtained by using a compound represented by the formula (12) as a starting material and oxidizing the compound by a method similar to the methods described in the literatures (Tetrahedron, 1978, vol. 34, p. 1651; Journal of American Chemical Society, 1972, vol. 94, p. 7586), i.e., Swern oxidation, Corey-Kim Oxidation, or the like.

The compounds represented by the formula (14) wherein $X^{031}$ is a group represented by the formula —O— can be obtained by a method similar to the methods described in the publications (for example, WO94/17088 and the like), i.e., by a method of reacting a compound represented by the formula (12) and a corresponding alkyl halide or the like in an inert solvent in the presence of a base.

The compounds represented by the formula (14) wherein $X^{031}$ is a group represented by the formula —OCO— can be obtained by a method similar to the methods described in the publications (U.S. Pat. No. 6,191,118, WO04/101584, <Scheme 2>

[Formula 12]

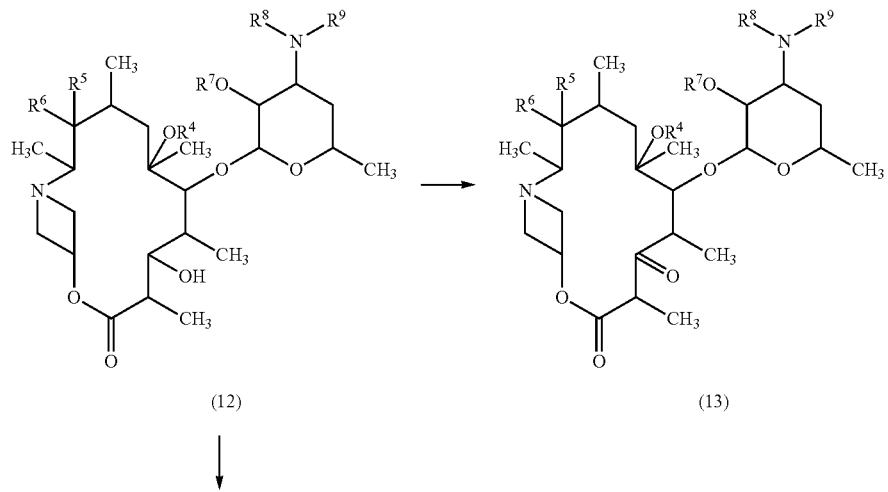

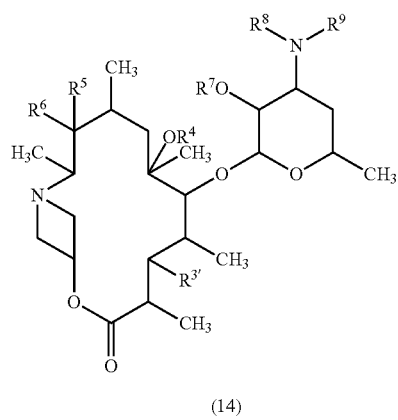

WO05/030786 and the like), specifically, by a method of reacting a compound represented by the formula (12) in an inert solvent in the presence of a corresponding carboxylic acid and a condensing agent, or with a corresponding acid anhydride or a corresponding acid chloride in an inert solvent in the presence or absence of a base. The reaction temperature is selected from the range of, for example, from 0° C. to the boiling temperature of the solvent. Further, the compounds represented by the formula (14) wherein $X^{031}$ is a group represented by the formula —OCON($R^{20}$)— can be obtained by a method similar to the method described in the publication (U.S. Pat. No. 5,523,399), specifically, by a method of reacting a compound represented by the formula (12) and carbonyldiimidazole in an inert solvent, and then adding a corresponding amine, a method of reacting triphosgene in an inert solvent in the presence of a base, and then adding a corresponding amine, or a method of reacting a compound represented by the formula (12) and a corresponding isocyanate in an inert solvent. The reaction temperature of the aforementioned reactions is preferably in the range of from room temperature to the boiling temperature of the solvent.

Further, among the compounds represented by the formula (9) shown in Scheme 1, those compounds shown in Scheme 3 can also be obtained by the steps shown in Scheme 3, as well as the steps shown in Scheme 1.

<Scheme 3>

[Formula 13]

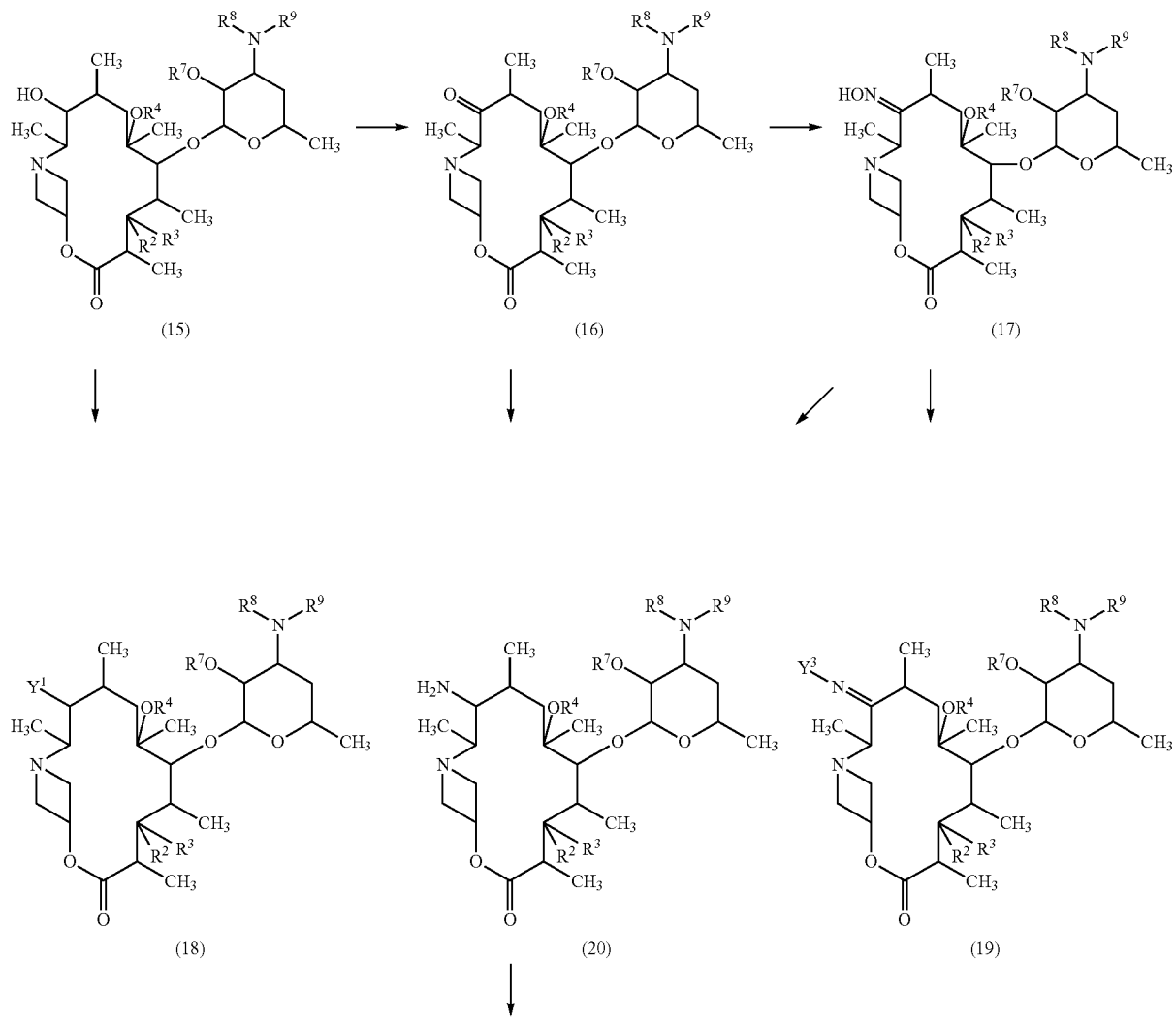

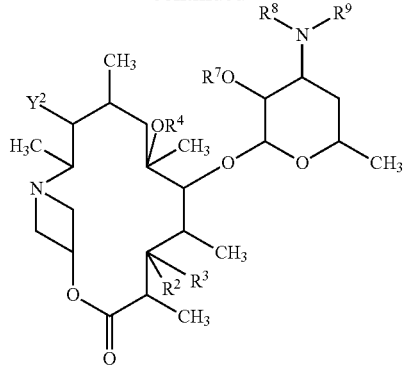

(21)

(In the formula, Y¹ is:
a group represented by the formula —$X^{051'}$—$R^{051}$, or
a group represented by the formula —$X^{051'}$-$A^{051}$-$X^{052}$— $R^{051}$,
wherein $X^{051'}$ is
a group represented by the formula —O— or
a group represented by the formula —$OCON(R^{22})$—, and
$A^{051}$, $X^{052}$, $R^{051}$, and $R^{22}$ have the same meanings as those defined above,
Y² is
a group represented by the formula —$X^{051''}$—$R^{051}$, or
a group represented by the formula —$X^{051''}$-$A^{051}$-$X^{052}$— $R^{051}$,
wherein $X^{051''}$ is
a group represented by the formula —$N(R^{22})$— or
a group represented by the formula —$N(R^{22})CO$—, and
$A^{051}$, $X^{052}$, $R^{051}$, and $R^{22}$ have the same meanings as those defined above,
Y³ is:
a group represented by the formula —$X^{053}$—$R^{052}$ or
a group represented by the formula —$X^{053}$-$A^{052}$-$X^{054}$— $R^{052}$, and
$X^{053}$, $A^{052}$, $X^{054}$, and $R^{052}$ have the same meanings as those defined above, and
the other symbols used in the formulas have the same meanings as those defined above.)

The compounds represented by the formula (16) can be obtained by using a compound represented by the formula (15) as a starting material and oxidizing the compound by a method similar to the methods described in the literatures (Tetrahedron, 1978, vol. 34, p. 1651; Journal of American Chemical Society, 1972, vol. 94, p. 7586), i.e., Swern oxidation, Corey-Kim Oxidation, or the like.

The compounds represented by the formula (17) can be obtained by reacting a compound represented by the formula (16) and a hydroxylamine salt such as hydroxylamine hydrochloride or hydroxylamine in a solvent (for example, methanol is preferred) in the presence or absence of a base (for example, imidazole is preferred). The reaction temperature of the aforementioned reaction is preferably in the range of from room temperature to the boiling temperature of the solvent.

The compounds represented by the formula (18) wherein $X^{051'}$ is a group represented by the formula —O— can be obtained by using a compound represented by the formula (15) as a starting material, and reacting the compound with a corresponding alkyl halide in an inert solvent (for example, tetrahydrofuran is preferred) in the presence or absence of a crown ether (for example, 18-crown-6-ether and the like) and in the presence of a base (for example, potassium hydroxide is preferred). The reaction temperature of the aforementioned reaction is preferably room temperature.

The compounds represented by the formula (18) wherein $X^{051'}$ is a group represented by the formula —$OCON(R^{22})$— can be obtained by a method of using a compound represented by the formula (15) as a starting material, reacting the compound with carbonyldiimidazole in the presence of a base (for example, pyridine is preferred) at a temperature in the range of from room temperature to 100° C., and reacting the resulting imidazocarbonyl compound with a corresponding amine in the presence of a base (for example, pyridine is preferred) at a temperature in the range of from room temperature to 50° C., or the compounds can also be obtained by a method of reacting a compound represented by the formula (15) with a corresponding isocyanate in a solvent (examples include, for example, toluene, pyridine, and the like, and pyridine is preferred) in the presence or absence of a base (for example, 1,4-diazabicyclo[2.2.2]octane is preferred). The reaction temperature of the aforementioned reactions is preferably in the range of from room temperature to the boiling temperature of the solvent.

The compounds represented by the formula (20) can be obtained by reacting a compound represented by the formula (16) with a reducing agent (examples include, for example, sodium triacetoxyborohydride, sodium cyanoborohydride, and sodium borohydride, and sodium cyanoborohydride is preferred) in a solvent (for example, methanol is preferred) in the presence of an ammonium salt (examples include, for example, ammonium acetate, ammonium carbonate, ammonium chloride, and the like, and ammonium acetate is preferred). The reaction temperature of the aforementioned reaction is preferably in the range of from room temperature to the boiling temperature of the solvent. Alternatively, the compounds represented by the formula (20) can also be obtained by using a compound represented by the formula (16) as a starting material according to a method similar to the methods described in the literatures (Tetrahedron Letters, 1971, vol. 2, p. 195; Tetrahedron Letters, 1972, vol. 1, p. 29), specifically, by reacting the carbonyl group with hydrazine in a polar solvent to convert the group into hydrazono group, and then reacting the resultant with sodium nitrite or the like, or by using a compound represented by the formula (17) as a starting material, reacting the compound with titanium chloride or the like to obtain an imino compound, and reducing the imino compound with a hydride reducing agent or the like.

The compounds represented by the formula (19) wherein $X^{053}$ is a group represented by the formula —O— can be obtained by using a compound represented by the formula (17) as a starting material according to a method similar to the method described in the publication (European Patent No. 284203 or WO93/13116), specifically, by reacting the compound with a corresponding alkyl halide or the like in an inert solvent in the presence or absence of crown ether (for example, 18-crown-6-ether and the like) and in the presence or absence of a base.

The compounds represented by the formula (19) wherein $X^{053}$ is a group represented by the formula —CO— can be obtained by using a compound represented by the formula (17) as a starting material, reacting the compound with titanium chloride or the like to obtain an imino compound, and reacting the imino compound with a corresponding acid chloride, acid anhydride, or the like in an inert solvent in the presence or absence of a base.

mentioned reaction is preferably a temperature in the range of from 0° C. to room temperature.

The compounds represented by the formula (21) wherein $X^{051"}$ is a group represented by the formula —N($R^{22}$)— can be obtained by reacting a compound represented by the formula (20) with a corresponding aldehyde reagent in a solvent (for example, methanol is preferred) in the presence of a hydride reducing agent (for example, sodium triacetoxyborohydride, sodium cyanoborohydride, and the like). The reaction temperature of the aforementioned reaction is preferably room temperature.

Further, among the compounds represented by the formula (9) shown in Scheme 1, those compounds shown in Scheme 4 can also be obtained by the steps shown in Scheme 4, as well as the steps shown in Scheme 1.

[Formula 14]

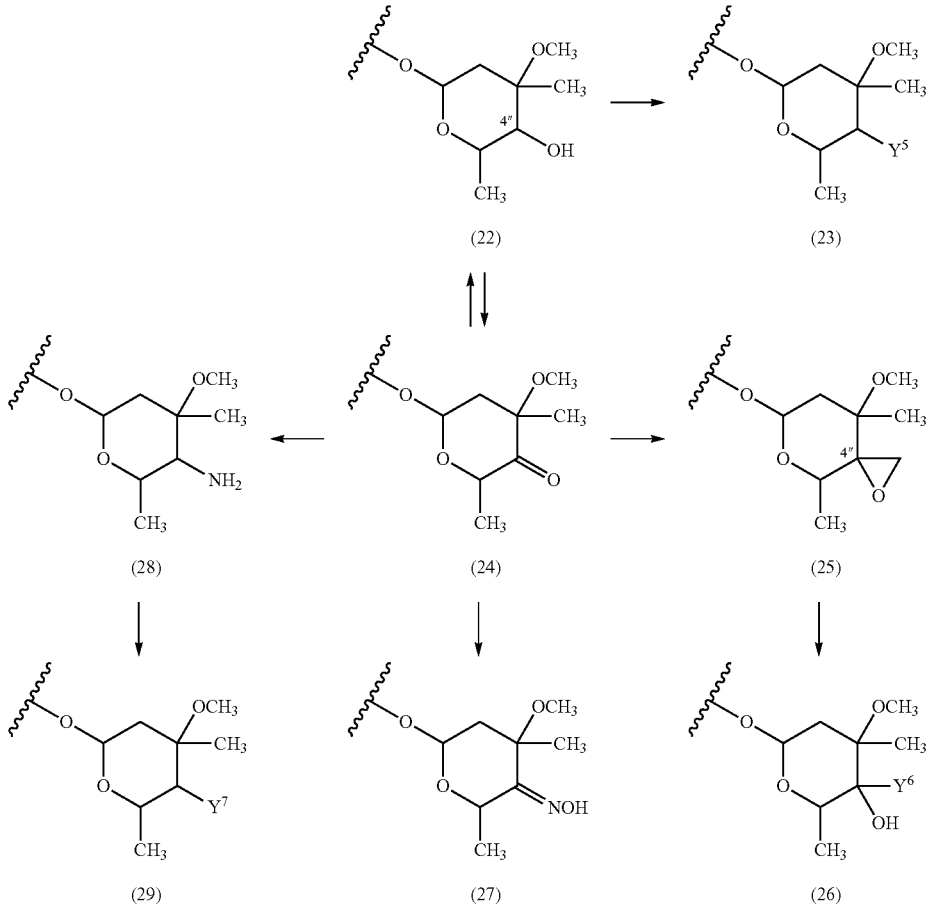

<Scheme 4>

The compounds represented by the formula (21) wherein $X^{051"}$ is a group represented by the formula —N($R^{22}$)CO— can be obtained by reacting a compound represented by the formula (20) with a corresponding acid chloride or acid anhydride in a solvent (for example, a mixed solvent of ether and water is preferred) in the presence or absence of a base (examples include, for example, an amine such as pyridine and triethylamine, sodium carbonate, and the like, and sodium carbonate is preferred). The reaction temperature of the afore- (The formulas (22) to (29) show conversion at the 4"-position of the compounds of the formula (I) wherein $R^2$ or $R^3$ is a group represented by the formula (II),
wherein, in the formulas, $Y^5$ is:
a group represented by the formula —$X^{331'}$—$R^{331}$,
a group represented by the formula —$X^{331'}$-$A^{331}$-$X^{332}$—$R^{331}$,
a group represented by the formula —$X^{331'}$-$A^{331}$-$X^{332}$-$A^{332}$-$X^{333}$—$R^{331}$, or a group represented by the formula —$X^{331'}$-$A^{331}$-$X^{332}$-$A^{332}$-$X^{333}$-$A^{333}$-$X^{334}$—$R^{331}$,
  wherein $X^{331'}$ is:
  a group represented by the formula —O—,
  a group represented by the formula —OCO—,
  a group represented by the formula —OCON($R^{20}$)—, or
  a group represented by the formula —OCSN($R^{20}$)—, and
  $A^{331}$, $X^{332}$, $A^{332}$, $X^{333}$, $A^{333}$, $X^{334}$, $R^{331}$, and $R^{20}$ have the same meanings as those defined above,
$Y^6$ is;
a group represented by the formula —$X^{335'}$—$R^{332}$,
a group represented by the formula —$X^{335'}$-$A^{334}$-$X^{336}$—$R^{332}$, or
a group represented by the formula —$X^{335'}$-$A^{334}$-$X^{336}$-$A^{335}$-$X^{337}$—$R^{332}$,
  wherein $X^{335'}$ is
  a single bond,
  a group represented by the formula —$CH_2N(R^{20})$—,
  a group represented by the formula —$CH_2O$—, or
  a group represented by the formula —$CH_2S(O)_p$—, and
  $A^{334}$, $X^{336}$, $A^{335}$, $X^{337}$, $R^{332}$, $R^{20}$, and p have the same meanings as those defined above, and
$Y^7$ is:
a group represented by the formula —$X^{331''}$—$R^{331}$,
a group represented by the formula —$X^{331''}$-$A^{331}$-$X^{332}$—$R^{331}$,
a group represented by the formula —$X^{331''}$-$A^{331}$-$X^{332}$-$A^{332}$-$X^{333}$—$R^{331}$, or
a group represented by the formula —$X^{331''}$-$A^{331}$-$X^{332}$-$A^{332}$-$X^{333}$-$A^{333}$-$X^{334}$—$R^{331}$,
  wherein $X^{331''}$ is:
  a group represented by the formula —$N(R^{20})$—, or
  a group represented by the formula —$N(R^{20})CO$—, and
  $A^{331}$, $X^{332}$, $A^{332}$, $X^{333}$, $A^{333}$, $X^{334}$, $R^{331}$, and $R^{20}$ have the same meanings as those defined above.)

The compounds represented by the formula (23) wherein $X^{331'}$ is a group represented by the formula —OCO— can be obtained by a method similar to the methods described in the publications (for example, European Patent No. 895999) by using a compound represented by the formula (22) as a starting material, specifically, by reacting the compound with a corresponding carboxylic acid in the presence of a condensing agent.

The compounds represented by the formula (23) wherein $X^{331'}$ is a group represented by the formula —O— can be obtained by using a compound represented by the formula (22) as a starting material, and reacting the compound with a corresponding alkyl halide or the like in a solvent (for example, tetrahydrofuran is preferred) in the presence or absence of a crown ether (for example, 18-crown-6-ether and the like) and in the presence of a base (for example, potassium hydroxide is preferred).

The compounds represented by the formula (23) wherein $X^{331'}$ is a group represented by the formula —OCON($R^{20}$)— can be obtained by a method similar to the methods described in the publications (for example, European Patent No. 895999) by using a compound represented by the formula (22) as a starting material, specifically, by reacting the compound, via an imidazocarbonyl compound, with a corresponding amine.

The compounds represented by the formula (23) wherein $X^{331'}$ is a group represented by the formula —OCSN($R^{20}$)— can be obtained by reacting a compound represented by the formula (22) and thiocarbonyldiimidazole in a solvent (for example, a mixed solvent of tetrahydrofuran and dimethylformamide is preferred) in the presence of a base (for example, sodium hydride is preferred) to obtain an imidazothiocarbonyl compound, and further reacting the resulting compound with a corresponding amine in the presence or absence of a solvent (for example, tetrahydrofuran is preferred). The reaction temperature of the reaction for obtaining the imidazothiocarbonyl compound is preferably in the range of from 0° C. to room temperature. The reaction temperature of the reaction with the corresponding amine is preferably in the range of from room temperature to the boiling temperature of the solvent.

The compounds represented by the formula (24) can be obtained by using a compound represented by the formula (22) as a starting material and oxidizing the compound by a method similar to the methods described in the literatures (Tetrahedron, 1978, vol. 34, p. 1651; Journal of American Chemical Society, 1972, vol. 94, p. 7586), i.e., Swern oxidation, Corey-Kim Oxidation, or the like.

The compounds represented by the formula (25) wherein the steric configuration of the 4"-position is the (R)-configuration can be obtained by a method similar to the methods described in the publications (for example, WO98/56801), specifically, by reacting a compound represented by the formula (24) with $(CH_3)_3S(O)X^2$ (examples of $X^2$ include, for example, a halogen, —$BF_4$ and —$PF_6$, and iodine is preferred) in a solvent (examples include, for example, tetrahydrofuran, ether, dimethylformamide, dimethyl sulfoxide, and the like, and two or more kinds of these may be used as a mixture) in the presence of an organic base or an inorganic base (for example, sodium hydride is preferred). The reaction temperature of the aforementioned reaction is chosen from the range of, for example, 0 to 60° C., and it is preferably in the range of from 0° C. to room temperature.

The compounds represented by the formula (25) wherein the steric configuration of the 4"-position is the (S)-configuration can be obtained by a method similar to the methods described in the publications (for example, WO98/56801), specifically, by reacting a compound represented by the formula (24) with $(CH_3)_3SX^3$ (examples of $X^3$ include, for example, a halogen, —$BF_4$ and —$PF_6$, and —$BF_4$ is preferred) in a solvent (examples include, for example, tetrahydrofuran, ether, dimethylformamide, dimethyl sulfoxide, and the like, and two or more kinds of these may be used as a mixture) in the presence of an organic base or an inorganic base. The reaction temperature of the aforementioned reaction is chosen from the range of, for example, −30 to 60° C., and it is preferably in the range of from −30° C. to room temperature.

The compounds represented by the formula (26) wherein $X^{335'}$ is a group represented by the formula —$CH_2N(R^{20})$— can be obtained by a method similar to the methods described in the publications (for example, WO98/56801), specifically, by reacting a compound represented by the formula (25) with a corresponding amine or the like in the presence or absence of a salt containing a halogen ion (examples include, for example, potassium iodide, ammonium chloride, pyridine hydrochloride, and the like) and in the presence or absence of a solvent (for example, water, methanol, ethanol, tetrahydrofuran, and the like are preferred). Further, the compounds represented by the formula (26) wherein $X^{335'}$ is a group represented by the formula —$CH_2O$—, or a group represented by the formula —$CH_2S$— can be obtained by using a corresponding alcohol reagent or thiol reagent instead of the amine reagent in the aforementioned reaction. The resulting sulfide compound wherein $X^{335'}$ is a group represented by the formula —$CH_2S$— can be converted into a sulfoxide or sulfone by oxidization with an oxidizing agent.

The compounds represented by the formula (27) can be obtained by reacting a compound represented by the formula

(24) and a hydroxylamine salt such as hydroxylamine hydrochloride or hydroxylamine in a solvent (for example, methanol is preferred) in the presence or absence of a base (for example, imidazole is preferred). The reaction temperature of the aforementioned reaction is preferably in the range of from room temperature to the boiling temperature of the solvent.

The compounds represented by the formula (28) can be obtained by reacting a compound represented by the formula (24) with a reducing agent (examples include, for example, sodium triacetoxyborohydride, sodium cyanoborohydride, and sodium borohydride, and sodium cyanoborohydride is preferred) in a solvent (for example, methanol is preferred) in the presence of an ammonium salt (examples include, for example, ammonium acetate, ammonium carbonate, ammonium chloride, and the like, and ammonium acetate is preferred). The reaction temperature of the aforementioned reaction is preferably in the range of from room temperature to 50° C.

The compounds represented by the formula (29) wherein $X^{331"}$ is a group represented by the formula $—N(R^{20})CO—$ can be obtained by reacting a compound represented by the formula (28) with a corresponding acid chloride, acid anhydride, or the like in an inert solvent in the presence or absence of a base. Those compounds wherein $X^{331"}$ is a group represented by the formula $—N(R^{20})—$ can be obtained by stirring a corresponding aldehyde reagent in the presence of a hydride reducing agent (for example, sodium triacetoxyborohydride, sodium cyanoborohydride, and the like) in a solvent. The reaction temperature of the aforementioned reaction is preferably in the range of from 0 to 50° C.

Further, among the compounds represented by the formula (9) shown in Scheme 1, those compounds shown in Scheme 5 can also be obtained by the steps shown in Scheme 5, as well as the steps shown in Scheme 1.

The compounds represented by the formula (31) can be obtained by reacting a compound represented by the formula (30) and a corresponding acid chloride, a corresponding acid anhydride, a corresponding isocyanate, a corresponding chloroformate, or the like in an inert solvent in the presence or absence of a base. The reaction temperature of the aforementioned reaction is preferably in the range of from 0° C. to the boiling temperature of the solvent. Among the compounds represented by the formula (31), those compounds wherein $R^{20}$ is a $C_{1-6}$ alkyl group which may be substituted with 1 to 3 groups selected from the group A can be obtained by monoalkylating the amino group of a compound represented by the formula (30), and then acylating the monoalkylated group.

The compounds represented by the formula (32) can be obtained by reacting a compound represented by the formula (30) with triphosgene or thiocarbonyldiimidazole in an inert solvent (for example, chloroform or dichloromethane is preferred) in the presence or absence of a base (for example, pyridine is preferred). The reaction temperature of the aforementioned reaction is preferably room temperature.

Further, among the compounds represented by the formula (9) shown in Scheme 1, those compounds shown in Scheme 6 can also be obtained by the steps shown in Scheme 6, as well as the steps shown in Scheme 1.

<Scheme 6>

[Formula 16]

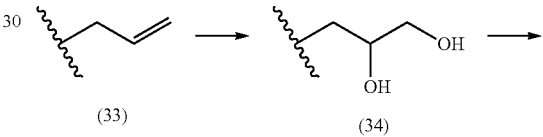

<Scheme 5>

[Formula 15]

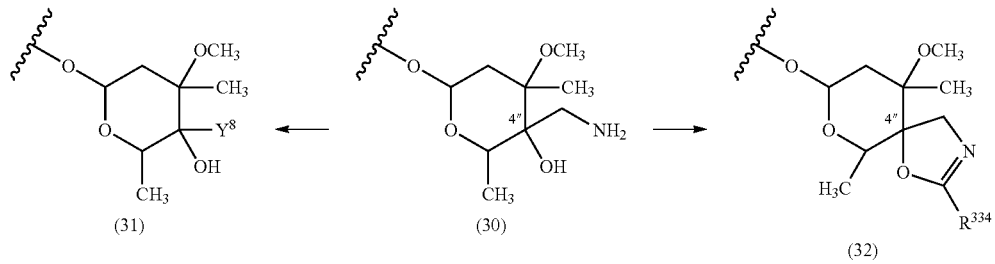

(The formulas (30) to (32) show conversion at the 4"-position of the compounds of the formula (I) wherein $R^2$ or $R^3$ is a group represented by the formula (II),
wherein, in the formula, $Y^8$ is:
a group represented by the formula $—X^{335"}—R^{332}$,
a group represented by the formula $—X^{335"}-A^{334}-X^{336}—R^{332}$, or
a group represented by the formula $—X^{335"}-A^{334}-X^{336}-A^{335}-X^{337}—R^{332}$,
  wherein $X^{335"}$ is:
  a group represented by the formula $—CH_2N(R^{28})CO—$,
  a group represented by the formula $—CH_2N(R^{20})CO_2—$, or
  a group represented by the formula $—CH_2N(R^{28})CON(R^{21})—$, and
$A^{334}$, $X^{336}$, $A^{335}$, $X^{337}$, $R^{332}$, $R^{334}$, $R^{20}$, and $R^{21}$ have the same meanings as those defined above.)

-continued

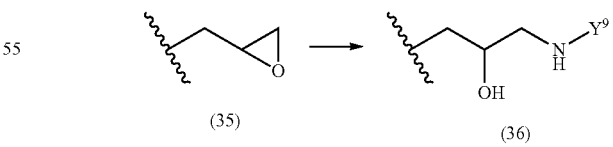

(The formulas (33) to (36) show conversion of $R^4$ of the compounds of the formula (I),
wherein, in the formula, $Y^9$ is:
a group represented by the formula $—R^{041}$, or
a group represented by the formula $-A^{041}-X^{042}—R^{041}$, and
$A^{041}$, $X^{042}$, and $R^{041}$ have the same meanings as those defined above.)

The compounds represented by the formula (34) can be obtained from a compound represented by the formula (33) by a method similar to the methods described in the publications (for example, WO97/42204), specifically, by reacting the compound in a solvent (for example, a mixed solvent of tetrahydrofuran and water, and the like) in the presence of osmium tetroxide and morpholine N-oxide.

The compounds represented by the formula (35) can be obtained by using a compound represented by the formula (34) as a starting material, reacting the compound with p-toluenesulfonyl chloride in an inert solvent (for example, chloroform is preferred) in the presence of a base (for example, triethylamine, 4-dimethylaminopyridine and the like) to obtain a sulfonate, and epoxylating the resulting sulfonate in a solvent (for example, methanol is preferred) in the presence of base (for example, potassium carbonate is preferred). The reaction temperature of the aforementioned reaction is preferably in the range of from 0° C. to room temperature.

The compounds represented by the formula (36) can be obtained by reacting a compound represented by the formula (35) and a corresponding amine reagent in a polar solvent (for example, ethanol is preferred) in the presence or absence of a perchlorate or an alkali metal salt (for example, lithium perchlorate and potassium iodide are preferred). The reaction temperature of the aforementioned reaction is chosen from the range of, for example, from room temperature to the boiling temperature of the solvent, and it is preferably in the range of from 50° C. to the boiling temperature of the solvent.

Hydroxyl groups, amino groups, carboxyl groups and oxime groups contained in the compounds represented by the formulas (1) to (36) mentioned in these synthesis methods may be protected with selectively removable protective groups known in this field, and by removing them at a desired stage, the 10a-azalide compounds represented by the formula (I), or intermediates for the synthesis of the 10a-azalide compounds represented by the formula (I) can be provided. Examples of the known protective group include a silyl type protective group such as trimethylsilyl group, triethylsilyl group and tert-butyldimethylsilyl group, an acyl type protective group such as acetyl group and benzoyl group, an ether type protective group such as benzyl group, p-methoxybenzyl group and 2-chlorobenzyl group, an acetal type protective group such as tetrahydropyranyl group, tetrahydrofuranyl group and 1-ethoxyethyl group, a carbonate type protective group such as benzyloxycarbonyl group and tert-butyloxycarbonyl group, and the like. However, besides those mentioned above, protective groups described in Protective Groups in Organic Syntheses (Third Edition, 1999, Ed. by P. G. M. Wuts, T. Green), and the like can also be used. Further, the substituents of the compounds represented by the formulas (1) to (36) mentioned in these synthesis methods can be interchangeably converted by known methods.

The intermediates and the objective compounds mentioned in the aforementioned preparation methods can be isolated and purified by purification methods commonly used in organic synthetic chemistry, for example, neutralization, filtration, extraction, washing, drying, concentration, recrystallization using a solvent such as ethyl acetate, ethyl acetate-hexane, isopropyl alcohol, ethanol, hydrated ethanol, acetone, hydrated acetone and the like, various chromatography techniques, and the like. The intermediates can also be used in subsequent reactions without particular purification.

A substance selected from the group consisting of the 10a-azalide compounds represented by the aforementioned formula (I), physiologically acceptable salts thereof, and hydrates and solvates thereof can be used as a medicament for prophylactic and/or therapeutic treatment of a microbial infectious disease as a novel macrolide antibiotic. Preferably, a pharmaceutical composition containing the aforementioned substance together with one or more kinds of usually used pharmaceutical additives can be prepared and administered for prophylactic and/or therapeutic treatment of a microbial infectious disease of a mammal including human. The administration route is not particularly limited, and administration route of oral administration, or parenteral administration may be chosen. Examples of the pharmaceutical composition suitable for oral administration include, for example, tablets, capsules, powders, granules, syrups, and the like, and examples of the pharmaceutical composition suitable for parenteral administration include, for example, injections for subcutaneous injection, intramuscular injection, or intravenous injection, drip infusions, suppositories, and the like, but the pharmaceutical composition is not limited to these examples. Injections or drip infusions can also be prepared as a pharmaceutical composition in the form of a lyophilized preparation. For manufacture of solid preparations such as tablets and capsules, usually used excipients, stabilizers. binders, coating agents, and the like can be suitably used, for manufacture of injections, drip infusions, and the like, usually used pharmaceutical additives, for example, excipients, pH modifiers, soothing agents, stabilizers, dissolving aids, and the like, can be suitably used, and these can be suitably chosen by those skilled in the art.

Although type of microbial infectious disease as the application object of the medicament of the present invention is not particularly limited, preferred examples include bacterial infectious diseases, mycoplasmal infectious diseases, chlamydial infectious diseases, and the like. Examples of the bacterial infectious diseases include Gram-positive or Gram-negative bacterial infectious diseases, and the medicament of the present invention can be used for the above diseases in a similar manner as that used for conventionally used macrolides. However, the medicament of the present invention is characterized by showing superior antibacterial activities even against, in particular, *Haemophilus influenzae*, erythromycin resistant pneumococci, and the like, against which the conventional macrolides cannot show sufficient antibacterial activity, and has an extremely wide antibacterial spectrum. Therefore, the medicament is usable even for an infectious disease of which causal bacterium is not specified.

The medicament of the present invention can be used for prophylactic and/or therapeutic treatment of infectious diseases caused by, for example, microorganisms of the genera *Staphylococcus*, and *Streptococcus*, pneumococci, *Moraxella (Branhamella) catarrhalis, Haemophilus influenzae*, microorganisms of the genera *Legionella, Campylobacter, Peptostreptococcus, Prevotella, Chlamydia*, and *Mycoplasma*, and the like, and can be used for, but not limited to, superficial skin infection, profound skin infection, lymphangitis and lymphadenitis, chronic pyoderma, secondary infection after traumatic injury, thermal burn, operative wound, and the like, perianal abscess, pharyngitis and laryngitis (laryngopharyngitis), tonsillitis, acute bronchitis, pneumonia, lung abscess, secondary infection in chronic respiratory diseases (including chronic bronchitis and diffuse panbronchiolitis), bronchiectasis, urethritis, cervicitis, enteritis infectious, otitis media, sinusitis, scarlet fever, pertussis, periodontitis, pericoronitis, jaw inflammation, disseminated *Mycobacterium avium* complex (MAC) disease accompanying acquired immunodeficiency syndrome (AIDS), *Helicobacter Pylori* infectious disease in gastric ulcer and duodenal ulcer, and the like.

Dose of the medicament of the present invention is not particularly limited, and the dose can be suitably chosen depending on type of infectious disease, purpose of administration (prophylactic or therapeutic treatment), age, weight and the like of patient, severity of infectious disease, and the like. For example, in the case of oral administration, 100 to 1,000 mg as a daily dose can be administered at one time or several times as divided portions. Moreover, the medicament of the present invention can be administered together with one or more kinds of other antibacterial agents or antibiotics.

EXAMPLES

The present invention will be more specifically explained with reference to reference examples, examples and test example. However, the scope of the present invention is not limited to these examples.

[Formula 17]

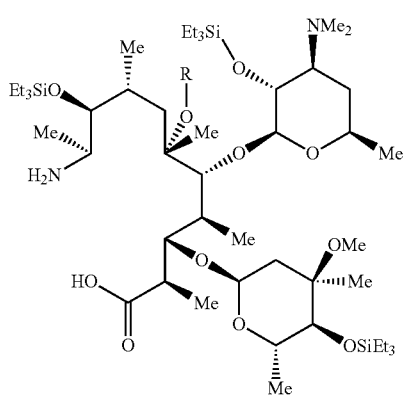

Formula (A)

Reference Example 1

Synthesis of Compound of the Formula (A) Wherein R is Methyl Group (1) (9S)-9-Dihydro-6-O-methylerythromycin A (84.5 g, 112.7 mmol) obtained by the method described in the literature (The Journal of Antibiotics, 1990, vol. 43, 10, p. 1334) and imidazole (80.6 g, 1183 mmol) were dissolved in dimethylformamide (1000 ml), the solution was cooled to 0° C., and triethylsilyl chloride (59.4 g, 394.4 mmol) was added dropwise to the solution. After the addition, the mixture was stirred at room temperature for 16 hours, then ethyl acetate (500 ml), hexane (500 ml), and distilled water (1000 ml) were added to the mixture, and the layers were separated. The organic layer was washed successively with saturated aqueous ammonium chloride (300 ml) and saturated brine, and dried over anhydrous magnesium sulfate, and then the solvent was evaporated under reduced pressure. The resulting residue was purified by silica gel column chromatography (hexane:ethyl acetate=100:1 to 5:1) to obtain a protected compound (107.9 g).

(2) A compound obtained in the same manner as that of (1) mentioned above (200 g) was dissolved in chloroform (400 ml), 90% lead tetraacetate (90.2 g) was added to the solution under ice cooling, and the mixture was stirred for 10 minutes. A solution of 2-methyl-2-butene (51.3 g) in tetrahydrofuran (800 ml), t-butyl alcohol (400 ml), and an aqueous solution (400 ml) of sodium chlorite (33.1 g) were further added successively to the mixture, and the resulting mixture was stirred at room temperature for 18 hours. Saturated aqueous sodium hydrogencarbonate (700 ml) was added to the reaction mixture, the resulting mixture was stirred, then ethyl acetate (1000 ml) was added to the mixture, and the layers were separated. The organic layer was washed successively with saturated aqueous sodium hydrogencarbonate (500 ml), and saturated brine (500 ml), then dried over anhydrous magnesium sulfate, and filtered. The resulting filtrate was concentrated under reduced pressure to obtain a 10-carboxy compound (218.9 g).

(3) A solution of the compound obtained in (2) mentioned above (218.9 g) in toluene (500 ml) was concentrated under reduced pressure, the resulting residue was dissolved in chloroform (500 ml), and triethylamine (28.1 ml) was added to the solution. Then, isobutyl chloroformate (25.0 g) was added dropwise to the mixture under ice cooling, and the mixture was stirred at the same temperature for 30 minutes. Then, 50% aqueous hydroxylamine (12.1 g) was added to the mixture under ice cooling, and the mixture was stirred at the same temperature for 1 hour. Saturated aqueous ammonium chloride (500 ml) was added to the reaction mixture, the layers were separated, and the organic layer was washed with saturated brine (500 ml), then dried over anhydrous magnesium sulfate, and filtered. The filtrate was concentrated under reduced pressure to obtain a 10-hydroxamic acid compound (219.9 g).

(4) A solution of the compound obtained in (3) mentioned above (219.9 g) in toluene (500 ml) was concentrated under reduced pressure, the resulting residue was dissolved in tetrahydrofuran (800 ml), triethylamine (77.0 ml), and p-toluenesulfonyl chloride (38.4 g) were successively added to the mixture, the resulting mixture was stirred at room temperature for 40 minutes, then an aqueous solution (260 ml) of lithium hydroxide (38.4 g) was further added to the mixture, and the resulting mixture was stirred at room temperature for 1 hour. Saturated aqueous ammonium chloride (500 ml) was added to the reaction mixture to neutralize the mixture, then the reaction mixture was concentrated under reduced pressure, chloroform (1000 ml) was added to the resulting residue, and the layers were separated. The organic layer was washed with saturated aqueous sodium hydrogencarbonate (500 ml), then dried over anhydrous magnesium sulfate, and filtered. The filtrate was concentrated under reduced pressure, and the resulting residue was purified by silica gel column chromatography (chloroform:methanol:28% aqueous ammonia=40:1:0.1 to 15:1:0.1) to obtain the title compound (44.3 g).

MS (ESI) m/z=993.8 [M+H]$^+$ $^1$H-NMR (500 MHz, CDCl$_3$) δ (ppm): 0.51-0.70 (m, 18H), 0.84-1.00 (m, 30H), 1.06-1.12 (m, 6H), 1.13-1.17 (m, 7H), 1.22 (d, J=6.50 Hz, 3H), 1.24 (d, J=6.88 Hz, 3H), 1.30 (s, 3H), 1.30-1.35 (m, 1H), 1.42 (dd, J=14.72, 4.78 Hz, 1H), 1.55-1.72 (m, 3H), 2.15-2.19 (m, 1H), 2.18 (s, 6H), 2.31-2.38 (m, 1H), 2.43-2.52 (m, 1H), 2.52-2.60 (m, 1H), 3.12 (dd, J=9.75, 7.07 Hz, 1H), 3.18 (d, J=9.17 Hz, 1H), 3.28 (s, 3H), 3.29 (s, 3H), 3.32-3.43 (m, 2H), 3.51-3.60 (m, 1H), 3.72 (d, J=7.65 Hz, 1H), 3.83-3.88 (m, 1H), 4.19-4.29 (m, 1H), 4.43 (d, J=7.26 Hz, 1H), 4.85 (d, J=4.59 Hz, 1H)

Reference Example 2

Synthesis of Compound of the Formula (A) Wherein R is Hydrogen Atom (1) Erythromycin A (10.0 g, 13.6 mmol) was dissolved in methanol (30 ml), the solution was cooled to 0° C., sodium borohydride (2.58 g, 68.1 mmol) was added to the solution, and the resulting mixture was stirred for 1 hour. Ethyl acetate (150 ml), distilled water (50 ml), and saturated brine (150 ml) were added to the reaction mixture, and the layers were separated. The organic layer was dried over anhydrous magnesium sulfate, and filtered, then the filtrate was cooled to 0° C., and a solution obtained by diluting a 4 N solution of hydrochloric acid in ethyl acetate (3.5 ml) with ethyl acetate (30 ml) was added dropwise to the filtrate with stirring. The resulting mixture was stirred at room temperature for 15 hours, and then the deposited solid was collected by filtration, and washed with ethyl acetate. The resulting solid was suspended in ethyl acetate (200 ml), sodium carbonate (1.18 g) and distilled water (50 ml) were added to the suspension, the resulting mixture was stirred, and the layers were separated. The organic layer was dried over anhydrous magnesium sulfate, and filtered. The solvent was evaporated under reduced pressure to obtain (9S)-9-dihydroerythromycin A (7.45 g).

(2) By using a compound obtained in the same manner as that of (1) mentioned above (1174.0 g) as a starting material, (9S)-9,2',4''-O-tris(triethylsilyl)-9-dihydroerythromycin A (574.8 g) was obtained in the same manner as that of Reference Example 1, (1).

(3) By using a compound obtained in the same manner as that of (2) mentioned above (200.0 g) as a starting material, the title compound (53.0 g) was obtained in the same manners as those of Reference Example 1, (2), (3) and (4).

MS (ESI) m/z=979.9 [M+H]$^+$ $^1$H-NMR (300 MHz, CDCl$_3$) δ (ppm): 0.49-0.76 (m, 18H), 0.84-1.04 (m, 30H), 1.03-1.37 (m, 23H), 1.37-1.72 (m, 3H), 1.77-1.93 (m, 1H), 2.01-2.18 (m, 1H), 2.19 (s, 6H), 2.32 (d, J=15.23 Hz, 1H), 2.38-2.56 (m, 2H), 3.13-3.29 (m, 3H), 3.30 (s, 3H), 3.37-3.54 (m, 1H), 3.56 (d, J=6.84 Hz, 1H), 3.62 (s, 1H), 3.64-3.80 (m, 1H), 4.13 (d, J=4.97 Hz, 1H), 4.17-4.30 (m, 1H), 4.60 (d, J=6.68 Hz, 1H), 4.64 (d, J=4.35 Hz, 1H)

Reference Example 3

Synthesis of N-ethyl-N-[(1S)-1-(2-methoxyphenyl)ethyl]ethane-1,2-diamine (1) (1S)-1-(2-Methoxyphenyl)ethylamine (8.86 g) obtained by the method described in the publication (Japanese Patent Unexamined Publication No. 54/154724) was dissolved in chloroform (100 ml), acetic anhydride (12.0 g) and 4-dimethylaminopyridine (14.3 g) were added to the solution, and the mixture was stirred at 70° C. for 30 minutes. The reaction mixture was left to cool, and then washed successively with 1 N hydrochloric acid, and 10% aqueous sodium hydroxide. The organic layer was dried over anhydrous magnesium sulfate, and filtered, and then the filtrate was concentrated under reduced pressure to obtain an acetyl compound (11.23 g).

(2) Lithium aluminum hydride (3.3 g) was suspended in tetrahydrofuran (200 ml), and the compound obtained in (1) mentioned above (11.2 g) was added to the suspension over 15 minutes under reflux by heating. The reaction mixture was stirred for 3 hours under reflux by heating, and then left to cool, distilled water (3.3 ml), 15% aqueous sodium hydroxide (3.3 ml), and distilled water (3.3 ml) were successively added to the mixture, and the resulting mixture was stirred for 2 hours. The reaction mixture was filtered, the resulting filtrate was further washed with tetrahydrofuran, and then the filtrate was concentrated under reduced pressure to obtain an N-ethyl compound (10.86 g).

(3) Phthalimidoacetaldehyde (125 mg) obtained by the method described in the literature (Tetrahedron Letters, 2001, vol. 42, p. 315) was dissolved in chloroform (20 ml), the compound obtained in (2) mentioned above (0.6 g) and sodium triacetoxyborohydride (1.06 g) were added to the solution, and the mixture was stirred at room temperature for 2 hours. Saturated aqueous sodium hydrogencarbonate and chloroform were added to the reaction mixture, the layers were separated, and the organic layer was dried over anhydrous magnesium sulfate, and filtered. The filtrate was concentrated under reduced pressure, and the resulting residue was purified by silica gel column chromatography (hexane:ethyl acetate=2:1) to obtain a phthalimide compound (0.93 g).

(4) The compound obtained in (3) mentioned above (0.93 g) was dissolved in ethanol (20 ml), hydrazine monohydrate (0.38 ml) was added to the solution, and the mixture was stirred under reflux by heating for 3 hours and at room temperature for 18 hours. The reaction mixture was concentrated under reduced pressure, 1 N hydrochloric acid was added the resulting residue to make the residue acidic, and the deposited solid was removed by filtration. The filtrate was neutralized with potassium carbonate, then chloroform was added to the mixture, the layers were separated, and the organic layer was dried over anhydrous magnesium sulfate, and filtered. The filtrate was concentrated under reduced pressure, and the resulting residue was purified by silica gel column chromatography (chloroform:methanol:28% aqueous ammonia=10:1:0.1) to obtain the title compound (484 mg).

MS (ESI) m/z=223.2 [M+H]$^+$ $^1$H-NMR (200 MHz, CDCl$_3$) δ (ppm): 0.98 (t, J=7.03 Hz, 3H), 1.29 (d, J=7.03 Hz, 3H), 2.38-2.72 (m, 6H), 3.82 (s, 3H), 4.37 (q, J=7.03 Hz, 1H), 6.83-6.97 (m, 2H), 7.15-7.25 (m, 1H), 7.36 (dd, J=7.47, 1.76 Hz, 1H)

Reference Example 4

Synthesis of N-ethyl-N-[1-(2-ethoxyphenyl)ethyl]-ethane-1,2-diamine (1) 2'-Ethoxyacetophenone (2.0 g) was dissolved in methanol (20 ml), ammonium acetate (9.4 g) was added to the solution, and the resulting mixture was stirred at room temperature for 1 hour. Sodium cyanoborohydride (536 mg) was added to the mixture, and the resulting mixture was stirred at room temperature for 2.5 days. Saturated aqueous sodium hydrogencarbonate and 5 N aqueous sodium hydroxide were added to the reaction mixture, and the resulting mixture was extracted with chloroform. The organic layer was dried over anhydrous sodium sulfate, and filtered. The filtrate was concentrated under reduced pressure, and the resulting residue was purified by silica gel column chromatography (chloroform to chloroform:methanol:28% aqueous ammonia=10:1:0.1) to obtain an amine compound (1.46 g).

(2) By using the compound obtained in (1) mentioned above (1.45 g) as a starting material, a phthalimide compound (2.51 g) was obtained in the same manner as that of Reference Example 3, (3).

(3) The compound obtained in (2) mentioned above (500 mg) was dissolved in chloroform (15 ml), acetaldehyde (0.25 ml) and sodium triacetoxyborohydride (656 mg) were added to the solution, and the resulting mixture was stirred at room temperature for 4 hours. Saturated aqueous sodium hydrogencarbonate was added to the reaction mixture, the resulting mixture was extracted with chloroform, and the organic layer was dried over anhydrous magnesium sulfate, and filtered. The filtrate was concentrated under reduced pressure to obtain an N-ethyl compound (487 mg).

(4) By using the compound obtained in (3) mentioned above (485 mg) as a starting material, the title compound (182 mg) was obtained in the same manner as that of Reference Example 3, (4).

MS (ESI) m/z=237.1 [M+H]$^+$ $^1$H-NMR (200 MHz, CDCl$_3$) δ (ppm): 1.01 (t, J=7.03 Hz, 3H), 1.30 (d, J=6.59 Hz, 3H), 1.42 (t, J=7.03 Hz, 3H), 2.33-2.75 (m, 6H), 3.94-4.12 (m, 2H), 4.43 (q, J=6.89 Hz, 1H), 6.78-6.97 (m, 2H), 7.11-7.23 (m, 1H), 7.35 (dd, J=7.47, 1.76 Hz, 1H)

Reference Example 5

Synthesis of N-ethyl-N-[1-(3-cyanophenyl)ethyl]-ethane-1,2-diamine (1) By using 3-acetylbenzonitrile (2.0 g) as a starting material, a phthalimide compound (1.92 g) was obtained in the same manners as those of Reference Example 4, (1) and Reference Example 3, (3).

(2) By using the compound obtained in (1) mentioned above (500 mg) as a starting material, the title compound (166.2 mg) was obtained in the same manners as those of Reference Example 4, (3) and Reference Example 3, (4).

MS (ESI) m/z=218.1 [M+H]$^+$ $^1$H-NMR (200 MHz, CDCl$_3$) δ (ppm): 1.02 (t, J=7.03 Hz, 3H), 1.34 (d, J=6.59 Hz, 3H), 2.29-2.75 (m, 6H), 3.90 (q, J=6.89 Hz, 1H), 7.34-7.48 (m, 1H), 7.48-7.57 (m, 1H), 7.57-7.70 (m, 2H)

Reference Example 6

Synthesis of N-ethyl-N-[1-(2-methoxyphenyl)propyl]ethane-1,2-diamine (1) By using 2'-methoxypropiophenone (2.0 g) obtained by the method described in the publication (International Patent Publication WO05/019184) as a starting material, an amine compound (1.78 g) was obtained in the same manner as that of Reference Example 4, (1).

(2) By using the compound obtained in (1) mentioned above (390 mg) as a starting material, the title compound (255.1 mg) was obtained in the same manners as those of Reference Example 3, (3), Reference Example 4, (3), and Reference Example 3, (4).

MS (ESI) m/z=237.1 [M+H]$^+$ $^1$H-NMR (200 MHz, CDCl$_3$) δ (ppm): 0.82 (t, J=7.25 Hz, 3H), 1.00 (t, J=7.03 Hz, 3H), 1.61-1.96 (m, 2H), 2.19-2.44 (m, 2H), 2.44-2.87 (m, 4H), 3.80 (s, 3H), 4.21 (dd, J=8.79, 6.59 Hz, 1H), 6.81-7.01 (m, 2H), 7.12-7.30 (m, 2H)

Reference Example 7

Synthesis of N-ethyl-N-[(1S)-1-(2-methoxyphenyl)ethyl]propane-1,3-diamine (1) The compound obtained in Reference Example 3, (2) (1.0 g) was dissolved in dimethylformamide (10 ml), N-(3-bromopropyl)phthalimide (1.65 g) and potassium carbonate (0.85 g) were added to the solution, and the resulting mixture was stirred at 100° C. for 2.5 hours. Distilled water and ethyl acetate was added to the reaction mixture, the layers were separated, and the organic layer was washed with saturated brine, then dried over anhydrous magnesium sulfate, and filtered. The filtrate was concentrated under reduced pressure, and the resulting residue was purified by silica gel column chromatography (chloroform to chloroform:methanol=100:1 to 20:1) to obtain a phthalimide compound (1.58 g).

(2) By using the compound obtained in the same manner as that of (1) mentioned above (1.73 g) as a starting material, the title compound (0.99 g) was obtained in the same manner as that of Reference Example 3, (4).

$^1$H-NMR (300 MHz, CDCl$_3$): δ (ppm): 1.01 (t, J=7.07 Hz, 3H), 1.28 (d, J=6.68 Hz, 3H), 1.49-1.61 (m, 2H), 2.42-2.74 (m, 6H), 3.81 (s, 3H), 4.32 (q, J=6.84 Hz, 1H), 6.86 (dd, J=8.24, 1.09 Hz, 1H), 6.89-6.98 (m, 1H), 7.16-7.23 (m, 1H), 7.40 (dd, J=7.62, 1.71 Hz, 1H)

Reference Example 8

Synthesis of N-isopropyl-N-(2-methoxybenzyl)ethane-1,2-diamine (1) 2-Methoxybenzaldehyde (2.5 g) and isopropylamine (1.65 ml) were dissolved in toluene (5 ml), anhydrous sodium sulfate (5 g) was added to the solution, and the resulting mixture was stirred at room temperature for 41 hour. The reaction mixture was filtered through Celite, then the filtrate was concentrated under reduced pressure, the resulting residue was dissolved in methanol (25 ml), sodium borohydride (700 mg) was added to the solution under ice cooling, and the resulting mixture was stirred at room temperature for 3 hours. The reaction mixture was concentrated under reduced pressure, concentrated hydrochloric acid (8 ml) was added to the residue, the mixture was washed twice with ethyl acetate, and then the aqueous layer was made alkaline with potassium carbonate, and extracted with chloroform. The organic layer was dried over anhydrous sodium sulfate, and filtered, and then the filtrate was concentrated under reduced pressure to obtain a crude product (3.19 g).

(2) By using the crude product obtained in (1) mentioned above (550 mg) as a starting material, the title compound (470 mg) was obtained in the same manners as those of Reference Example 3, (3) and (4).

MS (ESI) m/z=180 [M+H]$^+$ $^1$H-NMR (400 MHz, CDCl$_3$) δ (ppm): 1.08 (d, J=6.3 Hz, 6H), 2.79 (m, 1H), 3.78 (s, 2H), 3.84 (s, 3H), 6.86 (d, J=8.1 Hz, 1H), 6.91 (t, J=7.3 Hz, 1H), 7.20-7.26 (m, 2H)

Reference Example 9

Synthesis of N-ethyl-N-[(1S)-1-(2-methoxyphenyl)ethyl]butane-1,4-diamine

By using the compound obtained in Reference Example 3, (2) (1.0 g) and N-(4-bromobutyl)phthalimide (1.73 g) as starting materials, the title compound (0.98 g) was obtained in the same manners as those of Reference Example 7, (1) and Reference Example 3, (4).

$^1$H-NMR (300 MHz, CDCl$_3$) δ (ppm): 0.99 (t, J=7.07 Hz, 3H), 1.28 (d, J=6.68 Hz, 3H), 1.30-1.58 (m, 4H), 2.35-2.72 (m, 6H), 3.81 (s, 3H), 4.30 (q, J=6.74 Hz, 1H), 6.85 (dd, J=8.24, 1.09 Hz, 1H), 6.90-6.97 (m, 1H), 7.15-7.22 (m, 1H), 7.42 (dd, J=7.69, 1.79 Hz, 1H)

Reference Example 10

Synthesis of (2S)—N-ethyl-N-[(1S)-1-(2-methoxyphenyl)ethyl]propane-1,2-diamine (1) N-t-Butoxycarbonyl-(L)-alanine (422 mg), hydroxybenzotriazole (301 mg), and dicyclohexylcarbodiimide (460 mg) were dissolved in dimethylformamide (3 ml), the solution was stirred at room temperature for 10 minutes, then a solution of the compound obtained in Reference Example 3, (2) (200 mg) in dimethylformamide (3 ml) was added to the solution, and the resulting mixture was stirred at room temperature for 23.5 hours. The reaction mixture was filtered. Ethyl acetate and saturated aqueous sodium hydrogencarbonate were added to the filtrate, the layers were separated, and the organic layer was washed with saturated brine, then dried over anhydrous magnesium sulfate, and filtered. The filtrate was concentrated under reduced pressure, and the resulting residue was purified by silica gel column chromatography (hexane:ethyl acetate=7:1 to 5:1) to obtain an amide compound (352 mg).

(2) The compound obtained in (1) mentioned above (351 mg) was dissolved in methylene chloride (703 µl), anisole (351 µl) and trifluoroacetic acid (1.05 ml) were added to the solution, and the resulting mixture was stirred at room temperature for 2 hours. The reaction mixture was concentrated under reduced pressure, 1 N hydrochloric acid (100 µl), ethyl acetate, and distilled water were added to the resulting residue, and the layers were separated. 1 N Aqueous sodium hydroxide was added to the aqueous layer to make the aqueous layer alkaline, then ethyl acetate was added to the resulting mixture, and the layers were separated. The organic layer was dried over anhydrous magnesium sulfate, and filtered, and then the filtrate was concentrated under reduced pressure to obtain a deprotected compound (262 mg).

(3) By using the compound obtained in (2) mentioned above (262 mg) as a starting material, the title compound (92.1 mg) was obtained in the same manner as that of Reference Example 3, (2).

MS (FAB): m/z=237 [M+H]$^+$ $^1$H-NMR (400 MHz, CDCl$_3$) δ (ppm): 0.96 (t, J=7.08 Hz, 3H), 1.00 (d, J=6.35 Hz, 3H), 1.26 (d, J=7.08 Hz, 3H), 2.16 (dd, J=12.7, 9.77 Hz, 1H), 2.40 (dd, J=12.9, 3.91 Hz, 1H), 2.51 (q, J=7.08 Hz, 2H), 2.91-3.01 (m, 1H), 3.83 (s, 3H), 4.36 (q, J=6.84 Hz, 1H), 6.86 (d, J=8.30 Hz, 1H), 6.93 (dt, J=7.57, 1.22 Hz, 1H), 7.18-7.25 (m, 1H), 7.32 (dd, J=7.57, 1.71 Hz, 1H)

Reference Example 11

Synthesis of (2R)—N-ethyl-N-[(1S)-1-(2-methoxyphenyl)ethyl]propane-1,2-diamine

By using N-t-butoxycarbonyl-(D)-alanine (422 mg) and the compound obtained in Reference Example 3, (2) (200 mg) as starting materials, the title compound (66.6 mg) was obtained in the same manners as those of Reference Example 10, (1), (2) and Reference Example 3, (2).

MS (FAB): m/z=237 [M+H]$^+$ $^1$H-NMR (400 MHz, CDCl$_3$) δ (ppm): 0.95 (d, J=6.35 Hz, 3H), 0.97 (t, J=7.33 Hz, 3H), 1.32 (d, J=7.08 Hz, 3H), 2.15 (dd, J=12.9, 9.77 Hz, 1H), 2.30 (dd, J=12.9, 3.42 Hz, 1H), 2.33-2.44 (m, 1H), 2.56-2.68 (m, 1H), 2.89-3.01 (m, 1H), 3.81 (s, 3H), 4.41 (q, J=7.08 Hz, 1H), 6.87 (d, J=8.06 Hz, 1H), 6.93 (t, J=7.57 Hz, 1H), 7.18-7.24 (m, 1H), 7.33 (dd, J=7.57, 1.71 Hz, 1H)

Reference Example 12

Synthesis of N-ethyl-N-[(1R)-1-(2-methoxyphenyl)ethyl]ethane-1,2-diamine (1) By using (1R)-1-(2-methoxyphenyl)ethanamine (1.11 g) obtained by the method described in the literature (Tetrahedron Asym., 1996, vol. 7, p. 1539) as a starting material, an N-ethyl compound (1.31 g) was obtained in the same manners as those of Reference Example 3, (1) and (2).

(3) By using the compound obtained in (2) mentioned above (660 mg) as a starting material, the title compound (409 mg) was obtained in the same manners as those of Reference Example 3, (3) and (4).

MS (ESI) m/z=223 [M+H]$^+$ $^1$H-NMR (400 MHz, CDCl$_3$) δ (ppm): 0.98 (t, J=7.0 Hz, 3H), 1.29 (d, J=6.9 Hz, 3H), 2.42-2.65 (m, 4H), 2.67 (t, J=6.1 Hz, 3H), 3.82 (s, 3H), 4.37 (q, J=6.9 Hz, 1H), 6.84-6.95 (m, 2H), 7.18-7.23 (m, 1H), 7.36 (dd, J=7.5, 1.7 Hz, 1H)

Reference Example 13

Synthesis of 2-amino-N-ethyl-N-[(1S)-1-(2-methoxyphenyl)ethyl]acetamide (1) N-t-Butoxycarbonylglycine (440 mg) was dissolved in dimethylformamide (5 ml), hydroxybenzotriazole (339 mg) and dicyclohexylcarbodiimide (518 mg) were added to the solution, and the resulting mixture was stirred at room temperature for 10 minutes. A solution of the compound obtained in Reference Example 3, (2) (300 mg) in dimethylformamide (4 ml) was added to the reaction mixture, and the resulting mixture was stirred overnight at room temperature. Ethyl acetate was added to the reaction mixture, the resulting mixture was filtered, and the filtrate was washed with saturated aqueous sodium hydrogencarbonate and saturated brine. The organic layer was dried over anhydrous sodium sulfate, and filtered, then the filtrate was concentrated under reduced pressure, and the resulting residue was purified by silica gel column chromatography (hexane:ethyl acetate=7:3) to obtain an amide compound (465 mg).

(2) By using the compound obtained in (1) mentioned above (161 mg) as a starting material, the title compound (97 mg) was obtained in the same manner as that of Reference Example 10, (2).

MS (FAB) m/z 237 [M+H]$^+$ $^1$H-NMR (400 MHz, CDCl$_3$) δ (ppm): 0.73 and 0.82 (each t, J=7.1 Hz, 3H), 1.48-1.57 (m, 3H), 1.74 (m, 2H), 3.01-3.35 (m, 2H), 3.42 and 3.57 (each d, J=16.6 Hz, 1H), 3.46 (d, J=16.6 Hz, 0.25H), 3.77-3.86 (m, 3.75H), 5.18 and 5.92 (each q, J=7.1 Hz, 1H), 6.82-6.90 (m, 1H), 6.94-7.02 (m, 1H), 7.25-7.39 (m, 2H)

Reference Example 14

Synthesis of N-ethyl-N-[(1S)-1-(2-methoxyphenyl)ethyl]-N-methylethane-1,2-diamine By using the compound obtained in Reference Example 13, (1) (304 mg) as a starting material, the title compound (124 mg) was obtained in the same manner as that of Reference Example 3, (2).

MS (FAB) m/z 237 [M+H]$^+$ $^1$H-NMR (400 MHz, CDCl$_3$) δ (ppm): 0.96 (t, J=7.1 Hz, 3H), 1.29 (d, J=7.1 Hz, 3H), 1.92 (br, 1H), 2.36 (s, 3H), 2.42-2.66 (m, 6H), 3.81 (s, 3H), 4.36 (q, J=7.1 Hz, 1H), 6.85 (dd, J=8.2, 1.0 Hz, 1H), 6.92 (ddd, J=7.6, 7.3, 1.0 Hz, 1H), 7.19 (ddd, J=8.2, 7.3, 1.7 Hz, 1H), 7.35 (dd, J=7.6, 1.7 Hz, 1H)

Reference Example 15

Synthesis of N-ethyl-N-[(1S)-1-(3-hydroxyphenyl)ethyl]-ethane-1,2-diamine (1) By using (S)-1-(3-hydroxyphenyl)ethylamine (1.0 g) obtained by the method described in the literature (Journal of Medicinal Chemistry, 2004, vol. 47, p. 2887) as a starting material, a phthalimide compound (1.82 g) was obtained in the same manner as that of Reference Example 3, (3).
(2) By using the compound obtained in (1) mentioned above (800 mg) as a starting material, the title compound (166.6 mg) was obtained in the same manners as those of Reference Example 4, (3) and Reference Example 3, (4).
MS (ESI) m/z=209.0 [M+H]$^+$
$^1$H-NMR (200 MHz, CDCl$_3$) δ (ppm): 1.03 (t, J=7.03 Hz, 3H), 1.31 (d, J=6.59 Hz, 3H), 2.37-2.76 (m, 6H), 3.64-3.80 (m, 1H), 6.60-6.72 (m, 1H), 6.74-6.91 (m, 2H), 7.08-7.20 (m, 1H)

Reference Example 16

Synthesis of N-ethyl-N-[1-(1H-indol-4-yl)ethyl]ethane-1,2-diamine

By using 4-acetylindole (2.0 g) obtained by the method described in the literature (Journal of Heterocyclic Chemistry, 1983, vol. 20, p. 1393) as a starting material, the title compound (110 mg) was obtained in the same manners as those of Reference Example 4, (1), Reference Example 3, (3), Reference Example 4, (3) and Reference Example 3, (4).
MS (ESI) m/z=232.1 [M+H]$^+$
$^1$H-NMR (200 MHz, CDCl$_3$) δ (ppm): 1.10 (t, J=7.25 Hz, 3H), 1.45 (d, J=7.03 Hz, 3H), 2.42-2.84 (m, 6H), 4.33 (q, J=6.59 Hz, 1H), 6.74-6.85 (m, 1H), 7.01-7.33 (m, 4H), 8.23 (br s., 1H)

Reference Example 17

Synthesis of N-ethyl-N-[2-(2-methoxyphenyl)propan-2-yl]ethane-1,2-diamine (1) 2-Methoxybenzonitrile (6 g) was dissolved in diethyl ether (140 ml), a 3 M solution of methylmagnesium bromide in diethyl ether (45 ml) was added to the solution, and the resulting mixture was stirred at room temperature for 1 hour. Titanium tetraisopropoxide (13.1 ml) was added to the reaction mixture, and the resulting mixture was stirred for 4 hours under reflux by heating. 10% Aqueous sodium hydroxide (160 ml) and ethyl acetate (160 ml) were added to the reaction mixture, and the resulting mixture was stirred at room temperature for 1 hour. The reaction mixture was filtered through Celite, and then the layers of the filtrate were separated. The aqueous layer was extracted with chloroform, and the organic layer was dried over anhydrous magnesium sulfate, and filtered. The filtrate was concentrated under reduced pressure, and the resulting residue was purified by silica gel column chromatography (chloroform:methanol:28% aqueous ammonia=40:1:0.1 to 10:1:0.1) to obtain a dimethylamine compound (2.76 g).
(2) By using the compound obtained in (1) mentioned above (480 mg) as a starting material, a phthalimide compound (557 mg) was obtained in the same manner as that of Reference Example 3, (3).
(3) By using the compound obtained in (2) mentioned above (433 mg) as a starting material, the title compound (325 mg) was obtained in the same manners as those of Reference Example 4, (3) and Reference Example 3, (4).
MS (ESI) m/z=237.1 [M+H]$^+$
$^1$H-NMR (600 MHz, CDCl$_3$) δ (ppm): 0.94 (t, J=7.11 Hz, 3H), 1.46 (s, 6H), 2.46-2.66 (m, 4H), 2.75-2.80 (m, 1H), 3.26-3.31 (m, 1H), 3.80 (s, 3H), 6.82-6.92 (m, 2H), 7.13-7.21 (m, 1H), 7.37-7.42 (m, 1H)

Reference Example 18

Synthesis of N-ethyl-N-[1-(2-ethylphenyl)ethyl]ethane-1,2-diamine

By using 2'-ethylacetophenone (1.71 g) obtained by the method described in the literature (Organic Letters, 2004, vol. 6, p. 4395) as a starting material, the title compound (454 mg) was obtained in the same manners as those of Reference Example 4, (1), Reference Example 3, (3), Reference Example 4, (3) and Reference Example 3, (4).
MS (ESI) m/z=221.1 [M+H]$^+$
$^1$H-NMR (600 MHz, CDCl$_3$) δ (ppm): 0.97-1.03 (m, 3H), 1.18-1.24 (m, 3H), 1.28-1.33 (m, 3H), 2.34-2.86 (m, 7H), 3.11-3.25 (m, 1H), 4.03-4.11 (m, 1H), 7.10-7.18 (m, 3H), 7.38-7.47 (m, 1H)

Reference Example 19

Synthesis of N-[(1S)-1-(2-methoxyphenyl)ethyl]ethane-1,2-diamine (1) By using (1S)-1-(2-methoxyphenyl)ethylamine (1.0 g) obtained by the method described in the publication (Japanese Patent Unexamined Publication No. 54/154724) as a starting material, a phthalimide compound (792.8 mg) was obtained in the same manner as that of Reference Example 3, (3).
(2) By using the compound obtained in (1) mentioned above (390 mg) as a starting material, the title compound (295.1 mg) was obtained in the same manner as that of Reference Example 3, (4).
MS (ESI) m/z=195.0 [M+H]$^+$
$^1$H-NMR (200 MHz, CDCl$_3$) δ (ppm): 1.37 (d, J=7.03 Hz, 3H), 2.44-2.60 (m, 2H), 2.71-2.86 (m, 2H), 3.84 (s, 3H), 4.13 (q, J=6.59 Hz, 1H), 6.92 (br s., 2H), 7.14-7.36 (m, 2H)

Reference Example 20

Synthesis of N-[(1S)-1-(2-methoxyphenyl)ethyl]-N-methylethane-1,2-diamine (1) The compound obtained in Reference Example 19, (1) (400 mg) was dissolved in chloroform (10 ml), 37% aqueous formaldehyde (1.0 g) and sodium triacetoxyborohydride (314 mg) were added to the solution, and the resulting mixture was stirred at room temperature for 1 hour. Saturated aqueous sodium hydrogencarbonate was added to the reaction mixture, the resulting mixture was extracted with chloroform, and the organic layer was dried over anhydrous magnesium sulfate, and filtered. The filtrate was concentrated under reduced pressure to obtain a methyl compound (443.9 mg).
(2) By using the compound obtained in (1) mentioned above (440 mg) as a starting material, the title compound (285.6 mg) was obtained in the same manner as that of Reference Example 3, (4).
MS (ESI) m/z=209.0 [M+H]$^+$ ¹H-NMR (200 MHz, CDCl₃) δ (ppm): 1.30 (d, J=7.03 Hz, 3H), 2.19 (s, 3H), 2.26-2.61 (m, 2H), 2.63-2.84 (m, 2H), 3.82 (s, 3H), 4.16 (q, J=7.03 Hz, 1H), 6.78-7.02 (m, 2H), 7.11-7.29 (m, 1H), 7.36 (dd, J=7.69, 1.98 Hz, 1H)

Reference Example 21

Synthesis of N-ethyl-N-[1-(2-methoxypyridin-3-yl)ethyl]ethane-1,2-diamine (1) 2-Methoxynicotinic acid (3.0 g) was dissolved in chloroform (100 ml), N,O-dimethylhydroxylamine hydrochloride (3.82 g), N-ethyl-N'-(3-dimethylaminopropyl)carbodiimide hydrochloride (7.51 g), and triethylamine (27.3 ml) were added to the solution under ice cooling, and the resulting mixture was stirred at the same temperature for 6 hours. 4-Dimethylaminopyridine (0.1 g) was added to the reaction mixture at room temperature, and the resulting mixture was stirred overnight. Distilled water and ethyl acetate were added to the reaction mixture, and the layers were separated. The organic layer was washed with saturated brine, dried over anhydrous magnesium sulfate, and filtered. The filtrate was concentrated under reduced pressure, and the resulting residue was purified by silica gel column chromatography (chloroform to chloroform:methanol=50:1) to obtain an amide compound (1.0 g).

(2) The compound obtained in (1) mentioned above (600 mg) was dissolved in tetrahydrofuran (30 ml), a 3 M solution of methylmagnesium bromide in diethyl ether (1.1 ml) was added to the solution under ice cooling, and the resulting mixture was stirred at the same temperature for 1.5 hours. Saturated aqueous ammonium chloride and ethyl acetate were added to the reaction mixture, the layers were separated, and the organic layer was dried over anhydrous magnesium sulfate, and filtered. The filtrate was concentrated under reduced pressure, and the resulting residue was purified by silica gel column chromatography (chloroform to chloroform:methanol=100:1) to obtain a ketone compound (540 mg).

(3) By using the compound obtained in (2) mentioned above (540 mg) as a starting material, a phthalimide compound (572 mg) was obtained in the same manners as those of Reference Example 4, (1) and Reference Example 3, (3).

(4) By using the compound obtained in (3) mentioned above (200 mg) as a starting material, the title compound (118 mg) was obtained in the same manners as those of Reference Example 4, (3) and Reference Example 3, (4).

MS (ESI) m/z=224.1 [M+H]⁺

¹H-NMR (600 MHz, CDCl₃) δ (ppm): 0.98 (t, J=7.11 Hz, 3H), 1.28 (d, J=6.88 Hz, 3H), 2.44-2.77 (m, 6H), 3.95 (s, 3H), 4.23 (q, J=6.88 Hz, 1H), 6.87 (dd, J=7.34, 4.58 Hz, 1H), 7.61 (dd, J=7.11, 2.06 Hz, 1H), 8.05 (dd, J=5.04, 1.83 Hz, 1H)

Reference Example 22

Synthesis of N-ethyl-N-[1-(3-methoxypyridin-2-yl)ethyl]ethane-1,2-diamine (1) 1-(3-Methoxypyridin-2-yl)ethanol (1.0 g) obtained by the method described in the literature (Synthesis, 1982, vol. 3, p. 235) was dissolved in diethyl ether (30 ml), manganese dioxide (2.27 g) was added to the solution, and the resulting mixture was stirred at room temperature for 8 hours. The reaction mixture was filtered through Celite, then the filtrate was concentrated under reduced pressure, and the resulting residue was purified by silica gel column chromatography (chloroform to chloroform:methanol=100:1) to obtain a ketone compound (580 mg).

(2) By using the compound obtained in (1) mentioned above (580 mg) as a starting material, the title compound (66 mg) was obtained in the same manners as those of Reference Example 4, (1), Reference Example 3, (3), Reference Example 4, (3) and Reference Example 3, (4).

MS (ESI) m/z=224.1 [M+H]⁺

¹H-NMR (600 MHz, CDCl₃) δ (ppm): 0.97 (t, J=7.11 Hz, 3H), 1.36 (d, J=6.88 Hz, 3H), 2.48-2.71 (m, 6H), 3.84 (s, 3H), 4.53 (q, J=6.88 Hz, 1H), 7.12-7.14 (m, 2H), 8.17 (dd, J=3.90, 2.06 Hz, 1H)

Reference Example 23

Synthesis of N-[1-(2-bromophenyl)ethyl]-N-ethyl-ethane-1,2-diamine

By using 1-(2-bromophenyl)ethanamine (5.4 g) obtained by the method described in the literature (Tetrahedron Letters, 2007, vol. 48, p. 4589) as a starting material, the title compound (1.78 g) was obtained in the same manners as those of Reference Example 3, (3), Reference Example 4, (3) and Reference Example 3, (4).

MS (ESI) m/z=271.0 [M+H]⁺

¹H-NMR (200 MHz, CDCl₃) δ (ppm): 1.01 (t, J=7.25 Hz, 3H), 1.30 (d, J=6.59 Hz, 3H), 2.37-2.74 (m, 6H), 4.26 (q, J=6.59 Hz, 1H), 7.02-7.12 (m, 1H), 7.22-7.33 (m, 1H), 7.45-7.57 (m, 2H)

Reference Example 24

Synthesis of N-[1-(2-methoxypyridin-3-yl)ethyl]ethane-1,2-diamine

By using the compound obtained in Reference Example 21, (3) (160 mg) as a starting material, the title compound (56 mg) was obtained in the same manner as that of Reference Example 3, (4).

MS (ESI) m/z=196.0 [M+H]⁺

¹H-NMR (600 MHz, CDCl₃) δ (ppm): 1.34 (d, J=6.42 Hz, 3H), 2.46-2.51 (m, 1H), 2.53-2.58 (m, 1H), 2.76-2.80 (m, 2H), 3.96 (s, 3H), 4.00 (q, J=6.88 Hz, 1H), 6.88 (dd, J=6.88, 5.04 Hz, 1H), 7.61 (dd, J=7.34, 1.83 Hz, 1H), 8.04 (dd, J=5.04, 1.83 Hz, 1H)

Reference Example 25

Synthesis of 2-(8-methoxy-1,2,3,4-tetrahydroisoquinolin-2-yl)ethanamine

By using 8-methoxy-1,2,3,4-tetrahydroisoquinoline (330 mg) obtained by the method described in the literature (Tetrahedron Letters, 1991, vol. 32, p. 1965) as a starting material, the title compound (386 mg) was obtained in the same manners as those of Reference Example 3, (3) and (4).

MS (ESI) m/z=207.0 [M+H]⁺

¹H-NMR (600 MHz, CDCl₃) δ (ppm): 1.44 (br s., 2H), 2.62 (t, J=5.96 Hz, 2H), 2.70 (t, J=5.73 Hz, 2H), 2.85-2.92 (m, 4H), 3.57 (s, 2H), 3.80 (s, 3H), 6.65 (d, J=8.25 Hz, 1H), 6.72 (d, J=7.79 Hz, 1H), 7.10 (t, J=8.02 Hz, 1H)

Reference Example 26

Synthesis of N-[2-(2-methoxyphenyl)propan-2-yl] ethane-1,2-diamine

By using the compound obtained in Reference Example 17, (2) (62.2 mg) as a starting material, the title compound (34.7 mg) was obtained in the same manner as that of Reference Example 3, (4).

MS (ESI) m/z=209.0 [M+H]$^+$
$^1$H-NMR (600 MHz, CDCl$_3$) δ (ppm): 1.50 (s, 6H), 2.24 (t, J=6.19 Hz, 2H), 2.70 (t, J=6.19 Hz, 2H), 3.85 (s, 3H), 6.86-6.94 (m, 2H), 7.19-7.25 (m, 2H)

Reference Example 27

Synthesis of 5-[N-(2-aminoethyl)-N-ethylamino]-5,6,7,8-tetrahydronaphthalen-1-ol By using 5-hydroxy-1-tetralone (1.0 g) as a starting material, the title compound (119 mg) was obtained in the same manners as those of Reference Example 4, (1), Reference Example 3, (3), Reference Example 4, (3) and Reference Example 3, (4).

MS (ESI) m/z=235.1 [M+H]$^+$
$^1$H-NMR (600 MHz, CDCl$_3$) δ (ppm): 1.05 (t, J=7.11 Hz, 3H), 1.52-1.65 (m, 2H), 1.94-2.05 (m, 2H), 2.41-2.60 (m, 5H), 2.66 (dt, J=12.84, 4.81 Hz, 1H), 2.73 (dd, J=16.74, 3.90 Hz, 1H), 2.76-2.82 (m, 1H), 3.92 (dd, J=9.86, 4.81 Hz, 1H), 6.52 (d, J=7.79 Hz, 6.98 (t, J=7.79 Hz, 1H), 7.23-7.27 (m, 1H)

Reference Example 28

Synthesis of N-(3,4-dihydro-2H-chromen-4-yl)-N-ethylethane-1,2-diamine (1) By using 4-chromanone (2.0 g) as a starting material, a phthalimide compound (2.25 g) was obtained in the same manners as those of Reference Example 4, (1) and Reference Example 3, (3).

(2) By using the compound obtained in (1) mentioned above (1.09 g) as a starting material, the title compound (557 mg) was obtained in the same manners as those of Reference Example 4, (3) and Reference Example 3, (4).

MS (ESI) m/z=221.0 [M+H]$^+$
$^1$H-NMR (600 MHz, CDCl$_3$) δ (ppm): 1.05 (t, J=7.11 Hz, 3H), 1.43 (br s., 2H), 1.95-2.05 (m, 2H), 2.38-2.46 (m, 1H), 2.51-2.59 (m, 3H), 2.68 (dt, J=12.61, 5.16 Hz, 1H), 2.74-2.82 (m, 1H), 4.03-4.13 (m, 2H), 4.34 (dt, J=11.12, 4.07 Hz, 1H), 6.76 (d, J=8.25 Hz, 1H), 6.88 (t, J=8.02 Hz, D), 7.10 (t, J=7.11 Hz, 1H), 7.55 (d, J=7.79 Hz, 1H)

Reference Example 29

Synthesis of N-ethyl-N-(1,2,3,4-tetrahydronaphthalen-1-yl)ethane-1,2-diamine

By using 1,2,3,4-tetrahydro-1-naphthylamine (1.0 g) as a starting material, the title compound (921 mg) was obtained in the same manners as those of Reference Example 3, (3), Reference Example 4, (3) and Reference Example 3, (4).

MS (ESI) m/z=219.1 [M+H]$^+$
$^1$H-NMR (600 MHz, CDCl$_3$) δ (ppm): 1.05 (t, J=7.11 Hz, 3H), 1.55 (br s., 2H), 1.56-1.70 (m, 2H), 1.93-2.05 (m, 2H), 2.39-2.47 (m, 1H), 2.47-2.55 (m, 2H), 2.55-2.61 (m, 1H), 2.63-2.68 (m, 1H), 2.68-2.74 (m, 1H), 2.73-2.81 (m, 2H), 3.95 (dd, J=9.86, 5.27 Hz, 1H), 7.03 (d, J=7.34 Hz, 1H), 7.10 (t, J=7.11 Hz, 1H), 7.12-7.16 (m, 1H), 7.70 (d, J=7.79 Hz, 1H)

Reference Example 30

Synthesis of N-[1-(2-ethoxyphenyl)ethyl]ethane-1,2-diamine

By using the compound obtained in Reference Example 4, (2) (500 mg) as a starting material, the title compound (204.4 mg) was obtained in the same manner as that of Reference Example 3, (4).

MS (ESI) m/z=209.2 [M+H]$^+$
$^1$H-NMR (200 MHz, CDCl$_3$) δ (ppm): 1.34-1.49 (m, 6H), 2.46-2.59 (m, 2H), 2.72-2.83 (m, 2H), 3.97-4.15 (m, 3H), 6.79-6.99 (m, 2H), 7.12-7.33 (m, 2H)

Reference Example 31

Synthesis of N-ethyl-N-(1H-indol-3-ylmethyl)ethane-1,2-diamine (1) Indole-3-carboxyaldehyde (500 mg) was dissolved in chloroform (10 ml), t-butyl N-(2-aminoethyl)carbamate (0.6 ml), and sodium triacetoxyborohydride (876 mg) were added to the solution, and the resulting mixture was stirred at room temperature for 1.5 hours. Tetrahydrofuran (2 ml) was added to the reaction mixture, and the resulting mixture was stirred at room temperature for 1.5 hours. Saturated aqueous sodium hydrogencarbonate was added to the reaction mixture, the resulting mixture was extracted with chloroform, the organic layer was dried over anhydrous sodium sulfate, and filtered, and the filtrate was concentrated under reduced pressure. The resulting residue was purified by silica gel column chromatography (chloroform:methanol:28% aqueous ammonia=10:1:0.1) to obtain an alkyl compound (580 mg).

(2) By using the compound obtained in (1) mentioned above (300 mg) as a starting material, an N-ethyl compound (147.2 mg) was obtained in the same manner as that of Reference Example 4, (3).

(3) The compound obtained in (2) mentioned above (145 mg) was dissolved in methanol (2 ml), a 5 to 10% solution of hydrochloric acid in methanol (5 ml) was added to the solution, and the resulting mixture was stirred at room temperature for 3 days. Saturated aqueous sodium hydrogencarbonate and 5 N aqueous sodium hydroxide were added to the reaction mixture, and the resulting mixture was extracted with chloroform. The organic layer was concentrated under reduced pressure, and the resulting residue was purified by silica gel column chromatography (chloroform:methanol:28% aqueous ammonia=10:1:0.1 to 5:1:0.1) to obtain the title compound (64.8 mg).

MS (ESI) m/z=218.1 [M+H]$^+$
$^1$H-NMR (600 MHz, CD$_3$OD) δ (ppm): 1.12 (t, J=7.34 Hz, 3H), 2.48-2.74 (m, 6H), 3.78 (s, 2H), 6.96-7.01 (m, 1H), 7.03-7.09 (m, 1H), 7.15 (s, 1H), 7.31 (d, J=8.25 Hz, 1H), 7.62 (d, J=7.79 Hz, 1H), 7.88 (s, 1H)

Reference Example 32

Synthesis of N-[1-(2-methyl-3-hydroxyphenyl) ethyl]-ethane-1,2-diamine (1) By using 3-methoxy-2-methylbenzoic acid (2.0 g) as a starting material, a methyl ketone compound (887.3 mg) was obtained in the same manners as those of Reference Example 21, (1) and (2).

(2) The compound obtained in (1) mentioned above (840 mg) was dissolved in methylene chloride (10 ml), a solution of boron tribromide in methylene chloride (5.6 ml) was slowly added dropwise to the solution under ice cooling, and the resulting mixture was stirred at the same temperature for 2 hours. Methanol was added dropwise to the reaction mixture until fuming ceased, and then the resulting mixture was concentrated under reduced pressure. The resulting residue was purified by silica gel column chromatography (hexane:ethyl acetate=10:1 to 5:1) to obtain a hydroxy compound (96.5 mg).

(3) The compound obtained in (2) mentioned above (90 mg) was dissolved in methanol (1 ml), ethylenediamine (0.32 ml) was added to the solution, and the resulting mixture was stirred at room temperature overnight and at 50° C. for 2 hours. Sodium borohydride (22.7 mg) was added to the reaction mixture at room temperature, and the resulting mixture was stirred at the same temperature for 3 hours. 2 N Hydrochloric acid was added to the reaction mixture, the resulting mixture was washed with chloroform, and then the aqueous layer was made alkaline with 5 N aqueous sodium hydroxide, and concentrated under reduced pressure. The resulting residue was purified by silica gel column chromatography (chloroform:methanol:28% aqueous ammonia=10:1:0.1 to 5:1:0.1) to obtain the title compound (21.1 mg).

$^1$H-NMR (600 MHz, CDCl$_3$) δ (ppm): 1.31 (d, J=6.88 Hz, 3H), 2.22 (s, 3H), 2.48-2.54 (m, 1H), 2.56-2.62 (m, 1H), 2.74-2.79 (m, 2H), 4.06 (q, J=6.42 Hz, 1H), 6.64 (d, J=7.79 Hz, 1H), 6.99-7.03 (m, 1H), 7.03-7.08 (m, 1H)

Reference Example 33

Synthesis of N-ethyl-N-[1-(1H-indol-5-yl)ethyl]ethane-1,2-diamine (1) Indole-5-carboxylic acid (2.0 g) was dissolved in tetrahydrofuran (20 ml), a 1.09 M solution of methyllithium in diethyl ether (39.8 ml) was slowly added dropwise to the solution under ice cooling, and the resulting mixture was stirred at room temperature for 1.5 hours. Distilled water was added to the reaction mixture, the resulting mixture was extracted with chloroform, and the organic layer was dried over anhydrous sodium sulfate, and filtered. The filtrate was concentrated under reduced pressure to obtain a methyl ketone compound (1.35 g).

(2) By using the compound obtained in (1) mentioned above (500 mg) as a starting material, an amine compound (305 mg) was obtained in the same manner as that of Reference Example 4, (1).

(3) By using the compound obtained in (2) mentioned above (100 mg) as a starting material, the title compound (72.5 mg) was obtained in the same manners as those of Reference Example 3, (3), Reference Example 4, (3) and Reference Example 3, (4).

$^1$H-NMR (600 MHz, CDCl$_3$) δ (ppm): 1.04 (t, J=7.03 Hz, 3H), 1.41 (d, J=7.03 Hz, 3H), 2.38-2.73 (m, 6H), 3.98 (q, J=6.59 Hz, 1H), 6.48-6.56 (m, 1H), 7.14-7.25 (m, 1H), 7.24-7.38 (m, 2H), 7.56 (s, 1H), 8.07-8.22 (m, 1H)

Reference Example 34

Synthesis of N-[1-(1-methyl-1H-indol-4-yl)ethyl]ethane-1,2-diamine (1) 4-Acetylindole (2.0 g) was dissolved in dimethylformamide (50 ml), sodium hydride (451 mg) and methyl iodide (1.17 ml) were added to the solution, and the resulting mixture was stirred at room temperature for 18 hours. Distilled water and ethyl acetate were added to the reaction mixture, the layers were separated, and the organic layer was dried over anhydrous magnesium sulfate, and filtered. By using a crude product obtained by concentrating the filtrate under reduced pressure as a starting material, an amine compound (1.03 g) was obtained in the same manner as that of Reference Example 4, (1).

(2) By using the compound obtained in (1) mentioned above (100 mg) as a starting material, the title compound (66 mg) was obtained in the same manners as those of Reference Example 3, (3) and (4).

MS (ESI) m/z=218.1 [M+H]$^+$ $^1$H-NMR (200 MHz, CDCl$_3$) δ (ppm): 1.50 (d, J=6.59 Hz, 3H), 2.45-2.82 (m, 4H), 3.78 (s, 3H), 4.14-4.32 (m, 1H), 6.62 (d, J=3.08 Hz, 1H), 6.99-7.26 (m, 4H)

Reference Example 35

Synthesis of N-[1-(2-methoxyphenyl)propyl]ethane-1,2-diamine

By using 2'-methoxypropiophenone (200 mg) as a starting material, the title compound (91 mg) was obtained in the same manner as that of Reference Example 32, (3).

MS (ESI) m/z=209.0 [M+H]$^+$ $^1$H-NMR (200 MHz, CDCl$_3$) δ (ppm): 0.83 (t, 3H), 1.61-1.85 (m, 2H), 2.42-2.56 (m, 2H), 2.67-2.80 (m, 2H), 3.82 (s, 3H), 3.88 (t, J=6.81 Hz, 1H), 6.81-7.00 (m, 2H), 7.14-7.29 (m, 2H)

Reference Example 36

Synthesis of 2-(4-methoxy-1,3-dihydro-2H-isoindol-2-yl)ethanamine (1) 2,3-Dimethylanisole (1.0 g) was dissolved in carbon tetrachloride (10 ml), N-bromosuccinimide (2.63 g), and azobisisobutyronitrile (121 mg) were added to the solution, and the resulting mixture was stirred under reflux by heating for 6 hours. The reaction mixture was filtered, and the resulting filtrate was concentrated under reduced pressure to obtain a dibromo compound (2.27 g).

(2) The compound obtained in (1) mentioned above (144 mg) was dissolved in chloroform (1.5 ml), ethylenediamine (294 mg), and 10% aqueous sodium hydroxide (1.5 ml) were added to the solution, and the resulting mixture was stirred at room temperature for 6 hours. Saturated aqueous sodium hydrogencarbonate and chloroform were added to the reaction mixture, the layers were separated, and the organic layer was dried over anhydrous magnesium sulfate, and filtered. The filtrate was concentrated under reduced pressure, and the resulting residue was purified by silica gel column chromatography (chloroform to chloroform:methanol:28% aqueous ammonia=10:1:0.1) to obtain the title compound (80.3 mg).

MS (ESI) m/z=193.0 [M+H]$^+$ $^1$H-NMR (600 MHz, CDCl$_3$) δ (ppm): 1.43 (br s., 2H), 2.79-2.83 (m, 2H), 2.85-2.89 (m, 2H), 3.81 (s, 3H), 3.95 (d, J=13.75 Hz, 4H), 6.70 (d, J=8.25 Hz, 1H), 6.81 (d, J=7.79 Hz, 1H), 7.17 (t, J=7.79 Hz, 1H)

Reference Example 37

Synthesis of N-ethyl-N-[1-(1-methyl-1H-indol-4-yl)ethyl]ethane-1,2-diamine

By using the compound obtained in Reference Example 34, (1) (200 mg) as a starting material, the title compound (30 mg) was obtained in the same manners as those of Reference Example 3, (3), Reference Example 4, (3) and Reference Example 3, (4).

MS (ESI) m/z=246.1 [M+H]$^+$ $^1$H-NMR (200 MHz, CDCl$_3$) δ (ppm): 1.08 (t, J=7.25 Hz, 3H), 1.44 (d, J=7.03 Hz, 3H), 2.42-2.83 (m, 6H), 3.77 (s, 3H), 4.30 (q, J=6.59 Hz, 1H), 6.67-6.75 (m, 1H), 6.99-7.26 (m, 4H)

Reference Example 38

Synthesis of N-[(2-methoxypyridin-3-yl)propan-2-yl]ethane-1,2-diamine (1) 2-Chloro-3-cyanopyridine (10.0 g) was dissolved in methanol (200 ml), a 28% solution of sodium methoxide in methanol (27.8 g) was added to the solution, and the resulting mixture was stirred at room temperature for 18 hours. The reaction mixture was filtered, and then concentrated under reduced pressure, and the deposited crystals were collected by filtration to obtain a methoxy compound (4.15 g).

(2) By using the compound obtained in (1) mentioned above (4.15 g) as a starting material, a dimethyl compound (350 mg) was obtained in the same manner as that of Reference Example 17, (1).

(3) By using the compound obtained in (2) mentioned above (350 mg) as a starting material, the title compound (301 mg) was obtained in the same manners as those of Reference Example 3, (3) and (4).

MS (ESI) m/z=210.0 [M+H]$^+$ $^1$H-NMR (200 MHz, CDCl$_3$) δ (ppm): 1.48 (s, 6H), 2.19-2.28 (m, 2H), 2.67-2.76 (m, 2H), 4.00 (s, 3H), 6.80-6.90 (m, 1H), 7.45-7.57 (m, 1H), 8.01-8.07 (m, 1H)

Reference Example 39

Synthesis of N-[(1R)-1-(2-methoxypyridin-3-yl)ethyl]ethane-1,2-diamine (1) By using 2-methoxynicotinaldehyde (3.0 g) obtained by the method described in the literature (Journal of Organic Chemistry, 1988, vol. 53, p. 1367), and (R)-2-amino-2-phenylethanol (3.0 g) as starting materials, an amine compound (253 mg) was obtained by the method described in the literature (Helvetica Chimica Acta, 2004, vol. 87, p. 561).

(2) By using the compound obtained in (1) mentioned above (253 mg) as a starting material, a phthalimide compound (227 mg) was obtained in the same manner as that of Reference Example 3, (3).

(3) By using the compound obtained in (2) mentioned above (100 mg) as a starting material, the title compound (38 mg) was obtained in the same manner as that of Reference Example 3, (4).

MS (ESI) m/z=196.0 [M+H]$^+$ $^1$H-NMR (200 MHz, CDCl$_3$) δ (ppm): 1.34 (d, J=6.15 Hz, 3H), 2.40-2.63 (m, 2H), 2.71-2.84 (m, 2H), 3.91-4.08 (m, 4H), 6.87 (dd, J=7.25, 5.05 Hz, 1H), 7.61 (dd, J=7.47, 1.76 Hz, 1H), 8.01-8.09 (m, 1H)

Reference Example 40

Synthesis of N-[(1S)-1-(2-methoxypyridin-3-yl)ethyl]ethane-1,2-diamine (1) By using 2-methoxynicotinaldehyde (2.4 g) obtained by the method described in the literature (Journal of Organic Chemistry, 1988, vol. 53, p. 1367), and (S)-2-amino-2-phenylethanol (2.4 g) as starting materials, an amine compound (198 mg) was obtained in the same manner as that of the method described in the literature (Helvetica Chimica Acta, 2004, vol. 87, p. 561).

(2) By using the compound obtained in (1) mentioned above (100 mg) as a starting material, the title compound (39 mg) was obtained in the same manners as those of Reference Example 3, (3) and (4).

MS (ESI) m/z=196.0 [M+H]$^+$ $^1$H-NMR (200 MHz, CDCl$_3$) δ (ppm): 1.34 (d, J=6.59 Hz, 3H), 2.40-2.62 (m, 2H), 2.70-2.82 (m, 2H), 3.92-4.07 (m, 4H), 6.87 (dd, J=7.25, 5.05 Hz, 1H), 7.56-7.66 (m, 1H), 7.94-8.14 (m, 1H)

Reference Example 41

Synthesis of N-ethyl-N-[1-(2-methoxyphenyl)cyclopropyl]ethane-1,2-diamine

By using 1-(2-methoxyphenyl)-cyclopropylamine (347 mg) obtained by the method described in the literature (Journal of Organic Chemistry, 2003, vol. 68, p. 7133) as a starting material, the title compound (40 mg) was obtained in the same manners as those of Reference Example 3, (3), Reference Example 4, (3) and Reference Example 3, (4).

MS (ESI) m/z=235.1 [M+H]$^+$ $^1$H-NMR (200 MHz, CDCl$_3$) δ (ppm): 0.75-0.89 (m, 2H), 0.90-1.00 (m, 2H), 1.00-1.11 (m, 3H), 2.50-2.65 (m, 4H), 2.73-2.84 (m, 2H), 3.81 (s, 3H), 6.83-6.95 (m, 2H), 7.17-7.33 (m, 2H)

Reference Example 42

Synthesis of N-[2-(pyridin-3-yl)propan-2-yl]ethane-1,2-diamine (1) By using 3-cyanopyridine (5.0 g) as a starting material, a phthalimide compound (4.47 g) was obtained in the same manners as those of Reference Example 17, (1) and Reference Example 3, (3).

(2) By using the compound obtained in (1) mentioned above (2.0 g) as a starting material, the title compound (533.9 mg) was obtained in the same manner as that of Reference Example 3, (4).

MS (ESI) m/z=180.2 [M+H]$^+$ $^1$H-NMR (200 MHz, CDCl$_3$) δ (ppm): 1.49 (s, 6H), 2.39 (t, J=5.27 Hz, 2H), 2.75 (m, 2H), 719-7.31 (m, 1H), 7.73-7.84 (m, 1H), 8.47 (dd, J=4.83, 1.32 Hz, 1H), 8.69-8.75 (m, 1H)

Reference Example 43

Synthesis of N-[1-(quinolin-5-yl)ethyl]ethane-1,2-diamine (1) Quinoline-5-carboxyaldehyde (550 mg) was dissolved in tetrahydrofuran (15 ml), a 3 M solution of methylmagnesium bromide in diethyl ether (1.75 ml) was added dropwise to the solution under ice cooling, and the resulting mixture was stirred at the same temperature for 1.5 hours. A 3 M solution of methylmagnesium bromide in diethyl ether (0.8 ml) was further added dropwise to the mixture, and the resulting mixture was stirred for 1 hour. Saturated aqueous sodium hydrogencarbonate was added to the reaction mixture, the resulting mixture was extracted with ethyl acetate, and the organic layer was washed with saturated brine. The organic layer was concentrated under reduced pressure to obtain an alcohol compound (791.4 mg).

(2) A compound obtained in the same manner as that of (1) mentioned above (935 mg) was dissolved in tetrahydrofuran (5 ml), manganese dioxide (2.35 g) was added to the solution, and the resulting mixture was stirred at room temperature for 4.5 days. The reaction mixture was filtered, and the filtrate was concentrated under reduced pressure. The resulting residue was purified by silica gel column chromatography (chloroform:methanol:28% aqueous ammonia=30:1:0.1) to obtain a methyl ketone compound (329 mg).

(3) By using the compound obtained in (2) mentioned above (100 mg) as a starting material, the title compound (48.5 mg) was obtained in the same manner as that of Reference Example 32, (3).

MS (ESI) m/z=216.0 [M+H]$^+$ $^1$H-NMR (200 MHz, CDCl$_3$) δ (ppm): 1.51 (d, J=6.59 Hz, 3H), 2.33-2.85 (m, 4H), 4.57 (q, J=6.59 Hz, 1H), 7.41 (dd, J=8.79, 3.96 Hz, 1H), 7.66-7.72 (m, 2H), 7.96-8.05 (m, 1H), 8.61-8.73 (m, 1H), 8.92 (dd, J=3.96, 1.76 Hz, 1H)

Reference Example 44

Synthesis of N-[2-(2-methoxypyridin-3-yl)propan-2-yl]-N'-methylethane-1,2-diamine (1) t-Butyl (2-hydroxyethyl)methylcarbamate (1.0 g) obtained by the method described in the literature (Synthetic Communications, 1993, p. 2443) was dissolved in chloroform (5 ml), and a Dess-Martin reagent (2.54 g) was added to the solution under ice cooling. The resulting mixture was stirred at room temperature for 1.5 hours, then saturated aqueous sodium hydrogencarbonate and saturated aqueous sodium thiosulfate were added to the reaction mixture, and the resulting mixture was stirred for 30 minutes. The reaction mixture was extracted with chloroform, and the organic layer was dried over anhydrous sodium sulfate, and filtered. The filtrate was concentrated under reduced pressure to obtain an aldehyde compound (1.21 g).

(2) The compound obtained in Reference Example 38, (2) (50 mg), and the compound obtained in (1) mentioned above (46.9 mg) were dissolved in chloroform (3 ml), sodium triacetoxyborohydride (76.5 mg) was added to the solution, and the resulting mixture was stirred at room temperature for 1 hour. Saturated aqueous sodium hydrogencarbonate was added to the reaction mixture, the resulting mixture was extracted with chloroform, and the organic layer was concentrated under reduced pressure. The resulting residue was purified by silica gel column chromatography (chloroform:methanol=15:1 to 10:1) to obtain an alkyl compound (53.8 mg).

(3) By using the compound obtained in (2) mentioned above (51 mg) as a starting material, the title compound (29.8 mg) was obtained in the same manner as that of Reference Example 31, (3).

MS (ESI) m/z=224.1 [M+H]$^+$ $^1$H-NMR (200 MHz, CDCl$_3$) δ (ppm): 1.50 (s, 6H), 2.25-2.35 (m, 2H), 2.37 (s, 3H), 2.57-2.68 (m, 2H), 3.99 (s, 3H), 6.86 (dd, J=7.47, 4.83 Hz, 1H), 7.52 (dd, J=7.25, 1.98 Hz, 1H), 8.05 (dd, J=4.83, 1.76 Hz, 1H)

Reference Example 45

Synthesis of N-[2-(2-methoxyphenyl)propan-2-yl]-N'-methylethane-1,2-diamine (1) By using the compound obtained in Reference Example 17, (1) (100 mg), and the compound obtained in Reference Example 44, (1) (94.3 mg) as starting materials, an alkyl compound (114.8 mg) was obtained in the same manner as that of Reference Example 44, (2).

(2) By using the compound obtained in (1) mentioned above (55 mg) as a starting material, the title compound (35.9 mg) was obtained in the same manner as that of Reference Example 31, (3).

MS (ESI) m/z=223.0 [M+H]$^+$ $^1$H-NMR (200 MHz, CDCl$_3$) δ (ppm): 1.50 (s, 6H), 2.24-2.35 (m, 2H), 2.35 (s, 3H), 2.53-2.64 (m, 2H), 3.86 (s, 3H), 6.83-6.96 (m, 2H), 7.16-7.26 (m, 2H)

Reference Example 46

Synthesis of N-ethyl-N-[2-(2-methoxyphenyl)propan-2-yl]-N'-methylethane-1,2-diamine By using the compound obtained in Reference Example 45, (1) (55 mg) as a starting material, the title compound (36.7 mg) was obtained in the same manners as those of Reference Example 4, (3) and Reference Example 31, (3).

MS (ESI) m/z=251.1 [M+H]$^+$ $^1$H-NMR (200 MHz, CDCl$_3$) δ (ppm): 0.90 (t, J=7.25 Hz, 3H), 1.47 (s, 6H), 2.33-2.73 (m, 6H), 2.37 (s, 3H), 3.82 (s, 3H), 6.82-6.93 (m, 2H), 7.14-7.21 (m, 1H), 7.38 (dd, J=8.13, 1.98 Hz, 1H)

Reference Example 47

Synthesis of N-{1-[2-(1H-imidazol-1-yl)phenyl]ethyl}ethane-1,2-diamine

By using 1-(2-(1H-imidazol-1-yl)phenyl)ethanone (380 mg) obtained by the method described in the literature (Journal of the Chemical Society (C), 1970, p. 85) as a starting material, the title compound (52 mg) was obtained in the same manners as those of Reference Example 4, (1), Reference Example 3, (3) and (4).

MS (ESI) m/z=231.1 [M+H]$^+$ $^1$H-NMR (600 MHz, CDCl$_3$) δ (ppm): 1.29 (d, J=6.42 Hz, 3H), 2.30-2.37 (m, 1H), 2.42-2.47 (m, 1H), 2.65-2.73 (m, 2H), 3.59 (q, J=6.42 Hz, 1H), 7.05-7.07 (m, 1H), 7.19-7.23 (m, 2H), 7.30-7.34 (m, 1H), 7.49 (t, J=7.57 Hz, 1H), 7.58 (s, 1H), 7.66-7.69 (m, 1H)

Reference Example 48

Synthesis of N-[2-(2-ethoxypyridin-3-yl)propan-2-yl]ethane-1,2-diamine (1) Sodium (3.32 g) was dissolved in ethanol (300 ml), 2-chloro-3-cyanopyridine (10.0 g) was added to the solution, and the resulting mixture was stirred at room temperature for 18 hours. The reaction mixture was filtered, and then concentrated under reduced pressure, and the resulting residue was purified by silica gel column chromatography (hexane:ethyl acetate=2:1) to obtain an ethoxy compound (8.70 g).

(2) By using the compound obtained in (1) mentioned above (5.63 g) as a starting material, a dimethyl compound (123 mg) was obtained in the same manner as that of Reference Example 17, (1).

(3) By using the compound obtained in (2) mentioned above (116 mg) as a starting material, the title compound (67 mg) was obtained in the same manners as those of Reference Example 3, (3) and (4).

MS (ESI) m/z=224.2 [M+H]$^+$

¹H-NMR (200 MHz, CDCl₃) δ (ppm): 1.43 (t, J=7.03 Hz, 3H), 1.50 (s, 6H), 2.17-2.31 (m, 2H), 2.72 (t, J=6.15 Hz, 2H), 4.44 (q, J=7.03 Hz, 2H), 6.78-6.91 (m, 1H), 7.46-7.58 (m, 1H), 7.96-8.07 (m, 1H)

Reference Example 49

Synthesis of N-[2-(1-methyl-1H-indol-4-yl)propan-2-yl]ethane-1,2-diamine (1) 4-Cyanoindole (3.0 g) was dissolved in dimethylformamide (30 ml), sodium hydride (761 mg) and methyl iodide (1.97 ml) were added to the solution under ice cooling, and the resulting mixture was stirred at the same temperature for 30 minutes. Distilled water and ethyl acetate were added to the reaction mixture, the layers were separated, and the organic layer was dried over anhydrous magnesium sulfate, and filtered. By using a crude product obtained by concentrating the filtrate under reduced pressure as a starting material, a dimethyl compound (70 mg) was obtained in the same manner as that of Reference Example 17, (1).
(2) By using the compound obtained in (1) mentioned above (70 mg) as a starting material, the title compound (35 mg) was obtained in the same manners as those of Reference Example 3, (3) and (4).
MS (ESI) m/z=232.2 [M+H]⁺
¹H-NMR (200 MHz, CDCl₃) δ (ppm): 1.65 (s, 6H), 2.29-2.38 (m, 2H), 2.63-2.72 (m, 2H), 3.79 (s, 3H), 6.86-6.91 (m, 1H), 7.01-7.08 (m, 2H), 7.12-7.24 (m, 2H)

Reference Example 50

Synthesis of N-[2-(2-methoxyphenyl)propan-2-yl]-N,N'-dimethylethane-1,2-diamine

By using the compound obtained in Reference Example 45, (1) (300 mg) as a starting material, the title compound (130.5 mg) was obtained in the same manners as those of Reference Example 20, (1) and Reference Example 31, (3).
MS (ESI) m/z=237.2 [M+H]⁺
¹H-NMR (200 MHz, CDCl₃) δ (ppm): 1.45 (s, 6H), 2.13 (s, 3H), 2.36 (s, 3H), 2.48-2.63 (m, 4H), 3.82 (s, 3H), 6.83-6.95 (m, 2H), 7.14-7.25 (m, 1H), 7.41 (dd, J=7.91, 1.76 Hz, 1H)

Reference Example 51

Synthesis of N-[(1S)-1-phenylethyl]ethane-1,2-diamine

By using (5)-1-phenylethanamine (300 mg) as a starting material, the title compound (72 mg) was obtained in the same manners as those of Reference Example 3, (3) and (4).
MS (ESI) m/z=165.2 [M+H]⁺
¹H-NMR (200 MHz, CDCl₃) δ (ppm): 1.37 (d, J=6.59 Hz, 3H), 2.40-2.65 (m, 2H), 2.71-2.81 (m, 2H), 3.77 (q, J=6.59 Hz, 1H), 7.19-7.35 (m, 5H)

Reference Example 52

Synthesis of (2R)-2-[(2-aminoethyl)amino]-2-phenylethanol

By using (R)-2-amino-2-phenylethanol (300 mg) as a starting material, the title compound (72 mg) was obtained in the same manners as those of Reference Example 3, (3) and (4).
MS (ESI) m/z=181.1 [M+H]⁺

¹H-NMR (200 MHz, CDCl₃) δ (ppm): 2.52-2.84 (m, 4H), 3.50-3.82 (m, 3H), 7.21-7.40 (m, 5H)

Reference Example 53

Synthesis of (2S)-2-[(2-aminoethyl)amino]-2-phenylethanol

By using (S)-2-amino-2-phenylethanol (300 mg) as a starting material, the title compound (89 mg) was obtained in the same manners as those of Reference Example 3, (3) and (4).
MS (ESI) m/z=181.1 [M+H]⁺
¹H-NMR (200 MHz, CDCl₃) δ (ppm): 2.52-2.84 (m, 4H), 3.50-3.82 (m, 3H), 7.22-7.40 (m, 5H)

Reference Example 54

Synthesis of N-[(1R)-1-(2-methoxypyridin-3-yl)ethyl]-N'-methylethane-1,2-diamine By using the compound obtained in Reference Example 44, (1) (103 mg), and the compound obtained in Reference Example 39, (1) (100 mg) as starting materials, the title compound (80 mg) was obtained in the same manners as those of Reference Example 44, (2) and Reference Example 31, (3).
MS (ESI) m/z=210.2 [M+H]⁺
¹H-NMR (600 MHz, CDCl₃) δ (ppm): 1.33 (d, J=6.88 Hz, 3H), 2.41 (s, 3H), 2.52-2.71 (m, 4H), 3.94-4.02 (m, 4H), 6.87 (dd, J=7.11, 4.81 Hz, 1H), 7.61 (dd, J=7.34, 1.83 Hz, 1H), 8.04 (dd, J=5.04, 1.83 Hz, 1H)

Reference Example 55

Synthesis of N-[(1S)-1-(2-methoxypyridin-3-yl)ethyl]-N'-methylethane-1,2-diamine By using the compound obtained in Reference Example 44, (1) (74 mg), and the compound obtained in Reference Example 40, (1) (72 mg) as starting materials, the title compound (64 mg) was obtained in the same manners as those of Reference Example 44, (2) and Reference Example 31, (3).
MS (ESI) m/z=210.2 [M+H]⁺
¹H-NMR (600 MHz, CDCl₃) δ (ppm): 1.34 (d, J=6.42 Hz, 3H), 2.41 (s, 3H), 2.51-2.72 (m, 4H), 3.94-4.02 (m, 4H), 6.87 (dd, J=7.34, 5.04 Hz, 1H), 7.59-7.63 (m, 1H), 8.04 (dd, J=4.81, 2.06 Hz, 1H)

Reference Example 56

Synthesis of N-ethyl-N-[1-(3-methoxypyridin-4-yl)ethyl]ethane-1,2-diamine (1) By using 3-methoxyisonicotinonitrile (826 mg) obtained by the method described in the literature (YAKUGAKU ZASSHI, 1983, No. 103, p. 1129) as a starting material, a methylamine compound (69 mg) was obtained in the same manner as that of Reference Example 17, (1).
(2) By using the compound obtained in (1) mentioned above (35 mg) as a starting material, the title compound (36 mg) was obtained in the same manners as those of Reference Example 3, (3), Reference Example 4, (3) and Reference Example 3, (4).
MS (ESI) m/z=224.2 [M+H]⁺
¹H-NMR (200 MHz, CDCl₃) δ (ppm): 0.99 (t, J=7.03 Hz, 3H), 1.28 (d, J=6.59 Hz, 3H), 2.41-2.76 (m, 6H), 3.92 (s, 3H), 4.31 (q, J=6.59 Hz, 1H), 7.29 (d, J=4.83 Hz, 1H), 8.17-8.26 (m, 2H)

Reference Example 57

Synthesis of N-[2-(1-methyl-1H-indol-5-yl)propan-2-yl]ethane-1,2-diamine (1) 5-Cyanoindole (3.0 g) was dissolved in dimethylformamide (20 ml), sodium hydride (1.27 g) and methyl iodide (1.97 ml) were added to the solution under ice cooling, and the resulting mixture was stirred at the same temperature for 30 minutes. Distilled water and ethyl acetate were added to the reaction mixture, the layers were separated, and the organic layer was dried over anhydrous magnesium sulfate, and filtered. By using a crude product obtained by concentrating the filtrate under reduced pressure as a starting material, a dimethyl compound (615.9 mg) was obtained in the same manner as that of Reference Example 17, (1).

(2) By using the compound obtained in (1) mentioned above (100 mg) as a starting material, the title compound (75.8 mg) was obtained in the same manners as those of Reference Example 3, (3) and (4).

MS (ESI) m/z=232.2 [M+H]$^+$ $^1$H-NMR (200 MHz, CDCl$_3$) δ (ppm): 1.56 (s, 6H), 2.35-2.45 (m, 2H), 2.69-2.77 (m, 2H), 3.78 (s, 3H), 6.46 (d, J=3.08 Hz, 1H), 7.03 (d, J=3.08 Hz, 1H), 7.27-7.42 (m, 2H), 7.65 (s, 1H)

Reference Example 58

Synthesis of N-(2,3-dihydro-1-benzofuran-3-yl)-N-ethylethane-1,2-diamine

By using 3-amino-2,3-dihydrobenzofuran (152 mg) as a starting material, the title compound (68.1 mg) was obtained in the same manners as those of Reference Example 3, (3), Reference Example 4, (3) and Reference Example 3, (4).

MS (ESI) m/z=207.2 [M+H]$^+$ $^1$H-NMR (600 MHz, CDCl$_3$) δ (ppm): 1.06 (t, J=7.11 Hz, 3H), 1.36 (br s., 2H), 2.35-2.42 (m, 1H), 2.45-2.50 (m, 1H), 2.53 (q, J=7.03 Hz, 2H), 2.63-2.70 (m, 2H), 4.40-4.45 (m, 1H), 4.45-4.50 (m, 1H), 4.69 (dd, J=8.71, 4.13 Hz, 1H), 6.80 (d, J=8.25 Hz, 1H), 6.86-6.90 (m, 1H), 7.18 (t, J=7.34 Hz, 1H), 7.29 (d, J=8.25 Hz, 1H)

Reference Example 59

Synthesis of (2S)—N-[2-(2-methoxyphenyl)propan-2-yl]propane-1,2-diamine (1) By using the compound obtained in Reference Example 17, (1) (1.18 g) as a starting material, an amide compound (1.00 g) was obtained in the same manner as that of Reference Example 10, (1).

(2) The compound obtained in (1) mentioned above (1.00 g) was dissolved in tetrahydrofuran (15 ml), a 1 M solution of borane/tetrahydrofuran complex in tetrahydrofuran (15 ml) was added to the solution under ice cooling, and the resulting mixture was stirred overnight at room temperature. Methanol was added to the reaction mixture under ice cooling, the resulting mixture was concentrated under reduced pressure, and the resulting residue was purified by silica gel column chromatography (chloroform:methanol:28% aqueous ammonia=40:1:0.1 to 20:1:0.1) to obtain a reduced compound (241 mg).

(3) By using the compound obtained in (2) mentioned above (78.9 mg) as a starting material, the title compound (29.9 mg) was obtained in the same manner as that of Reference Example 31, (3).

MS (ESI) m/z=223.2 [M+H]$^+$ $^1$H-NMR (600 MHz, CDCl$_3$) δ (ppm): 0.95 (d, J=6.42 Hz, 3H), 1.49 (s, 3H), 1.50 (s, 3H), 1.95 (dd, J=11.23, 8.02 Hz, 1H), 2.14 (dd, J=11.00, 4.58 Hz, 1H), 2.82-2.89 (m, 1H), 3.85 (s, 3H), 6.86-6.93 (m, 2H), 7.20-7.26 (m, 2H)

Reference Example 60

Synthesis of N-(3,3-dimethyl-3,4-dihydro-2H-chromen-4-yl)ethane-1,2-diamine

By using 3,3-dimethylchroman-4-one (0.52 g) obtained by the method described in the literature (Synthetic Communications, 2005, vol. 36, p. 465) as a starting material, the title compound (43 mg) was obtained in the same manners as those of Reference Example 4, (1), Reference Example 3, (3) and (4).

MS (ESI) m/z=221.2 [M+H]$^+$ $^1$H-NMR (600 MHz, CDCl$_3$) δ (ppm): 0.93 (s, 3H), 1.02 (s, 3H), 1.39 (br s., 2H), 2.74-2.82 (m, 3H), 2.96-3.06 (m, 1H), 3.16 (s, 1H), 3.70 (dd, J=11.00, 1.38 Hz, 1H), 3.98 (d, J=10.55 Hz, 1H), 6.79 (d, J=7.34 Hz, 1H), 6.83-6.89 (m, 1H), 7.13 (t, J=8.48 Hz, 1H), 7.21 (d, J=9.17 Hz, 1H)

Reference Example 61

Synthesis of (2S)—N-[2-(2-methoxyphenyl)propan-2-yl]-N-methylpropane-1,2-diamine By using the compound obtained in Reference Example 59, (2) (82.8 mg) as a starting material, the title compound (21.8 mg) was obtained in the same manners as those of Reference Example 20, (1) and Reference Example 31, (3).

MS (ESI) m/z=237.2 [M+H]$^+$ $^1$H-NMR (600 MHz, CDCl$_3$) δ (ppm): 0.94 (d, J=6.42 Hz, 3H), 1.44 (s, 6H), 1.70 (br s., 2H), 2.10 (s, 3H), 2.13 (dd, J=12.38, 3.67 Hz, 1H), 2.19-2.26 (m, 1H), 2.87-2.96 (m, 1H), 3.80 (s, 3H), 6.85-6.90 (m, 2H), 7.16-7.22 (m, 1H), 7.34-7.38 (m, 1H)

Reference Example 62

Synthesis of (2S)—N-[2-(2-methoxyphenyl)propan-2-yl]-N'-methylpropane-1,2-diamine (1) By using the compound obtained in Reference Example 17, (1) (0.90 g), and (S)-2-[t-butoxycarbonyl(methyl)amino]propanoic acid (2.22 g) as starting materials, a reduced compound (504 mg) was obtained in the same manners as those of Reference Example 10, (1) and Reference Example 59, (2).

(2) By using the compound obtained in (1) mentioned above (160 mg) as a starting material, the title compound (88.1 mg) was obtained in the same manner as that of Reference Example 31, (3).

MS (ESI) m/z=237.2 [M+H]$^+$ $^1$H-NMR (600 MHz, CDCl$_3$) δ (ppm): 0.91 (d, J=6.42 Hz, 3H), 1.47 (s, 3H), 1.47 (s, 3H), 2.04-2.13 (m, 2H), 2.34 (s, 3H), 2.42-2.48 (m, 1H), 3.84 (s, 3H), 6.86-6.92 (m, 2H), 7.18-7.23 (m, 2H)

Reference Example 63

Synthesis of (2S)—N-ethyl-N-[2-(2-methoxyphenyl)propan-2-yl]propane-1,2-diamine

By using the compound obtained in Reference Example 59, (2) (94 mg) as a starting material, the title compound (35.1 mg) was obtained in the same manners as those of Reference Example 4, (3) and Reference Example 31, (3).
MS (ESI) m/z=251.2 [M+H]$^+$
$^1$H-NMR (600 MHz, CDCl$_3$) δ (ppm): 0.89 (t, J=7.11 Hz, 3H), 0.95 (d, J=6.42 Hz, 3H), 1.45 (s, 3H), 1.46 (s, 3H), 1.62 (br s., 2H), 2.18 (dd, J=13.07, 10.32 Hz, 1H), 2.29 (dq, J=14.21, 7.03 Hz, 1H), 2.43 (dd, J=13.07, 3.90 Hz, 1H), 2.57-2.65 (m, 1H), 2.79-2.88 (m, 1H), 3.81 (s, 3H), 6.87 (d, J=7.34 Hz, 2H), 7.18-7.21 (m, 1H), 7.35 (dd, J=8.25, 1.83 Hz, 1H)

Reference Example 64

Synthesis of N-[2-(2-methoxypyridin-3-yl)propan-2-yl]-N,N'-dimethylethane-1,2-diamine By using the compound obtained in Reference Example 44, (2) (290 mg) as a starting material, the title compound (46.3 mg) was obtained in the same manners as those of Reference Example 20, (1) and Reference Example 31, (3).
MS (ESI) m/z=238.2 [M+H]$^+$
$^1$H-NMR (200 MHz, CDCl$_3$) δ (ppm): 1.43 (s, 6H), 2.14 (s, 3H), 2.39 (s, 3H), 2.47-2.69 (m, 4H), 3.96 (s, 3H), 6.84 (dd, J=7.47, 4.83 Hz, 1H), 7.69 (dd, J=7.47, 1.76 Hz, 1H), 8.04 (dd, J=4.83, 2.20 Hz, 1H)

Reference Example 65

Synthesis of N,N'-dimethyl-N-[(1-methyl-1H-indol-3-yl)methyl]ethane-1,2-diamine (1) 1-Methylindole-3-carboxyaldehyde (2.0 g) was dissolved in chloroform (30 ml), 40% aqueous methylamine (5.42 ml), and sodium triacetoxyborohydride (3.2 g) were added to the solution, and the resulting mixture was stirred at room temperature for 7 hours. Saturated aqueous sodium hydrogencarbonate was added to the reaction mixture, the resulting mixture was extracted with chloroform, and the organic layer was concentrated under reduced pressure. The resulting residue (1.0 g) was dissolved in methanol (5 ml), sodium borohydride (263.6 mg) was slowly added to the solution under ice cooling, and the resulting mixture was stirred at room temperature for 2 hours. Distilled water was added to the reaction mixture, the resulting mixture was extracted with chloroform, and the organic layer was dried over anhydrous sodium sulfate, and filtered. The filtrate was concentrated under reduced pressure to obtain an alkyl compound (923 mg).
(2) By using the compound obtained in (1) mentioned above (100 mg), and the compound obtained in Reference Example 44, (1) (94.4 mg) as starting materials, the title compound (25.3 mg) was obtained in the same manners as those of Reference Example 44, (2) and Reference Example 31, (3).
MS (ESI) m/z=232.2 [M+H]$^+$
$^1$H-NMR (600 MHz, CDCl$_3$) δ (ppm): 2.23 (s, 3H), 2.35 (s, 3H), 2.55-2.58 (m, 2H), 2.66-2.70 (m, 2H), 3.69 (s, 2H), 3.76 (s, 3H), 6.96 (s, 1H), 7.10 (t, J=7.34 Hz, 1H), 7.19-7.23 (m, 1H), 7.28 (d, J=8.25 Hz, 1H), 7.67 (d, J=7.79 Hz, 1H)

Reference Example 66

Synthesis of N-[2-(3-methoxyphenyl)propan-2-yl]-N,N'-dimethylethane-1,2-diamine (1) By using 3-methoxybenzonitrile (5.0 g) as a starting material, a dimethylamine compound (2.58 g) was obtained in the same manner as that of Reference Example 17, (1).

(2) By using the compound obtained in (1) mentioned above (200 mg), and the compound obtained in Reference Example 44, (1) (209.7 mg) as starting materials, the title compound (21.6 mg) was obtained in the same manners as those of Reference Example 44, (2), Reference Example 20, (1) and Reference Example 31, (3).
MS (ESI) m/z=237.2 [M+H]$^+$
$^1$H-NMR (200 MHz, CDCl$_3$) δ (ppm): 1.34 (s, 6H), 2.16 (s, 3H), 2.33 (s, 3H), 2.38-2.48 (m, 2H), 2.53-2.65 (m, 2H), 3.81 (s, 3H), 7.26 (s, 4H)

Reference Example 67

Synthesis of (2S)—N-[2-(2-methoxyphenyl)propan-2-yl]-N,N'-dimethylpropane-1,2-diamine By using the compound obtained in Reference Example 62, (1) (104 mg) as a starting material, the title compound (72 mg) was obtained in the same manners as those of Reference Example 20, (1) and Reference Example 31, (3).
MS (ESI) m/z=251.2 [M+H]$^+$
$^1$H-NMR (200 MHz, CDCl$_3$) δ (ppm): 0.93 (d, 3H), 1.42 (s, 3H), 1.46 (s, 3H), 2.06 (s, 3H), 2.07-2.20 (m, 1H), 2.41 (s, 3H), 2.44-2.59 (m, 2H), 3.83 (s, 3H), 6.83-6.93 (m, 2H), 7.15-7.25 (m, 1H), 7.28-7.36 (m, 1H)

Reference Example 68

Synthesis of N-[(1S)-1-(2-methoxyphenyl)ethyl]-N'-methylethane-1,2-diamine (1) By using N-t-butoxycarbonylglycine (556 mg), and (1S)-1-(2-methoxyphenyl)ethanamine (320 mg) obtained by the method described in the publication (Japanese Patent Unexamined Publication No. 54/154724) as starting materials, an amide compound (651 mg) was obtained in the same manner as that of Reference Example 10, (1).
(2) By using the compound obtained in (1) mentioned above (291 mg) as a starting material, the title compound (52.3 mg) was obtained in the same manner as that of Reference Example 3, (2).
MS (FAB) m/z 209 [M+H]$^+$
$^1$H-NMR (400 MHz, CDCl$_3$) δ (ppm): 1.36 (d, J=6.6 Hz, 3H), 1.87 (br, 1H), 2.40 (s, 3H), 2.54-2.72 (m, 4H), 3.83 (s, 3H), 4.12 (q, J=6.6 Hz, 1H), 6.86 (dd, J=8.1, 1.0 Hz, 1H), 6.94 (ddd, J=7.6, 7.3, 1.0 Hz, 1H), 7.20 (ddd, J=8.1, 7.3, 1.7 Hz, 1H), 7.30 (dd, J=7.6, J=1.7 Hz, 1H)

Reference Example 69

Synthesis of (2S)—N-[(1S)-1-(2-methoxyphenyl)ethyl]propane-1,2-diamine

By using N-t-butoxycarbonyl-(L)-alanine (431 mg), and (1S)-1-(2-methoxyphenyl)ethanamine (200 mg) obtained by the method described in the publication (Japanese Patent Unexamined Publication No. 54/154724) as starting materials, the title compound (33.6 mg) was obtained in the same manners as those of Reference Example 10, (1), (2), and Reference Example 3, (2).
MS (ESI) m/z=209 [M+H]$^+$
$^1$H-NMR (400 MHz, CDCl$_3$) δ (ppm): 1.01 (d, J=6.34 Hz, 3H), 1.35 (d, J=6.84 Hz, 3H), 2.24 (dd, J=11.7, 8.30 Hz, 1H), 2.43 (dd, J=11.5, 4.64 Hz, 1H), 2.85-2.97 (m, 1H), 3.83 (s, 3H), 4.08 (q, J=6.84 Hz, 1H), 6.87 (d, J=8.05 Hz, 1H), 6.91-6.98 (m, 1H), 7.21 (dt, J=7.81, 1.70 Hz, 1H), 7.31 (dd, J=7.33, 1.47 Hz, 1H)

Reference Example 70

Synthesis of (2S)—N-ethyl-N-[(1S)-1-(2-methoxyphenyl)ethyl]-3-methylbutane-1,2-diamine By using N-t-butoxycarbonyl-(L)-valine (727 mg), and the compound obtained in Reference Example 3, (2) (200 mg) as starting materials, the title compound (78.7 mg) was obtained in the same manners as those of Reference Example 10, (1), (2), and Reference Example 3, (2).
MS (ESI) m/z=265 [M+H]$^+$
$^1$H-NMR (400 MHz, CDCl$_3$) δ (ppm): 0.87 (d, J=6.84 Hz, 3H), 0.89 (d, J=6.83 Hz, 3H), 0.97 (t, J=7.08 Hz, 3H), 1.27 (d, J=7.08 Hz, 3H), 1.45-1.57 (m, 1H), 2.20 (dd, J=12.7, 10.3 Hz, 1H), 2.45-2.60 (m, 4H), 3.82 (s, 3H), 4.37 (q, J=6.83 Hz, 1H), 6.83-6.97 (m, 2H), 7.18-7.24 (m, 1H), 7.30-7.35 (m, 1H)

Reference Example 71

Synthesis of (2S)-3-(1H-imidazol-4-yl)-N-[(1S)-1-(2-methoxyphenyl)ethyl]propane-1,2-diamine (1) N-t-Butoxycarbonyl-(L)-histidine (427 mg), hydroxybenzotriazole (282 mg), and diisopropylcarbodiimide (264 mg) were dissolved in dimethylformamide (5 ml), a solution of (1S)-1-(2-methoxyphenyl)ethanamine (210 mg) obtained by the method described in the publication (Japanese Patent Unexamined Publication No. 54/154724) in dimethylformamide (3 ml) was added to the solution, and the resulting mixture was stirred at room temperature for 15 hours. The reaction mixture was filtered, ethyl acetate and saturated aqueous sodium hydrogencarbonate were added to the filtrate, the layers were separated, and the organic layer was washed with saturated brine, then dried over anhydrous magnesium sulfate, and filtered. The filtrate was concentrated under reduced pressure, and the resulting residue was purified by silica gel column chromatography (chloroform:methanol:28% aqueous ammonia=30:1:0.1) to obtain an amide compound (441 mg).

(2) The compound obtained in (1) mentioned above (50 mg) was dissolved in methylene chloride (1 anisole (50 μl), and trifluoroacetic acid (1 ml) were added to the solution, and the resulting mixture was stirred at room temperature for 3 hours. The reaction mixture was concentrated under reduced pressure, the resulting residue was dissolved in methylene chloride (5 ml), and then 5 N aqueous sodium hydroxide was added to the solution to make the solution alkaline. Methylene chloride was added to the resulting mixture, the layers were separated, the organic layer was dried over anhydrous magnesium sulfate, and filtered, and then the filtrate was concentrated under reduced pressure to obtain a deprotected compound (40 mg).

(3) The compound obtained in (2) mentioned above (39 mg) was dissolved in tetrahydrofuran (2 ml), a 2 M solution of borane/methyl sulfide in tetrahydrofuran (340 μl) was added to the solution under an argon atmosphere, and the resulting mixture was stirred for 1 hour and 25 minutes under reflux by heating. The reaction mixture was left to cool to room temperature, methanol (200 μl), and a 4 N solution of hydrochloric acid in ethyl acetate (200 μl) were successively added to the reaction mixture, and then the resulting mixture was stirred for 1 hour, and concentrated under reduced pressure. 5 N Aqueous sodium hydroxide, and methylene chloride were added to the residue, the layers were separated, and then the organic layer was dried over anhydrous magnesium sulfate, and filtered. The filtrate was concentrated under reduced pressure, and the resulting residue was purified by preparative thin layer chromatography (chloroform:methanol:28% aqueous ammonia=7:1:0.1) to obtain the title compound (21 mg).
MS (FAB): m/z=275 [M+H]$^+$
$^1$H-NMR (400 MHz, CDCl$_3$) δ (ppm): 1.37 (d, J=6.84 Hz, 3H), 2.37 (dd, J=12.0, 7.32 Hz, 1H), 2.40 (m, 2H), 2.76 (dd, J=14.7, 4.15 Hz, 1H), 3.07 (m, 1H), 3.82 (s, 3H), 4.07 (q, J=6.59 Hz, 1H), 6.76 (s, 1H), 6.87 (d, J=8.30 Hz, 1H), 6.95 (t, J=7.32 Hz, 1H), 7.23 (dt, J=7.81, 1.71 Hz, 1H), 7.28 (m, 1H), 7.48 (s, 1H)

Reference Example 72

Synthesis of N'-ethyl-N-[(1S)1-(2-methoxyphenyl)ethyl]ethane-1,2-diamine (1) By using the compound obtained in Reference Example 68, (1) (360 mg) as a starting material, a deprotected compound (202 mg) was obtained in the same manner as that of Reference Example 10, (2).

(2) By using the compound obtained in (1) mentioned above (193 mg) as a starting material, an acetyl compound (228 mg) was obtained in the same manner as that of Reference Example 3, (1).

(3) By using the compound obtained in (2) mentioned above (291 mg) as a starting material, the title compound (15.5 mg) was obtained in the same manner as that of Reference Example 3, (2).
MS (FAB) m/z 223 [M+H]$^+$
$^1$H-NMR (400 MHz, CDCl$_3$) δ (ppm): 1.09 (t, J=7.1 Hz, 3H), 1.36 (d, J=6.6 Hz, 3H), 1.85 (br, 2H), 2.56-2.72 (m, 6H), 3.84 (s, 3H), 4.10 (q, J=4.10 Hz, 1H), 6.87 (dd, J=8.3, 1.0 Hz, 1H), 6.94 (ddd, J=8.3, 7.6, 7.6 Hz, 1H), 7.20 (ddd, J=8.3, 7.6, 1.7 Hz, 1H), 7.29 (dd, J=7.6, 1.7 Hz, 1H)

Reference Example 73

Synthesis of (2R)-3-(1H-imidazol-4-yl)-N-[(1S)-1-(2-methoxyphenyl)ethyl]propane-1,2-diamine By using N-t-butoxycarbonyl-(D)-histidine (405 mg), and (1S)-1-(2-methoxyphenyl)ethanamine compound (200 mg) obtained by the method described in the publication (Japanese Patent Unexamined Publication No. 54/154724) as starting materials, the title compound (88 mg) was obtained in the same manner as that of Reference Example 71.
MS (FAB): m/z=275 [M+H]$^+$
$^1$H-NMR (400 MHz, CDCl$_3$) δ (ppm): 1.37 (d, J=6.84 Hz, 3H), 2.37 (dd, J=12.0, 7.32 Hz, 1H), 2.40 (m, 2H), 2.76 (dd, J=14.7, 4.15 Hz, 1H), 3.07 (m, 1H), 3.82 (s, 3H), 4.07 (q, J=6.59 Hz, 1H), 6.76 (s, 1H), 6.87 (d, J=8.30 Hz, 1H), 6.95 (t, J=7.32 Hz, 1H), 7.23 (dt, J=7.81, 1.71 Hz, 1H), 7.28 (m, 1H), 7.48 (s, 1H)

Reference Example 74

Synthesis of (2R)-2-amino-3-{ethyl[(1S)-1-(2-methoxyphenyl)ethyl]amino}propan-1-ol (1) By using N-(t-butoxycarbonyl)-O-benzyl-(L)-serine (247 mg), and the compound obtained in Reference Example 3, (2) (100 mg) as starting materials, an amide compound (197 mg) was obtained in the same manner as that of Reference Example 10, (1).

(2) The compound obtained in (1) mentioned above (197 mg) was dissolved in methanol (4 ml), 10% palladium-carbon (20 mg) was added to the solution under an argon atmosphere, and the resulting mixture was stirred at room temperature for 2 hours under a hydrogen atmosphere of 1 atm. The reaction mixture was filtered, and then the filtrate was concentrated under reduced pressure to obtain a debenzylated compound (155 mg).

(3) By using the compound obtained in (2) mentioned above (155 mg) as a starting material, the title compound (68.6 mg) was obtained in the same manners as those of Reference Example 10, (2) and Reference Example 3, (2).

MS (FAB): m/z=253 [M+H]$^+$ $^1$H-NMR (400 MHz, CDCl$_3$) δ (ppm): 1.06 (t, J=7.1 Hz, 3H), 1.36 (d, J=6.8 Hz, 1H), 2.37-2.57 (m, 3H), 2.63-2.75 (m, 1H), 3.02-3.11 (m, 1H), 3.47-3.58 (m, 2H), 3.83 (s, 3H), 4.45 (q, J=6.8 Hz, 1H), 6.88 (d, J=8.3 Hz, 1H), 6.96 (dt, J=7.6, 1.0 Hz, 1H), 7.21-7.31 (m, 2H)

Reference Example 75

Synthesis of (2S)-2-amino-3-{ethyl[(1S)-1-(2-methoxyphenyl)ethyl]amino}propan-1-ol By using N-(t-butoxycarbonyl)-O-benzyl-(D)-serine (247 mg), and the compound obtained in Reference Example 3, (2) (29 mg) as starting materials, the title compound (29.0 mg) was obtained in the same manners as those of Reference Example 10, (1), Reference Example 74, (2), Reference Example 10, (2) and Reference Example 3, (2).

MS (ESI) m/z=253 [M+H]$^+$ $^1$H-NMR (400 MHz, CDCl$_3$) δ (ppm): 1.05 (t, J=7.1 Hz, 3H), 1.35 (d, J=7.1 Hz, 3H), 2.38-2.57 (m, 3H), 2.62-2.73 (m, 1H), 3.04-3.13 (m, 1H), 3.54 (d, J=6.3 Hz, 2H), 3.83 (s, 3H), 4.44 (q, J=7.1 Hz, 1H), 6.90 (d, J=8.3 Hz, 1H), 6.96 (dt, J=7.6, 1.0 Hz, 1H), 7.22-7.26 (m, 1H), 7.31 (dd, J=7.6, 1.7 Hz, 1H)

Reference Example 76

Synthesis of (2R)—N-ethyl-3-methoxy-N-[(1S)-1-(2-methoxyphenyl)ethyl]propane-1,2-diamine By using N-(t-butoxycarbonyl)-O-methyl-(L)-serine (238 mg) as a starting material, the title compound (71.1 mg) was obtained in the same manners as those of Reference Example 10, (1), (2), and Reference Example 3, (2).

MS (FAB): m/z=267 [M+H]$^+$ $^1$H-NMR (400 MHz, CDCl$_3$) δ (ppm): 0.96 (t, J=7.1 Hz, 3H), 1.27 (d, J=7.1 Hz, 3H), 2.30 (dd, J=12.9, 8.8 Hz, 1H), 2.43-2.59 (m, 3H), 3.02-3.10 (m, 1H), 3.20 (dd, J=9.0, 6.6 Hz, 1H), 3.34 (s, 3H), 3.41 (dd, J=9.0, 3.9 Hz, 1H), 3.82 (s, 3H), 4.36 (q, J=6.8 Hz, 1H), 6.87 (dd, J=8.1, 1.0 Hz, 1H), 6.93 (dt, J=7.3, 1.0 Hz, 1H), 7.18-7.23 (m, 1H), 7.33 (dd, J=7.6, 1.7 Hz, 1H)

Reference Example 77

Synthesis of (S)—N-(azetidin-3-ylmethyl)-1-(2-methoxyphenyl)ethanamine (1) Azetidine-3-carboxylic acid (125 mg) was dissolved in a mixed solvent of dioxane and distilled water (3:1, 2.5 ml), di-t-butyl dicarbonate (324 mg), and triethylamine (207 μl) were added to the solution, and the resulting mixture was stirred at room temperature for 3.5 hours. 1 N Aqueous sodium hydroxide (1 ml) was added to the reaction mixture, the resulting mixture was washed with hexane, then 1 N hydrochloric acid (0.8 ml), and 1 N potassium hydrogensulfate (2 ml) were added to the aqueous layer, ethyl acetate was added to the resulting mixture, and the layers were separated. The organic layer was dried over anhydrous magnesium sulfate, and filtered, and then the filtrate was concentrated under reduced pressure to obtain a protected compound (247 mg).

(2) By using the compound obtained in (1) mentioned above (351 mg), and (1S)-1-(2-methoxyphenyl)ethylamine (187 mg) obtained by the method described in the publication (Japanese Patent Unexamined Publication No. 54/154724) as starting materials, an amide compound (407 mg) was obtained in the same manner as that of Reference Example 10, (1).

(3) By using the compound obtained in (2) mentioned above (398 mg) as a starting material, a deprotected compound (275 mg) was obtained in the same manner as that of Reference Example 10, (2).

(4) The compound obtained in (3) mentioned above (229 mg) was dissolved in tetrahydrofuran (2.3 ml), a 1 N solution of borane-tetrahydrofuran complex in tetrahydrofuran (5.85 ml) was added to the solution under ice cooling, and the resulting mixture was stirred at room temperature for 2 hours and 30 minutes. Methanol (790 μl) was added to the reaction mixture, the resulting mixture was stirred at the same temperature for 14 hours, then ethylenediamine (652 μl) was added to the reaction mixture, start of foaming was confirmed, and then the resulting mixture was stirred at 130° C. for 1 hour and 30 minutes under microwave irradiation. The reaction mixture was concentrated under reduced pressure, and the resulting residue was purified by silica gel column chromatography (chloroform:methanol: 28% aqueous ammonia=30:1:0.1 to 1:1:0.1) to obtain the title compound (154 mg).

MS (ESI) m/z=221 [M+H]$^+$ $^1$H-NMR (400 MHz, CDCl$_3$) δ (ppm): 1.35 (d, J=6.59 Hz, 3H), 2.61-2.73 (m, 2H), 2.78-2.89 (m, 1H), 3.30-3.38 (m, 2H), 3.69 (dt, J=7.82, 2.45 Hz, 2H), 3.83 (s, 3H), 4.06 (q, J=6.84 Hz, 1H), 6.87 (d, J=8.06 Hz, 1H), 6.95 (t, J=7.57 Hz, 1H), 7.19-7.24 (m, HD, 7.26-7.31 (m, 1H)

Reference Example 78

Synthesis of (R)-3-{[2-(2-methoxyphenyl)propan-2-yl]methylamino}-2-(methylamino)propan-1-ol (1) N-t-Butoxycarbonyl-O-benzyl-(L)-serine (958 mg), hydroxybenzotriazole (438 mg), and diisopropylcarbodiimide (502 μl) were dissolved in dimethylformamide (2 ml), the solution was stirred at room temperature for 10 minutes, then a solution of the compound obtained in Reference Example 17, (1) (179 mg) in dimethylformamide (1.57 ml) was added to the solution, and the resulting mixture was stirred at the same temperature for 6 hours. Diethyl ether was added to the reaction mixture, the resulting mixture was filtered, a mixed solvent of hexane and ethyl acetate (2:1) and saturated aqueous sodium hydrogencarbonate were added to the filtrate, the layers were separated, and the organic layer was washed with saturated brine, then dried over anhydrous sodium sulfate, and filtered. The filtrate was concentrated under reduced pressure, and the resulting residue was purified by silica gel column chromatography (hexane:ethyl acetate=7:1 to 2:1) to obtain an amide compound (458 mg).

(2) By using the compound obtained in (1) mentioned above (458 mg) as a starting material, a debenzylated compound (341 mg) was obtained in the same manner as that of Reference Example 74, (2).

(3) By using the compound obtained in (2) mentioned above (323 mg) as a starting material, a reduced compound (216 mg) was obtained in the same manner as that of Reference Example 77, (4).

(4) By using the compound obtained in (3) mentioned above (58.4 mg) as a starting material, the title compound (18.2 mg) was obtained in the same manners as those of Reference Example 20, (1) and Reference Example 3, (2).

MS (ESI) m/z=267 [M+H]$^+$ $^1$H-NMR (400 MHz, CDCl$_3$) δ (ppm): 1.43 (s, 3H), 1.50 (s, 3H), 2.09 (s, 3H), 2.45 (s, 3H), 2.50-2.65 (m, 2H), 2.66-2.75 (m, 1H), 3.51 (dd, J=10.8, 7.57 Hz, 1H), 3.61-3.73 (m, 2H), 3.83 (s, 3H), 6.86-6.92 (m, 2H), 7.20-7.30 (m, 2H)

Reference Example 79

Synthesis of (R)-3-{ethyl[2-(2-methoxyphenyl)propan-2-yl]amino}-2-(methylamino)propan-1-ol By using the compound obtained in Reference Example 78, (3) (58.4 mg) as a starting material, the title compound (13 mg) was obtained in the same manners as those of Reference Example 4, (3) and Reference Example 3, (2).

MS (ESI) m/z=281 [M+H]$^+$ $^1$H-NMR (400 MHz, CDCl$_3$) δ (ppm): 0.85 (t, J=7.08 Hz, 3H), 1.47 (s, 3H), 1.50 (s, 3H), 2.37-2.64 (m, 4H), 2.45 (s, 3H), 2.77-2.87 (m, 1H), 3.52 (d, J=11.2 Hz, 1H), 3.63 (dd, J=10.8, 5.62 Hz, 1H), 3.68-3.72 (m, 1H), 3.85 (s, 3H), 6.87-6.93 (m, 2H), 7.21-7.32 (m, 2H)

Reference Example 80

Synthesis of (2R)-3-{[(1S)-1-(2-methoxyphenyl)ethyl]methylamino}-2-(methylamino)propan-1-ol (1) By using N-(t-butoxycarbonyl)-O-benzyl-(L)-serinol (338 mg) as a starting material, an aldehyde compound (263 mg) was obtained in the same manner as that of Reference Example 44, (1).

(2) By using the compound obtained in (1) mentioned above (262 mg), and (1S)-1-(2-methoxyphenyl)ethylamine (142 mg) obtained by the method described in the publication (Japanese Patent Unexamined Publication No. 54/154724) as starting materials, an alkyl compound (366 mg) was obtained in the same manner as that of Reference Example 44, (2).

(3) The compound obtained in (2) mentioned above (336 mg) was dissolved in methanol (6 ml), 10% palladium-carbon (10 mg) was added to the solution under an argon atmosphere, and the resulting mixture was stirred at room temperature for 30 minutes under a hydrogen atmosphere of 1 atm. Acetic acid (46 µl) was added to the reaction mixture, the resulting mixture was stirred at room temperature for 30 minutes under a hydrogen atmosphere of 1 atm, then 5 N hydrochloric acid (162 µl) was added to the reaction mixture, and the resulting mixture was stirred at room temperature for 1 hour under a hydrogen atmosphere of 1 atm. 10% Palladium-carbon (120 mg) was further added to the reaction mixture, the resulting mixture was stirred at room temperature for 2 hours under a hydrogen atmosphere of 1 atm., the reaction mixture was filtered through Celite, and then the filtrate was concentrated under reduced pressure to obtain a debenzylated compound (265 mg).

(4) By using the compound obtained in (3) mentioned above (81.0 mg) as a starting material, the title compound (18.6 mg) was obtained in the same manners as those of Reference Example 20, (1) and Reference Example 3, (2).

MS (FAB): m/z=253 [M+H]$^+$ $^1$H-NMR (400 MHz, CDCl$_3$) δ (ppm): 1.32 (d, J=7.1 Hz, 3H), 2.21 (s, 3H), 2.38-2.46 (m, 4H), 2.62 (dd, J=12.5, 6.3 Hz, 1H), 2.68-2.75 (m, 1H), 3.50-3.60 (m, 2H), 3.84 (s, 3H), 4.17 (q, J=7.1 Hz, 1H), 6.89 (d, J=8.3 Hz, 1H), 6.96 (dt, J=7.6, 1.0 Hz, 1H), 7.21-7.33 (m, 2H)

Reference Example 81

Synthesis of (2R)-3-{ethyl[(1S)-1-(2-methoxyphenyl)ethyl]amino}-2-(methylamino)propan-1-ol By using the compound obtained in Reference Example 80, (3) (85.0 mg) as a starting material, the title compound (13.9 mg) was obtained in the same manners as those of Reference Example 4, (3) and Reference Example 3, (2).

MS (ESI) m/z=267 [M+H]$^+$ $^1$H-NMR (400 MHz, CDCl$_3$) δ (ppm): 1.04 (t, J=7.1 Hz, 3H), 1.33 (d, J=7.1 Hz, 3H), 1.38 (s, 3H), 2.39-2.50 (m, 2H), 2.60-2.72 (m, 3H), 3.50-3.59 (m, 2H), 4.44 (q, J=6.8 Hz, 1H), 6.88 (dd, J=8.3, 1.0 Hz, 1H), 6.94 (ddd, J=7.6, 7.3, 1.0 Hz, 1H), 7.24 (ddd, J=8.3, 7.3, 1.7 Hz, 1H), 7.28 (dd, J=7.6, 1.7 Hz, 1H)

Reference Example 82

Synthesis of (R)-3-[2-(2-methoxyphenyl)propan-2-ylamino]-2-(methylamino)propan-1-ol (1) The compound obtained in Reference Example 78, (1) (500 mg) was dissolved in methanol (4.3 ml), 5 N hydrochloric acid (2.5 ml) was added to the solution, and the resulting mixture was stirred at room temperature for 27 hours. 5 N Aqueous sodium hydroxide (2.15 ml) was added to the reaction mixture, ethyl acetate was added to the resulting mixture, the layers were separated, and the organic layer was dried over anhydrous sodium sulfate, and filtered. The filtrate was concentrated under reduced pressure to obtain a deprotected compound (397 mg).

(2) A mixture of acetic anhydride (213 µl) and formic acid (430 µl) was stirred at 50° C. for 10 minutes, left to cool to room temperature, and then added to a solution of the compound obtained in (1) mentioned above (397 mg) in dimethylformamide (3.87 ml), and the resulting mixture was stirred at room temperature for 1 hour. Distilled water (1 ml) was added to the reaction mixture, a mixed solvent of hexane and ethyl acetate (1:1) was added to the resulting mixture, the layers were separated, and the resulting organic layer was azeotroped with toluene to obtain a formyl compound (431 mg).

(3) By using the compound obtained in (2) mentioned above (100 mg) as a starting material, the title compound (47.9 mg) was obtained in the same manners as those of Reference Example 74, (2) and Reference Example 77, (4).

MS (ESI) m/z=253 [M+H]$^+$ $^1$H-NMR (400 MHz, CDCl$_3$) δ (ppm): 1.51 (s, 3H), 1.52 (s, 3H), 2.31-2.52 (m, 3H), 2.37 (s, 3H), 3.62-3.72 (m, 2H), 3.87 (s, 3H), 6.87-6.95 (m, 2H), 7.20-7.27 (m, 2H)

Reference Example 83

Synthesis of (2R,3R)-3-amino-4-{ethyl[(S)-1-(2-methoxyphenyl)ethyl]amino}butan-2-ol By using N-(carbobenzoxy)-O-benzyl-(L)-threonine (249 mg) as a starting material, the title compound (31.9 mg) was obtained in the same manners as those of Reference Example 10, (1), Reference Example 74, (2), and Reference Example 3, (2).

MS (FAB): m/z=267 [M+H]+
$^1$H-NMR (400 MHz, CDCl$_3$) δ (ppm): 1.02 (t, J=7.1 Hz, 3H), 1.11 (d, J=6.3 Hz, 3H), 1.30 (d, J=6.8 Hz, 3H), 2.44 (dd, J=13.2, 7.8 Hz, 1H), 2.51-2.64 (m, 3H), 2.60-2.77 (m, 1H), 3.45 (dq, J=6.3, 3.9 Hz, 1H), 3.83 (s, 3H), 4.42 (q, J=6.8 Hz, 1H), 6.88 (d, J=8.3 Hz, 1H), 6.93 (dt, J=7.3, 1.0 Hz, 1H), 7.21-7.25 (m, 1H), 7.30 (dd, J=7.3, 1.5 Hz, 1H)

Reference Example 84

Synthesis of (S)-3-amino-4-{ethyl[(S)-1-(2-methoxyphenyl)ethyl]amino}butan-1-ol (1) By using N-t-butoxycarbonyl-O-benzyl-(L)-homoserine (300 mg), and (1S)-1-(2-methoxyphenyl)ethylamine (147 mg) obtained by the method described in the publication (Japanese Patent Unexamined Publication No. 54/154724) as starting materials, a reduced compound (91.3 mg) was obtained in the same manners as those of Reference Example 78, (1), Reference Example 74, (2) and Reference Example 77, (4).
(2) By using the compound obtained in (1) mentioned above (51.5 mg) as a starting material, an N-ethyl compound (31.7 mg) was obtained in the same manner as that of Reference Example 4, (3).
(3) By using the compound obtained in (2) mentioned above (48.4 mg) as a starting material, the title compound (31.9 mg) was obtained in the same manner as that of Reference Example 82, (1).

MS (ESI) m/z=267 [M+H]+
$^1$H-NMR (400 MHz, CDCl$_3$) δ (ppm): 1.00 (t, J=7.08 Hz, 3H), 1.30 (d, J=6.83 Hz, 3H), 1.37-1.47 (m, 1H), 1.59-1.67 (m, 1H), 2.21 (dd, J=13.2, 8.30 Hz, 1H), 2.36-2.49 (m, 2H), 2.54-2.65 (m, 1H), 2.94-3.03 (m, 1H), 3.76-3.80 (m, 2H), 3.83 (s, 3H), 4.43 (q, J=7.08 Hz, 1H), 6.87 (d, J=8.06 Hz, 1H), 6.94 (t, J=7.32 Hz, 1H), 7.20-7.32 (m, 2H)

Reference Example 85

Synthesis of N-[2-(2-methoxyphenyl)propan-2-yl]azetidin-3-amine (1) 3-Hydroxyazetidine tartrate (3 g) was dissolved in tetrahydrofuran (60 ml), 1 N aqueous sodium hydroxide (26.9 ml), and di-t-butyl dicarbonate (2.96 g) were successively added to the solution, and the resulting mixture was stirred at room temperature for 1 hour. Tetrahydrofuran in the reaction mixture was concentrated under reduced pressure, ethyl acetate was added to the residue, the layers were separated, and then the organic layer was dried over anhydrous sodium sulfate, and filtered. The filtrate was concentrated under reduced pressure, and the resulting residue was purified by silica gel column chromatography (hexane to hexane:ethyl acetate=1:1) to obtain a protected compound (2.27 g).
(2) The compound obtained in (1) mentioned above (300 mg) was dissolved in chloroform (3 ml), dimethyl sulfoxide (3.69 ml), triethylamine (1.21 ml), and sulfur trioxide/pyridine complex (690 mg) were successively added to the solution, and the resulting mixture was stirred at room temperature for 4 hours. Distilled water was added to the reaction mixture, chloroform was added to the resulting mixture, the layers were separated, and the organic layer was dried over anhydrous sodium sulfate, and filtered. The filtrate was concentrated under reduced pressure, and the resulting residue was purified by silica gel column chromatography (hexane to hexane ethyl acetate=1:1) to obtain a ketone compound (234 mg).
(3) The compound obtained in (2) mentioned above (203 mg), the compound obtained in Reference Example 17, (1) (587 mg), and Molecular Sieves 4A (800 mg) were suspended in dimethylformamide (2 ml), acetic acid (338 μl) was added to the suspension, and the resulting mixture was stirred at 80° C. for 3 hours, and then left to cool to room temperature. Sodium triacetoxyborohydride (752 mg) was added to the reaction mixture, the resulting mixture was stirred at room temperature for 3.5 hours, and then filtered. Saturated aqueous sodium hydrogencarbonate was added to the filtrate, the layers were separated, and the organic layer was dried over anhydrous sodium sulfate, and filtered. The filtrate was concentrated under reduced pressure, and the resulting residue was purified by silica gel column chromatography (chloroform to chloroform:methanol:28% aqueous ammonia=20:1:0.1) to obtain an alkyl compound (280 mg).
(4) By using the compound obtained in (3) mentioned above (150 mg) as a starting material, the title compound (80.6 mg) was obtained in the same manner as that of Reference Example 82, (1).

MS (ESI) m/z=221 [M+H]+
$^1$H-NMR (400 MHz, CDCl$_3$) δ (ppm): 1.48 (s, 6H), 3.23-3.32 (m, 4H), 3.54-3.63 (m, 1H), 3.88 (s, 3H), 6.84-6.92 (m, 2H), 7.19-7.24 (m, 2H)

Reference Example 86

Synthesis of (S)—N-ethyl-N-[(5)-1-(2-methoxyphenyl)ethyl]-N'',N''-dimethylpropane-1,2,3-triamine By using N-a-carbobenzoxy-N-β-(t-butoxycarbonyl)-(L)-α,β-diaminopropionic acid (238 mg) as a starting material, the title compound (32 mg) was obtained in the same manners as those of Reference Example 10, (1), Reference Example 82, (1), Reference Example 20, (1), Reference Example 74, (2), and Reference Example 3, (2).

MS (FAB): m/z=280 [M+H]+
$^1$H-NMR (400 MHz, CDCl$_3$) δ (ppm): 0.98 (t, J=7.1 Hz, 3H), 1.29 (d, J=6.8 Hz, 3H), 2.15-2.27 (m, 8H), 2.31 (dd, J=12.9, 9.3 Hz, 1H), 2.51 (dd, J=13.2, 4.2 Hz, 1H), 2.55 (q, J=7.1 Hz, 2H), 3.01-3.10 (m, 1H), 3.84 (s, 3H), 4.37 (q, J=6.8 Hz, 1H), 6.87 (d, J=8.3 Hz, 1H), 6.94 (t, J=7.6 Hz, 1H), 7.20-7.25 (m, 1H), 7.34 (dd, J=7.6 Hz, 1.5 Hz, 1H)

Reference Example 87

Synthesis of 3-(2-{methyl[2-(methylamino)ethyl]amino}propan-2-yl)phenol (1) 3-Hydroxybenzonitrile (871 mg) was dissolved in dimethylformamide (13 ml), potassium carbonate (1.11 g), and benzyl bromide (0.956 ml) were added to the solution, and the resulting mixture was stirred at room temperature for 2 hours. Distilled water was added to the reaction mixture, the resulting mixture was extracted with ethyl acetate, and the organic layer was dried over anhydrous sodium sulfate, and filtered. The filtrate was concentrated under reduced pressure, and the resulting residue was purified by silica gel column chromatography (hexane to hexane:ethyl acetate=13:1) to obtain a benzyl compound (1.46 g).
(2) Under an argon atmosphere, tetrahydrofuran (18 ml) was added to cerium(III) chloride (3.44 g), and the resulting mixture was stirred at 45° C. for 3 hours. A solution of the compound obtained in (1) mentioned above (1.46 g) in tetrahydrofuran (3 ml) was added to the reaction mixture at room temperature, a 1.09 M solution of methyllithium in diethyl ether (16.0 ml) was added dropwise to the mixture at −10° C. over 30 minutes, and then the resulting mixture was stirred for 1.5 hours. 28% Aqueous ammonia (5 ml) was added to the reaction mixture, the resulting mixture was stirred at room temperature for 1 hour, methanol (10 ml), and Celite were further added to the reaction mixture, and the resulting mixture was stirred for 1 hour, and then filtered through Celite. The filtrate was concentrated under reduced pressure, the resulting residue was dissolved in diethyl ether, and the solution was washed with 1 N aqueous sodium hydroxide. The organic layer was dried over anhydrous sodium sulfate, and filtered, then the filtrate was concentrated under reduced pressure, and the resulting residue was purified by silica gel column chromatography (chloroform to chloroform:methanol:28% aqueous ammonia=9:1:0.1) to obtain a dimethylamine compound (1.45 g).
(3) By using the compound obtained in (2) mentioned above (237 mg), and the compound obtained in Reference Example 44, (1) (170 mg) as starting materials, an N-methyl compound (221 mg) was obtained in the same manners as those of Reference Example 44, (2), and Reference Example 20, (1).
(4) By using the compound obtained in (3) mentioned above (113 mg) as a starting material, the title compound (21.1 mg) was obtained in the same manners as those of Reference Example 74, (2), and Reference Example 10, (2).
MS (FAB): m/z=223 [M+H]$^+$
$^1$H-NMR (400 MHz, CDCl$_3$) δ (ppm): 1.32 (s, 6H), 2.17 (s, 3H), 2.30 (s, 3H), 2.50-2.56 (m, 2H), 2.63-2.68 (m, 2H), 6.59 (ddd, J=8.1, 2.4, 0.7 Hz, 1H), 6.77-6.83 (m, 1H), 7.01 (t, J=2.0 Hz, 1H), 7.11 (t, J=7.8 Hz, 1H)

Reference Example 88

Synthesis of N-{2-(2-benzyloxyphenyl)propan-2-yl}-N,N'-dimethylethane-1,2-diamine (1) By using 2-hydroxybenzonitrile (800 mg) as a starting material, a benzyl compound (1.39 g) was obtained in the same manner as that of Reference Example 87, (1).
(2) By using the compound obtained in (1) mentioned above (1.39 g) as a starting material, a dimethylamine compound (880 mg) was obtained in the same manner as that of Reference Example 87, (2).
(3) By using the compound obtained in (2) mentioned above (279 mg), and the compound obtained in Reference Example 44, (1) (200 mg) as starting materials, an N-methyl compound (279 mg) was obtained in the same manners as those of Reference Example 44, (2), and Reference Example 20, (1).
(4) By using the compound obtained in (3) mentioned above (139 mg) as a starting material, the title compound (97.8 mg) was obtained in the same manner as that of Reference Example 10, (2).
MS (FAB): m/z=313 [M+H]$^+$
$^1$H-NMR (400 MHz, CDCl$_3$) δ (ppm): 1.48 (s, 6H), 2.12 (s, 3H), 2.18 (s, 3H), 2.45-2.55 (m, 4H), 5.10 (s, 2H), 6.88-6.97 (m, 2H), 7.15-7.22 (m, 1H), 7.28-7.34 (m, 1H), 7.36-7.50 (m, 5H)

Reference Example 89

Synthesis of N-ethyl-N-[(1R)-1-(2-methoxypyridin-3-yl)ethyl]-N'-methylethane-1,2-diamine (1) By using 2-methoxynicotinaldehyde (3.0 g) obtained by the method described in the literature (Journal of Organic Chemistry, 1988, vol. 53, p. 1367), and (R)-2-phenylglycinol (3.0 g) as starting materials, an amine compound (253 mg) was obtained in the same manner as that described in the literature (Helvetica Chimia Acta, 2004, vol. 87, p. 561).
(2) By using the compound obtained in (1) mentioned above (140 mg), and the compound obtained in Reference Example 44, (1) (287 mg) as starting materials, the title compound (73.0 mg) was obtained in the same manners as those of Reference Example 44, (2), Reference Example 4, (3) and Reference Example 31, (3).
MS (ESI) m/z=238.2 [M+H]$^+$
$^1$H-NMR (200 MHz, CDCl$_3$) δ (ppm): 0.97 (t, J=7.03 Hz, 3H), 1.27 (d, J=7.03 Hz, 3H), 2.38 (s, 3H), 2.40-2.66 (m, 6H), 3.95 (s, 3H), 4.15-4.30 (m, 1H), 6.81-6.91 (m, 1H), 7.56-7.66 (m, 1H), 8.00-8.08 (m, 1H)

Reference Example 90

Synthesis of N-ethyl-N-[(1S)-1-(2-methoxypyridin-3-yl)ethyl]-N'-methylethane-1,2-diamine By using 2-methoxynicotinaldehyde (3.0 g) obtained by the method described in the literature (Journal of Organic Chemistry, 1988, vol. 53, p. 1367), and (S)-2-phenylglycinol (2.4 g) as starting materials, the title compound (67.0 mg) was obtained in the same manners as those of Reference Example 89, (1), Reference Example 44, (2), Reference Example 4, (3) and Reference Example 31, (3).
MS (ESI) m/z=238.2 [M+H]$^+$
$^1$H-NMR (200 MHz, CDCl$_3$) δ (ppm): 0.97 (t, J=7.03 Hz, 3H), 1.27 (d, J=6.59 Hz, 3H), 2.38 (s, 3H), 2.44-2.62 (m, 6H), 3.95 (s, 3H), 4.23 (q, J=6.74 Hz, 1H), 6.86 (dd, J=7.25, 5.05 Hz, 1H), 7.61 (dd, J=7.47, 1.76 Hz, 1H), 8.04 (dd, J=4.83, 1.76 Hz, 1H)

Reference Example 91

Synthesis of N-methyl-N'-[1-(1-methyl-1H-indol-4-yl-ethyl]ethane-1,2-diamine (1) 4-Acetylindole (2.0 g) was dissolved in dimethylformamide (50 ml), sodium hydride (844 mg), and methyl iodide (1.31 ml) were added to the solution, and the resulting mixture was stirred at room temperature for 1 hour. Distilled water and ethyl acetate were added to the reaction mixture, the layers were separated, and the organic layer was dried over anhydrous magnesium sulfate, and filtered. The filtrate was concentrated under reduced pressure, and the resulting crude product was purified by silica gel column chromatography (hexane:ethyl acetate=4:1) to obtain a methyl compound (2.2 g).
(2) By using the compound obtained in (1) mentioned above (2.2 g) as a starting material, an amine compound (1.0 g) was obtained in the same manner as that of Reference Example 4, (1).
(3) By using the compound obtained in (2) mentioned above (212 mg), and the compound obtained in Reference Example 44, (1) (200 mg) as starting materials, the title compound (92.5 mg) was obtained in the same manners as those of Reference Example 44, (2) and Reference Example 31, (3).
MS (ESI) m/z=232.2 [M+H]+
1H-NMR (200 MHz, CDCl3) δ (ppm): 1.49 (d, J=6.59 Hz, 3H), 2.36 (s, 3H), 2.54-2.67 (m, 4H), 3.78 (s, 3H), 4.21 (q, J=6.59 Hz, 1H), 6.57-6.64 (m, 1H), 6.99-7.23 (m, 4H)

Reference Example 92

Synthesis of N-[1-(biphenyl-2-yl)ethyl]-N'-methyl-ethane-1,2-diamine (1) Di-t-butyl dicarbonate (1.26 ml) was added to a solution of 1-(2-bromophenyl)ethanamine (1.0 g) obtained by the method described in the literature (Tetrahedron Letters, 2007, vol. 48, p. 4589) in chloroform (10 ml), and the resulting mixture was stirred at room temperature for 2 hours. The reaction mixture was concentrated under reduced pressure, and the resulting residue was purified by silica gel column chromatography (chloroform:methanol=50:1) to obtain a protected compound (1.52 g).
(2) Phenylboronic acid (113.8 mg), sodium carbonate (211.8 mg), and distilled water (5 ml) were added to a solution of the compound obtained in (1) mentioned above (200 mg) in dimethoxyethane (5 ml), the mixture was degassed, and then the system was substituted with nitrogen. Tetrakistriphenylphosphine palladium (77 mg) was added to the reaction mixture, the resulting mixture was degassed, then the system was substituted with nitrogen, and the mixture was refluxed by heating for 2 hours. Ethyl acetate was added to the reaction mixture, the layers were separated, and the organic layer was washed with saturated brine, then dried over anhydrous magnesium sulfate, and filtered. The filtrate was concentrated under reduced pressure, and the resulting residue was purified by silica gel column chromatography (hexane:ethyl acetate=10:1 to 2:1) to obtain a coupling compound (170 mg).
(3) By using the compound obtained in (2) mentioned above (170 mg) as a starting material, an amine compound (90 mg) was obtained in the same manner as that of Reference Example 31, (3).
(4) By using the compound obtained in (3) mentioned above (90 mg), and the compound obtained in Reference Example 44, (1) (75.1 mg) as starting materials, the title compound (65.7 mg) was obtained in the same manners as those of Reference Example 44, (2) and Reference Example 31, (3).
MS (ESI) m/z=255.2 [M+H]+
1H-NMR (200 MHz, CDCl3) δ (ppm): 1.27 (d, J=6.59 Hz, 3H), 2.32 (s, 3H), 2.38-2.55 (m, 4H), 3.89 (q, J=6.45 Hz, 1H), 7.13-7.60 (m, 9H)

Reference Example 93

Synthesis of N-methyl-N'-{1-[2-(pyridin-3-yl)phenyl]ethyl}ethane-1,2-diamine

By using the compound obtained in Reference Example 92, (1) (200 mg), and 3-pyridylboronic acid (114.7 mg) as starting materials, the title compound (29.7 mg) was obtained in the same manners as those of Reference Example 92, (2), Reference Example 31, (3), Reference Example 44, (2) and Reference Example 31, (3).
MS (ESI) m/z=256.2 [M+H]+
1H-NMR (200 MHz, CDCl3) δ (ppm): 1.28 (d, J=6.15 Hz, 3H), 2.33 (s, 3H), 2.38-2.60 (m, 4H), 3.82 (q, J=6.45 Hz, 1H), 7.13-7.50 (m, 5H), 7.56-7.67 (m, 2H), 8.53-8.65 (m, 2H)

Reference Example 94

Synthesis of N-methyl-N'-{1-[2-(pyridin-2-yl)phenyl]ethyl}ethane-1,2-diamine (1) By using 2-acetylphenylboronic acid (1.67 g), and 2-bromopyridine (1.0 g) as starting materials, an amine compound (410 mg) was obtained in the same manners as those of Reference Example 92, (2), and Reference Example 4, (1).
(2) By using the compound obtained in (1) mentioned above (200 mg), and the compound obtained in Reference Example 44, (1) (166.0 mg) as starting materials, the title compound (136.0 mg) was obtained in the same manners as those of Reference Example 44, (2) and Reference Example 31, (3).
MS (ESI) m/z=256.2 [M+H]+
1H-NMR (200 MHz, CDCl3) δ (ppm): 1.32 (d, J=6.59 Hz, 3H), 2.34 (s, 3H), 2.42-2.62 (m, 4H), 3.95 (q, J=6.59 Hz, 1H), 7.21-7.48 (m, 5H), 7.59 (d, J=7.47 Hz, 1H), 7.68-7.81 (m, 1H), 8.63-8.72 (m, 1H)

Reference Example 95

Synthesis of N-(3,4-dihydro-2H-chromen-4-yl-N,N'-dimethylethane-1,2-diamine (1) By using 4-chromanone (2.0 g) as a starting material, an amine compound (1.42 g) was obtained in the same manner as that of Reference Example 4, (1).
(2) By using the compound obtained in (1) mentioned above (194 mg), and the compound obtained in Reference Example 44, (1) (150 mg) as starting materials, the title compound (93.1 mg) was obtained in the same manners as those of Reference Example 44, (2), Reference Example 20, (1) and Reference Example 31, (3).
MS (ESI) m/z=221.2 [M+H]+
1H-NMR (600 MHz, CDCl3) δ (ppm): 1.91-1.97 (m, 1H), 2.03-2.11 (m, 1H), 2.19 (s, 3H), 2.43 (s, 3H), 2.59-2.69 (m, 4H), 3.95 (dd, J=9.40, 5.73 Hz, 1H), 4.10 (dt, J=10.77, 2.29 Hz, 1H), 4.30-4.36 (m, 1H), 6.74-6.78 (m, 1H), 6.86-6.91 (m, 1H), 7.08-7.12 (m, 1H), 7.48 (d, J=7.34 Hz, 1H)

Reference Example 96

Synthesis of N-methyl-N'-[2-(1-methyl-1H-indol-5-yl)propan-2-yl]ethane-1,2-diamine (1) By using 4-cyanoindole (2.2 g) as a starting material, a dimethylamine compound (180 mg) was obtained in the same manners as those of Reference Example 91, (1), and Reference Example 17, (1).
(2) By using the compound obtained in (1) mentioned above (100 mg), and the compound obtained in Reference Example 44, (1) (92.0 mg) as starting materials, the title compound (41.0 mg) was obtained in the same manners as those of Reference Example 44, (2) and Reference Example 31, (3).
MS (ESI) m/z=246.2 [M+H]+
1H-NMR (200 MHz, CDCl3) δ (ppm): 1.63 (s, 6H), 2.27 (s, 3H), 2.33-2.43 (m, 2H), 2.49-2.60 (m, 2H), 3.77 (s, 3H), 6.82-6.90 (m, 1H), 6.99-7.26 (m, 4H)

Reference Example 97

Synthesis of N-methyl-N'-[2-(1-methyl-1H-indol-4-yl)propan-2-yl]ethane-1,2-diamine (1) Sodium hydride (1.27 g) was washed with hexane, and then dimethylformamide (20 ml) was added thereto under ice cooling. 5-Cyanoindole (3.0 g) and methyl iodide (1.97 ml) were successively added to the reaction mixture, and the resulting mixture was stirred at room temperature for 30 minutes. Distilled water was added to the reaction mixture, the resulting mixture was extracted with ethyl acetate, and the organic layer was washed with distilled water and saturated brine. The organic layer was dried over anhydrous magnesium sulfate, and then filtered, and the filtrate was concentrated under reduced pressure to obtain a methyl compound (4.16 g).
(2) By using the compound obtained in (1) mentioned above (4.16 g) as a starting material, a dimethylamine compound (379.2 mg) was obtained in the same manner as that of Reference Example 17, (1).
(3) By using the compound obtained in (2) mentioned above (100 mg), and the compound obtained in Reference Example 44, (1) (87.4 mg) as starting materials, the title compound (36.3 mg) was obtained in the same manners as those of Reference Example 44, (2) and Reference Example 31, (3).
MS (ESI) m/z=246.2 [M+H]$^+$
$^1$H-NMR (200 MHz, CDCl$_3$) δ (ppm): 1.54 (s, 6H), 2.35 (s, 3H), 2.38-2.49 (m, 2H), 2.55-2.68 (m, 2H), 3.78 (s, 3H), 6.42-6.49 (m, 1H), 7.03 (d, J=3.08 Hz, 1H), 7.19-7.41 (m, 2H), 7.59-7.69 (m, 1H)

Reference Example 98

Synthesis of N-methyl-N'-[1-(quinolin-5-yl)ethyl]ethane-1,2-diamine

By using the compound obtained in Reference Example 43, (2) (70 mg), and N-(2-aminoethyl)-N-methylcarbamic acid t-butyl ester (213.7 mg) as starting materials, the title compound (9.0 mg) was obtained in the same manners as those of Reference Example 32, (3), and Reference Example 31, (3).
MS (ESI) m/z=230.2 [M+H]$^+$
$^1$H-NMR (200 MHz, CDCl$_3$) δ (ppm): 1.51 (d, J=6.59 Hz, 3H), 2.39 (s, 3H), 2.55-2.84 (m, 4H), 4.56 (q, J=6.59 Hz, 1H), 7.41 (dd, J=8.57, 4.18 Hz, 1H), 7.63-7.76 (m, 2H), 7.91-8.08 (m, 1H), 8.66 (d, J=8.35 Hz, 1H), 8.91 (dd, J=4.18, 1.54 Hz, 1H)

Reference Example 99

Synthesis of 2-(8-methoxy-3,4-dihydroisoquinolin-2(1H)-yl)-N-methylethanamine

By using 8-methoxy-1,2,3,4-tetrahydroisoquinoline (150 mg) obtained by the method described in the literature (Tetrahedron Letters, 1991, vol. 32, p. 1965), and the compound obtained in Reference Example 44, (1) (239 mg) as starting materials, the title compound (154 mg) was obtained in the same manners as those of Reference Example 44, (2) and Reference Example 31, (3).
MS (ESI) m/z=221.2 [M+H]$^+$
$^1$H-NMR (600 MHz, CDCl$_3$) δ (ppm): 2.45 (s, 3H), 2.68-2.73 (m, 4H), 2.76-2.79 (m, 2H), 2.87 (t, J=5.73 Hz, 2H), 3.56 (s, 2H), 3.80 (s, 3H), 6.65 (d, J=8.25 Hz, 1H), 6.71 (d, J=7.34 Hz, 1H), 7.10 (t, J=8.02 Hz, 1H)

Reference Example 100

Synthesis of N-(5-methoxy-1,2,3,4-tetrahydronaphthalen-1-yl)-N,N'-dimethylethane-1,2-diamine (1) By using 5-methoxy-1-tetralone (2.0 g) as a starting material, an amine compound (1.58 g) was obtained in the same manner as that of Reference Example 4, (1).
(2) By using the compound obtained in (1) mentioned above (307 mg), and the compound obtained in Reference Example 44, (1) (200 mg) as starting materials, the title compound (105 mg) was obtained in the same manners as those of Reference Example 44, (2), Reference Example 20, (1) and Reference Example 31, (3).
MS (ESI) m/z=249.3 [M+H]$^+$
$^1$H-NMR (600 MHz, CDCl$_3$) δ (ppm): 1.55-1.66 (m, 2H), 1.88-1.95 (m, 1H), 1.97-2.03 (m, 1H), 2.16 (s, 3H), 2.42 (s, 3H), 2.44-2.50 (m, 1H), 2.59-2.70 (m, 4H), 2.73-2.80 (m, 1H), 3.80 (s, 3H), 3.81-3.86 (m, 1H), 6.67 (d, J=8.25 Hz, 1H), 7.13 (t, J=8.02 Hz, 1H), 7.28 (d, J=7.79 Hz, 1H)

Reference Example 101

Synthesis of N-methyl-N'-[1-(quinolin-3-yl)ethyl]ethane-1,2-diamine (1) By using quinoline-3-carboxyaldehyde (1.0 g) as a starting material, a methyl ketone compound (0.83 g) was obtained by the same reactions as those of Reference Example 43, (1) and (2).
(2) By using the compound obtained in (1) mentioned above (200 mg), and N-(2-aminoethyl)-N-methylcarbamate t-butyl ester (610.5 mg) as starting materials, the title compound (160.0 mg) was obtained in the same manners as those of Reference Example 32, (3), and Reference Example 31, (3).
MS (ESI) m/z=230.2 [M+H]$^+$
$^1$H-NMR (200 MHz, CDCl$_3$) δ (ppm): 1.48 (d, J=6.59 Hz, 3H), 2.41 (s, 3H), 2.51-2.81 (m, 4H), 4.00 (q, J=6.30 Hz, 1H), 7.48-7.59 (m, 1H), 7.62-7.74 (m, 1H), 7.77-7.86 (m, 1H), 8.03-8.15 (m, 2H), 8.91 (d, J=2.20 Hz, 1H)

Reference Example 102

Synthesis of N-(3-methoxyphenyl)-N,N-dimethylethane-1,2-diamine

By using m-anisidine (57 mg), and the compound obtained in Reference Example 44, (1) (80.0 mg) as starting materials, the title compound (32.6 mg) was obtained in the same manners as those of Reference Example 44, (2), Reference Example 20, (1) and Reference Example 31, (3).
MS (ESI) m/z=195.2 [M+H]$^+$
$^1$H-NMR (600 MHz, CDCl$_3$) δ (ppm): 2.46 (s, 3H), 2.79 (t, J=6.65 Hz, 2H), 2.94 (s, 3H), 3.44 (t, J=6.65 Hz, 2H), 3.79 (s, 3H), 6.26-6.30 (m, 2H), 6.37-6.40 (m, 1H), 7.13 (t, J=8.25 Hz, 1H)

Reference Example 103

Synthesis of N-(2-methoxyphenyl)-N,N'-dimethylethane-1,2-diamine

By using o-anisidine (57 mg), and the compound obtained in Reference Example 44, (1) (80.0 mg) as a starting material, the title compound (50.6 mg) was obtained in the same manners as those of Reference Example 44, (2), Reference Example 20, (1) and Reference Example 31, (3).

MS (ESI) m/z=195.2 [M+H]$^+$ $^1$H-NMR (600 MHz, CDCl$_3$) δ (ppm): 2.43 (s, 3H), 2.76 (t, J=6.42 Hz, 2H), 2.79 (s, 3H), 3.16 (t, J=6.42 Hz, 2H), 3.86 (s, 3H), 6.83-6.93 (m, 2H), 6.96-7.01 (m, 2H)

Reference Example 104

Synthesis of 2-[4-(pyridin-3-yl)-1H-imidazol-1-yl]ethanamine (1) A solution of 3-(1H-imidazol-4-yl)pyridine (3.0 g) in dimethylformamide (10 ml) and N-(2-bromoethyl)phthalimide (5.26 g) were added to a suspension of sodium hydride (763 mg) in dimethylformamide (10 ml) under ice cooling, and the resulting mixture was stirred at the same temperature for 1 hour, at room temperature for 4 hours, and at 50° C. for 2 hours. After the reaction mixture was cooled, saturated aqueous sodium hydrogencarbonate, and ethyl acetate were added to the reaction mixture, the layers were separated, and the resulting organic layer was washed with distilled water and saturated brine, dried over anhydrous magnesium sulfate, and filtered. The filtrate was concentrated under reduced pressure, and the resulting residue was purified by silica gel column chromatography (chloroform:methanol=9:1) to obtain a phthalimide compound (193.7 mg).
(2) By using the compound obtained in (1) mentioned above (193.7 mg) as a starting material, the title compound (115 mg) was obtained in the same manner as that of Reference Example 3, (4).

MS (ESI) m/z=189.1 [M+H]$^+$ $^1$H-NMR (600 MHz, CDCl$_3$) δ (ppm): 3.11-3.14 (m, 2H), 4.03-4.07 (m, 2H), 7.28-7.32 (m, 1H), 7.33-7.35 (m, 1H), 7.60-7.61 (m, 1H), 8.07-8.11 (m, 1H), 8.46-8.49 (m, 1H), 8.96-8.98 (m, 1H)

Reference Example 105

Synthesis of 3-[4-(pyridin-3-yl)-1H-imidazol-1-yl]propan-1-amine

By using N-(3-bromopropyl)phthalimide (5.55 g) as a starting material, the title compound (380 mg) was obtained in the same manners as those of Reference Example 104, (1), and Reference Example 3, (4).

MS (ESI) m/z=203.2 [M+H]$^+$ $^1$H-NMR (600 MHz, CDCl$_3$) δ (ppm): 1.93-1.99 (m, 2H), 2.77 (t, J=6.65 Hz, 2H), 4.11 (t, J=6.88 Hz, 2H), 7.28-7.31 (m, 2H), 7.55-7.58 (m, 1H), 8.07-8.11 (m, 1H), 8.45-8.49 (m, 1H), 8.94-8.99 (m, 1H)

Reference Example 106

Synthesis of 4-[4-(pyridin-3-yl)-1H-imidazol-1-yl]butan-1-amine

By using N-(4-bromobutyl)phthalimide (5.84 g) as a starting material, the title compound (1.2 g) was obtained in the same manners as those of Reference Example 104, (1), and Reference Example 3, (4).

MS (ESI) m/z=217.2 [M+H]$^+$ $^1$H-NMR (600 MHz, CDCl$_3$) δ (ppm): 1.43-1.54 (m, 2H), 1.84-1.95 (m, 2H), 2.75 (t, J=7.11 Hz, 2H), 4.01 (t, J=7.11 Hz, 2H), 7.27-7.31 (m, 2H), 7.53-7.55 (m, 1H), 8.09 (dt, J=8.02, 1.95 Hz, 1H), 8.47 (dd, J=4.81, 1.60 Hz, 1H), 8.97 (d, J=2.29 Hz, 1H)

Reference Example 107

Synthesis of 3-(quinolin-4-yl)propan-1-amine (1) 4-Quinolinecarboxyaldehyde (4.46 g) was dissolved in toluene (50 ml), (carboethoxymethylene)triphenylphosphorane (9.85 g), and benzoic acid (0.345 g) were added to the solution, and the resulting mixture was stirred under reflux by heating for 5 hours. The reaction mixture was cooled, then saturated aqueous sodium hydrogencarbonate, and ethyl acetate were added to the reaction mixture, and the layers were separated. The organic layer was washed with saturated brine, dried over anhydrous magnesium sulfate, and filtered. The filtrate was concentrated under reduced pressure, and the resulting residue was purified by silica gel column chromatography (hexane:ethyl acetate=1:1) to obtain an ester compound (6.6 g).
(2) The compound obtained in (1) mentioned above (6.6 g) was dissolved in toluene (300 ml), the solution was cooled to −78° C., then a 0.99 M solution of diisobutylaluminum hydride in toluene (64.5 ml) was added to the solution, and the resulting mixture was stirred for 1 hour. 1 N Hydrochloric acid was added to the reaction mixture to make the mixture acidic, and then the resulting mixture was stirred overnight. The organic layer was separated, the aqueous layer was extracted with chloroform, and then the organic layer was dried over anhydrous magnesium sulfate, and filtered. The filtrate was concentrated under reduced pressure, and the resulting residue was purified by silica gel column chromatography (chloroform to chloroform:methanol=9:1) to obtain an alcohol compound (3.3 g).
(3) The compound obtained in (2) mentioned above (1.0 g) was dissolved in tetrahydrofuran (20 ml), triphenylphosphine (2.1 g), and phthalimide (1.19 g) were added to the solution, then a 40% solution of diethyl azodicarboxylate in toluene (3.5 ml) was added to the reaction mixture under ice cooling, and the resulting mixture was stirred for 30 minutes. The resulting mixture was further stirred at room temperature for 1 hour, then saturated aqueous sodium hydrogencarbonate, and ethyl acetate were added to the reaction mixture, and the layers were separated. The organic layer was washed with saturated brine, dried over anhydrous magnesium sulfate, and filtered. The filtrate was concentrated under reduced pressure, and the resulting residue was roughly purified by silica gel column chromatography (hexane:ethyl acetate=2:1 to 1:1) to obtain a phthalimide compound.
(4) The compound obtained in (3) mentioned above was dissolved in ethanol (30 ml), hydrazine monohydrate (5 ml) was added to the solution, and the resulting mixture was stirred at room temperature for 18 hours. The reaction mixture was filtered, then the filtrate was concentrated under reduced pressure, and the resulting residue was roughly purified by silica gel column chromatography (chloroform:methanol:28% aqueous ammonia=20:1:0.1 to 10:1:0.1). 1 N Hydrochloric acid and chloroform were added to the resulting crude product, the layers were separated, and the aqueous layer was made basic with 4 N aqueous sodium hydroxide, and then extracted with chloroform. The organic layer was dried over anhydrous magnesium sulfate, and filtered, and then the filtrate was concentrated under reduced pressure to obtain the title compound (180 mg).

MS (ESI) m/z=187.2 [M+H]$^+$ $^1$H-NMR (200 MHz, CDCl$_3$) δ (ppm): 1.89-1.95 (m, 2H), 2.84 (t, J=6.88 Hz, 2H), 3.11-3.16 (m, 2H), 7.24 (d, J=4.58 Hz, 1H), 7.53-7.58 (m, 1H), 7.67-7.72 (m, 1H), 8.02-8.13 (m, 2H), 8.80 (d, J=4.13 Hz, 1H)

Reference Example 108

Synthesis of N-[1-(4-methoxypyrimidin-5-yl)ethyl]-N'-methylethane-1,2-diamine (1) 2,4-Dichloropyrimidine (5.0 g) was dissolved in methanol (15 ml), a 28% solution of sodium methoxide in methanol (6.7 ml) was added dropwise to the solution under ice cooling, and the resulting mixture was stirred overnight at room temperature. A 28% solution of sodium methoxide in methanol (3 ml) was further added dropwise to the reaction mixture at room temperature, and the resulting mixture was stirred for 6 hours. Distilled water was added to the reaction mixture, the resulting mixture was extracted with ethyl acetate, and the organic layer was concentrated under reduced pressure. The resulting residue was purified by silica gel column chromatography (hexane:ethyl acetate=5:1 to 2:1) to obtain a methoxy compound (329 mg).

(2) A 2.77 M solution of n-butyllithium in hexane (4.0 ml), and 2,2,6,6-tetramethylpiperidine (2.1 ml) were successively added dropwise to tetrahydrofuran (30 ml) under ice cooling, and the resulting mixture was stirred at the same temperature for 45 minutes. The reaction mixture was cooled to −70° C., a solution of the compound obtained in (1) mentioned above (700 mg) in tetrahydrofuran (10 ml) was added to the reaction mixture, and the resulting mixture was stirred for 1.5 hours. Vaporized acetaldehyde was bubbled in the reaction mixture until the color of the reaction mixture changed to red, and then the resulting mixture was stirred at −70° C. for 1 hour. Concentrated hydrochloric acid (5 ml), and a mixed solvent of ethanol (5 ml) and tetrahydrofuran (10 ml) were slowly added dropwise to the reaction mixture, and the resulting mixture was gradually warmed to room temperature. Saturated aqueous sodium hydrogencarbonate was added to the reaction mixture, and the resulting mixture was concentrated under reduced pressure. Chloroform was added to the resulting aqueous layer for extraction, and the organic layer was concentrated under reduced pressure. The resulting residue was purified by silica gel column chromatography (hexane:ethyl acetate=1:1) to obtain an alcohol compound (1.45 g).

(3) The compound obtained in (2) mentioned above (600 mg) was dissolved in ethanol (1.5 ml), sodium acetate (108.7 mg) and 5% palladium-carbon (20 mg) were added to the solution, and the resulting mixture was stirred at room temperature for 1 hour under a hydrogen atmosphere. The reaction mixture was filtered, and the filtrate was concentrated under reduced pressure. The resulting residue was dissolved in chloroform, the solution was filtered, and then the filtrate was concentrated under reduced pressure to obtain a dechlorated compound (731.3 mg).

(4) By using the compound obtained in (3) mentioned above (800 mg) as a starting material, a methyl ketone compound (440.0 mg) was obtained in the same manner as that of Reference Example 43, (2).

(5) By using the compound obtained in (4) mentioned above (200 mg), and N-(2-aminoethyl)-N-methylcarbamate t-butyl ester (687 mg) as starting materials, an alkyl compound (33.7 mg) was obtained in the same manner as that of Reference Example 32, (3)

(6) Trifluoroacetic acid (0.5 ml) was added to the compound obtained in (5) mentioned above (30 mg), and the resulting mixture was stirred at room temperature for 30 minutes. The reaction mixture was concentrated under reduced pressure, 1 N aqueous sodium hydroxide and chloroform were added to the reaction mixture, the layers were separated, and the organic layer was concentrated under reduced pressure. The resulting residue was purified by silica gel column chromatography (chloroform:methanol: 28% aqueous ammonia=10:1:0.1) to obtain the title compound (12.5 mg).

MS (ESI) m/z=221.2 [M+H]$^+$ $^1$H-NMR (600 MHz, CDCl$_3$) δ (ppm): 1.36 (d, J=6.42 Hz, 3H), 2.40 (s, 3H), 2.51-2.57 (m, 1H), 2.57-2.71 (m, 3H), 3.93 (q, J=6.72 Hz, 1H), 4.00 (s, 3H), 8.44 (s, 1H), 8.66 (s, 1H)

Reference Example 109

Synthesis of (3R)—N-[1-(2-methoxyphenyl)ethyl]-N-methylpyrrolidin-3-amine (1) (R)-3-amino-1-N-(t-butoxycarbonyl)pyrrolidine (100 mg) was dissolved in chloroform (1 ml), 2'-methoxyacetophenone (96.8 mg) was added to the solution, and the resulting mixture was stirred at room temperature for 2 hours. Sodium triacetoxyborohydride (170.7 mg) was added to the reaction mixture, and the resulting mixture was stirred overnight at room temperature. Saturated aqueous sodium hydrogencarbonate and chloroform were added to the reaction mixture, and the layers were separated. The organic layer was dried over anhydrous magnesium sulfate, and filtered. The filtrate was concentrated under reduced pressure, and the resulting residue was purified by silica gel column chromatography (chloroform) to obtain an alkylated compound (124 mg).

(2) By using the compound obtained in (1) mentioned above (120 mg) as a starting material, the title compound (93.0 mg) was obtained in the same manners as those of Reference Example 20, (1) and Reference Example 31, (3).

MS (ESI) m/z=235.2 [M+H]$^+$ $^1$H-NMR (600 MHz, CDCl$_3$) δ (ppm): 1.30-1.33 (m, 3H), 1.69-1.91 (m, 7H), 2.16-2.18 (m, 3H), 3.82 (s, 3H), 4.33-4.43 (m, 1H), 6.88 (d, J=7.79 Hz, 1H), 6.92-6.96 (m, 1H), 7.19-7.24 (m, 1H), 7.31-7.35 (m, 1H)

Reference Example 110

Synthesis of N-[2-(2-fluorophenyl)propan-2-yl]-N,N'-dimethylethane-1,2-diamine (1) By using 2-fluorobenzonitrile (2.0 g) as a starting material, a dimethylamine compound (257 mg) was obtained in the same manner as that of Reference Example 17, (1).

(2) By using the compound obtained in (1) mentioned above (200 mg), and the compound obtained in Reference Example 44, (1) (215 mg) as starting materials, the title compound (44.0 mg) was obtained in the same manners as those of Reference Example 44, (2), Reference Example 20, (1) and Reference Example 31, (3).

MS (ESI) m/z=225.2 [M+H]$^+$ $^1$H-NMR (200 MHz, CDCl$_3$) δ (ppm): 1.45 (d, J=1.32 Hz, 6H), 2.17 (s, 3H), 2.34 (s, 3H), 2.43-2.63 (m, 4H), 6.92-7.11 (m, 2H), 7.13-7.26 (m, 1H), 7.36-7.48 (m, 1H)

Reference Example 111

Synthesis of N-[2-(2-bromophenyl)propan-2-yl]-N,N'-dimethylethane-1,2-diamine

By using 2-bromobenzonitrile (3.0 g) as a starting material, the title compound (56.0 mg) was obtained in the same manners as those of Reference Example 17, (1), Reference Example 44, (2), Reference Example 20, (1) and Reference Example 31, (3).

MS (ESI) m/z=285.1 [M+H]$^+$
$^1$H-NMR (200 MHz, CDCl$_3$) δ (ppm): 1.51 (s, 6H), 2.09 (s, 3H), 2.33 (s, 3H), 2.44-2.54 (m, 2H), 2.56-2.66 (m, 2H), 6.99-7.10 (m, 1H), 7.19-7.28 (m, 1H), 7.38-7.45 (m, 1H), 7.57-7.65 (m, 1H)

Reference Example 112

Synthesis of 2-{[2-(2-methoxyphenyl)propan-2-yl]oxy}ethanamine (1) A 3 M solution of methylmagnesium bromide in diethyl ether (22 ml) was added dropwise to a solution of 2'-hydroxyacetophenone (3.0 g) in tetrahydrofuran (50 ml) under ice cooling, and the resulting mixture was stirred at room temperature for 2 hours. Saturated aqueous ammonium chloride was added to the reaction mixture, the resulting mixture was extracted with ethyl acetate, and the organic layer was concentrated under reduced pressure. The resulting residue was purified by silica gel column chromatography (hexane ethyl acetate=3:1) to obtain an alcohol compound (3.86 g).

(2) A mixture of the compound obtained in (1) mentioned above (500 mg), ethylene glycol (3 ml), and p-toluenesulfonic acid (10 mg) was stirred at room temperature for 2 days. Sodium acetate (296.4 mg) was added to the reaction mixture, the resulting mixture was stirred at room temperature for 2 hours, then distilled water was added to the reaction mixture, the resulting mixture was extracted with ethyl acetate, and the organic layer was concentrated under reduced pressure. The resulting residue was purified by silica gel column chromatography (hexane:ethyl acetate=1:1) to obtain an ether compound (430.7 mg).

(3) Methyl iodide (0.13 ml) and cesium carbonate (335.4 mg) were added to a solution of the compound obtained in (2) mentioned above (200 mg) in acetone (5 ml), and the resulting mixture was stirred overnight at room temperature. Distilled water was added to the reaction mixture, the resulting mixture was extracted with ethyl acetate, and the organic layer was concentrated under reduced pressure to obtain a methyl compound (219.3 mg).

(4) Phthalimide (225.7 mg), and triphenylphosphine (402.3 mg) were added to a solution of the compound obtained in (3) mentioned above (215 mg) in tetrahydrofuran (2 ml), a 2.2 M solution of diethyl azodicarboxylate in toluene (0.7 ml) was added to the mixture under ice cooling, and the resulting mixture was stirred overnight at room temperature. Distilled water was added to the reaction mixture, the resulting mixture was extracted with ethyl acetate, and the organic layer was washed with saturated brine and concentrated under reduced pressure. The resulting residue was purified by silica gel column chromatography (hexane:ethyl acetate=5:1 to 3:1) to obtain a phthalimide compound (380 mg).

(5) By using the compound obtained in (4) mentioned above (230 mg) as a starting material, the title compound (178.5 mg) was obtained in the same manner as that of Reference Example 3, (4).

MS (ESI) m/z=210.2 [M+H]$^+$
$^1$H-NMR (200 MHz, CDCl$_3$) δ (ppm): 2.26 (s, 6H), 2.55 (t, J=6.37 Hz, 2H), 3.41 (t, J=6.37 Hz, 2H), 3.82 (s, 3H), 6.84-6.99 (m, 2H), 7.17-7.25 (m, 1H), 7.44 (dd, J=7.47, 1.76 Hz, 1H)

Reference Example 113

Synthesis of N,N'-dimethyl-N-[2-(2-methylphenyl)propan-2-yl]ethane-1,2-diamine (1) By using 2-methylbenzonitrile (2.0 g) as a starting material, a dimethylamine compound (236.2 mg) was obtained in the same manner as that of Reference Example 17, (1).

(2) By using the compound obtained in (1) mentioned above (230 mg), and the compound obtained in Reference Example 44, (1) (253.6 mg) as starting materials, the title compound (100.1 mg) was obtained in the same manners as those of Reference Example 44, (2), Reference Example 20, (1), and Reference Example 108, (6).

MS (ESI) m/z=221.3 [M+H]$^+$
$^1$H-NMR (200 MHz, CDCl$_3$) δ (ppm): 1.42 (s, 6H), 2.10 (s, 3H), 2.34 (s, 3H), 2.43-2.65 (m, 4H), 2.67 (s, 3H), 7.04-7.17 (m, 3H), 7.26-7.35 (m, 1H)

Reference Example 114

Synthesis of N-[2-(2-chlorophenynl)propan-2-yl]-N,N'-dimethylethane-1,2-diamine (1) By using 2-chlorobenzonitrile (2.0 g) as a starting material, a dimethylamine compound (118.1 mg) was obtained in the same manner as that of Reference Example 17, (1).

(2) By using the compound obtained in (1) mentioned above (115 mg), and the compound obtained in Reference Example 44, (1) (115.1 mg) as starting materials, the title compound (95.2 mg) was obtained in the same manners as those of Reference Example 44, (2), Reference Example 20, (1), and Reference Example 108, (6).

MS (ESI) m/z=241.2 [M+H]$^+$
$^1$H-NMR (200 MHz, CDCl$_3$) δ (ppm): 1.50 (s, 6H), 2.10 (s, 3H), 2.32 (s, 3H), 2.43-2.65 (m, 4H), 7.07-7.24 (m, 2H), 7.31-7.47 (m, 2H)

Reference Example 115

Synthesis of N-(2-methoxyphenyl)-N,N'-dimethylpropane-1,3-diamine (1) Di-t-butyl dicarbonate (5.1 ml) was added to a solution of 3-(methylamino)-1-propanol (1.8 g) in chloroform (30 ml), and the resulting mixture was stirred overnight at room temperature. The reaction mixture was concentrated under reduced pressure, and the resulting residue was purified by silica gel column chromatography (hexane:acetone:triethylamine=50:10:0.2 to 20:10:0.2) to obtain a protected compound (2.6 g).

(2) By using the compound obtained in (1) mentioned above (300 mg) as a starting material, an aldehyde compound (358.0 mg) was obtained in the same manner as that of Reference Example 44, (1).

(3) By using the compound obtained in (2) mentioned above (150 mg), and o-anisidine (100.3 mg) as starting materials, the title compound (60.0 mg) was obtained in the same manners as those of Reference Example 44, (2), Reference Example 20, (1) and Reference Example 31, (3).
MS (ESI) m/z=209.3 [M+H]$^+$
$^1$H-NMR (200 MHz, CDCl$_3$) δ (ppm): 1.68-1.86 (m, 2H), 2.43 (s, 3H), 2.67 (t, J=6.81 Hz, 2H), 2.77 (s, 3H), 3.02-3.14 (m, 2H), 3.87 (s, 3H), 6.80-7.05 (m, 4H)

Reference Example 116

Synthesis of N-methyl-N'-[1-(1-methyl-1H-indol-7-yl)ethyl]ethane-1,2-diamine (1) By using indole-7-carboxylic acid (1.0 g) as a starting material, a methyl ketone compound (582 mg) was obtained in the same manner as that of Reference Example 33, (1).
(2) By using the compound obtained in (1) mentioned above (500 mg) as a starting material, an amine compound (110 mg) was obtained in the same manner as that of Reference Example 34, (1).
(3) By using the compound obtained in (2) mentioned above (106 mg), and the compound obtained in Reference Example 44, (1) (111 mg) as starting materials, the title compound (71.0 mg) was obtained in the same manners as those of Reference Example 44, (2) and Reference Example 31, (3).
MS (ESI) m/z=232.2 [M+H]$^+$
$^1$H-NMR (600 MHz, CDCl$_3$) δ (ppm): 1.49 (d, J=6.42 Hz, 3H), 2.38 (s, 3H), 2.60-2.74 (m, 4H), 4.05 (s, 3H), 4.64-4.73 (m, 1H), 6.45 (d, J=2.75 Hz, 1H), 6.94 (d, J=3.21 Hz, 1H), 7.07 (t, J=7.57 Hz, 1H), 7.29 (d, J=7.34 Hz, 1H), 7.48 (d, J=7.79 Hz, 1H)

Reference Example 117

Synthesis of (2R)-2-amino-3-{[2-(2-methoxyphenyl)propan-2-yl]amino}propan-1-ol (1) By using N-(t-butoxycarbonyl)-O-benzyl-(L)-serine (1.34 g), and the compound obtained in Reference Example 17, (1) (500 mg) as starting materials, an amide compound (1.44 g) was obtained in the same manner as that of Reference Example 10, (1).
(2) By using the compound obtained in (1) mentioned above (500 mg) as a starting material, an amine compound (187 mg) was obtained in the same manners as those of Reference Example 74, (2), and Reference Example 59, (2).
(3) By using the compound obtained in (2) mentioned above (48.2 mg) as a starting material, the title compound (23.2 mg) was obtained in the same manner as that of Reference Example 108, (6).
MS (ESI) m/z=239.2 [M+H]$^+$
$^1$H-NMR (600 MHz, CDCl$_3$) δ (ppm): 1.62 (s, 3H), 1.63 (s, 3H), 2.39-2.50 (m, 2H), 3.00-3.08 (m, 1H), 3.50 (dd, J=11.00, 6.42 Hz, 1H), 3.59 (dd, J=11.00, 4.59 Hz, 1H), 3.89 (s, 3H), 6.92 (d, J=8.25 Hz, 1H), 6.96 (t, J=7.57 Hz, 1H), 7.20-7.24 (m, 1H), 7.26-7.32 (m, 1H)

Reference Example 118

Synthesis of (2R)-2-amino-3-{[2-(2-methoxyphenyl)propan-2-yl](methyl)amino}propan-1-ol By using the compound obtained in Reference Example 117, (2) (67.4 mg) as a starting material, the title compound (34.5 mg) was obtained in the same manners as those of Reference Example 20, (1), and Reference Example 108, (6).
MS (ESI) m/z=253.2 [M+H]$^+$
$^1$H-NMR (600 MHz, CDCl$_3$) δ (ppm): 1.50 (s, 3H), 1.51 (s, 3H), 2.16 (s, 3H), 2.48-2.57 (m, 1H), 2.73-2.84 (m, 1H), 3.21-3.32 (m, 1H), 3.58-3.66 (m, 1H), 3.68-3.73 (m, 1H), 3.85 (s, 3H), 6.85-6.97 (m, 2H), 7.20-7.30 (m, 2H)

Reference Example 119

Synthesis of N-(2-{2-[(dimethylamino)methyl]phenyl}propan-2-yl)-N,N'-dimethylethane-1,2-diamine (1) 50% Aqueous dimethylamine (1.4 ml) was added to a solution of 2-cyanobenzyl bromide (1.0 g) in dioxane (30 ml) at room temperature, and the resulting mixture was stirred for 1 hour. The reaction mixture was concentrated under reduced pressure, saturated aqueous sodium hydrogencarbonate was added to the resulting residue, the resulting mixture was extracted with ethyl acetate, and the resulting organic layer was dried over anhydrous magnesium sulfate, and filtered. The filtrate was concentrated under reduced pressure to obtain a crude product of alkylated compound (750 mg).
(2) By using the compound obtained in (1) mentioned above (500 mg) as a starting material, a dimethylamine compound (37.0 mg) was obtained in the same manner as that of Reference Example 87, (2).
(3) By using the compound obtained in (2) mentioned above (35.0 mg), and the compound obtained in Reference Example 44, (1) (31.5 mg) as starting materials, the title compound (14.0 mg) was obtained in the same manners as those of Reference Example 44, (2), Reference Example 20, (1), and Reference Example 108, (6).
MS (ESI) m/z=264.3 [M+H]$^+$
$^1$H-NMR (200 MHz, CDCl$_3$) δ (ppm): 1.43 (s, 6H), 2.01 (s, 3H), 2.27 (s, 6H), 2.44 (s, 3H), 2.53-2.73 (m, 4H), 3.98 (s, 2H), 7.09-7.35 (m, 3H), 7.69-7.78 (m, 1H)

Reference Example 120

Synthesis of (3S)—N-[1-(2-methoxyphenyl)ethyl]-N-methylpyrrolidin-3-amine

By using (S)-3-amino-1-N-t-butoxycarbonylpyrrolidine (500 mg) as a starting material, the title compound (83.0 mg) was obtained in the same manners as those of Reference Example 109, (1), Reference Example 20, (1), and Reference Example 31, (3).
MS (ESI) m/z=235.2 [M+H]$^+$
$^1$H-NMR (600 MHz, CDCl$_3$) δ (ppm): 1.30-1.33 (m, 3H), 1.69-1.91 (m, 7H), 2.16-2.18 (m, 3H), 3.82 (s, 3H), 4.33-4.43 (m, 1H), 6.88 (d, J=7.79 Hz, 1H), 6.92-6.96 (m, 1H), 7.19-7.24 (m, 1H), 7.31-7.35 (m, 1H)

Reference Example 121

Synthesis of N-methyl-N'-{2-[2-(methylsulfanyl)phenyl]propan-2-yl}ethane-1,2-diamine (1) By using 2-(methylthio)benzonitrile (1.0 g) as a starting material, a dimethylamine compound (1.3 g) was obtained in the same manner as that of Reference Example 87, (2).
(2) By using the compound obtained in (1) mentioned above (200 mg), and the compound obtained in Reference Example 44, (1) (191.0 mg) as starting materials, the title compound (117.0 mg) was obtained in the same manners as those of Reference Example 44, (2), and Reference Example 108, (6).

MS (ESI) m/z=239.2 [M+H]$^+$ $^1$H-NMR (200 MHz, CDCl$_3$) δ (ppm): 1.59 (s, 6H), 2.32-2.40 (m, 5H), 2.49 (s, 3H), 2.58-2.66 (m, 2H), 7.04-7.34 (m, 4H)

Reference Example 122

Synthesis of (2S)—N-[2-(2-methoxypyridin-3-yl) propan-2-yl]-N-methylpropane-1,2-diamine By using the compound obtained in Reference Example 38, (2) (604 mg), and N-t-butoxycarbonyl-(L)-alanine (1.37 g) as starting materials, the title compound (23.2 mg) was obtained in the same manners as those of Reference Example 10, (1), Reference Example 59, (2), Reference Example 20, (1), and Reference Example 108, (6).

MS (ESI) m/z=238.2 [M+H]$^+$ $^1$H-NMR (600 MHz, CDCl$_3$) δ (ppm): 0.95 (d, J=5.96 Hz, 3H), 1.41 (s, 6H), 2.10 (s, 3H), 2.11-2.26 (m, 2H), 2.84-3.03 (m, 1H), 3.92 (s, 3H), 6.82 (dd, J=7.57, 4.81 Hz, 1H), 7.64 (dd, J=7.79, 1.83 Hz, 1H), 8.03 (dd, J=5.04, 1.83 Hz, 1H)

Reference Example 123

Synthesis of 2-methoxy-N-methyl-N-[2-(methylamino)ethyl]benzenesulfonamide (1) Triethylamine (0.11 ml) was added to a solution of 2-methoxybenzenesulfonyl chloride (150 mg), and N-(2-aminoethyl)-N-methylcarbamic acid t-butyl ester (126.4 mg) in chloroform (5 ml), and the resulting mixture was stirred at room temperature for 3 days. Distilled water was added to the reaction mixture, the resulting mixture was extracted with chloroform, the organic layer was concentrated under reduced pressure, and the resulting residue was purified by silica gel column chromatography (hexane:ethyl acetate=1:1) to obtain a sulfonamide compound (188.5 mg).

(2) Sodium hydride (14 mg) was added to a solution of the compound obtained in (1) mentioned above (80 mg) in dimethylformamide (1 ml), the resulting mixture was stirred, then methyl iodide (22 µl) was added to the mixture, and the resulting mixture was stirred at room temperature for 1 hour. Distilled water and saturated brine were added to the reaction mixture, the resulting mixture was extracted with ethyl acetate, and the organic layer was concentrated under reduced pressure. The resulting residue was purified by silica gel column chromatography (hexane:ethyl acetate=2:1 to 1:1) to obtain a methylated compound (82.3 mg).

(3) By using the compound obtained in (2) mentioned above (80 mg) as a starting material, the title compound (54.5 mg) was obtained in the same manner as that of Reference Example 108, (6).

MS (ESI) m/z=259.1 [M+H]$^+$ $^1$H-NMR (200 MHz, CDCl$_3$) δ (ppm): 2.44 (s, 3H), 2.71-2.81 (m, 2H), 2.86 (s, 3H), 3.23-3.35 (m, 2H), 3.93 (s, 3H), 6.96-7.11 (m, 2H), 7.45-7.58 (m, 1H), 7.94 (dd, J=7.69, 1.54 Hz, 1H)

Reference Example 124

Synthesis of 2-(8-methoxy-1-methyl-3,4-dihydroisoquinolin-2(1H)-yl)-N-methylethanamine (1) Chloroform, and 10% aqueous sodium hydroxide were added to 8-methoxy-3,4-dihydroisoquinoline hydrochloride (150 mg) obtained by the method described in the literature (Tetrahedron Letters, 1991, vol. 32, p. 1965), and the layers were separated. The organic layer was dried over anhydrous magnesium sulfate, and filtered. The filtrate was concentrated under reduced pressure, the resulting residue was dissolved in tetrahydrofuran (3 ml), a 1.09 M solution of methyllithium in diethyl ether (1.6 ml) was added dropwise to the solution under ice cooling, and the resulting mixture was stirred at the same temperature for 1 hour. Saturated aqueous sodium hydrogencarbonate was added to the reaction mixture, the resulting mixture was extracted with chloroform, and the organic layer was dried over anhydrous magnesium sulfate, and filtered. The filtrate was concentrated under reduced pressure, and the resulting residue was purified by silica gel column chromatography (chloroform:methanol:28% aqueous ammonia=40:1:0.1 to 20:1:0.1) to obtain an alkyl compound (49.8 mg).

(2) By using the compound obtained in (1) mentioned above (46.8 mg), and the compound obtained in Reference Example 44, (1) (137 mg) as starting materials, the title compound (35.4 mg) was obtained in the same manners as those of Reference Example 44, (2), and Reference Example 108, (6).

MS (ESI) m/z=235.2 [M+H]$^+$ $^1$H-NMR (600 MHz, CDCl$_3$) δ (ppm): 1.24 (d, J=6.42 Hz, 3H), 2.43 (s, 3H), 2.55-2.73 (m, 4H), 2.73-2.79 (m, 2H), 2.90-2.99 (m, 1H), 3.03-3.11 (m, 1H), 3.80 (s, 3H), 4.06 (q, J=6.57 Hz, 1H), 6.66 (d, J=8.25 Hz, 1H), 6.69 (d, J=7.79 Hz, 1H), 7.09 (t, J=7.79 Hz, 1H)

Reference Example 125

Synthesis of N-methyl-N-[2-(2-methoxyphenyl)propan-2-yl]ethane-1,2-diamine

By using the compound obtained in Reference Example 17, (2) (500 mg) as a starting material, the title compound (316 mg) was obtained in the same manners as those of Reference Example 20, (1), and Reference Example 3, (4).

MS (ESI) m/z=223.1 [M+H]$^+$ $^1$H-NMR (600 MHz, CDCl$_3$) δ (ppm): 1.45 (s, 6H), 2.14 (s, 3H), 2.20-2.35 (m, 2H), 2.37-2.47 (m, 2H), 2.61-2.77 (m, 2H), 3.81 (s, 3H), 6.84-6.94 (m, 2H), 7.15-7.27 (m, 1H), 7.38-7.45 (m, 1H)

Reference Example 126

Synthesis of N-(azetidin-3-ylmethyl)-2-(2-methoxyphenyl)propan-2-amine (1) A solution of the compound obtained in Reference Example 17, (1) (500 mg), 1-(t-butoxycarbonyl)azetidine-3-carboxylic acid (730.7 mg), N-ethyl-N'-(3-dimethylaminopropyl)-carbodiimide hydrochloride (870.2 mg), 1-hydroxybenzotriazole (695.1 mg), and 4-dimethylaminopyridine (554.5 mg) in chloroform (15 ml) was stirred at room temperature for 4 hours. Distilled water was added to the reaction mixture, the resulting mixture was extracted with chloroform, the organic layer was concentrated under reduced pressure, and the resulting residue was purified by silica gel column chromatography (chloroform:methanol=50:1 to 30:1) to obtain an amide compound (1.03 g).

(2) A 0.99 M solution of borane/tetrahydrofuran complex in tetrahydrofuran (5.8 ml) was added dropwise to a solution of the compound obtained in (1) mentioned above (200 mg) in tetrahydrofuran (8 ml) under ice cooling, and the resulting mixture was stirred overnight at room temperature. Methanol was added to the reaction mixture, the resulting mixture was concentrated under reduced pressure, then the resulting residue was dissolved in methanol (8 ml), ethylenediamine (0.38 ml) was added to the solution, and the resulting mixture was stirred at 65° C. for 8 hours. The reaction mixture was concentrated under reduced pressure, then distilled water was added to the resulting residue, the resulting mixture was extracted with chloroform, and the organic layer was concentrated under reduced pressure. The resulting residue was purified by silica gel column chromatography (chloroform:methanol: 28% aqueous ammonia=10:1:0.1) to obtain a reduced compound (189.8 mg).

(3) The compound obtained in (2) mentioned above (100 mg) was dissolved in chloroform (5 ml), trifluoroacetic acid (0.22 ml) was added to the solution, and the resulting mixture was stirred overnight at room temperature. Trifluoroacetic acid (0.5 ml) was further added to the reaction mixture, the resulting mixture was stirred at room temperature for 3 hours, then toluene was added to the reaction mixture, and the resulting mixture was concentrated under reduced pressure. Saturated aqueous sodium hydrogencarbonate was added to the resulting residue, the resulting mixture was extracted with chloroform, and the organic layer was concentrated under reduced pressure. The resulting residue was purified by silica gel column chromatography (NH silica gel, chloroform:methanol=10:1) to obtain the title compound (67.0 mg).
MS (ESI) m/z=235.2 [M+H]$^+$
$^1$H-NMR (200 MHz, CDCl$_3$) δ (ppm): 1.49 (s, 6H), 2.40 (d, J=7.47 Hz, 2H), 2.65-2.88 (m, 1H), 3.21 (dd, J=7.69, 6.81 Hz, 2H), 3.56-3.68 (m, 2H), 3.86 (s, 3H), 6.84-6.99 (m, 2H), 7.17-7.30 (m, 2H)

Reference Example 127

Synthesis of N-(azetidin-3-ylmethyl)-2-(2-methoxyphenyl)-N-methylpropan-2-amine

By using the compound obtained in Reference Example 126, (2) (1.2 g) as a starting material, the title compound (0.70 g) was obtained in the same manners as those of Reference Example 20, (1), and Reference Example 126, (3).
MS (ESI) m/z=249.2 [M+H]$^+$
$^1$H-NMR (200 MHz, CDCl$_3$) δ (ppm): 1.42 (s, 6H), 2.13 (s, 3H), 2.53 (d, J=7.03 Hz, 2H), 2.79-3.02 (m, 1H), 3.19-3.32 (m, 2H), 3.52-3.65 (m, 2H), 3.79 (s, 3H), 6.82-6.96 (m, 2H), 7.14-7.25 (m, 1H), 7.55 (dd, J=8.35, 1.76 Hz, 1H)

Reference Example 128

Synthesis of N-[2-(2-methoxyphenyl)propan-2-yl]pyrrolidin-3-amine (1) Acetic acid (0.19 ml) and sodium triacetoxyborohydride (686.6 mg) were added to a solution of 1-N-(t-butoxycarbonyl)-3-pyrrolidinone (500 mg) and the compound obtained in Reference Example 17, (1) (490.6 mg) in chloroform (1 ml), and the resulting mixture was stirred at room temperature for 3 days. Saturated aqueous sodium hydrogencarbonate and 5 N aqueous sodium hydroxide were added to the reaction mixture, the resulting mixture was extracted with chloroform, the organic layer was concentrated under reduced pressure, and the resulting residue was purified by silica gel column chromatography (chloroform:methanol=30:1 to 10:1) to obtain an amine compound (460 mg).

(2) By using the compound obtained in (1) mentioned above (460 mg) as a starting material, the title compound (82.6 mg) was obtained in the same manner as that of Reference Example 126, (3).
MS (ESI) m/z=235.2 [M+H]$^+$
$^1$H-NMR (200 MHz, CDCl$_3$) δ (ppm): 1.22-1.47 (m, 1H), 1.47-1.53 (m, 6H), 1.65-1.91 (m, 1H), 2.39-2.59 (m, 1H), 2.64-3.14 (m, 4H), 3.87 (s, 3H), 6.82-6.98 (m, 2H), 7.16-7.30 (m, 2H)

Reference Example 129

Synthesis of (3S)-1-[(1S)-1-(2-methoxyphenyl)ethyl]pyrrolidin-3-amine (1) A solution of di-t-butyl dicarbonate (3.3 g) in chloroform (10 ml) was added dropwise to a solution of (L)-aspartic acid dimethyl ester hydrochloride (3.0 g) and triethylamine (4.65 ml) in chloroform (30 ml) under ice cooling. The resulting mixture was stirred at room temperature for 3 hours, then di-t-butyl dicarbonate (1.65 g) and triethylamine (2.3 ml) were added to the mixture, and the resulting mixture was stirred at room temperature for 2 hours. Saturated aqueous sodium hydrogencarbonate was added to the reaction mixture, the resulting mixture was extracted with chloroform, and the organic layer was dried over anhydrous sodium sulfate, and filtered. The filtrate was concentrated under reduced pressure to obtain a protected compound (5.35 g).

(2) Sodium borohydride (0.29 g) was added to a solution of the compound obtained in (1) mentioned above (1.0 g) in tetrahydrofuran (10 ml), and methanol (1.2 ml) was added dropwise to the mixture at 50° C. with stirring. The resulting mixture was stirred at the same temperature for 5 hours, then saturated aqueous sodium hydrogencarbonate was added to the reaction mixture, the resulting mixture was extracted with ethyl acetate, and the organic layer was concentrated under reduced pressure. The resulting residue was purified by silica gel column chromatography (chloroform:methanol=10:1) to obtain a diol compound (596.7 mg).

(3) Triethylamine (1.62 ml), and methanesulfonyl chloride (0.67 ml) were successively added dropwise to a solution of the compound obtained in (2) mentioned above (595 mg) in chloroform (10 ml) under ice cooling, and the resulting mixture was stirred at 0° C. for 1 hour and at room temperature for 2 hours. Saturated aqueous sodium hydrogencarbonate was added to the reaction mixture, the resulting mixture was extracted with chloroform, and the organic layer was dried over anhydrous sodium sulfate, and filtered. The filtrate was concentrated under reduced pressure to obtain a dimesyl compound (952.3 mg).

(4) A solution of the compound obtained in (3) mentioned above (79.7 mg) and (1S)-1-(2-methoxyphenyl)-ethylamine (100 mg) obtained by the method described in the publication (Japanese Patent Unexamined Publication No. 54/154724)) in chloroform (1 ml) was stirred at 65° C. for 3 days. The reaction mixture was concentrated under reduced pressure, and then the resulting residue was purified by silica gel column chromatography (chloroform:methanol:28% aqueous ammonia=10:1:0.1 to 5:1:0.1) and preparative thin layer chromatography (chloroform:methanol:28% aqueous ammonia=10:1:0.1) to obtain the title compound (14.6 mg).

MS (ESI) m/z=221.2 [M+H]+

¹H-NMR (200 MHz, CDCl₃) δ (ppm): 1.31 (d, J=6.59 Hz, 3H), 1.36-1.56 (m, 1H), 1.99-2.51 (m, 3H), 2.62-2.88 (m, 2H), 3.36-3.55 (m, 1H), 3.73-3.87 (m, 1H), 3.82 (s, 3H), 6.79-7.00 (m, 2H), 7.10-7.24 (m, 1H), 7.49 (dd, J=7.47, 1.76 Hz, 1H)

Reference Example 130

Synthesis of N-(azetidin-3-ylmethyl)-N-ethyl-2-(2-methoxyphenyl)propan-2-amine

By using the compound obtained in Reference Example 126, (2) (150 mg) as a starting material, the title compound (57.7 mg) was obtained in the same manners as those of Reference Example 4, (3), and Reference Example 126, (3).

MS (ESI) m/z=263.2 [M+H]+

¹H-NMR (200 MHz, CDCl₃) δ (ppm): 0.94 (t, J=7.25 Hz, 3H), 1.45 (s, 6H), 2.50 (q, J=7.33 Hz, 2H), 2.59-2.72 (m, 2H), 2.74-3.01 (m, 1H), 3.26 (t, J=7.25 Hz, 2H), 3.43-3.66 (m, 2H), 3.79 (s, 3H), 6.74-6.97 (m, 2H), 7.10-7.24 (m, 1H), 7.39-7.54 (m, 1H)

Reference Example 131

Synthesis of N-[2(2-methoxyphenyl)propan-2-yl]azetidine-3-carboxamide

By using the compound obtained in Reference Example 126, (1) (100 mg) as a starting material, the title compound (53.4 mg) was obtained in the same manner as that of Reference Example 126, (3).

¹H-NMR (200 MHz, CDCl₃) δ (ppm): 1.77 (s, 6H), 3.20-3.39 (m, 1H), 3.65 (t, J=7.69 Hz, 2H), 3.74-3.89 (m, 2H), 3.82 (s, 3H), 6.25 (br s, 1H), 6.83-7.01 (m, 2H), 7.17-7.30 (m, 1H), 7.37 (dd, J=7.91, 1.76 Hz, 1H)

Reference Example 132

Synthesis of 2-(2-methoxyphenyl)-N-(pyrrolidin-3-ylmethyl)propan-2-amine

By using 1-(t-butoxycarbonyl)pyrrolidine-3-carboxylic acid (0.72 g), and the compound obtained in Reference Example 17, (1) (0.5 g) as starting materials, the title compound (171.4 mg) was obtained in the same manner as that of Reference Example 126.

MS (ESI) m/z=249.2 [M+H]+

¹H-NMR (600 MHz, CDCl₃) δ (ppm): 1.13-1.22 (m, 1H), 1.44-1.51 (m, 6H), 1.81-1.89 (m, 1H), 2.05-2.20 (m, 3H), 2.37 (dd, J=10.77, 6.65 Hz, 1H), 2.81 (dd, J=7.79, 6.42 Hz, 2H), 3.01 (dd, J=11.00, 7.34 Hz, 1H), 3.85 (s, 3H), 6.84-6.94 (m, 2H), 7.18-7.24 (m, 2H)

Reference Example 133

Synthesis of (3R)-1-[(1S)-1-(2-methoxyphenyl)ethyl]pyrrolidin-3-amine (1) Thionyl chloride (1.64 ml) was added dropwise to a solution of (D)-aspartic acid (2.0 g) in methanol (20 ml) at room temperature, and the resulting mixture was stirred at the same temperature for 3 days. The reaction mixture was concentrated under reduced pressure to obtain a crude product containing a dimethyl ester compound.

(2) By using the compound obtained in (1) mentioned above as a starting material, a protected compound (4.77 g) was obtained in the same manner as that of Reference Example 129, (1).

(3) By using the compound obtained in (2) mentioned above (1.0 g) as a starting material, a dimesyl compound (1.13 g) was obtained in the same manners as those of Reference Example 129, (2) and (3).

(4) By using the compound obtained in (3) mentioned above (79.7 mg), and (1S)-1-(2-methoxyphenyl)ethylamine (100 mg) obtained by the method described in the publication (Japanese Patent Unexamined Publication No. 54/154724) as starting materials, a cyclized compound (27.6 mg) was obtained in the same manner as that of Reference Example 129, (4).

(5) By using the compound obtained in (4) mentioned above (27 mg) as a starting material, the title compound (18.1 mg) was obtained in the same manner as that of Reference Example 126, (3).

MS (ESI) m/z=221.1 [M+H]+

¹H-NMR (600 MHz, CDCl₃) δ (ppm): 1.30 (d, J=6.42 Hz, 3H), 1.39-1.49 (m, 1H), 2.10-2.20 (m, 1H), 2.33 (dd, J=9.17, 4.58 Hz, 1H), 2.46-2.56 (m, 1H), 2.59-2.66 (m, 1H), 2.66-2.73 (m, 1H), 3.41-3.50 (m, 1H), 3.81 (s, 3H), 3.75-3.86 (m, 1H), 6.85 (d, J=8.25 Hz, 1H), 6.94 (t, J=7.34 Hz, 1H), 7.15-7.21 (m, 1H), 7.45-7.52 (m, 1H)

Reference Example 134

Synthesis of 3-({[2-(2-methoxyphenyl)propan-2-yl](methyl)amino}methyl)azetidin-3-ol (1) Methyltriphenylphosphonium bromide (7.51 g) was dissolved in diethyl ether (30 ml), t-butoxypotassium (2.36 g) was added to the solution under ice cooling, and the resulting mixture was stirred at 35° C. for 1 hour. A solution of t-butyl 3-oxoazetidine-1-carboxylate (1.2 g) in diethyl ether (10 ml) was added to the reaction mixture at room temperature, and the resulting mixture was stirred at 35° C. for 6 hours. The reaction mixture was filtered thorough Celite, and then the filtrate was washed with distilled water and saturated brine, dried over anhydrous magnesium sulfate, and then filtered. The filtrate was concentrated under reduced pressure, and the resulting residue was purified by silica gel column chromatography (hexane:ethyl acetate=5:1) to obtain a methylene compound (1.35 g).

(2) The compound obtained in (1) mentioned above (1.35 g) was dissolved in chloroform (50 ml), m-chloroperbenzoic acid (3.18 g) was added to the solution under ice cooling, and the resulting mixture was stirred overnight at room temperature. Saturated aqueous sodium hydrogencarbonate, and saturated aqueous sodium thiosulfate were added to the reaction mixture, and the resulting mixture was extracted with chloroform. The organic layer was dried over anhydrous magnesium sulfate, and filtered. The filtrate was concentrated under reduced pressure, and the resulting residue was purified by silica gel column chromatography (hexane:ethyl acetate=10:1 to 5:1) to obtain an epoxy compound (294 mg).

(3) The compound obtained in (2) mentioned above (31 mg), and the compound obtained in Reference Example 17, (1) (56.6 mg) were dissolved in tetrahydrofuran (1 ml), and the resulting solution was stirred under reflux by heating for 4 hours. The reaction mixture was concentrated under reduced pressure, and the resulting residue was purified by silica gel column chromatography (chloroform:methanol: 28% aqueous ammonia=10:1:0.1) to obtain an adduct compound (69.9 mg).

(4) By using the compound obtained in (3) mentioned above (66.7 mg) as a starting material, the title compound (34.4 mg) was obtained in the same manners as those of Reference Example 20, (1), and Reference Example 108, (6).

MS (ESI) m/z=265.1 [M+H]$^+$ $^1$H-NMR (600 MHz, CDCl$_3$) δ (ppm): 1.46 (s, 6H), 2.04 (s, 3H), 2.81 (s, 2H), 3.41 (d, J=9.17 Hz, 2H), 3.76 (d, J=8.71 Hz, 2H), 3.83 (s, 3H), 6.86-6.93 (m, 2H), 7.19-7.24 (m, 2H)

Reference Example 135

Synthesis of N-(1H-imidazol-4-ylmethyl)-2-(2-methoxyphenyl)propan-2-amine

By using imidazole-4-carboxaldehyde (200 mg), and the compound obtained in Reference Example 17, (1) (343.9 mg) as starting materials, the title compound (134.0 mg) was obtained in the same manner as that of Reference Example 44, (2).

MS (ESI) m/z=246.1 [M+H]$^+$ $^1$H-NMR (200 MHz, CDCl$_3$) δ (ppm): 1.54 (s, 6H), 3.38 (s, 2H), 3.85 (s, 3H), 6.74 (s, 1H), 6.89-7.02 (m, 2H), 7.20-7.33 (m, 2H), 7.50 (s, 1H)

Reference Example 136

Synthesis of (3R)-1-[2-(2-methoxyphenyl)propan-2-yl]pyrrolidin-3-amine

By using the compound obtained in Reference Example 133, (3) (145.8 mg), and the compound obtained in Reference Example 17, (1) (100 mg) as starting materials, the title compound (30.1 mg) was obtained in the same manners as those of Reference Example 129, (4), and Reference Example 126, (3).

MS (ESI) m/z=235.2 [M+H]$^+$ $^1$H-NMR (200 MHz, CDCl$_3$) δ (ppm): 1.35-1.63 (m, 1H), 1.47 (s, 6H), 1.93-2.23 (m, 1H), 2.29-2.46 (m, 1H), 2.50-2.71 (m, 1H), 2.72-2.94 (m, 2H), 3.28-3.51 (m, 1H), 3.81 (s, 3H), 6.82-6.99 (m, 2H), 7.11-7.25 (m, 1H), 7.50-7.64 (m, 1H)

Reference Example 137

Synthesis of (S)—N-ethyl-N-[1-(2-methoxyphenyl)ethyl]-2-methylpropane-1,2-diamine (1) Di-t-butyl dicarbonate (2.2 g) was dissolved in dichloromethane (40 ml), and 2-amino-2-methylpropanol (1.0 g) was added to the solution under ice cooling. The resulting mixture was stirred at room temperature for 2 hours, then ethyl acetate and saturated aqueous sodium hydrogencarbonate were added to the reaction mixture, and the layers were separated. The organic layer was dried over anhydrous magnesium sulfate, and filtered, and then the filtrate was concentrated under reduced pressure to obtain a protected compound (1.90 g).

(2) By using the compound obtained in (1) mentioned above (200 mg) as a starting material, an aldehyde compound (200 mg) was obtained in the same manner as that of Reference Example 44, (1).

(3) By using the compound obtained in (2) mentioned above (200 mg), and (1S)-1-(2-methoxyphenyl)ethylamine (176 mg) obtained by the method described in the publication (Japanese Patent Unexamined Publication No. 54/154714) as starting materials, an alkyl compound (288 mg) was obtained in the same manner as that of Reference Example 44, (2).

(4) By using the compound obtained in (3) mentioned above (300 mg) as a starting material, the title compound (150 mg) was obtained in the same manner as that of Reference Example 10, (2).

MS (ESI) m/z=251 [M+H]$^+$ $^1$H-NMR (400 MHz, CDCl$_3$) δ (ppm): 0.95 (s, 3H), 0.98 (s, 3H), 1.01 (t, J=7.08 Hz, 3H), 1.30 (d, J=6.84 Hz, 3H), 1.82 (br s, 1H), 2.33 (d, 14.2 Hz, 1H), 2.38 (d, 14.2 Hz, 1H), 2.48-2.57 (m, 1H), 2.59-2.68 (m, 1H), 3.82 (s, 3H), 4.45 (q, J=7.08 Hz, 1H), 6.86 (d, J=8.06 Hz, 1H), 6.93 (t, J=7.57 Hz, 1H), 7.22 (dt, J=7.57, 1.22 Hz, 1H), 7.31 (d, J=7.57 Hz, 1H)

Reference Example 138

(S)—N-(2-Methoxyethyl)-N-[1-(2-methoxyphenyl)ethyl]-N'-methylethane-1,2-diamine (1) By using the compound obtained in Reference Example 44, (1) (750 mg), and (1S)-1-(2-methoxyphenyl)ethylamine (320 mg) obtained by the method described in the publication (Japanese Patent Unexamined Publication No. 54/154714) as starting materials, an alkyl compound (456 mg) was obtained in the same manner as that of Reference Example 137, (3).

(2) The compound obtained in (1) mentioned above (70 mg), bromoethyl methyl ether (316 mg), and triethylamine (460 mg) were dissolved in dimethylformamide (1 ml), and the resulting solution was stirred at 60° C. for 7 hours. Ethyl acetate and saturated aqueous sodium hydrogencarbonate were added to the reaction mixture, the layers were separated, and then the organic layer was washed with saturated brine. The organic layer was dried over anhydrous magnesium sulfate, and filtered, then the filtrate was concentrated under reduced pressure, and the resulting residue was purified by preparative thin layer chromatography (chloroform:methanol:28% aqueous ammonia=30:1:0.1) to obtain an N-methoxyethyl compound (38 mg).

(3) By using the compound obtained in (2) mentioned above (37 mg) as a starting material, the title compound (22 mg) was obtained in the same manner as that of Reference Example 10, (2).

MS (ESI) m/z=267 [M+H]$^+$ $^1$H-NMR (400 MHz, CDCl$_3$) δ (ppm): 1.32 (d, J=6.84 Hz, 3H), 2.33 (s, 3H), 2.51-2.74 (m, 6H), 3.24-3.38 (m, 2H), 3.27 (s, 3H), 3.80 (s, 3H), 4.39 (q, J=6.84 Hz, 1H), 6.86 (d, J=8.30 Hz, 1H), 6.92 (dt, J=7.32, 0.73 Hz, 1H), 7.21 (dt, J=7.32, 1.71 Hz, 1H), 7.31 (dd, J=7.57, 1.71 Hz, 1H)

Reference Example 139

Synthesis of N—[(S)-1-(2-methoxyphenyl)ethyl]propane-1,2-diamine (1) (1S)-1-(2-Methoxyphenyl)ethylamine (250 mg) obtained by the method described in the publication (Japanese Patent Unexamined Publication No. 54/154724), and phthalimide acetone (403 mg) were dissolved in methanol (7.5 ml), acetic acid (285 µl), and sodium triacetoxyborohydride (156 mg) were added to the solution, and the resulting mixture was stirred at room temperature for 24 hours. Sodium triacetoxyborohydride (260 mg) was added to the reaction mixture, the resulting mixture was further stirred at room temperature for 22 hours, then saturated aqueous sodium hydrogencarbonate and chloroform were added to the reaction mixture, the layers were separated, and the organic layer was dried over anhydrous sodium sulfate, and filtered. The filtrate was concentrated under reduced pressure, and the resulting residue was purified by silica gel column chromatography (chloroform:methanol=80:1) to obtain a phthalimide compound (351 mg).

(2) By using the compound obtained in (1) mentioned above (240 mg) as a starting material, the title compound (102 mg) was obtained in the same manner as that of Reference Example 3, (4).

MS (GC) m/z=209 [M+H]$^+$
$^1$H-NMR (400 MHz, CDCl$_3$) δ (ppm): 0.97 and 0.98 (each d, J=6.1 Hz, 3H), 1.33 and 1.36 (each d, J=6.6 Hz, 3H), 2.32-2.58 (m, 2H), 2.62-2.71 (m, 1H), 3.84 (s, 3H), 4.18 and 4.27 (each q, J=6.6 Hz, 1H), 6.86 (d, J=8.3 Hz, 1H), 6.91-6.97 (m, 1H), 7.18-7.23 (m, 1H), 7.26-7.32 (m, 1H)

Reference Example 140

Synthesis of N-ethyl-N—[(S)-1-(2-methoxyphenyl)ethyl]propane-1,2-diamine

By using the compound obtained in Reference Example 139, (1) (190 mg) as a starting material, the title compound (61 mg) was obtained in the same manners as those of Reference Example 4, (3) and Reference Example 3, (4).

MS (ESI) m/z=236 [M+H]$^+$
$^1$H-NMR (400 MHz, CDCl$_3$) δ (ppm): 0.66 and 0.95 (each d, J=6.1 Hz, 3H), 1.04 (t, J=6.9 Hz, 3H), 1.30 and 1.36 (each d, J=6.8 Hz, 3H), 2.25-2.85 (m, 5H), 3.81 and 3.83 (each s, 3H), 4.47 (q, J=6.9 Hz, 1H), 6.82-6.87 (m, 1H), 6.89-6.96 (m, 1H), 7.17-7.23 (m, 1H), 7.36-7.41 (m, 1H)

Reference Example 141

Synthesis of (R)-2-amino-3-[(S)-1-(2-methoxyphenyl)ethylamino]propanol (1) By using (1S)-1-(2-methoxyphenyl)ethylamine (162 mg) obtained by the method described in the publication (Japanese Patent Unexamined Publication No. 54/154724), and the compound obtained in Reference Example 80, (1) (320 mg) as starting materials, an alkyl compound (375 mg) was obtained in the same manner as that of Reference Example 44, (2).
(2) By using the compound obtained in (1) mentioned above (370 mg) as a starting material, a debenzylated compound (215 mg) was obtained in the same manner as that of Reference Example 74, (2).
(3) By using the compound obtained in (2) mentioned above (80 mg) as a starting material, the title compound (52 mg) was obtained in the same manner as that of Reference Example 10, (2).

MS (FAB) m/z=224 [M+H]$^+$
$^1$H-NMR (400 MHz, CDCl$_3$) δ (ppm): 1.36 (d, J=6.8 Hz, 3H), 2.50-2.65 (m, 2H), 2.89-3.00 (m, 1H), 3.53-3.67 (m, 2H), 3.84 (s, 3H), 4.02-4.14 (m, 1H), 6.87 (d, J=7.8 Hz, 1H), 6.94 (t, J=7.1 Hz, 1H), 7.18-7.27 (m, 2H)

Reference Example 142

Synthesis of (R)-2-amino-3-{N—[(S)-1-(2-methoxyphenyl)ethyl]-N-methylamino}propanol By using the compound obtained in Reference Example 141, (2) (90 mg) as a starting material, the title compound (53 mg) was obtained in the same manners as those of Reference Example 20, (1), and Reference Example 10, (2).

MS (FAB) m/z=239 [M+H]$^+$
$^1$H-NMR (400 MHz, CDCl$_3$) δ (ppm): 1.32 (d, J=6.8 Hz, 3H), 2.22 (s, 3H), 2.43-2.53 (m, 2H), 3.08-3.16 (m, 1H), 3.28 (dd, J=10.5, 7.3 Hz, 1H), 3.46 (dd, J=10.5, 7.6 Hz, 1H), 3.53-3.67 (m, 2H), 3.83 (s, 3H), 4.17 (q, 6.8 Hz, 1H), 6.89 (dd, J=8.3, 1.0 Hz, 1H), 6.96 (dd, J=8.3, 1.0 Hz, 1H), 7.21-7.27 (m, 1H), 7.30 (dd, J=8.3, 1.7 Hz, 1H)

Reference Example 143

(S)-3-[(S)-1-(2-Methoxyphenyl)ethylamino]-2-(methylamino)propan-1-ol (1) By using N-t-butoxycarbonyl-O-benzyl-(D)-serine (842 mg), and (1S)-1-(2-methoxyphenyl)ethylamine (431 mg) obtained by the method described in the publication (Japanese Patent Unexamined Publication No. 54/154714) as starting materials, a debenzylated compound (636 mg) was obtained in the same manners as those of Reference Example 78, (1), Reference Example 82, (1), (2), and Reference Example 74, (2).
(2) The compound obtained in (3) mentioned above (633 mg) was dissolved in tetrahydrofuran (30 ml), and a 1 M solution of borane/tetrahydrofuran complex in tetrahydrofuran (19 ml) was added to the solution under ice cooling. The resulting mixture was stirred at room temperature for 4 hours, and then cooled on ice again, and 5 N aqueous sodium hydroxide was slowly added to the mixture. Ethyl acetate was added to the reaction mixture, the layers were separated, and then ethyl acetate was added to the aqueous layer for extraction. The organic layers were combined, washed with saturated brine, then dried over anhydrous magnesium sulfate, and filtered. The filtrate was concentrated under reduced pressure, ethanol (1 ml) and ethylenediamine (0.5 ml) were added to the resulting residue, and the resulting mixture was stirred at 60° C. for 2 hours. The reaction mixture was purified by preparative thin layer chromatography (chloroform:methanol:28% aqueous ammonia=10:1:0.3) to obtain the title compound (145 mg).

MS (ESI) m/z=239 [M+H]$^+$
$^1$H-NMR (400 MHz, CDCl$_3$) δ (ppm): 1.35 (d, J=6.59 Hz, 3H), 2.40 (s, 3H), 2.53-2.57 (m, 1H), 2.61-2.64 (m, 2H), 3.58-3.68 (m, 2H), 3.83 (s, 3H), 4.08 (q, J=6.84 Hz, 1H), 6.87 (d, J=8.06 Hz, 1H), 6.95 (t, J=7.57 Hz, 1H), 7.21 (dt, J=8.06, 1.71 Hz, 1H), 7.26 (dd, J=7.33, 1.71, 1H)

Reference Example 144

Synthesis of (S)-2-amino-3-[(S)-1-(2-methoxyphenyl)ethylamino]propanol (1) By using N-(t-butoxycarbonyl)-O-benzyl-(D)-serinol (400 mg) as a starting material, an aldehyde compound (480 mg) was obtained in the same manner as that of Reference Example 44, (1).

(2) By using the compound obtained in (1) mentioned above (480 mg), and (1S)-1-(2-methoxyphenyl)ethylamine (215 mg) obtained by the method described in the publication (Japanese Patent Unexamined Publication No. 54/154724) as starting materials, a debenzylated compound (530 mg) was obtained in the same manners as those of Reference Example 44, (2), and Reference Example 74, (2).

(3) By using the compound obtained in (2) mentioned above (150 mg) as a starting material, the title compound (88 mg) was obtained in the same manner as that of Reference Example 10, (2).

MS (ESI) m/z=225 [M+H]$^+$ $^1$H-NMR (400 MHz, CDCl$_3$) δ (ppm): 1.36 (d, J=6.6 Hz, 3H), 2.56-2.61 (m, 1H), 2.94 (quint, J=5.4 Hz, 1H), 3.58 (d, J=5.4 Hz, 2H), 3.83 (s, 3H), 4.06 (q, J=6.6 Hz, 1H), 6.87 (d, J=8.1 Hz, 1H), 6.94 (dt, J=7.3, 1.0 Hz, 1H), 7.19-7.25 (m, 2H)

Reference Example 145

Synthesis of (S)-2-amino-3-{N—[(S)-1-(2-methoxyphenyl)ethyl]-N-methylamino}propanol By using the compound obtained in Reference Example 144, (2) (155 mg) as a starting material, the title compound (90 mg) was obtained in the same manners as those of Reference Example 20, (1), and Reference Example 10, (2).

MS (ESI) m/z=239 [M+H]$^+$ $^1$H-NMR (400 MHz, CDCl$_3$) δ (ppm): 1.33 (d, J=6.8 Hz, 3H), 2.28 (s, 3H), 2.39-2.51 (m, 2H), 3.04-3.14 (m, 1H), 3.28 (dd, J=10.2, 7.3 Hz, 1H), 3.42-3.48 (m, 1H), 3.53-3.67 (m, 2H), 3.82 (s, 3H), 4.16 (q, 6.8 Hz, 1H), 6.89 (d, J=8.3 Hz, 1H), 6.94 (t, J=7.3 Hz, 1H), 7.23-7.28 (m, 2H)

Reference Example 146

Synthesis of (R)-2-amino-3-[N-ethyl-N-(2-methoxybenzyl)amino]propanol (1) By using 2-methoxybenzylamine (98 mg), and the compound obtained in Reference Example 80, (1) (235 mg) as starting materials, an alkyl compound (250 mg) was obtained in the same manner as that of Reference Example 44, (2).

(2) By using the compound obtained in (1) mentioned above (100 mg) as a starting material, the title compound (22 mg) was obtained in the same manners as those of Reference Example 74, (2), Reference Example 4, (3), and Reference Example 10, (2).

MS (FAB) m/z=239 [M+H]$^+$ $^1$H-NMR (400 MHz, CDCl$_3$) δ (ppm): 1.09 (t, J=7.1 Hz, 3H), 2.43-2.52 (m, 2H), 2.54-2.69 (m, 2H), 3.06-3.14 (m, 1H), 3.38 (dd, J=10.5, 7.4 Hz, 1H), 3.49 (d, J=13.5 Hz, 1H), 3.49-3.54 (m, 1H), 3.72 (d, J=13.5 Hz, 1H), 3.83 (s, 3H), 6.87 (d, J=8.5 Hz, 1H), 6.92 (dt, J=7.2, 1.2 Hz, 1H), 7.22-7.28 (m, 210

Reference Example 147

Synthesis of (R)-2-amino-3-{N-ethyl-[(R)-1-(2-methoxypyridin-3-yl)ethyl]amino}propanol By using the compound obtained in Reference Example 40, (1) (50 mg), and the compound obtained in Reference Example 80, (1) (102 mg) as starting materials, the title compound (28 mg) was obtained in the same manners as those of Reference Example 44, (2), Reference Example 74, (2), Reference Example 4, (3), and Reference Example 10, (2).

MS (FAB) m/z=254 [M+H]$^+$ $^1$H-NMR (400 MHz, CDCl$_3$) δ (ppm): 1.05 (t, J=7.08 Hz, 3H), 1.32 (d, J=7.08 Hz, 3H), 2.39-2.53 (m, 3H), 2.59-2.70 (m, 1H), 3.02-3.12 (m, 1H), 3.51 (d, J=6.10 Hz, 2H), 3.95 (s, 3H), 4.31 (q, J=7.08 Hz, 2H), 6.88 (dd, J=7.33, 4.88 Hz, 1H), 7.56 (dd, J=7.33, 1.95 Hz, 1H), 8.07 (dd, J=4.88, 1.95 Hz, 1H)

Reference Example 148

Synthesis of (R)-2-amino-3-{N-ethyl-[2-(2-methoxypyridin-3-yl)propan-2-yl]amino}propanol By using the compound obtained in Reference Example 38, (2) (100 mg), and the compound obtained in Reference Example 80, (1) (188 mg) as starting materials, the title compound (105 mg) was obtained in the same manners as those of Reference Example 44, (2), Reference Example 74, (2), Reference Example 4, (3), and Reference Example 10, (2).

MS (ESI) m/z=268 [M+H]$^+$ $^1$H-NMR (400 MHz, CDCl$_3$) δ (ppm): 0.88 (t, J=7.1 Hz, 3H), 1.45 (s, 3H), 1.51 (s, 3H), 2.37-2.53 (m, 2H), 2.56-2.69 (m, 2H), 3.05-3.14 (m, 1H), 3.56 (d, J=5.8 Hz, 2H), 3.96 (s, 3H), 6.85 (dd, J=7.5, 4.8 Hz, 1H), 7.58 (dd, J=7.5, 1.8 Hz, 1H), 8.07 (dd, J=4.8, 1.8 Hz, 1H)

Reference Example 149

Synthesis of N-[2-(2-methoxyphenyl)propan-2-yl]piperidin-4-amine (1) The compound obtained in Reference Example 17, (1) (415 mg), and N-t-butoxycarbonylpiperidone (200 mg) were dissolved in dimethylformamide (2 ml), Molecular Sieves 4A (800 mg), acetic acid (0.29 ml), and sodium triacetoxyborohydride (640 mg) were added to the solution, and the resulting mixture was stirred at room temperature for 16 hours. Chloroform was added to the reaction mixture, the resulting mixture was filtered through Celite, and then the filtrate was washed with saturated aqueous sodium hydrogencarbonate, distilled water, and saturated brine. The organic layer was dried over anhydrous sodium sulfate, and filtered, then the filtrate was concentrated under reduced pressure, and the resulting residue was purified by silica gel column chromatography (chloroform: ethyl acetate=1:3 to ethyl acetate:methanol=30:1) to obtain an alkyl compound (96 mg).

(2) By using the compound obtained in (1) mentioned above (118 mg) as a starting material, the title compound (80 mg) was obtained in the same manner as that of Reference Example 10, (2).

MS (FAB) m/z=249 [M+H]$^+$ $^1$H-NMR (400 MHz, CDCl$_3$) δ (ppm): 1.10-1.21 (m, 2H), 1.46-1.57 (m, 2H), 1.51 (s, 6H), 2.15-2.22 (m, 1H), 2.40 (dt, J=12.2, 2.44 Hz, 2H), 2.87-2.93 (m, 2H), 3.85 (s, 3H), 6.85-6.89 (m, 1H), 6.91 (dt, J=7.57, 1.22 Hz, 1H), 7.20-7.27 (m, 1H), 7.27 (dd, J=7.57, 1.71 Hz, 1H)

Reference Example 150

Synthesis of N-methyl-N'-(2-phenylpropan-2-yl)ethane-1,2-diamine

By using the compound obtained in Reference Example 44, (1) (96 mg), and cumylamine (77 mg) as starting materials, the title compound (56 mg) was obtained in the same manners as those of Reference Example 44, (2), and Reference Example 10, (2).

MS (FAB) m/z=193 [M+H]$^+$ $^1$H-NMR (400 MHz, CDCl$_3$) δ (ppm): 1.10-1.21 (m, 2H), 1.46-1.57 (m, 2H), 1.51 (s, 6H), 2.15-2.22 (m, 1H), 2.40 (dt, J=12.2, 2.44 Hz, 2H), 2.87-2.93 (m, 2H), 3.85 (s, 3H), 6.85-6.89 (m, 1H), 6.91 (dt, J=7.57, 1.22 Hz, 1H), 7.20-7.27 (m, 1H), 7.27 (dd, J=7.57, 1.71 Hz, 1H)

Reference Example 151

Synthesis of 2-{[N-(2-methoxyphenyl)propan-2-yl]-N-methylamino}ethanethiol (1) The compound obtained in Reference Example 17, (1) (400 mg) was dissolved in dimethylformamide (10 ml), sodium hydrogencarbonate (305 mg) and ethyl bromoacetate (485 mg) were added to the solution, and the resulting mixture was stirred overnight at room temperature. Saturated aqueous sodium hydrogencarbonate was added to the reaction mixture, ethyl acetate was added to the resulting mixture, the layers were separated, and then the organic layer was washed with saturated brine. The organic layer was dried over anhydrous magnesium sulfate, and filtered, then the filtrate was concentrated under reduced pressure, and the resulting residue was purified by silica gel column chromatography (n-hexane:ethyl acetate:triethylamine=4:1:0.1) to obtain an ethyl ester compound (254 mg).

(2) By using the compound obtained in (1) mentioned above (254 mg) as a starting material, an alcohol compound (217 mg) was obtained in the same manners as those of Reference Example 20, (1) and Reference Example 3, (2).

(3) The compound obtained in (2) mentioned above (50 mg) was dissolved in methylene chloride (2 ml), triethylamine (0.057 ml), and methanesulfonyl chloride (0.026 ml) were added to the solution under ice cooling, the resulting mixture was stirred at the same temperature for 2 hours, then potassium thioacetate (128 mg), and dimethylformamide (1 ml) were added to the mixture, and the resulting mixture was stirred at room temperature for 1 hour. The reaction mixture was diluted with ethyl acetate, then saturated aqueous sodium hydrogencarbonate was added to the reaction mixture, the layers were separated, and the organic layer was washed with saturated brine. The organic layer was dried over anhydrous magnesium sulfate, and filtered, then the filtrate was concentrated under reduced pressure, and the resulting residue was purified by silica gel column chromatography (hexane:ethyl acetate:triethylamine=3:1:0.1) to obtain the title compound (39 mg).

MS (ESI) m/z=282 [M+H]$^+$ $^1$H-NMR (400 MHz, CDCl$_3$) δ (ppm): 1.44 (s, 6H), 2.29 (s, 3H), 2.30 (s, 3H), 2.57 (t, J=6.84 Hz, 2H), 2.98 (t, J=7.08 Hz, 2H), 3.81 (s, 3H), 6.88-6.94 (m, 2H), 7.20 (dt, J=8.06, 1.71 Hz, 1H), 7.56 (dd, J=7.81, 1.71 Hz, 1H)

Reference Example 152

Synthesis of N-{2-[2-(dimethylamino)phenyl]propan-2-yl}-N'-methylethane-1,2-diamine (1) By using 2-(2-dimethylamino)benzonitrile (500 mg) as a starting material, a dimethylamine compound (24.3 mg) was obtained in the same manner as that of Reference Example 87, (2).

(2) By using the compound obtained in (1) mentioned above (24 mg), and the compound obtained in Reference Example 44, (1) (23.3 mg) as starting materials, the title compound (8.8 mg) was obtained in the same manners as those of Reference Example 44, (2), and Reference Example 108, (6).

MS (ESI) m/z=236.2 [M+H]$^+$ $^1$H-NMR (200 MHz, CDCl$_3$) δ (ppm): 1.54 (s, 6H), 2.36-2.48 (m, 2H), 2.40 (s, 3H), 2.58-2.70 (m, 2H), 2.63 (s, 6H), 7.06-7.41 (m, 4H)

Examples 1 to 9

Preparation methods of the compounds represented by the formula (B) having $R^{5B}$, $R^{6B}$, and X defined in Table 1 are shown below.

[Formula 18]

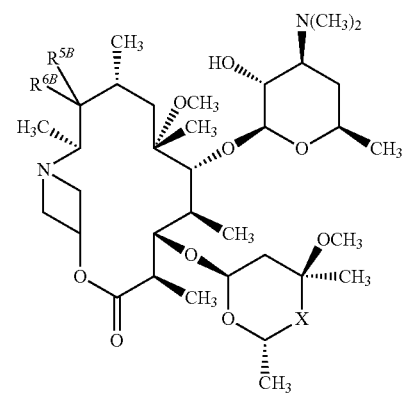

Formula (B)

TABLE 1
| Example | R5B | R6B | X | ESI MS (M + H) | ¹H-NMR, CDCl₃, δ (ppm) |
|---|---|---|---|---|---|
| 1 |  |  | 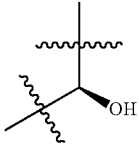 | 689 | (400 MHz): 0.99 (d, J = 7.06 Hz, 3 H) 1.02 (d, J = 6.58 Hz, 3 H) 1.13 (d, J = 7.55 Hz, 3 H) 1.17-1.37 (m, 2 H) 1.23 (d, J = 5.85 Hz, 3 H) 1.25 (d, J = 6.09 Hz, 3 H) 1.27 (s, 3 H) 1.31 (d, J = 6.09 Hz, 3 H) 1.39 (s, 3 H) 1.58-1.67 (m, 2 H) 2.10-2.21 (m, 1 H) 2.21 (d, J = 10.2 Hz, 1 H) 2.40 (d, J = 14.6 Hz, 1 H) 2.40-2.49 (m, 1 H) 2.61 (dd, J = 13.4, 6.82 Hz, 1 H) 2.83-3.08 (m, 5 H) 3.12-3.26 (m, 3 H) 3.30-3.44 (m, 2 H) 3.35 (s, 3 H) 3.35 (s, 3 H) 3.45-3.56 (m, 1 H) 3.59 (dd, J = 8.77, 4.87 Hz, 1 H) 3.71 (dd, J = 9.74, 1.70 Hz, 1 H) 3.89 (d, J = 6.33 Hz, 1 H) 4.04-4.14 (m, 1 H) 4.52 (d, J = 7.30 Hz, 1 H) 4.64 (t, J = 4.63 Hz, 1 H) 4.90 (d, J = 10.5 Hz, 1 H) 4.96 (d, J = 4.63 Hz, 1 H) |
| 2 |  |  | 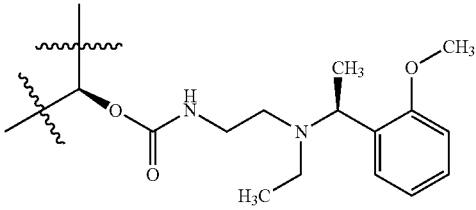 | 937 | (400 MHz): 0.89 (d, J = 7.06 Hz, 3 H) 0.95 (t, J = 6.33 Hz, 3 H) 1.02 (d, J = 6.82 Hz, 3 H) 1.14 (d, J = 7.55 Hz, 3 H) 1.17 (s, 3 H) 1.17-1.37 (m, 5 H) 1.18 (d, J = 6.82 Hz, 3 H) 1.20 (d, J = 6.58 Hz, 3 H) 1.25 (d, J = 7.07 Hz, 3 H) 1.38 (s, 3 H) 1.52-1.73 (m, 2 H) 2.09-2.19 (m, 1 H) 2.27 (s, 6 H) 2.38-2.71 (m, 7 H) 2.84-2.99 (m, 3 H) 3.03 (d, J = 3.16 Hz, 1 H) 3.14-3.46 (m, 7 H) 3.32 (s, 3 H) 3.36 (s, 3 H) 3.58-3.65 (m, 1 H) 3.66-3.76 (m, 2 H) 3.85 (s, 3 H) 3.99 (d, J = 6.09 Hz, 1 H) 4.33-4.46 (m, 2 H) 4.52 (d, J = 9.99 Hz, 1 H) 4.59 (d, J = 7.31 Hz, 1 H) 4.64 (t, J = 4.63 Hz, 1 H) 4.99 (d, J = 5.11 Hz, 1 H) 5.42-5.63 (m, 1 H) 6.87 (d, J = 8.28 Hz, 1 H) 6.93 (t, J = 7.55 Hz, 1 H) 7.19-7.33 (m, 2 H) |

TABLE 1-continued

| Example | R5B | R6B | X | ESI MS (M + H) | 1H-NMR, CDCl3, δ (ppm) |
|---|---|---|---|---|---|
| 3 | HO— (wedge) | —H | [structure with NH-CH2-CH2-N(Et)-CH(CH3)-(2-methoxyphenyl)] | 923 | (400 MHz): 0.88 (d, J = 7.31 Hz, 3 H) 0.96 (t, J = 7.06 Hz, 3 H) 1.01 (d, J = 6.82 Hz, 3 H) 1.10 (s, 3 H) 1.12 (d, J = 7.55 Hz, 3 H) 1.14 (d, J = 6.33 Hz, 3 H) 1.17-1.35 (m, 2 H) 1.19 (d, J = 6.09 Hz, 3 H) 1.25 (d, J = 6.82 Hz, 3 H) 1.28 (d, J = 6.83 Hz, 3 H) 1.39 (s, 3 H) 1.57-1.74 (m, 2 H) 1.99 (dd, J = 14.9, 5.11 Hz, 1 H) 2.08 (d, J = 14.1 Hz, 1 H) 2.10-2.19 (m, 1 H) 2.25-2.30 (m, 1 H) 2.29 (s, 6 H) 2.41-2.65 (m, 8 H) 2.83-2.95 (m, 4 H) 3.02 (dd, J = 10.2, 3.41 Hz, 1 H) 3.13-3.24 (m, 3 H) 3.28-3.43 (m, 2 H) 3.30 (s, 3 H) 3.37 (s, 3 H) 3.46-3.55 (m, 1 H) 3.56-3.63 (m, 1 H) 3.71 (dd, J = 9.50, 1.70 Hz, 1 H) 3.81 (s, 3 H) 3.92 (d, J = 6.33 Hz, 1 H) 4.25 (q, J = 6.33 Hz, 1 H) 4.37 (q, J = 6.82 Hz, 1 H) 4.49 (d, J = 7.31 Hz, 1 H) 4.63 (t, J = 4.63 Hz, 1 H) 4.97 (d, J = 10.2 Hz, 1 H) 5.03 (d, J = 4.14 Hz, 1 H) 6.86 (dd, J = 8.28, 0.97 Hz, 1 H) 6.93 (dt, J = 7.55, 0.98 Hz, 1 H) 7.18-7.23 (m, 1 H) 7.31 (dd, J = 7.56, 1.47 Hz, 1 H) |
| 4 | =O | =O | [structure with O-C(=O)-NH-CH2-CH2-N(Et)-CH(CH3)-(2-methoxyphenyl)] | 935 | (500 MHz): 0.94 (t, J = 6.9 Hz, 3 H) 1.10-1.33 (m, 20 H) 1.20 (d, J = 6.2 Hz, 3 H) 1.30 (d, J = 6.8 Hz, 3 H) 1.38 (s, 3 H) 1.52-1.67 (m, 2 H) 2.19-2.24 (m, 1 H) 2.26 (s, 6 H) 2.38-2.67 (m, 7 H) 2.77-2.89 (m, 2 H) 3.13-3.34 (m, 5 H) 3.17 (s, 3 H) 3.31 (s, 3 H) 3.51 (q, J = 6.9 Hz, 1 H) 3.54-3.65 (m, 2 H) 3.70 (d, J = 9.5 Hz, 1 H) 3.73 (d, J = 7.7 Hz, 1 H) 3.77-3.91 (m, 2 H) 3.86 (s, 3 H) 4.32-4.41 (m, 2 H) 4.49 (d, J = 7.2 Hz, 1 H) 4.53 (d, J = 9.7 Hz, 1 H) 4.75-4.80 (m, 1 H) 4.90 (d, J = 4.8 Hz, 1 H) 5.52-5.60 (m, 1 H) 6.88 (d, J = 8.2 Hz, 1 H) 6.92 (t, J = 7.3 Hz, 1 H) 7.22 (t, J = 7.3 Hz, 1 H) 7.26-7.31 (m, 1 H) |

TABLE 1-continued

| Example | R5B | R6B | X | ESI MS (M + H) | $^1$H-NMR, CDCl$_3$, δ (ppm) |
|---|---|---|---|---|---|
| 5 | O= | O= | (structure with OH, NH, N-ethyl, CH$_3$, 2-methoxyphenyl) | 921 | (500 MHz): 0.96 (t, J = 6.9 Hz, 3 H) 1.09 (s, 3 H) 1.11-1.26 (m, 19 H) 1.29 (d, J = 6.8 Hz, 3 H) 1.39 (s, 3 H) 1.59-1.64 (m, 2 H) 1.93 (dd, J = 14.9, 5.2 Hz, 1 H) 2.06 (d, J = 14.8 Hz, 1 H) 2.20 (dd, J = 15.1, 5.1 Hz, 1 H) 2.27-2.67 (m, 8 H) 2.29 (s, 6 H) 2.78-2.86 (m, 3 H) 3.18 (s, 3 H) 3.19-3.30 (m, 2 H) 3.27 (s, 3 H) 3.42-3.50 (m, 2 H) 3.59 (dd, J = 9.9, 2.9 Hz, 1 H) 3.70 (d, J = 9.3 Hz, 1 H) 3.74 (d, J = 7.9 Hz, 1 H) 3.76-3.86 (m, 2 H) 3.81 (s, 3 H) 4.23 (q, J = 6.3 Hz, 1 H) 4.37 (q, J = 6.9 Hz, 1 H) 4.40 (d, J = 7.3 Hz, 1 H) 4.74-4.79 (m, 1 H) 4.93 (d, J = 4.9 Hz, 1 H) 6.86 (d, J = 8.2 Hz, 1 H) 6.90-6.95 (m, 1 H) 7.18-7.23 (m, 1 H) 7.31 (dd, J = 7.5, 1.3 Hz, 1 H) |
| 6 | HO-N= | HO-N= | (carbamate structure with N-ethyl, CH$_3$, 2-methoxyphenyl) | 950 | (500 MHz): 0.94 (d, J = 6.9 Hz, 3 H) 0.97-1.80 (m, 25 H) 1.31 (d, J = 6.8 Hz, 3 H) 1.40 (s, 3 H) 2.26 (s, 6 H) 2.33-2.71 (m, 7 H) 3.07-3.44 (m, 6 H) 3.31 (s, 3 H) 3.54-3.91 (m, 4 H) 3.86 (s, 3 H) 4.31-4.42 (m, 2 H) 4.45-4.56 (m, 2 H) 4.75-4.81 (m, 1 H) 4.86-4.95 (m, 1 H) 6.87 (d, J = 8.5 Hz, 1 H) 6.92 (t, J = 7.4 Hz, 1 H) 7.19-7.32 (m, 2 H) |
| 7 | HO-N= | HO-N= | (structure with OH, NH, N-ethyl, CH$_3$, 2-methoxyphenyl) | 936 | (500 MHz): 0.96 (t, J = 7.00 Hz, 3 H) 1.07-1.46 (m, 14 H) 1.10 (s, 3 H) 1.15 (d, J = 6.4 Hz, 3 H) 1.19 (d, J = 6.1 Hz, 3 H) 1.29 (d, J = 6.8 Hz, 3 H) 1.41 (s, 3 H) 1.58-1.65 (m, 1 H) 1.89-2.08 (m, 2 H) 2.30 (s, 6 H) 2.30-2.86 (m, 12 H) 3.13-3.51 (m, 8 H) 3.27 (s, 3 H) 3.66-3.76 (m, 3 H) 3.81 (s, 3 H) 4.19-4.27 (m, 1 H) 4.33-4.43 (m, 2 H) 4.73-4.41 (m, 1 H) 4.89-4.97 (m, 1 H) 6.86 (d, J = 8.1 Hz, 1 H) 6.93 (t, J = 6.8 Hz, 1 H) 7.18-7.23 (m, 1 H) 7.29-7.34 (m, 1 H) |

TABLE 1-continued

| Example | R5B | R6B | X | ESI MS (M + H) | $^1$H-NMR, CDCl$_3$, δ (ppm) |
|---|---|---|---|---|---|
| 8 | H$_2$N– (structure) | –H | (structure with carbamate, N-ethyl, ethylene diamine, α-methylbenzyl with 2-methoxyphenyl) | 936 | (400 MHz): 0.89-0.98 (m, 6 H) 1.06-1.38 (m, 26 H) 1.50-1.68 (m, 2 H) 2.26 (s, 6 H) 2.37-2.71 (m, 7 H) 2.84-2.91 (m, 1 H) 3.10-3.33 (m, 8 H) 3.31 (s, 3 H) 3.45-3.51 (m, 1 H) 3.62-3.91 (m, 4 H) 3.84 (s, 3 H) 4.29-4.44 (m, 2 H) 4.52 (d, J = 9.76 Hz, 1 H) 4.59 (d, J = 7.08 Hz, 1 H) 4.87-4.99 (m, 1 H) 5.36-5.69 (m, 1 H) 6.87 (d, J = 8.05 Hz, 1 H) 6.93 (t, J = 7.57 Hz, 1 H) 7.18-7.34 (m, 2 H) |
| 9 | H$_2$N– (structure) | –H | (structure with OH, N-ethyl, ethylene diamine, α-methylbenzyl with 2-methoxyphenyl) | 922 | (400 MHz): 0.96 (t, J = 7.08 Hz, 3 H) 0.99-1.36 (m, 17 H) 1.10 (s, 3 H) 1.20 (d, J = 6.10 Hz, 3 H) 1.29 (d, J = 6.79 Hz, 3 H) 1.33 (s, 3 H) 1.57-1.67 (m, 1 H) 1.79-2.25 (m, 4 H) 2.29 (s, 6 H) 2.41-2.67 (m, 8 H) 2.76-2.99 (m, 2 H) 2.87 (d, J = 13.7 Hz, 1 H) 3.13-3.47 (m, 4 H) 3.18 (s, 3 H) 3.30 (s, 3 H) 3.47-3.58 (m, 1 H) 3.72-3.80 (m, 3 H) 3.81 (s, 3 H) 4.22 (q, J = 6.10 Hz, 1 H) 4.37 (q, J = 6.59 Hz, 1 H) 4.50 (d, J = 7.32 Hz, 1 H) 4.87-4.98 (m, 2 H) 6.86 (d, J = 7.57 Hz, 1 H) 6.93 (dt, J = 7.32, 0.97 Hz, 1 H) 7.18-7.24 (m, 1 H) 7.29-7.34 (m, 1 H) |

Example 1

(1) The compound obtained in Reference Example 1 (21.7 g), and epichlorohydrin (20.2 g) were dissolved in tetrahydrofuran (200 ml), and the resulting solution was stirred at 100° C. for 15 minutes under microwave irradiation. The reaction mixture was concentrated under reduced pressure, and the resulting residue was purified by silica gel column chromatography (chloroform:methanol:28% aqueous ammonia=100:1:0.1 to 5:1:0.1) to obtain a low polar lactonization precursor (7.98 g), and a highly polar lactonization precursor (3.76 g). As another method different from the aforementioned method, the aforementioned compound was also obtained by the following method. Namely, the compound obtained in Reference Example 1 (62.5 g), and epichlorohydrin (58.2 g) were dissolved in tetrahydrofuran (312 ml), and the resulting solution was stirred at an internal temperature of 70.5° C. for 2 hours and 30 minutes under reflux by heating. The reaction mixture was concentrated under reduced pressure, and the resulting residue was purified by silica gel column chromatography (chloroform:methanol:28% aqueous ammonia=90:1:0.1 to 20:1:0.1) to obtain a mixture of isomers of lactonization precursor (50.9 g).

(2) The highly polar lactonization precursor obtained in (1) mentioned above (1.5 g), and triphenylphosphine (1.45 g) were dissolved in tetrahydrofuran (19.5 ml), diisopropyl azodicarboxylate (1.07 ml) was added to the solution under ice cooling, and the resulting mixture was stirred at room temperature for 3.5 hours. The reaction mixture was concentrated, and the resulting residue was purified by silica gel column chromatography (chloroform:ethyl acetate=30:1 to 4:1) to obtain an optically active lactone compound (331 mg). As another method different from the aforementioned method, the aforementioned compound was also obtained by the following method. Namely, triphenylphosphine (48.2 g) was dissolved in toluene (625 ml), a solution of di-t-butyl azodicarboxylate (42.3 g) in toluene (500 ml) was added to the solution under ice cooling, the resulting mixture was stirred for 30 minutes, then a solution of the mixture of isomers of lactonization precursor obtained in (1) mentioned above (49.9 g) in toluene (875 ml) was added dropwise to the mixture over 3.5 hours, and then the resulting mixture was further stirred for 1 hour. Saturated aqueous sodium hydrogencarbonate and ethyl acetate were added to the reaction mixture, the layers were separated, and the organic layer was dried over anhydrous magnesium sulfate, and filtered. The filtrate was concentrated under reduced pressure, and the resulting residue was purified by silica gel column chromatography (hexane:acetone:triethylamine=500:10:0.2 to 400:10:0.2) to obtain a mixture of isomers of lactone compound (22.7 g).

(3) The optically active lactone compound (200 mg) obtained in (2) mentioned above was dissolved in tetrahydrofuran (4 ml), hydrogen fluoride-pyridine complex (73 μl) was added to the solution, and the resulting mixture was stirred at room temperature for 14 hours. Saturated aqueous sodium hydrogencarbonate and ethyl acetate were added to the reaction mixture, the layers were separated, the organic layer was concentrated under reduced pressure, and the resulting residue was purified by silica gel column chromatography (chloroform:methanol:28% aqueous ammonia=90:1:0.1 to 8:1:0.1) to obtain a deprotected compound (129 mg).
(4) The compound obtained in (3) mentioned above (50 mg) was dissolved in dimethylformamide (5 ml), potassium iodide (114 mg), and diisopropylethylamine (240 μl) were added to the solution, and the resulting mixture was stirred at 90° C. for 3.5 hours under microwave irradiation. Distilled water and ethyl acetate were added to the reaction mixture, the layers were separated, and then the organic layer was dried over anhydrous magnesium sulfate, and filtered. The filtrate was concentrated under reduced pressure, and the resulting residue was purified by silica gel column chromatography (chloroform:methanol:28% aqueous ammonia=100:1:0.1 to 8:1:0.1) to obtain the compound shown in Table 1 (31.7 mg).

Example 2

(1) The mixture of isomers of lactone compound obtained in Example 1, (2) (22.7 g) was dissolved in dimethylformamide (450 ml), potassium iodide (35.2 g), and diisopropylethylamine (37 ml) were added to the solution, and the resulting mixture was stirred at 120° C. for 1 hour. The reaction mixture was left to cool, then ethyl acetate and 8% aqueous sodium hydrogencarbonate were added to the reaction mixture, the layers were separated, and the organic layer was dried over anhydrous magnesium sulfate, and filtered. The filtrate was concentrated under reduced pressure, and the resulting residue was purified by silica gel column chromatography (hexane:acetone:triethylamine=500:10:0.2 to 100:10:0.2) to obtain an azetidine compound (16.4 g).
(2) The azetidine compound obtained in (1) mentioned above (16.4 g) was dissolved in tetrahydrofuran (164 ml), ethanol (655 ml), and 1 N hydrochloric acid (81.9 ml) were added to the solution, and then the resulting mixture was stirred at room temperature for 40 minutes. 1 N Aqueous sodium hydroxide (90.6 ml) was added to the reaction mixture, the resulting mixture was concentrated under reduced pressure, ethyl acetate and saturated aqueous sodium hydrogencarbonate were added to the resulting residue, the layers were separated, and then the organic layer was dried over anhydrous magnesium sulfate, and filtered. The filtrate was concentrated under reduced pressure, and the resulting residue was purified by silica gel column chromatography (hexane:acetone:triethylamine=500:10:0.2 to 100:10:0.2) to obtain a 4"-hydroxy compound (7.78 g).
(3) The compound obtained in (2) mentioned above (2 g), and 1,1'-carbonyldiimidazole (1.06 g) were dissolved in a mixed solvent of tetrahydrofuran and dimethylformamide (2:1, 40 ml), 60% sodium hydride (262 mg) was added to the solution under ice cooling, and the resulting mixture was stirred at the same temperature for 30 minutes. Saturated aqueous ammonium chloride (50 ml) and hexane (40 ml) were added to the reaction mixture, the layers were separated, and then the organic layer was further washed twice with saturated aqueous ammonium chloride. The organic layer was washed with saturated brine (50 ml), dried over anhydrous magnesium sulfate, and filtered, and then the filtrate was concentrated under reduced pressure to obtain a 4"-imidazolide compound (2.3 g).
(4) A solution of the compound obtained in Reference Example 3 (147 mg) in tetrahydrofuran was added to the compound obtained in (3) mentioned above (370 mg), the reaction mixture was concentrated under reduced pressure, and the resulting residue was left at room temperature for 16 hours. The reaction mixture was purified by silica gel column chromatography (hexane:acetone:28% aqueous ammonia=60:10:0.2 to 40:10:0.2) to obtain a carbamate compound (300 mg).
(5) By using the compound obtained in (4) mentioned above (7.2 mg) as a starting material, the compound shown in Table 1 (4.3 mg) was obtained in the same manner as that of Example 1, (3).

Example 3

(1) N-Chlorosuccinimide (3.49 g) was dissolved in chloroform (150 ml), and the solution was cooled to −20° C. Dimethyl sulfide (2.46 ml) was added to the solution, the resulting mixture was stirred for 10 minutes, then a solution of the compound obtained in Example 2, (2) (4 g) in chloroform (50 ml) was added to the reaction mixture, and the resulting mixture was stirred for 10 minutes. Triethylamine (6.38 ml) was added to the reaction mixture, the resulting mixture was stirred for 30 minutes, then saturated aqueous sodium hydrogencarbonate was added to the reaction mixture, the resulting mixture was warmed to room temperature, chloroform was added to the mixture, and the layers were separated. The organic layer was dried over anhydrous magnesium sulfate, and filtered, then the filtrate was concentrated under reduced pressure, and the resulting residue was purified by silica gel column chromatography (hexane:acetone:triethylamine=500:10:0.2 to 70:10:0.2) to obtain a 4"-ketone compound (3.68 g).
(2) 60% Sodium hydride (200 mg) was suspended in tetrahydrofuran (30 ml), trimethylsulfoxonium iodide (1.1 g) was added to the suspension, and the resulting mixture was stirred at room temperature for 2 hours. The compound obtained in (1) mentioned above (3.05 g) was dissolved in a mixed solvent of dimethyl sulfoxide and tetrahydrofuran (2:1, 45.5 ml), the solution was added to the reaction mixture, and the resulting mixture was stirred for 3 hours. Saturated aqueous ammonium chloride and ethyl acetate were added to the reaction mixture, the layers were separated, and the organic layer was dried over anhydrous magnesium sulfate, and filtered. The filtrate was concentrated under reduced pressure, and the resulting residue was purified by silica gel column chromatography (hexane to hexane:acetone:triethylamine=70:10:0.2) to obtain a 4"-epoxy compound (2.23 g).
(3) By using the compound obtained in (2) mentioned above (2.23 g) as a starting material, a deprotected compound (1.75 g) was obtained in the same manner as that of Example 1, (3).
(4) A solution of the compound obtained in Reference Example 3 (476 mg) in ethanol (1.5 ml) was added to the compound obtained in (3) mentioned above (300 mg), and the resulting mixture was stirred at 120° C. for 15 minutes under microwave irradiation. The reaction mixture was concentrated under reduced pressure, and the resulting residue was purified by preparative thin layer chromatography (chloroform:methanol:28% aqueous ammonia=8:1:0.1) to obtain the compound shown in Table 1 (292 mg).

Example 4

(1) The compound obtained in Example 2 (199 mg) was dissolved in acetone (2 ml), acetic anhydride (22.1 μl) was added to the solution, and the resulting mixture was stirred at room temperature for 13 hours. The reaction mixture was concentrated under reduced pressure, then saturated aqueous sodium hydrogencarbonate and ethyl acetate were added to the reaction mixture, the layers were separated, and the organic layer was dried over anhydrous magnesium sulfate, and filtered. The filtrate was concentrated under reduced pressure to obtain a 2'-O-acetyl compound (183 mg).

(2) N-Chlorosuccinimide (283 mg) was dissolved in chloroform (7 ml), and the solution was cooled to −20° C. Dimethyl sulfide (315 µl) was added to the solution, the resulting mixture was stirred for 15 minutes, then a solution of the compound obtained in (1) mentioned above (183 mg) in chloroform (3.4 ml) was added to the mixture, and the resulting mixture was stirred for 45 minutes. Triethylamine (592 µl) was added to the reaction mixture, the resulting mixture was further stirred for 10 minutes, then saturated aqueous sodium hydrogencarbonate was added to the mixture, the resulting mixture was warmed to room temperature, chloroform was added to the mixture, and the layers were separated. The organic layer was dried over anhydrous magnesium sulfate, and filtered, and then the filtrate was concentrated under reduced pressure to obtain a crude product of 9-ketone compound. This crude product was dissolved in methanol (4.1 ml), and the resulting solution was stirred under reflux by heating for 5 hours. The reaction mixture was concentrated under reduced pressure, and the resulting residue was purified by silica gel column chromatography (ethyl acetate:methanol:28% aqueous ammonia=10:1:0.1 to 5:1:0.1) to obtain the compound shown in Table 1 (167 mg).

Example 5

(1) By using the compound obtained in Example 3, (3) (100 mg) as a starting material, a 9-ketone compound (71.2 mg) was obtained in the same manner as that of Example 4.
(2) By using the compound obtained in (1) mentioned above (71.2 mg), and the compound obtained in Reference Example 3 (113.3 mg) as starting materials, the compound shown in Table 1 (51.1 mg) was obtained in the same manner as that of Example 3, (4).

Example 6

The compound obtained in Example 4 (10 mg), hydroxylamine hydrochloride (3.7 mg), and imidazole (4.37 mg) were dissolved in methanol, and the resulting solution was stirred at 65° C. for 2.5 hours. The reaction mixture was concentrated under reduced pressure, saturated aqueous ammonium chloride and chloroform were added to the resulting residue, and the layers were separated. The organic layer was dried over anhydrous magnesium sulfate, and filtered, then the filtrate was concentrated under reduced pressure, and the resulting residue was purified by preparative thin layer chromatography (chloroform:methanol:28% aqueous ammonia=7:1:0.1) to obtain the compound shown in Table 1 (3.3 mg).

Example 7

By using the compound obtained in Example 5 (10 mg) as a starting material, the compound shown in Table 1 (2.3 mg) was obtained in the same manner as that of Example 6.

Example 8

The compound obtained in Example 4 (20 mg) was dissolved in methanol (400 µl), ammonium acetate (65.9 mg), and sodium cyanoborohydride (21.5 mg) were added to the solution, and the resulting mixture was stirred at 65° C. for 11.5 hours. Saturated aqueous sodium hydrogencarbonate and ethyl acetate were added to the reaction mixture, the layers were separated, and the organic layer was dried over anhydrous magnesium sulfate, and filtered. The filtrate was concentrated under reduced pressure, and the resulting residue was purified by preparative thin layer chromatography (chloroform:methanol:28% aqueous ammonia=5:1:0.1) to obtain the compound shown in Table 1 (3.2 mg).

Example 9

By using the compound obtained in Example 5 (30 mg) as a starting material, the compound shown in Table 1 (5.5 mg) was obtained in the same manner as that of Example 8.

Example 10

A preparation method of the compound represented by the formula (C) is shown below.

[Formula 19]

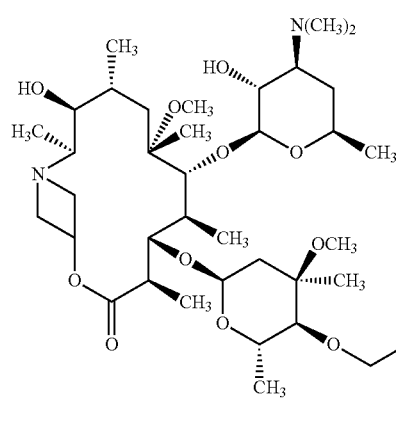
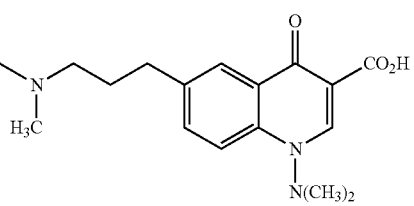

Formula (C)

Example 10

(1) A solution of tris(dibenzylideneacetone)dipalladium (10 mg) and 1,4-bis(diphenylphosphino)butane (9.3 mg) in tetrahydrofuran (1 ml) was degassed, the system was substituted with nitrogen, then a solution of the compound obtained in Example 2, (2) (100 mg) in tetrahydrofuran (2 ml) was added to the reaction mixture, the reaction mixture was degassed, and the system was substituted with nitrogen. Allyl t-butyl carbonate (34.5 mg) was added to the reaction mixture, the resulting mixture was degassed, the system was substituted with nitrogen, and then the mixture was stirred at 70° C. for 5 hours. The reaction mixture was concentrated under reduced pressure, and then the resulting residue was purified by silica gel column chromatography (chloroform:methanol=10:1 to hexane:acetone:triethylamine=30:10:0.2) to obtain an allyl compound (78.5 mg).

(2) The compound obtained in (1) mentioned above (75 mg) was dissolved in a mixed solvent of tetrahydrofuran and distilled water (2:1, 7.5 ml), 4-methylmorpholine N-oxide (45.9 mg), and 4% aqueous osmium tetroxide (0.1 ml) were added to the solution, and the resulting mixture was stirred at room temperature for 5 hours. Saturated aqueous sodium hydrogencarbonate and powdery sodium hydrogensulfite were added to the reaction mixture, and the resulting mixture was extracted with ethyl acetate. The organic layer was concentrated under reduced pressure, and the resulting residue was purified by silica gel column chromatography (chloroform:methanol:28% aqueous ammonia=10:1:0.1) to obtain a diol compound (58.7 mg).

(3) The compound obtained in (2) mentioned above (45 mg) was dissolved in chloroform (3 ml), 90% lead tetraacetate (22.4 mg) was added to the solution under ice cooling, and the resulting mixture was stirred at room temperature for 20 minutes. A solution of ethyl 6-(3-methylaminopropyl)-1-(dimethylamino)-4-oxo-1,4-dihydro-3-quinolinecarboxylate (15.0 mg) obtained by the method described in the publication (International Patent Publication WO98/30549) in chloroform (1 ml) and sodium triacetoxyborohydride (11.5 mg) were successively added to the reaction mixture, and the resulting mixture was stirred at room temperature for 2 hours. Saturated aqueous sodium hydrogencarbonate was added to the reaction mixture, the resulting mixture was extracted with chloroform, and the organic layer was concentrated under reduced pressure. The resulting residue was purified by preparative thin layer chromatography (chloroform:methanol:28% aqueous ammonia=10:1:0.1) to obtain an alkyl compound (35.1 mg).

(4) The compound obtained in (3) mentioned above (15 mg) was dissolved in tetrahydrofuran (1 ml), hydrogen fluoride-pyridine complex (2.0 mg) was added to the solution, and the resulting mixture was stirred overnight at room temperature. 5 N Aqueous sodium hydroxide was added to the reaction mixture, the resulting mixture was extracted with chloroform, and the organic layer was concentrated under reduced pressure. The resulting residue was purified by preparative thin layer chromatography (chloroform:methanol:28% aqueous ammonia=10:1:0.1) to obtain a deprotected compound (7.0 mg).

(5) The compound obtained in (4) mentioned above (7.0 mg) was dissolved in tetrahydrofuran (0.5 ml), 0.5 N aqueous lithium hydroxide was added to the solution, and the resulting mixture was stirred at room temperature for 4 hours. Dry ice powder was added portionwise to the reaction mixture, and then the reaction mixture was concentrated under reduced pressure. Chloroform and distilled water were added to the resulting residue for extraction, and the organic layer was concentrated under reduced pressure to obtain the compound represented by the formula (C) (5.5 mg).

MS (ESI) m/z 1018.6 [M+H]$^+$ $^1$H-NMR (600 MHz, CDCl$_3$) δ (ppm): 0.88 (d, J=6.88 Hz, 3H), 1.00 (d, J=6.88 Hz, 3H), 1.12 (d, J=7.34 Hz, 3H), 1.13-1.16 (m, 110, 1.17 (d, J=5.96 Hz, 3H), 1.20-1.30 (m, 9H), 1.34-1.37 (m, 1H), 1.37 (s, 3H), 1.50-1.59 (m, 2H), 1.79-1.88 (m, 2H), 2.10-2.17 (m, 1H), 2.22-2.29 (m, 9H), 2.33-2.46 (m, 4H), 2.49-2.63 (m, 3H), 2.71-3.00 (m, 6H), 2.97 (s, 6H), 2.99-3.04 (m, 1H), 3.11-3.21 (m, 3H), 3.32 (s, 3H), 3.34 (s, 3H), 3.37-3.43 (m, 1H), 3.55-3.60 (m, 1H), 3.63-3.81 (m, 4H), 3.86 (d, J=5.96 Hz, 1H), 4.22-4.31 (m, 1H), 4.59 (d, J=6.88 Hz, 1H), 4.62 (t, J=4.36 Hz, 1H), 4.86-4.95 (m, 1H), 7.66 (d, J=8.71 Hz, 1H), 8.16 (d, J=8.25 Hz, 1H), 8.29 (s, 1H), 9.02 (s, 1H)

Examples 11 to 14

Preparation methods of the compounds represented by the formula (D) having X defined in Table 2 are shown below.

[Formula 20]

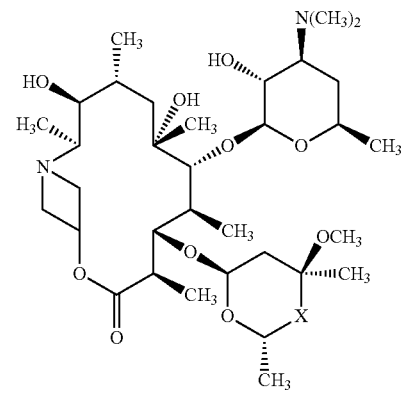

Formula (D)

TABLE 2

| Example | Reference Example | X | ESI MS (M + H) | $^1$H-NMR, CDCl$_3$, δ (ppm) |
|---|---|---|---|---|
| 11 | | ![structure with OH] | 675.4 | (600 MHz): 0.92-0.99 (m, 3 H) 1.08 (d, J = 5.96 Hz, 3 H) 1.13 (d, J = 7.34 Hz, 3 H) 1.17-1.30 (m, 8 H) 1.31 (d, J = 6.88 Hz, 3 H) 1.37 (d, J = 6.42 Hz, 3 H) 1.45 (br. s., 3 H) 1.60-1.63 (m, 1 H) 1.64-1.69 (m, 1 H) 1.74-1.83 (m, 1 H) 1.98-2.06 (m, 1 H) 2.16-2.23 (m, 2 H) 2.28 (s, 6 H) 2.36 (d, J = 15.13 Hz, 1 H) 2.40-2.45 (m, 1 H) 2.50-2.58 (m, 1 H) 2.78-2.84 (m, 1 H) 3.03 (t, J = 9.86 Hz, 1 H) 3.17-3.41 (m, 5 H) 3.32 (s, 3 H) 3.43 (s, 1 H) 3.45-3.52 (m, 1 H) 3.73 (d, J = 5.96 Hz, 1 H) 4.04-4.10 (m, 1 H) 4.38-4.42 (m, 2 H) 4.72-4.75 (m, 1 H) 4.99 (d, J = 5.04 Hz, 1 H) |

| Example | Reference Example | X | ESI MS (M + H) | 1H-NMR, CDCl3, δ (ppm) |
|---|---|---|---|---|
| 12 | 3 | (structure) | 923.6 | (600 MHz): 0.91-0.97 (m, 6 H) 1.08 (d, J = 6.42 Hz, 3 H) 1.14 (d, J = 7.34 Hz, 3 H) 1.15-1.33 (m, 16 H) 1.42-1.46 (m, 4 H) 1.52-1.56 (m, 1 H) 1.65-1.70 (m, 1 H) 1.73-1.80 (m, 1 H) 1.99-2.05 (m, 1 H) 2.16-2.22 (m, 1 H) 2.25 (s, 6 H) 2.36-2.66 (m, 9 H) 2.79-2.84 (m, 1 H) 3.18-3.31 (m, 7 H) 3.32 (s, 3 H) 3.63-3.68 (m, 1 H) 3.74-3.78 (m, 1 H) 3.85 (s, 3 H) 4.35-4.44 (m, 3 H) 4.47 (d, J = 6.88 Hz, 1 H) 4.55 (d, J = 9.63 Hz, 1 H) 4.72-4.75 (m, 1 H) 5.02 (d, J = 4.59 Hz, 1 H) 5.51 (br. s., 1 H) 6.87 (d, J = 8.25 Hz, 1 H) 6.92 (t, J = 7.57 Hz, 1 H) 7.19-7.23 (m, 1 H) 7.28 (d, J = 7.79 Hz, 1 H) |
| 13 | 3 | (structure) | 909.6 | (600 MHz): 0.92-0.99 (m, 6 H) 1.06-1.13 (m, 12 H) 1.18-1.22 (m, 6 H) 1.22-1.27 (m, 2 H) 1.28 (d, J = 6.88 Hz, 3 H) 1.31 (d, J = 6.88 Hz, 3 H) 1.44 (br. s., 3 H) 1.59-1.64 (m, 1 H) 1.72-1.80 (m, 1 H) 1.94-2.05 (m, 2 H) 2.15-2.21 (m, 1 H) 2:27 (s, 6 H) 2.29-2.33 (m, 1 H) 2.40-2.64 (m, 8 H) 2.76-2.87 (m, 2 H) 3.16-3.44 (m, 5 H) 3.28 (s, 3 H) 3.48-3.54 (m, 1 H) 3.74 (d, J = 7.34 Hz, 1 H) 3.81 (s, 3 H) 4.23-4.27 (m, 1 H) 4.34-4.39 (m, 2 H) 4.41 (d, J = 6.88 Hz, 1 H) 4.73 (br. s., 1 H) 5.04 (d, J = 4.58 Hz, 1 H) 6.86 (d, J = 7.79 Hz, 1 H) 6.93 (t, J = 7.11 Hz, 1 H) 7.18-7.22 (m, 1 H) 7.32 (dd, J = 7.57, 1.60 Hz, 1 H) |
| 14 | 26 | (structure) | 895.5 | (500 MHz): 0.94 (d, J = 6.31 Hz, 3 H) 1.05-1.12 (m, 9 H) 1.15-1.26 (m, 7 H) 1.31 (d, J = 7.13 Hz, 3 H) 1.39-1.52 (m, 10 H) 1.58-1.65 (m, 1 H) 1.71-1.80 (m, 1 H) 1.92-2.05 (m, 2 H) 2.12-2.35 (m, 5 H) 2.28 (s, 6 H) 2.38-2.47 (m, 1 H) 2.51-2.59 (m, 1 H) 2.61-2.67 (m, 2 H) 2.74-2.84 (m, 1 H) 2.88 (d, J = 13.44 Hz, 1 H) 3.16-3.40 (m, 6 H) 3.26 (s, 3 H) 3.45-3.53 (m, 1 H) 3.73 (d, J = 7.68 Hz, 1 H) 3.87 (s, 3 H) 4.24 (q, J = 6.31 Hz, 1 H) 4.33-4.40 (m, 2 H) 4.70-4.76 (m, 1 H) 5.01-5.05 (m, 1 H) 6.88-6.95 (m, 2 H) 7.21-7.26 (m, 2 H) |

Example 11

(1) By using the compound obtained in Reference Example 2 (5.0 g) as a starting material, a cyclized compound (304 mg) was obtained in the same manners as those of Example 1 (1), (2), and Example 2, (1).

(2) By using the compound obtained in (1) mentioned above (91 mg) as a starting material, the compound shown in Table 2 (46.5 mg) was obtained in the same manner as that of Example 1, (3).

Example 12

(1) By using the compound obtained in Example 11, (1) (300 mg) as a starting material, a 4"-hydroxy compound (157 mg) was obtained in the same manner as that of Example 2, (2).

(2) By using the compound obtained in (1) mentioned above (30 mg) as a starting material, an imidazole compound (33 mg) was obtained in the same manner as that of Example 2, (3).

(3) By using the compound obtained in (2) mentioned above (33 mg) and the compound obtained in Reference Example 3 (15 mg) as starting materials, the compound shown in Table 2 (14 mg) was obtained in the same manners as those of Example 2, (4), and Example 1, (3).

Example 13

(1) By using the compound obtained in Example 12, (1) (50 mg) as a starting material, a 4"-epoxy compound (19 mg) was obtained in the same manners as those of Example 3 (1), (2), and Example 1, (3).

(2) The compound obtained in (1) mentioned above (19 mg), and the compound obtained in Reference Example 3 (18 mg) were dissolved in ethanol (0.2 ml), and the resulting mixture was stirred overnight at 100° C. in a sealed tube. The reaction mixture was concentrated under reduced pressure, and the resulting residue was purified by preparative thin layer chromatography (chloroform:methanol: 28% aqueous ammonia=10:1:0.1) to obtain the compound shown in Table 2 (9.6 mg).

Example 14

By using the compound obtained in Example 13, (1) (50 mg), and the compound obtained in Reference Example 26 (60.7 mg) as starting materials, the compound shown in Table 2 (39.9 mg) was obtained in the same manner as that of Example 13, (2).

Examples 15 to 29

Preparation methods of the compounds represented by the formula (E) having R defined in Tables 3-1 and 3-2 are shown below.

[Formula 21]

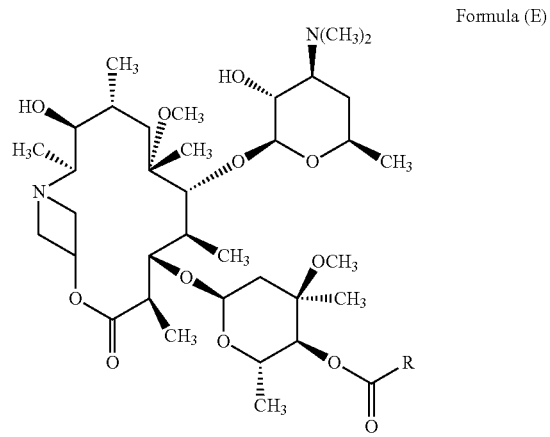

Formula (E)

TABLE 3-1

| Example | Reference Example | R | ESI MS (M + H) | 1H-NMR, CDCl3, δ (ppm) |
|---|---|---|---|---|
| 15 | 4 | 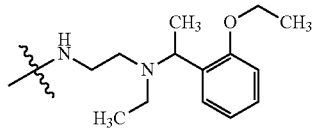 | 951.5 | (600 MHz): 0.88 (d, J = 7.34 Hz, 3 H) 1.01 (d, J = 6.42 Hz, 3 H) 1.08-1.27 (m, 19 H) 1.28-1.46 (m, 10 H) 1.47-1.70 (m, 2 H) 2.09-2.17 (m, 1 H) 2.21-2.33 (m, 6 H) 2.35-2.71 (m, 9 H) 2.85-2.98 (m, 3 H) 2.99-3.06 (m, 1 H) 3.11-3.28 (m, 3 H) 3.29-3.38 (m, 6 H) 3.38-3.43 (m, 1 H) 3.55-3.61 (m, 1 H) 3.70 (d, J = 9.63 Hz, 1 H) 3.73-3.82 (m, 1 H) 3.86-3.92 (m, 1 H) 3.96-4.12 (m, 3 H) 4.35-4.41 (m, 1 H) 4.50 (d, J = 10.09 Hz, 1 H) 4.57-4.61 (m, 1 H) 4.61-4.67 (m, 1 H) 4.96-5.02 (m, 1 H) 6.81-6.95 (m, 2 H) 7.14-7.22 (m, 1 H) 7.25-7.30 (m, 1 H) |
| 16 | 5 | 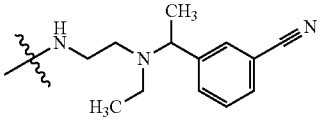 | 932.5 | (600 MHz): 0.89 (d, J = 5.96 Hz, 3 H) 0.95-1.04 (m, 6 H) 1.08-1.22 (m, 12 H) 1.19-1.24 (m, 1 H) 1.24 (d, J = 6.42 Hz, 3 H) 1.30-1.40 (m, 7 H) 1.54-1.69 (m, 2 H) 2.08-2.17 (m, 1 H) 2.22-2.65 (m, 9 H) 2.29 (br. s., 6 H) 2.86-2.98 (m, 3 H) 2.99-3.06 (m, 1 H) 3.10-3.27 (m, 3 H) 3.28-3.37 (m, 6 H) 3.37-3.44 (m, 1 H) 3.55-3.62 (m, 1 H) 3.65-3.77 (m, 2 H) 3.84-3.93 (m, 2 H) 4.31-4.44 (m, 1 H) 4.49-4.55 (m, 1 H) 4.56-4.67 (m, 2 H) 4.95-5.03 (m, 1 H) 7.41 (t, J = 7.34 Hz, 1 H) 7.53 (d, J = 7.79 Hz, 1 H) 7.57 (d, J = 7.79 Hz, 1 H) 7.60 (br. s., 1 H) |
| 17 | 6 | 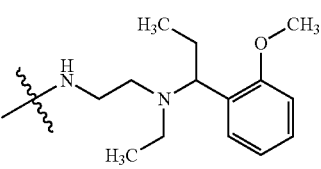 | 951.7 | (600 MHz): 0.75-0.84 (m, 3 H) 0.88 (d, J = 6.88 Hz, 3 H) 1.01 (d, J = 6.42 Hz, 3 H) 1.08-1.30 (m, 19 H) 1.33-1.41 (m, 4 H) 1.55-1.90 (m, 4 H) 2.10-2.17 (m, 1 H) 2.19-2.69 (m, 9 H) 2.21-2.33 (m, 6 H) 2.88-2.98 (m, 3 H) 2.99-3.06 (m, 1 H) 3.10-3.25 (m, 3 H) 3.30-3.33 (m, 3 H) 3.34-3.38 (m, 3 H) 3.38-3.43 (m, 1 H) 3.56-3.62 (m, 1 H) 3.66-3.72 (m, 1 H) 3.80 (br. s., 3 H) 3.81-3.86 (m, 1 H) 3.86-3.92 (m, 1 H) 4.14-4.21 (m, 1 H) 4.34-4.44 (m, 1 H) 4.52 (d, J = 9.63 Hz, 1 H) 4.58-4.67 (m, 2 H) 4.97-5.03 (m, 1 H) 6.83-6.97 (m, 2 H) 7.16-7.24 (m, 2 H) |
| 18 | 7 | 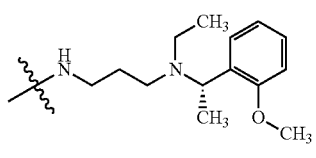 | 951 FAB MASS | (400 MHz): 0.90 (t, J = 7.1 Hz, 3 H) 1.03 (d, J = 7.1 Hz, 3 H) 1.05-1.30 (m, 20 H) 1.31-1.42 (m, 6 H) 1.53-1.77 (m, 4 H) 2.14 (m, 1 H) 2.27 (br s, 1 H) 2.31 (s, 6 H) 2.34-2.75 (m, 7 H) 2.84-2.99 (m, 3 H) 3.09-3.25 (m, 4 H) 3.26-3.39 (m, 7 H) 3.44 (br s, 1 H) 3.54-3.64 (m, 1 H) 3.65-3.78 (m, 2 H) 3.83 (s, 3 H) 3.90 (d, J = 6.1 Hz, 1 H) 4.30-4.50 (m, 2 H) 4.54 (d, J = 10.0 Hz, 1 H) 4.62 (d, J = 7.1 Hz, 1 H) 4.65 (t, J = 4.4 Hz, 1 H) 4.94 (br s, 1 H) 4.98 (d, J = 4.9 Hz, 1 H) 5.80 (br s, 1 H) 6.87 (d, J = 8.1 Hz, 1 H) 6.95 (t, J = 7.6 Hz, 1 H) 7.23-7.32 (m, 2 H) |
| 19 | 8 | 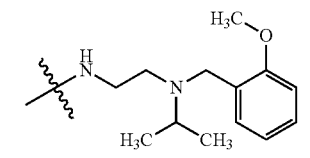 | 937 | (400 MHz): 0.94 (d, J = 8.00 Hz, 3 H) 1.02 (d, J = 6.60 Hz, 3 H) 1.12 (d, J = 7.30 Hz, 3 H) 1.17 (d, J = 7.00 Hz, 3 H) 1.21-1.44 (m, 14 H) 1.59 (dd, J = 15.1, 4.90 Hz, 1 H) 1.63-1.70 (m, 1 H) 2.10-2.58 (m, 12 H) 2.72-3.07 (m, 7 H) 3.10-3.25 (m, 3 H) 3.29 (s, 3 H) 3.34 (s, 3 H) 3.44-3.55 (m, 1 H) 3.62 (d, J = 9.80 Hz, 1 H) 3.78 (q, J = 7.30 Hz, 1H) 3.99-4.12 (m, 1 H) 4.50 (d, J = 7.00 Hz, 1 H) 4.88-5.10 (m, 4 H) 5.68-5.84 (m, 1 H) 6.77 (d, J = 8.24 Hz, 1 H) 7.09 (d, J = 7.97 Hz, 1 H) 7.27-7.29 (m, 1 H) |
| 20 | 9 | 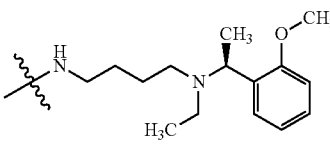 | 955 FAB MASS | (400 MHz): 0.90 (t, J = 7.1 Hz, 3 H) 1.02 (d, J = 6.6 Hz, 3 H) 1.14 (d, J = 7.6 Hz, 3 H) 1.15-1.40 (m, 20 H) 1.46 (m, 4 H) 1.60-1.71 (m, 2 H) 2.30 (s, 6 H) 2.37-2.74 (m, 7 H) 2.83-2.99 (m, 3 H) 3.03-3.25 (m, 6 H) 3.29-3.37 (m, 7 H) 3.38-3.46 (m, 1 H) 3.60 (dd, J = 8.5, 4.6 Hz, 1 H) 3.64-3.75 (m, 2 H) 3.81 (s, 3 H) 3.89 (d, J = 6.3 Hz, 1 H) 4.37-4.52 (m, 2 H) 4.63 (d, J = 9.8 Hz, 1 H) 4.68 (d, J = 7.1 Hz, 1 H) 4.74 (t, J = 4.6 Hz, 1H) 4.80-4.95 (m, 2 H) 4.98 (d, J = 4.9 Hz, 1 H) 6.86 (d, J = 8.1 Hz, 1H) 6.94 (t, J = 7.3 Hz, 1H) 7.16-7.23 (m, 1 H) |
| 21 | 10 | 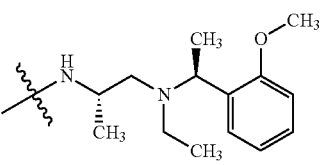 | 951 | (400 MHz): 0.89 (d, J = 7.32 Hz, 3 H) 0.89-0.97 (m, 3 H) 1.02 (d, J = 6.59 Hz, 3 H) 1.09-1.36 (m, 11 H) 1.17 (s, 3 H) 1.19 (d, J = 6.35 Hz, 3 H) 1.25 (d, J = 7.08 Hz, 3 H) 1.30 (d, J = 6.59 Hz, 3 H) 1.38 (s, 3 H) 1.52-1.63 (m, 1 H) 1.67 (dd, J = 14.9, 5.12 Hz, 1 H) 2.09-2.20 (m, 1 H) 2.29 (s, 6 H) 2.34-2.66 (m, 7 H) 2.83-2.99 (m, 3 H) 2.99-3.06 (m, 1 H) 3.13-3.24 (m, 3 H) 3.28-3.46 (m, 2 H) 3.32 (s, 3 H) 3.36 (s, 3 H) 3.56-3.74 (m, 4 H) 3.84 (s, 3 H) 3.90 (d, J = 6.35 Hz, 1 H) 4.29-4.42 (m, 2 H) 4.54 (d, J = 9.76 Hz, 1 H) 4.57 (d, J = 7.32 Hz, 1 H) 4.64 (t, J = 4.39 Hz, 1 H) 4.85-4.99 (m, 1 H) 4.98 (d, J = 4.89 Hz, 1 H) 5.12-5.26 (m, 1 H) 6.86 (d, J = 8.30 Hz, 1 H) 6.92 (t, J = 7.33 Hz, 1 H) 7.18-7.35 (m, 2 H) |
| 22 | 11 | 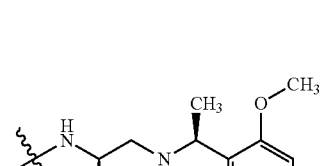 | 951 | (400 MHz): 0.89 (d, J = 7.32 Hz, 3 H) 0.90-0.98 (m, 3 H) 1.02 (d, J = 6.59 Hz, 3 H) 1.09-1.36 (m, 8 H) 1.09 (d, J = 5.37 Hz, 3 H) 1.14 (d, J = 7.08 Hz, 3 H) 1.18 (s, 3 H) 1.25 (d, J = 7.08 Hz, 3 H) 1.31 (d, J = 6.83 Hz, 3 H) 1.38 (s, 3 H) 1.60-1.71 (m, 2 H) 2.09-2.20 (m, 1 H) 2.27-2.64 (m, 7 H) 2.31 (s, 6 H) 2.87-3.07 (m, 3 H) 3.12-3.45 (m, 5 H) 3.33 (s, 3 H) 3.36 (s, 3 H) 3.57-3.93 (m, 5 H) 3.83 (s, 3 H) 4.34-4.45 (m, 3 H) 4.52 (d, J = 9.03 Hz, 1 H) 4.61-4.68 (m, 2 H) 4.88-4.99 (m, 1 H) 5.01 (d, J = 4.15 Hz, 1 H) 5.14-5.23 (m, 1 H) 6.88 (d, J = 7.81 Hz, 1 H) 6.93 (t, J = 7.33 Hz, 1 H) 7.18-7.32 (m, 2 H) |

TABLE 3-2

| Example | Reference Example | R | ESI MS (M + H) | $^1$H-NMR, CDCl$_3$, δ (ppm) |
|---|---|---|---|---|
| 23 | 19 | (2-methoxyphenyl)ethyl-NH-CH₂CH₂-NH- | 909 | (400 MHz): 0.89 (d, J = 7.08 Hz, 3 H) 1.02 (d, J = 6.59 Hz, 3 H) 1.14 (d, J = 7.57 Hz, 3 H) 1.17-1.37 (m, 11 H) 1.25 (d, J = 7.08 Hz, 3 H) 1.35 (d, J = 6.83 Hz, 3 H) 1.38 (s, 3 H) 1.57-1.71 (m, 2 H) 2.09-2.19 (m, 1 H) 2.31 (s, 6 H) 2.45 (d, J = 15.1 Hz, 1 H) 2.51-2.66 (m, 4 H) 2.86-3.08 (m, 4 H) 3.12-3.45 (m, 7 H) 3.33 (s, 3 H) 3.36 (s, 3 H) 3.56-3.64 (m, 1 H) 3.66-3.77 (m, 2 H) 3.83 (s, 3 H) 3.89 (d, J = 6.10 Hz, 1 H) 4.06 (q, J = 6.59 Hz, 1 H) 4.32-4.44 (m, 1 H) 4.52 (d, J = 9.77 Hz, 1 H) 4.60 (d, J = 7.08 Hz, 1 H) 4.62 (t, J = 4.64 Hz, 1 H) 4.87-4.97 (m, 1 H) 4.99 (d, J = 4.88 Hz, 1 H) 5.27-5.36 (m, 1 H) 6.87 (d, J = 8.55 Hz, 1 H) 6.93 (t, J = 7.57 Hz, 1 H) 7.17-7.28 (m, 2 H) |
| 24 | 20 | (2-methoxyphenyl)ethyl-N(CH₃)-CH₂CH₂-NH- | 923 | (400 MHz): 0.89 (d, J = 7.08 Hz, 3 H) 1.02 (d, J = 6.59 Hz, 3 H) 1.14 (d, J = 7.57 Hz, 3 H) 1.17-1.37 (m, 11 H) 1.25 (d, J = 6.83 Hz, 3 H) 1.33 (d, J = 6.83 Hz, 3 H) 1.38 (s, 3 H) 1.59-1.72 (m, 2 H) 2.10-2.15 (m, 1 H) 2.14 (s, 3 H) 2.29 (s, 6 H) 2.40-2.64 (m, 5 H) 2.85-3.07 (m, 4 H) 3.13-3.45 (m, 7 H) 3.34 (s, 3 H) 3.37 (s, 3 H) 3.56-3.65 (m, 1 H) 3.66-3.78(m, 2 H) 3.85 (s, 3 H) 3.87-3.92 (m, 1 H) 4.16-4.28 (m, 1 H) 4.36-4.45 (m, 1 H) 4.53 (d, J = 9.76 Hz, 1 H) 4.60 (d, J = 7.32 Hz, 1 H) 4.64 (t, J = 4.64 Hz, 1 H) 4.87-4.97 (m, 1 H) 4.99 (d, J = 4.64 Hz, 1 H) 5.38-5.51 (m, 1 H) 6.88 (d, J = 8.06 Hz, 1 H) 6.93 (t, J = 7.33 Hz, 1 H) 7.19-7.30 (m, 2 H) |
| 25 | | (CH₃)₂N-CH₂CH₂-NH- | 803 | (400 MHz): 0.89 (d, J = 7.08 Hz, 3 H) 1.02 (d, J = 6.84 Hz, 3 H) 1.15 (d, J = 7.57 Hz, 3 H) 1.16-1.28 (m, 7 H) 1.19 (d, J = 7.08 Hz, 3 H) 1.34-1.40 (m, 1 H) 1.38 (s, 3 H) 1.62-1.72 (m, 2 H) 2.09-2.18 (m, 1 H) 2.22 (s, 6 H) 2.29-2.48 (m, 3 H) 2.32 (s, 6 H) 2.53-2.65 (m, 2 H) 2.87-3.07 (m, 4 H) 3.14-3.45 (m, 7 H) 3.33 (s, 3 H) 3.36 (s, 3 H) 3.56-3.64 (m, 1 H) 3.67-3.78 (m, 2 H) 3.89 (d, J = 6.10 Hz, 1 H) 4.32-4.43 (m, 1 H) 4.52 (d, J = 9.76 Hz, 1 H) 4.62 (d, J = 7.08 Hz, 1 H) 4.64 (t, J = 5.13 Hz, 1 H) 4.88-4.97 (m, 1 H) 5.00 (d, J = 4.88 Hz, 1 H) 5.31 (t, J = 4.64 Hz, 1 H) |
| 26 | 12 | (2-methoxyphenyl)ethyl-N(Et)-CH₂CH₂-NH- | 937 FAB MASS | (400 MHz): 0.89 (d, J = 7.1 Hz, 3 H) 0.93 (t, J = 7.1 Hz, 3 H) 1.02 (d, J = 6.9 Hz, 3 H) 1.10-1.23 (m, 10 H) 1.21 (d, J = 7.1 Hz, 3 H) 1.30 (d, J = 6.8 Hz, 3 H) 1.38 (s, 3 H) 1.57-1.65 (m, 1 H) 1.67 (dd, J = 15.3, 5.3 Hz, 1 H) 2.08-2.20 (m, 1 H) 2.28 (s, 6 H) 2.45 (d, J = 14.9 Hz, 1 H) 2.51-2.66 (m, 4 H) 2.86-3.00 (m, 2 H) 3.00-3.07 (m, 2 H) 3.13-3.24 (m, 3 H) 3.25-3.31 (m, 2 H) 3.34 (s, 3 H) 3.36 (s, 3 H) 3.39-3.44 (m, 1 H) 3.55-3.64 (m, 1 H) 3.68-3.82 (m, 2 H) 3.85 (s, 3 H) 3.90 (d, J = 6.3 Hz, 1 H) 4.32-4.45 (m, 2 H) 4.53 (d, J = 9.7 Hz, 1 H) 4.61-4.67 (m, 2 H) 4.90-4.98 (m, 1 H) 5.01 (d, J = 4.9 Hz, 1 H) 5.53 (br s, 1 H) 6.87 (d, J = 8.3 Hz, 1 H) 6.94 (t, J = 7.3 Hz, 1 H) 7.19-7.31 (m, 2 H) |
| 27 | 13 | (2-methoxyphenyl)ethyl-N(Et)-C(O)-CH₂-NH- | 951 | (400 MHz): 0.74 (t, J = 7.1 Hz, 2.25 H) 0.84 (t, J = 7.1 Hz, 0.75 H) 0.91 (d, J = 7.1 Hz, 3 H) 1.04 (d, J = 6.8 Hz, 3 H) 1.15 (d, J = 7.6 Hz, 3H) 1.16-1.44 (m, 17 H) 1.52 and 1.56 (each d, J = 7.1 Hz, 3 H) 1.66 (dd, J = 14.9, 4.9 Hz, 1 H) 1.84 (d, J = 11.2 Hz, 1 H) 2.14 (m, 1 H) 2.37 (s, 6 H) 2.45 (d, J = 15.1 Hz, 1 H) 2.57-2.70 (m, 2 H) 2.83-3.14 (m, 6 H) 3.18-3.28 (m, 5 H) 3.34 (s, 3 H) 3.37 (s, 3 H) 3.49-3.66 (m, 2 H) 3.72 (d, J = 9.8 Hz, 1 H) 3.80 and 3.83(each s, 3 H) 3.90 (d, J = 5.6 Hz, 1 H) 4.00-4.20 (m, 1 H) 4.37-4.48 (m, 2 H) 4.50-4.58 (m, 1 H) 4.60-4.70 (m, 2 H) 5.03 (d, J = 4.6 Hz, 1 H) 5.17-5.97 (m, 2 H) 6.83-6.92 (m, 1 H) 6.94-7.04 (m, 1 H) 7.23-7.38 (m, 2 H) |
| 28 | 14 | (2-methoxyphenyl)ethyl-N(Et)-CH₂CH₂-N(CH₃)- | 951 FAB MASS | (400 MHz): 0.88 (d, J = 7.3 Hz, 3 H) 0.97-1.07 (m, 6 H) 1.10-1.35 (m, 20 H) 1.38 (m, 3 H) 1.49-1.70 (m, 2 H) 1.08-2.20 (m, 1 H) 2.18 (s, 3 H) 3.29 (s, 3 H) 2.43 (d, J = 15.1 Hz, 1 H) 2.43-2.80 (m, 6 H) 2.83 (s, 3 H) 2.88-3.07 (m, 4 H) 3.12-3.44 (m, 11 H) 3.56-3.79 (m, 3 H) 3.81 (s, 3 H) 3.89 (d, J = 5.9 Hz, 1 H) 4.30-4.47 (m, 2 H) 4.56 (d, J = 9.8 Hz, 1 H) 4.58-4.75 (m, 2 H) 4.92-5.05 (m, 2 H) 6.86 (d, J = 8.1 Hz, 1 H) 6.94 (d, J = 7.3 Hz, 1 H) 7.16-7.23 (m, 1 H) 7.33-7.39 (m, 1 H) |
| 29 | 15 | (3-hydroxyphenyl)ethyl-N(Et)-CH₂CH₂-NH- | 923.4 | (600 MHz): 0.89 (d, J = 6.88 Hz, 3 H) 0.97-1.05 (m, 6 H) 1.07-1.32 (m, 20 H) 1.38 (br. s., 3 H) 1.57-1.75 (m, 2 H) 2.10-2.18 (m, 1 H) 2.24-2.74 (m, 6 H) 2.37 (br. s., 6 H) 2.79-2.99 (m, 5 H) 3.00-3.05 (m, 1 H) 3.11-3.23 (m, 2 H) 3.26-3.44 (m, 3 H) 3.33 (s, 3 H) 3.41 (br. s., 3 H) 3.55-3.62 (m, 1 H) 3.66-3.80 (m, 3 H) 3.86 (d, J = 6.42 Hz, 1 H) 4.28-4.42 (m, 1 H) 4.53 (d, J = 10.09 Hz, 1 H) 4.57-4.66 (m, 2 H) 4.98 (d, J = 4.58 Hz, 1 H) 6.67-6.77 (m, 2 H) 6.95 (br. s., 1 H) 7.13 (t, J = 7.79 Hz, 1 H) |

In Examples 15 to 29, by using the compound obtained in Example 2, (3) and corresponding amine reagents, the compounds shown in Table 3 were synthesized in the same manners as those of Example 2, (4), and Example 1, (3).

Example 30

A preparation method of the compound represented by the formula (F) is shown below.

[Formula 22]

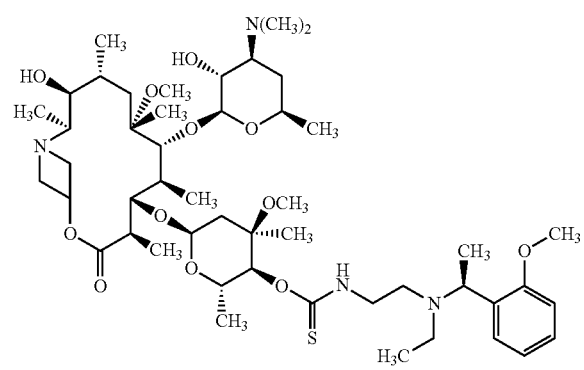

Formula (F)

Example 30

(1) The compound obtained in Example 2, (2) (35 mg), and 1,1'-thiocarbonyldiimidazole (27 mg) were dissolved in dimethylformamide (0.7 ml), sodium hydride (6.1 mg) was added to the solution, and the resulting mixture was stirred at room temperature for 1.5 hours. 1,1'. Thiocarbonyldiimidazole (84 mg), and sodium hydride (12.2 mg) were added to the reaction mixture, the resulting mixture was further stirred at room temperature for 27 hours, then 20% aqueous ammonium chloride and distilled water were added to the reaction mixture, and the resulting mixture was extracted with ethyl acetate. The organic layer was washed with distilled water and saturated brine, dried over anhydrous sodium sulfate, and filtered. The filtrate was concentrated under reduced pressure, and the resulting residue was purified by preparative thin layer chromatography (hexane:aqueous acetone=3:2) to obtain a thiocarbonylimidazole compound (16 mg).

(2) By using the compound obtained in (1) mentioned above (16 mg), and the compound obtained in Reference Example 3 (6.3 mg) as starting materials, the compound represented by the formula (F) (23 mg) was obtained in the same manners as those of Example 2, (4), and Example 1, (3).

MS (FAB): m/z=953 [M+H]$^+$ $^1$H-NMR (400 MHz, CDCl$_3$) δ (ppm): 0.86-0.98 (m, 6H), 1.02 (d, J=6.6 Hz, 3H), 1.09-1.18 (m, 10H), 1.18-1.36 (m, 9H), 1.38 (s, 3H), 1.45-1.51 (m, 1H), 1.68 (dd, J=15.1 Hz, J=5.1 Hz, 1H), 2.08-2.23 (m, 1H), 2.28 and 2.27 (each s, 6H), 2.38-2.654 (m, 5H), 2.68-2.79 (m, 15H), 2.84-3.05 (m, 4H), 3.12-3.24 (m, 5H), 3.32 (s, 3H), 3.34 and 3.36 (each s, 3H), 3.37-3.45 (m, 1H), 3.56-3.74 (m, 3H), 3.86 and 3.94 (each s, 3H), 3.87-3.92 (m, 1H), 4.33-4.43 (m, 1H), 4.44-4.54 (m, 1H), 4.58 (d, J=7.3 Hz, 1H), 4.61-4.70 (m, 2H), 4.85-5.04 (m, 2H), 5.44 and 5.50 (each d, J=9.7 Hz, 1H), 6.88 (d, J=7.6 Hz, 1H), 6.93 (t, J=7.6 Hz, 1H), 7.20-7.33 (m, 2H)

Examples 31 to 106

Preparation methods of the compounds represented by the formula (G) having R defined in Tables 4-1 to 4-11 are shown below.

[Formula 23]

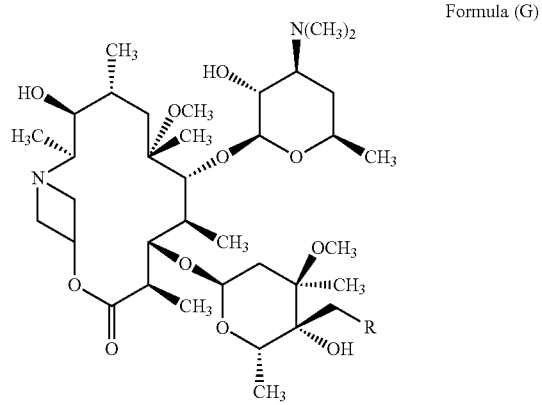

Formula (G)

TABLE 4-1

| Example | Reference Example | R | ESI MS (M + H) | $^1$H-NMR, CDCl$_3$, δ (ppm) |
|---|---|---|---|---|
| 31 | 16 | ![structure] | 932.6 | (600 MHz): 0.88 (d, J = 6.88 Hz, 3 H) 0.92-1.28 (m, 22 H) 1.33-1.40 (m, 4 H) 1.4 1-1.47 (m, 3 H) 1.59-1.68 (m, 1 H) 1.89-2.17 (m, 4 H) 2.27-2.35 (m, 6 H) 2.41-2.80 (m, 9 H) 2.84-2.93 (m, 3 H) 3.00-3.05 (m, 1 H) 3.13-3.50 (m, 11 H) 3.57-3.62 (m, 1 H) 3.65-3.71 (m, 1 H) 3.87-3.93 (m, 1 H) 4.07-4.40 (m, 2 H) 4.44-4.49 (m, 1 H) 4.63 (t, J = 4.81 Hz, 1 H) 4.93-5.02 (m, 2 H) 6.72-6.76 (m, 1 H) 7.03-7.07 (m, 1 H) 7.11-7.16 (m, 1 H) 7.16-7.19 (m, 1 H) 7.29 (d, J = 8.25 Hz, 1 H) 8.25 (br. s., 1 H) |

TABLE 4-1-continued

| Example | Reference Example | R | ESI MS (M + H) | ¹H-NMR, CDCl₃, δ (ppm) |
|---|---|---|---|---|
| 32 | 15 | [structure] | 909.6 | (600 MHz): 0.88 (d, J = 6.88 Hz, 3 H) 1.01 (d, J = 6.88 Hz, 3 H) 1.04 (t, J = 7.11 Hz, 3 H) 1.09 (d, J = 7.34 Hz, 3 H) 1.15 (s, 9 H) 1.25 (d, J = 6.88 Hz, 3 H) 1.24-1.35 (m, 2 H) 1.35 (d, J = 6.88 Hz, 3 H) 1.37 (s, 3 H) 1.65-1.73 (m, 1 H) 1.95-2.06 (m, 2 H) 2.06-2.18 (m, 2 H) 2.18-2.31 (m, 1 H) 2.34-2.75 (m, 7 H) 2.44 (s, 6 H) 2.81-2.98 (m, 4 H) 2.98-3.05 (m, 1 H) 3.10-3.21 (m, 2 H) 3.26-3.44 (m, 2 H) 3.31 (s, 3 H) 3.33 (s, 3 H) 3.48-3.56 (m, 1 H) 3.56-3.62 (m, 1 H) 3.64-3.69 (m, 1 H) 3.80 (q, J = 6.72 Hz, 1 H) 3.90 (d, J = 5.50 Hz, 1 H) 4.23 (q, J = 6.11 Hz, 1 H) 4.48 (d, J = 6.88 Hz, 1 H) 4.63 (t, J = 4.81 Hz, 1 H) 4.97-5.02 (m, 1 H) 6.66-6.75 (m, 2 H) 6.80 (d, J = 7.79 Hz, 1 H) 7.15 (t, J = 7.79 Hz, 1 H) |
| 33 | 4 | [structure] | 937.8 | (600 MHz): 0.87 (d, J = 7.34 Hz, 3 H) 0.95-1.04 (m, 6 H) 1.05-1.15 (m, 9 H) 1.16-1.32 (m, 10 H) 1.33-1.37 (m, 1 H) 1.36-1.39 (m, 3 H) 1.39-1.43 (m, 3 H) 1.58-1.65 (m, 1 H) 1.94-2.10 (m, 2 H) 2.09-2.18 (m, 1 H) 2.22-2.27 (m, 1 H) 2.27-2.30 (m, 6 H) 2.36-2.72 (m, 8 H) 2.79-2.92 (m, 4 H) 2.98-3.04 (m, 1 H) 3.10-3.24 (m, 3 H) 3.25-3.30 (m, 3 H) 3.36 (s, 3 H) 3.37-3.42 (m, 1 H) 3.44-3.53 (m, 1 H) 3.55-3.63 (m, 1 H) 3.65-3.73 (m, 1 H) 3.91 (d, J = 6.42 Hz, 1 H) 3.94-4.08 (m, 2 H) 4.17-4.27 (m, 1 H) 4.42 (q, J = 7.03 Hz, 1 H) 4.48 (d, J = 7.34 Hz, 1 H) 4.62 (t, J = 4.58 Hz, 1 H) 4.98-5.06 (m, 1 H) 6.83 (d, J = 8.25 Hz, 1 H) 6.87-6.94 (m, 1 H) 7.17 (t, J = 7.79 Hz, 1 H) 7.29 (d, J = 8.71 Hz, 1 H) |
| 34 | 5 | [structure] | 918.6 | (600 MHz): 0.88 (d, J = 6.88 Hz, 3 H) 0.97-1.03 (m, 6 H) 1.08-1.16 (m, 9 H) 1.18-1.21 (m, 3 H) 1.24 (d, J = 7.34 Hz, 3 H) 1.22-1.28 (m, 1 H) 1.30-1.35 (m, 4 H) 1.35-1.40 (m, 3 H) 1.62 (d, J = 12.38 Hz, 1 H) 1.94-2.09 (m, 2 H) 2.09-2.16 (m, 1 H) 2.22-2.26 (m, 1 H) 2.26-2.32 (m, 6 H) 2.40-2.66 (m, 8 H) 2.82-2.97 (m, 4 H) 2.99-3.05 (m, 1 H) 3.11-3.24 (m, 3 H) 3.28-3.31 (m, 3 H) 3.34-3.37 (m, 3 H) 3.37-3.42 (m, 1 H) 3.46-3.54 (m, 1 H) 3.56-3.62 (m, 1 H) 3.69 (d, J = 9.63 Hz, 1 H) 3.85-3.90 (m, 1 H) 3.91 (d, J = 6.42 Hz, 1 H) 4.25 (q, J = 6.42 Hz, 1 H) 4.47 (d, J = 7.34 Hz, 1 H) 4.62 (t, J = 4.81 Hz, 1 H) 5.02 (d, J = 5.04 Hz, 1 H) 7.38-7.43 (m, 1 H) 7.52 (d, J = 7.79 Hz, 1 H) 7.58 (d, J = 7.79 Hz, 1 H) 7.62 (s, 1 H) |
| 35 | 6 | [structure] | 937.5 | (600 MHz): 0.79-0.83 (m, 3 H) 0.87 (d, J = 7.34 Hz, 3 H) 1.00 (d, J = 6.88 Hz, 6 H) 1.07-1.16 (m, 9 H) 1.17-1.27 (m, 7 H) 1.32-1.40 (m, 4 H) 1.53-1.71 (m, 2 H) 1.78-1.90 (m, 1 H) 1.96-2.16 (m, 3 H) 2.24-2.34 (m, 2 H) 2.26-2.30 (m, 6 H) 2.41-2.49 (m, 1 H) 2.49-2.71 (m, 6 H) 2.83-2.94 (m, 4 H) 2.99-3.04 (m, 1 H) 3.12-3.24 (m, 3 H) 3.26-3.31 (m, 3 H) 3.34-3.37 (m, 3 H) 3.37-3.41 (m, 1 H) 3.47-3.54 (m, 1 H) 3.56-3.61 (m, 1 H) 3.67-3.72 (m, 1 H) 3.78 (s, 3 H) 3.90-3.93 (m, 1 H) 4.15-4.29 (m, 2 H) 4.47-4.52 (m, 1 H) 4.62 (t, J = 4.58 Hz, 1 H) 5.00-5.05 (m, 1 H) 6.87 (d, J = 8.25 Hz, 1 H) 6.88-6.94 (m, 1 H) 7.16-7.23 (m, 2 H) |
| 36 | 17 | [structure] | 937.6 | (600 MHz): 0.87 (d, J = 7.34 Hz, 3 H) 0.93 (t, J = 7.11 Hz, 3 H) 1.00 (d, J = 6.42 Hz, 3 H) 1.11 (t, J=3.67 Hz, 6 H) 1.15 (d, J = 6.42 Hz, 3 H) 1.19 (d, J = 5.96 Hz, 3 H) 1.19-1.22 (m, 1 H) 1.24 (d, J = 6.88 Hz, 3 H) 1.35 (d, J = 14.67 Hz, 1 H) 1.38 (s, 3 H) 1.45 (d, J = 5.04 Hz, 6 H) 1.58-1.63 (m, 1 H) 1.96-2.09 (m, 2 H) 2.10-2.17 (m, 1 H) 2.25 (d, J = 13.75 Hz, 1 H) 2.28 (s, 6 H) 2.39-2.67 (m, 8 H) 2.83-2.93 (m, 4 H) 2.97-3.03 (m, 1 H) 3.12-3.23 (m, 3 H) 3.29 (s, 3 H) 3.36 (s, 3 H) 3.37-3.41 (m, 1 H) 3.46-3.52 (m, 1 H) 3.56-3.61 (m, 1 H) 3.70 (dd, J = 9.63, 1.83 Hz, 1 H) 3.79 (s, 3 H) 3.92 (d, J = 6.42 Hz, 1 H) 4.23 (q, J = 5.96 Hz, 1 H) 4.49 (d, J = 7.34 Hz, 1 H) 4.62 (t, J = 4.58 Hz, 1 H) 4.91-4.97 (m, 1 H) 5.03 (d, J = 4.58 Hz, 1 H) 6.85-6.90 (m, 2 H) 7.16-7.21 (m, 1 H) 7.37 (dd, J = 8.25, 1.83 Hz, 1 H) |

TABLE 4-1-continued

| Example | Reference Example | R | ESI MS (M + H) | ¹H-NMR, CDCl₃, δ (ppm) |
|---|---|---|---|---|
| 37 | 18 | (structure: —NH–CH₂CH₂–N(Et)–CH(CH₃)–(2-ethylphenyl)) | 921.7 | (600 MHz): 0.87 (d, J = 6.88 Hz, 3 H) 0.94-1.25 (m, 24 H) 1.24-1.26 (m, 1 H) 1.27-1.31 (m, 3 H) 1.32-1.37 (m, 1 H) 1.38 (s, 3 H) 1.57-1.67 (m, 1 H) 1.93-2.20 (m, 3 H) 2.29 (br. s., 6 H) 2.34-2.73 (m, 9 H) 2.76-2.91 (m, 4 H) 2.99-3.05 (m, 1 H) 3.10-3.24 (m, 3 H) 3.24-3.30 (m, 3 H) 3.33-3.37 (m, 3 H) 3.37-3.44 (m, 1 H) 3.46-3.51 (m, 1 H) 3.55-3.63 (m, 1 H) 3.65-3.72 (m, 1 H) 3.86-3.94 (m, 1 H) 4.02-4.08 (m, 1 H) 4.08-4.14 (m, 1 H) 4.14-4.18 (m, 1 H) 4.19-4.24 (m, 1 H) 4.44-4.50 (m, 1 H) 4.60-4.65 (m, 1 H) 4.87-4.97 (m, 1 H) 4.98-5.04 (m, 1 H) 7.10-7.19 (m, 3 H) 7.32-7.41 (m, 1 H) |

TABLE 4-2

| Example | Reference Example | R | ESI MS (M + H) | ¹H-NMR, CDCl₃, δ (ppm) |
|---|---|---|---|---|
| 38 | 19 | (structure: —NH–CH₂CH₂–NH–CH(CH₃)–(2-methoxyphenyl)) | 895.5 | (600 MHz): 0.87 (d, J = 6.88 Hz, 3 H) 1.00 (d, J = 6.42 Hz, 3 H) 1.08-1.13 (m, 6 H) 1.15 (d, J = 6.42 Hz, 3 H) 1.18 (d, J = 6.42 Hz, 3 H) 1.19-1.22 (m, 1 H) 1.24 (d, J = 6.88 Hz, 3 H) 1.34 (d, J = 6.88 Hz, 3 H) 1.34-1.37 (m, 1 H) 1.38 (s, 3 H) 1.58-1.64 (m, 1 H) 1.96-2.01 (m, 1 H) 2.02-2.07 (m, 1 H) 2.09-2.17 (m, 1 H) 2.29 (s, 6 H) 2.29-2.33 (m, 1 H) 2.41-2.49 (m, 1 H) 2.50-2.61 (m, 3 H) 2.62-2.71 (m, 2 H) 2.82-2.94 (m, 4 H) 2.98-3.04 (m, 1 H) 3.11-3.24 (m, 3 H) 3.28 (s, 3 H) 3.35 (s, 3 H) 3.37-3.42 (m, 1 H) 3.46-3.54 (m, 1 H) 3.56-3.61 (m, 1 H) 3.67-3.72 (m, 1 H) 3.82 (s, 3 H) 3.90 (d, J = 5.96 Hz, 1 H) 4.07 (q, J = 6.88 Hz, 1 H) 4.26 (q, J = 6.27 Hz, 1 H) 4.47 (d. J = 7.34 Hz, 1 H) 4.62 (t, J = 4.81 Hz, 1 H) 5.01 (d, J = 3.67 Hz, 1 H) 6.86 (d, J = 8.25 Hz, 1 H) 6.91-6.95 (m, 1 H) 7.18-7.23 (m, 1 H) 7.23-7.28 (m, 1 H) |
| 39 | 20 | (structure: —NH–CH₂CH₂–N(CH₃)–CH(CH₃)–(2-methoxyphenyl)) | 909.5 | (600 MHz): 0.87 (d, J = 7.34 Hz, 3 H) 1.00 (d, J = 6.42 Hz, 3 H) 1.05-1.18 (m, 12 H) 1.18-1.26 (m, 1 H) 1.22-1.26 (m, 3 H) 1.27-1.31 (m, 3 H) 1.32-1.41 (m, 4 H) 1.57-1.65 (m, 1 H) 1.96-2.08 (m, 2 H) 2.09-2.15 (m, 1 H) 2.15-2.19 (m, 1 H) 2.22-2.28 (m, 1 H) 2.27-2.31 (m, 6 H) 2.37-2.73 (m, 6 H) 2.81-2.93 (m, 4 H) 2.97-3.05 (m, 1 H) 3.11-3.23 (m, 3 H) 3.26-3.30 (m, 3 H) 3.34-3.37 (m, 3 H) 3.37-3.43 (m, 1 H) 3.46-3.53 (m, 1 H) 3.55-3.61 (m, 1 H) 3.67-3.72 (m, 1 H) 3.81 (s, 3 H) 3.91 (d, J = 6.42 Hz, 1 H) 4.08-4.18 (m, 1 H) 4.24 (q, J = 6.11 Hz, 1 H) 4.47 (d, J = 7.34 Hz, 1 H) 4.62 (t, J = 4.81 Hz, 1 H) 5.02 (d, J = 4.58 Hz, 1 H) 6.86 (d, J = 8.25 Hz, 1 H) 6.93 (t, J = 8.02 Hz, 1 H) 7.20 (t, J = 7.57 Hz, 1 H) 7.31 (d, J = 7.34 Hz, 1 H) |
| 40 | 21 | (structure: —NH–CH₂CH₂–N(Et)–CH(CH₃)–(2-methoxy-3-pyridyl)) | 924.5 | (500 MHz): 0.86-0.91 (m, 3 H) 0.93-1.05 (m, 9 H) 1.06-1.29 (m, 16 H) 1.32-1.41 (m, 4 H) 1.52-1.66 (m, 1 H) 1.96-2.31 (m, 5 H) 2.29 (s, 6 H) 2.41-2.73 (m, 8 H) 2.84-2.95 (m, 4 H) 2.98-3.06 (m, 1 H) 3.12-3.45 (m, 10 H) 3.46-3.55 (m, 1 H) 3.56-3.63 (m, 1 H) 3.67-3.74 (m, 1 H) 3.89-3.97 (m, 4 H) 4.19-4.29 (m, 1 H) 4.45-4.53 (m, 1 H) 4.60-4.67 (m, 1 H) 5.00-5.06 (m, 1 H) 6.81-6.91 (m, 1 H) 7.54-7.60 (m, 1 H) 8.03-8.08 (m, 1 H) |
| 41 | 22 | (structure: —NH–CH₂CH₂–N(Et)–CH(CH₃)–(3-methoxy-2-pyridyl)) | 924.5 | (500 MHz): 0.88 (d, J = 6.88 Hz, 3 H) 0.99-1.29 (m, 22 H) 1.31-1.41 (m, 7 H) 1.59-1.69 (m, 1 H) 1.96-2.18 (m, 3 H) 2.25-2.34 (m, 6 H) 2.41-2.75 (m, 8 H) 2.82-2.95 (m, 4 H) 3.00-3.05 (m, 1 H) 3.13-3.34 (m, 6 H) 3.36 (s, 3 H) 3.38-3.44 (m, 1 H) 3.45-3.53 (m, 1 H) 3.57-3.63 (m, 1 H) 3.67-3.73 (m, 1 H) 3.79-3.86 (m, 1 H) 3.82 (s, 3 H) 3.91 (d, J = 6.12 Hz, 1 H) 4.16-4.25 (m, 1 H) 4.45-4.56 (m, 2 H) 4.63 (t, J = 4.59 Hz, 1 H) 4.99-5.05 (m, 1 H) 7.09-7.18 (m, 2 H) 8.13-8.21 (m, 1 H) |
| 42 | 23 | (structure: —NH–CH₂CH₂–N(Et)–CH(CH₃)–(2-bromophenyl)) | 971.5 | (500 MHz): 0.89 (d, J = 7.26 Hz, 3 H) 0.97-1.17 (m, 15 H) 1.17-1.32 (m, 10 H) 1.34-1.41 (m, 4 H) 1.62-1.69 (m, 1 H) 1.94-2.33 (m, 6 H) 2.30 (s, 6 H) 2.42-2.70 (m, 6 H) 2.78 (d, J = 13.76 Hz, 1 H) 2.83-2.94 (m, 3 H) 3.02 (br. s., 1 H) 3.13-3.25 (m, 3 H) 3.28-3.31 (m, 3 H) 3.37 (s, 3 H) 3.39-3.44 (m, 1 H) 3.47-3.53 (m, 1 H) 3.57-3.63 (m, 1 H) 3.68-3.72 (m, 1 H) 3.91 (dd, J = 6.31, 2.10 Hz, 1 H) 4.17-4.30 (m, 2 H) 4.46-4.51 (m, 1 H) 4.63 (t, J = 4.59 Hz, 1 H) 5.00-5.04 (m, 1 H) 7.06-7.11 (m, 1 H) 7.25-7.30 (m, 1 H) 7.40-7.45 (m, 1 H) 7.50-7.54 (m, 1 H) |

TABLE 4-2-continued

| Example | Reference Example | R | ESI MS (M + H) | ¹H-NMR, CDCl₃, δ (ppm) |
|---|---|---|---|---|
| 43 | 24 | [structure: ethyl-NH-CH₂CH₂-NH-CH(CH₃)- (2-methoxypyridin-3-yl)] | 896.5 | (500 MHz): 0.87 (d, J = 7.26 Hz, 3 H) 1.00 (d, J = 6.50 Hz, 3 H) 1.07-1.26 (m, 16 H) 1.30-1.40 (m, 7 H) 1.58-1.65 (m, 1 H) 1.95-2.08 (m, 2 H) 2.09-2.18 (m, 1 H) 2.29 (s, 6 H) 2.30-2.36 (m, 1 H) 2.41-2.74 (m, 6 H) 2.83-2.96 (m, 4 H) 2.99-3.04 (m, 1 H) 3.12-3.23 (m, 3 H) 3.28 (s, 3 H) 3.35 (s, 3 H) 3.37-3.43 (m, 1 H) 3.47-3.54 (m, 1 H) 3.56-3.61 (m, 1 H) 3.67-3.72 (m, 1 H) 3.90 (d, J = 6.12 Hz, 1 H) 3.92-3.99 (m, 1 H) 3.95 (s, 3 H) 4.23-4.30 (m, 1 H) 4.46 (d, J = 7.26 Hz, 1 H) 4.62 (t, J = 4.59 Hz, 1 H) 5.01 (d, J = 4.20 Hz, 1 H) 6.86 (dd, J = 7.26, 4.97 Hz, 1 H) 7.55 (d, J = 7.26 Hz, 1 H) 8.04 (dd, J = 4.97, 1.91 Hz, 1 H) |
| 44 | 25 | [structure: ethyl-NH-CH₂CH₂-N(8-methoxy-1,2,3,4-tetrahydroisoquinolin-2-yl)] | 907.5 | (600 MHz): 0.87 (d, J = 6.88 Hz, 3 H) 1.00 (d, J = 6.88 Hz, 3 H) 1.09-1.12 (m, 6 H) 1.13 (d, J = 6.42 Hz, 3 H) 1.17 (d, J = 6.42 Hz, 3 H) 1.20 (d, J = 11.00 Hz, 1 H) 1.23 (d, J = 6.88 Hz, 3 H) 1.33-1.37 (m, 1 H) 1.37 (s, 3 H) 1.60-1.64 (m, 1 H) 1.94-2.00 (m, 1 H) 2.03-2.07 (m, 1 H) 2.09-2.15 (m, 1 H) 2.29 (s, 6 H) 2.38 (d, J = 13.75 Hz, 1 H) 2.43-2.49 (m, 1 H) 2.57 (q, J = 6.88 Hz, 1 H) 2.62-2.72 (m, 4 H) 2.76-2.92 (m, 7 H) 2.94 (d, J = 13.75 Hz, 1 H) 3.01 (dd, J = 10.09, 3.67 Hz, 1 H) 3.12-3.22 (m, 3 H) 3.26 (s, 3 H) 3.34 (s, 3 H) 3.37-3.41 (m, 1 H) 3.49-3.60 (m, 4 H) 3.69 (dd, J = 9.63, 1.83 Hz, 1 H) 3.80 (s, 3 H) 3.90 (d, J = 5.96 Hz, 1 H) 4.26 (q, J = 6.27 Hz, 1 H) 4.47 (d, J = 7.34 Hz, 1 H) 4.62 (t, J = 4.58 Hz, 1 H) 4.91 (d, J = 10.55 Hz, 1 H) 5.01 (d, J = 4.58 Hz, 1 H) 6.65 (d, J = 7.79 Hz, 1 H) 6.72 (d, J = 7.79 Hz, 1 H) 7.11 (t, J = 7.79 Hz, 1 H) |

TABLE 4-3

| Example | Reference Example | R | ESI MS (M + H) | ¹H-NMR, CDCl₃, δ (ppm) |
|---|---|---|---|---|
| 45 | 26 | [structure: ethyl-NH-CH₂CH₂-NH-C(CH₃)₂-(2-methoxyphenyl)] | 909.5 | (600 MHz): 0.87 (d, J = 7.34 Hz, 3 H) 1.00 (d, J = 6.42 Hz, 3 H) 1.09-1.11 (m, 6 H) 1.12 (d, J = 6.42 Hz, 3 H) 1.17 (d, J = 5.96 Hz, 3 H) 1.19-1.21 (m, 1 H) 1.23 (d, J = 6.88 Hz, 3 H) 1.33-1.36 (m, 1 H) 1.37 (s, 3 H) 1.49 (s, 6 H) 1.58-1.62 (m, 1 H) 2.03 (s, 2 H) 2.10-2.17 (m, 1 H) 2.26 (d, J = 13.76 Hz, 1 H) 2.26-2.30 (m, 2 H) 2.28 (s, 6 H) 2.40-2.47 (m, 1 H) 2.57 (q, J = 6.72 Hz, 1 H) 2.64 (t, J = 5.50 Hz, 2 H) 2.83-2.91 (m, 3 H) 2.91-2.94 (m, 1 H) 2.99-3.03 (m, 1 H) 3.12-3.22 (m, 3 H) 3.27 (s, 3 H) 3.35 (s, 3 H) 3.37-3.41 (m, 1 H) 3.45-3.51 (m, 1 H) 3.56-3.61 (m, 1 H) 3.66-3.71 (m, 1 H) 3.86 (s, 3 H) 3.89 (d, J = 6.42 Hz, 1 H) 4.22 (q, J = 6.11 Hz, 1 H) 4.46 (d, J = 6.88 Hz, 1 H) 4.62 (t, J = 4.81 Hz, 1 H) 4.91 (d, J = 10.55 Hz, 1 H) 5.01 (d, J = 5.04 Hz, 1 H) 6.87-6.93 (m, 2 H) 7.20-7.24 (m, 2 H) |
| 46 | 27 | [structure: ethyl-NH-CH₂CH₂-N(ethyl)-(5-hydroxy-1,2,3,4-tetrahydronaphthalen-1-yl)] | 935.5 | (600 MHz): 0.87 (d, J = 7.34 Hz, 3 H) 0.98-1.02 (m, 6 H) 1.03-1.06 (m, 6 H) 1.08 (s, 3 H) 1.10-1.12 (m, 1 H) 1.13 (t, J = 7.11 Hz, 3 H) 1.21-1.26 (m, 3 H) 1.22-1.24 (m, 1 H) 1.32 (s, 3 H) 1.42-1.47 (m, 1 H) 1.55-1.66 (m, 2 H) 1.93-2.02 (m, 3 H) 2.07-2.15 (m, 1 H) 2.20-2.40 (m, 4 H) 2.44-2.51 (m, 1 H) 2.52-2.66 (m, 6 H) 2.54 (br. s., 6 H) 2.78 (d, J = 16.51 Hz, 1 H) 2.83-2.92 (m, 3 H) 2.93-2.98 (m, 1 H) 3.00-3.04 (m, 1 H) 3.09-3.18 (m, 3 H) 3.33 (s, 3 H) 3.34 (s, 3 H) 3.38-3.43 (m, 2 H) 3.55-3.61 (m, 1 H) 3.65 (dd, J = 9.63, 2.29 Hz, 1 H) 3.83 (d, J = 5.50 Hz, 1 H) 3.93-3.99 (m, 1 H) 4.02 (q, J = 6.42 Hz, 1 H) 4.41 (d, J = 7.34 Hz, 1 H) 4.62 (t, J = 4.58 Hz, 1 H) 4.96 (d, J = 10.09 Hz, 1 H) 5.03 (d, J = 4.58 Hz, 1 H) 6.62 (d, J = 7.79 Hz, 1 H) 7.03 (t, J = 7.79 Hz, 1 H) 7.24-7.28 (m, 1 H) |
| 47 | 27 | [structure: ethyl-NH-CH₂CH₂-N(ethyl)-(5-hydroxy-1,2,3,4-tetrahydronaphthalen-1-yl) isomer] | 935.5 | (600 MHz): 0.88 (d, J = 7.34 Hz, 3 H) 0.99-1.05 (m, 6 H) 1.10 (d, J = 7.79 Hz, 3 H) 1.13-1.17 (m, 6 H) 1.19 (d, J = 6.42 Hz, 3 H) 1.22-1.24 (m, 1 H) 1.24 (d, J = 7.34 Hz, 3 H) 1.35 (d, J = 14.21 Hz, 1 H) 1.38 (s, 3 H) 1.51-1.68 (m, 4 H) 1.96-2.08 (m, 3 H) 2.10-2.17 (m, 1 H) 2.22 (d, J = 12.38 Hz, 1 H) 2.29 (br. s., 6 H) 2.36-2.60 (m, 7 H) 2.62-2.68 (m, 1 H) 2.71-2.78 (m, 2 H) 2.85-2.93 (m, 3 H) 2.98 (d, J = 13.30 Hz, 1 H) 3.01-3.05 (m, 1 H) 3.13-3.20 (m, 2 H) 3.22 (dd, J = 10.09, 7.34 Hz, 1 H) 3.29 (s, 3 H) 3.36 (s, 3 H) 3.38-3.42 (m, 1 H) 3.46-3.53 (m, 1 H) 3.56-3.62 (m, 1 H) 3.69 (dd, J = 9.86, 2.06 Hz, 1 H) 3.88-3.91 (m, 1 H) 3.92 (d, J = 5.96 Hz, 1 H) 4.22-4.26 (m, 1 H) 4.48 (d, J = 6.88 Hz, 1 H) 4.63 (t, J = 4.58 Hz, 1 H) 5.02 (d, J = 4.58 Hz, 1 H) 5.04-5.07 (m, 1 H) 6.62 (d, J = 7.79 Hz, 1 H) 7.00 (t, J = 8.02 Hz, 1 H) 7.23 (d, J = 7.79 Hz, 1 H) |

TABLE 4-3-continued

| Example | Reference Example | R | ESI MS (M + H) | ¹H-NMR, CDCl₃, δ (ppm) |
|---|---|---|---|---|
| 48 | 28 | | 921.5 | (600 MHz): 0.87 (d, J = 8.25 Hz, 3 H) 1.00 (d, J = 6.88 Hz, 3 H) 1.02-1.07 (m, 3 H) 1.09-1.20 (m, 12 H) 1.21-1.23 (m, 1 H) 1.24 (d, J = 7.34 Hz, 3 H) 1.33-1.37 (m, 1 H) 1.38 (d, J = 5.04 Hz, 3 H) 1.58-1.64 (m, 1 H) 1.95-2.10 m, 4 H) 2.10-2.16 (m, 1 H) 2.21-2.37 (m, 1 H) 2.26-2.31 (m, 6 H) 2.40-2.48 (m, 2 H) 2.50-2.59 (m, 4 H) 2.61-2.69 (m, 1 H) 2.71-2.81 (m, 1 H) 2.80-3.03 (m, 5 H) 3.12-3.23 (m, 3 H) 3.29 (s, 3 H) 3.34-3.38 (m, 3 H) 3.39 (d, J = 4.58 Hz, 1 H) 3.46-3.54 (m, 1 H) 3.58 (br. s., 1 H) 3.68-3.74 (m, 1 H) 3.91 (d, J = 5.96 Hz, 1 H) 4.01-4.13 (m, 2 H) 4.21-4.30 (m, 1 H) 4.31-4.38 (m, 1 H) 4.47 (d, J = 6.88 Hz, 1 H) 4.62 (t, J = 4.58 Hz, 1 H) 4.88-4.95 (m, 1 H) 5.01-5.07 (m, 1 H) 6.73-6.79 (m, 1 H) 6.84-6.88 (m, 1 H) 7.07-7.12 (m, 1 H) 7.43-7.50 (m, 1 H) |
| 49 | 29 | | 919.5 | (600 MHz): 0.85-0.89 (m, 3 H) 1.00 (d, J = 6.42 Hz, 3 H) 1.03 (q, J = 6.88 Hz, 3 H) 1.09-1.20 (m, 12 H) 1.21-1.23 (m, 1 H) 1.24 (d, J = 7.34 Hz, 3 H) 1.34 (d, J = 5.04 Hz, 1 H) 1.38 (d, J = 5.50 Hz, 3 H) 1.55-1.70 (m, 4 H) 1.95-2.09 (m, 3 H) 2.10-2.17 (m, 1 H) 2.22-2.35 (m, 1 H) 2.27-2.29 (m, 6 H) 2.39-2.62 (m, 7 H) 2.68-2.80 (m, 3 H) 2.79-3.01 (m, 1 H) 2.84-2.92 (m, 3 H) 3.01-3.03 (m, 1 H) 3.12-3.23 (m, 3 H) 3.29 (s, 3 H) 3.35-3.38 (m, 3 H) 3.38-3.41 (m, 1 H) 3.46-3.53 (m, 1 H) 3.56-3.61 (m, 1 H) 3.67-3.73 (m, 1 H) 3.92 (d, J = 5.96 Hz, 1 H) 3.92-3.95 (m, 1 H) 4.22-4.29 (m, 1 H) 4.48 (d, J = 7.34 Hz, 1 H) 4.62 (t, J = 4.81 Hz, 1 H) 4.89-4.95 (m, 1 H) 5.01-5.05 (m, 1 H) 7.00-7.15 (m, 3 H) 7.57-7.63 (m, 1 H) |
| 50 | 30 | | 909.5 | (600 MHz): 0.87 (d, J = 6.88 Hz, 3 H) 1.00 (d, J = 6.88 Hz, 3 H) 1.08-1.15 (m, 9 H) 1.16-1.20 (m, 3H) 1.20-1.23 (m, 1 H) 1.24 (d, J = 7.34 Hz, 3 H) 1.32-1.39 (m, 7 H) 1.41 (t, J = 6.88 Hz, 3 H) 1.60 (d, J = 12.84 Hz, 1 H) 1.96-2.02 (m, 1 H) 2.02-2.07 (m, 1 H) 2.09-2.16 (m, 1 H) 2.28 (s, 6 H) 2.29-2.33 (m, 1 H) 2.40-2.48 (m, 1 H) 2.52-2.60 (m, 3 H) 2.62-2.74 (m, 2 H) 2.82-2.95 (m, 4 H) 2.98-3.04 (m, 1 H) 3.12-3.23 (m, 3 H) 3.26-3.29 (m, 3 H) 3.34-3.36 (m, 3 H) 3.37-3.42 (m, 1 H) 3.46-3.54 (m, 1 H) 3.56-3.61 (m, 1 H) 3.69 (d, J = 9.63 Hz, 1 H) 3.90 (d, J = 6.42 Hz, 1 H) 4.00-4.09 (m, 3 H) 4.22-4.28 (m, 1 H) 4.47 (d, J = 7.34 Hz, 1 H) 4.62 (t, J = 4.81 Hz, 1 H) 5.01 (d, J = 5.04 Hz, 1 H) 6.84 (d, J = 7.79 Hz, 1 H) 6.91 (t, J = 7.34 Hz, 1 H) 7.15-7.20 (m, 1 H) 7.21-7.25 (m, 1 H) |

TABLE 4-4

| Example | Reference Example | R | ESI MS (M + H) | ¹H-NMR, CDCl₃, δ (ppm) |
|---|---|---|---|---|
| 51 | 31 | | 918.5 | (600 MHz): 0.88 (d, J = 7.34 Hz, 3 H) 0.96-1.03 (m, 6 H) 1.04-1.28 (m, 16 H) 1.30-1.39 (m, 4 H) 1.54-1.69 (m, 1 H) 1.91-2.21 (m, 4 H) 2.29 (br. s., 6 H) 2.41-2.75 (m, 8 H) 2.76-2.94 (m, 4 H) 2.98-3.05 (m, 1 H) 3.10-3.31 (m, 3 H) 3.25 (br. s., 3 H) 3.35 (s, 3 H) 3.38-3.43 (m, 1 H) 3.43-3.50 (m, 1 H) 3.55-3.62 (m, 1 H) 3.67 (d, J = 9.63 Hz, 1 H) 3.69-3.82 (m, 2 H) 3.89 (d, J = 5.96 Hz, 1 H) 4.14-4.23 (m, 1 H) 4.46 (d, J = 7.34 Hz, 1 H) 4.62 (t, J = 4.81 Hz, 1 H) 4.97-5.02 (m, 1 H) 7.04-7.13 (m, 2 H) 7.17 (t, J = 8.02 Hz, 1 H) 7.36 (d, J = 9.17 Hz, 1 H) 7.67 (d, J = 7.79 Hz, 1 H) |
| 52 | 32 | | 895.5 | (600 MHz): 0.84-0.90 (m, 3 H) 1.01 (d, J = 6.88 Hz, 3 H) 1.03-1.18 (m, 9 H) 1.18-1.26 (m, 7 H) 1.27-1.40 (m, 7 H) 1.47-1.64 (m, 1 H) 1.74-2.40 (m, 6 H) 2.22 (s, 3 H) 2.30-2.51 (m, 6 H) 2.41-2.72 (m, 4 H) 2.72-2.96 (m, 4 H) 2.98-3.05 (m, 1 H) 3.10-3.53 (m, 5 H) 3.27-3.32 (m, 3 H) 3.32-3.36 (m, 3 H) 3.55-3.62 (m, 1 H) 3.64-3.71 (m, 1 H) 3.83-3.93 (m, 1 H) 4.00-4.07 (m, 1 H) 4.06-4.28 (m, 1 H) 4.38-4.49 (m, 1 H) 4.62 (t, J = 4.58 Hz, 1 H) 4.98-5.04 (m, 1 H) 6.66 (t, J = 7.11 Hz, 1 H) 6.95-7.10 (m, 2 H) |
| 53 | 33 | | 932.5 | (600 MHz): 0.88 (d, J = 6.88 Hz, 3 H) 0.96-1.05 (m, 6 H) 1.06-1.27 (m, 16 H) 1.32-1.43 (m, 7 H) 1.55-1.65 (m, 1 H) 1.93-2.08 (m, 2 H) 2.09-2.17 (m, 1 H) 2.18-2.26 (m, 1 H) 2.26-2.33 (m, 6 H) 2.42-2.66 (m, 8 H) 2.78-2.93 (m, 4 H) 2.98-3.05 (m, 1 H) 3.10-3.25 (m, 3 H) 3.36 (s, 3 H) 3.38-3.42 (m, 1 H) 3.45-3.52 (m, 1 H) 3.56-3.61 (m, 1 H) 3.69 (d, J = 10.09 Hz, 1 H) 3.88-4.01 (m, 2 H) 4.18-4.26 (m, 1 H) 4.45-4.50 (m, 1 H) 4.63 (t, J = 4.58 Hz, 1 H) 4.99-5.04 (m, 1 H) 6.48-6.51 (m, 1 H) 7.16-7.21 (m, 2 H) 7.30-7.35 (m, 1 H) 7.52 (d, J = 6.42 Hz, 1 H) |

TABLE 4-4-continued

| Example | Reference Example | R | ESI MS (M + H) | ¹H-NMR, CDCl₃, δ (ppm) |
|---|---|---|---|---|
| 54 | 34 | *(structure: -NH-CH₂CH₂-NH-CH(CH₃)- attached to 1-methylindol-4-yl)* | 918.5 | (600 MHz): 0.88 (d, 3 H) 1.01 (d, J = 6.88 Hz, 3 H) 1.07-1.23 (m, 13 H) 1.25 (d, J = 6.88 Hz, 3 H) 1.34-1.38 (m, 1 H) 1.38 (s, 3 H) 1.49 (d, J = 6.88 Hz, 3 H) 1.51-1.64 (m, 1 H) 1.96-2.07 (m, 2 H) 2.11-2.17 (m, 1 H) 2.24-2.31 (m, 1 H) 2.29 (s, 6 H) 2.41-2.49 (m, 1 H) 2.55-2.71 (m, 5 H) 2.84-2.94 (m, 4 H) 2.99-3.05 (m, 1 H) 3.12-3.24 (m, 3 H) 3.28 (s, 3 H) 3.36 (s, 3 H) 3.38-3.43 (m, 1 H) 3.46-3.53 (m, 1 H) 3.57-3.62 (m, 1 H) 3.70 (d, J = 10.55 Hz, 1 H) 3.80 (s, 3 H) 3.91 (d, J = 6.42 Hz, 1 H) 4.16-4.28 (m, 2 H) 4.47 (d, J = 6.88 Hz, 1 H) 4.63 (t, J = 4.58 Hz, 1 H) 4.90-4.95 (m, 1 H) 5.02 (d, J = 5.50 Hz, 1 H) 6.60 (t, J = 2.75 Hz, 1 H) 7.04-7.09 (m, 2 H) 7.18-7.25 (m, 3 H) |
| 55 | 35 | *(structure: -NH-CH₂CH₂-NH-CH(CH₂CH₃)- attached to 2-methoxyphenyl)* | 909.5 | (600 MHz): 0.81-0.85 (m, 3 H) 0.88 (d, J = 7.34 Hz, 3 H) 1.01 (d, J = 6.88 Hz, 3 H) 1.09-1.24 (m, 13 H) 1.25 (d, J = 6.88 Hz, 3 H) 1.34-1.40 (m, 4 H) 1.59-1.78 (m, 3 H) 1.97-2.02 (m, 1 H) 2.04-2.08 (m, 1 H) 2.11-2.17 (m, 1 H) 2.28-2.33 (m, 1 H) 2.30 (s, 6 H) 2.42-2.72 (m, 6 H) 2.84-2.94 (m, 4 H) 3.00-3.05 (m, 1 H) 3.14-3.25 (m, 3 H) 3.29 (s, 3 H) 3.36 (s, 3 H) 3.39-3.43 (m, 1 H) 3.48-3.55 (m, 1 H) 3.58-3.62 (m, 1 H) 3.70 (d, J = 9.63 Hz, 1 H) 3.80-3.85 (m, 1 H) 3.82 (s, 3 H) 3.91 (d, J = 6.42 Hz, 1 H) 4.24-4.29 (m, 1 H) 4.48 (d, J = 7.34 Hz, 1 H) 4.63 (t, J = 4.81 Hz, 1 H) 4.93 (d, J = 10.09 Hz, 1 H) 5.02 (d, J = 4.59 Hz, 1 H) 6.87 (d, J = 8.25 Hz, 1 H) 6.93 (t, J = 7.34 Hz, 1 H) 7.18-7.24 (m, 2 H) |
| 56 | 36 | *(structure: -NH-CH₂CH₂-N-isoindoline with 7-methoxy)* | 893.5 | (600 MHz): 0.87 (d, J = 7.34 Hz, 3 H) 1.00 (d, J = 6.88 Hz, 3 H) 1.08-1.13 (m, 6 H) 1.14 (d, J = 6.42 Hz, 3 H) 1.19 (d, J = 6.42 Hz, 3 H) 1.20-1.21 (m, 1 H) 1.23 (d, J = 6.88 Hz, 3 H) 1.33-1.37 (m, 1 H) 1.37 (s, 3 H) 1.65 (d, J = 12.38 Hz, 1 H) 1.96-2.01 (m, 1 H) 2.03-2.09 (m, 1 H) 2.10-2.15 (m, 1 H) 2.30 (s, 6 H) 2.39 (d, J = 13.75 Hz, 1 H) 2.44-2.50 (m, 1 H) 2.57 (q, J = 6.72 Hz, 1 H) 2.75-2.92 (m, 7 H) 2.97 (d, J = 13.75 Hz, 1 H) 2.99-3.04 (m, 1 H) 3.13-3.23 (m, 3 H) 3.28 (s, 3 H) 3.35 (s, 3 H) 3.37-3.42 (m, 1 H) 3.49-3.56 (m, 1 H) 3.56-3.61 (m, 1 H) 3.69 (dd, J = 9.63, 2.29 Hz, 1 H) 3.81 (s, 3 H) 3.88-3.97 (m, 5 H) 4.27 (q, J = 6.42 Hz, 1 H) 4.48 (d, J = 7.34 Hz, 1 H) 4.62 (t, J = 4.58 Hz, 1 H) 4.91 (d, J = 9.63 Hz, 1 H) 5.01 (d, J = 4.59 Hz, 1 H) 6.71 (d, J = 8.25 Hz, 1 H) 6.80 (d, J = 7.34 Hz, 1 H) 7.18 (t, J = 7.79 Hz, 1 H) |
| 57 | | *(structure: -NH-CH₂- attached to 2-phenylthiazol-4-yl)* | 891.4 | (600 MHz): 0.87 (d, J = 6.88 Hz, 3 H) 1.00 (d, J = 6.88 Hz, 3 H) 1.08-1.11 (m, 6 H) 1.12 (s, 3 H) 1.13-1.16 (m, 1 H) 1.17 (d, J = 6.42 Hz, 3 H) 1.23 (d, J = 7.34 Hz, 3 H) 1.33-1.36 (m, 1 H) 1.36 (s, 3 H) 1.46-1.51 (m, 1 H) 1.95-2.01 (m, 1 H) 2.04-2.07 (m, 1 H) 2.09-2.16 (m, 1 H) 2.22 (s, 6 H) 2.35-2.41 (m, 1 H) 2.43 (d, J = 13.30 Hz, 1 H) 2.55-2.61 (m, 1 H) 2.81-2.92 (m, 3 H) 2.94 (d, J = 13.30 Hz, 1 H) 2.98-3.03 (m, 1 H) 3.12-3.20 (m, 3 H) 3.28 (s, 3 H) 3.34 (s, 3 H) 3.37-3.42 (m, 1 H) 3.45-3.52 (m, 1 H) 3.55-3.61 (m, 1 H) 3.67-3.71 (m, 1 H) 3.85-3.98 (m, 3 H) 4.33 (q, J = 6.27 Hz, 1 H) 4.45 (d, J = 7.34 Hz, 1 H) 4.62 (t, J = 4.58 Hz, 1 H) 5.01 (d, J = 4.58 Hz, 1 H) 7.04 (s, 1 H) 7.39-7.46 (m, 3 H) 7.89-7.95 (m, 2 H) |

TABLE 4-5

| Example | Reference Example | R | ESI MS (M + H) | ¹H-NMR, CDCl₃, δ (ppm) |
|---|---|---|---|---|
| 58 | 37 | *(structure: -NH-CH₂CH₂-N(CH₂CH₃)-CH(CH₃)- attached to 1-methylindol-4-yl)* | 946.5 | (600 MHz): 0.86-1.28 (m, 25 H) 1.33-1.46 (m, 7 H) 1.57-1.68 (m, 1 H) 1.87-2.06 (m, 2 H) 2.09-2.17 (m, 1 H) 2.25-2.81 (m, 16 H) 2.84-2.93 (m, 3 H) 3.00-3.05 (m, 1 H) 3.12-3.51 (m, 10 H) 3.57-3.62 (m, 1 H) 3.66-3.73 (m, 1 H) 3.76-3.80 (m, 3 H) 3.86-3.93 (m, 1 H) 4.07-4.38 (m, 2 H) 4.43-4.50 (m, 1 H) 4.61-4.65 (m, 1 H) 4.90-4.97 (m, 1 H) 4.97-5.05 (m, 1 H) 6.63-6.72 (m, 1 H) 6.98-7.09 (m, 2 H) 7.14-7.25 (m, 3 H) |

TABLE 4-5-continued

| Example | Reference Example | R | ESI MS (M + H) | ¹H-NMR, CDCl₃, δ (ppm) |
|---|---|---|---|---|
| 59 | 38 | | 910.5 | (600 MHz): 0.88 (d, J = 7.34 Hz, 3 H) 1.01 (d, J = 6.42 Hz, 3 H) 1.09-1.13 (m, 6 H) 1.14 (d, J = 6.42 Hz, 3 H) 1.19 (d, J = 6.42 Hz, 3 H) 1.20-1.26 (m, 4 H) 1.36 (d, J = 14.67 Hz, 1 H) 1.38 (s, 3 H) 1.47 (s, 6 H) 1.58-1.66 (m, 1 H) 1.98-2.07 (m, 2 H) 2.11-2.18 (m, 1 H) 2.23-2.29 (m, 3 H) 2.30 (s, 6 H) 2.40-2.49 (m, 1 H) 2.55-2.68 (m, 3 H) 2.84-2.97 (m, 4 H) 3.00-3.05 (m, 1 H) 3.13-3.25 (m, 3 H) 3.29 (s, 3 H) 3.36 (s, 3 H) 3.38-3.43 (m, 1 H) 3.47-3.53 (m, 1 H) 3.57-3.62 (m, 1 H) 3.70 (dd, J = 9.86, 2.06 Hz, 1 H) 3.91 (d, J = 5.96 Hz, 1 H) 4.00 (s, 3 H) 4.24 (q, J = 6.11 Hz, 1 H) 4.48 (d, J = 7.34 Hz, 1 H) 4.63 (t, J = 4.58 Hz, 1 H) 4.89-4.95 (m, 1 H) 5.02 (d, J = 4.59 Hz, 1 H) 6.87 (dd, J = 7.34, 4.58 Hz, 1 H) 7.50 (dd, J = 7.34, 1.83 Hz, 1 H) 8.05 (dd, J = 5.04, 1.83 Hz, 1 H) |
| 60 | 39 | | 896.5 | (500 MHz): 0.87 (d, J = 7.13 Hz, 3 H) 1.00 (d, J = 6.58 Hz, 3 H) 1.08-1.27 (m, 16 H) 1.30-1.40 (m, 7 H) 1.57-1.65 (m, 1 H) 2.03 (d, J = 1.37 Hz, 2 H) 2.08-2.17 (m, 1 H) 2.29 (s, 6 H) 2.33 (d, J = 13.71 Hz, 1 H) 2.40-2.74 (m, 6 H) 2.82-2.96 (m, 4 H) 2.98-3.05 (m, 1 H) 3.12-3.24 (m, 3 H) 3.28 (s, 3 H) 3.35 (s, 3 H) 3.38-3.43 (m, 1 H) 3.46-3.55 (m, 1 H) 3.56-3.61 (m, 1 H) 3.67-3.72 (m, 1 H) 3.90 (d, J = 6.31 Hz, 1 H) 3.93-4.00 (m, 1 H) 3.95 (s, 3 H) 4.26 (q, J = 6.31 Hz, 1 H) 4.46 (d, J = 7.13 Hz, 1 H) 4.62 (t, J = 4.66 Hz, 1 H) 5.01 (d, J = 3.84 Hz, 1 H) 6.86 (dd, J = 7.27, 5.07 Hz, 1 H) 7.55 (dd, J = 7.27, 1.78 Hz, 1 H) 8.04 (dd, J = 4.94, 1.92 Hz, 1 H) |
| 61 | 40 | | 896.5 | (500 MHz): 0.87 (d, J = 7.13 Hz, 3 H) 1.00 (d, J = 6.86 Hz, 3 H) 1.08-1.26 (m, 16 H) 1.30-1.39 (m, 7 H) 1.58-1.65 (m, 1 H) 1.95-2.08 (m, 2 H) 2.08-2.16 (m, 1 H) 2.29 (s, 6 H) 2.32 (d, J = 13.71 Hz, 1 H) 2.41-2.61 (m, 4 H) 2.64-2.71 (m, 2 H) 2.82-2.94 (m, 4 H) 2.99-3.03 (m, 1 H) 3.12-3.23 (m, 3 H) 3.28 (s, 3 H) 3.35 (s, 3 H) 3.37-3.42 (m, 1 H) 3.47-3.54 (m, 1 H) 3.56-3.61 (m, 1 H) 3.67-3.71 (m, 1 H) 3.90 (d, J = 6.31 Hz, 1 H) 3.92-3.97 (m, 1 H) 3.95 (s, 3 H) 4.27 (q, J = 6.31 Hz, 1 H) 4.46 (d, J = 7.13 Hz, 1 H) 4.62 (t, J = 4.66 Hz, 1 H) 5.01 (d, J = 3.57 Hz, 1 H) 6.86 (dd, J = 7.13, 4.94 Hz, 1 H) 7.55 (dd, J = 7.27, 1.78 Hz, 1 H) 8.04 (dd, J = 5.07, 1.78 Hz, 1H) |
| 62 | 41 | | 935.7 | (600 MHz): 0.89 (d, J = 7.34 Hz, 7 H) 0.99-1.05 (m, 6 H) 1.13 (d, J = 7.79 Hz, 3 H) 1.14 (s, 3 H) 1.16 (d, J = 5.96 Hz, 3 H) 1.20-1.25 (m, 1 H) 1.24 (d, J = 5.96 Hz, 3 H) 1.26 (d, J = 6.88 Hz, 3 H) 1.37 (d, J = 14.67 Hz, 1 H) 1.40 (s, 3 H) 1.63-1.67 (m, 1 H) 1.99-2.18 (m, 3 H) 2.29 (s, 6 H) 2.30-2.35 (m, 1 H) 2.45-2.68 (m, 7 H) 2.71-2.77 (m, 1 H) 2.84-2.95 (m, 4 H) 3.00-3.05 (m, 1 H) 3.14-3.25 (m, 3 H) 3.31 (s, 3 H) 3.37 (s, 3 H) 3.38-3.43 (m, 1 H) 3.52-3.57 (m, 1 H) 3.58-3.62 (m, 1 H) 3.72 (dd, J = 9.63, 1.83 Hz, 1 H) 3.80 (s, 3 H) 3.93 (d, J = 5.96 Hz, 1 H) 4.25-4.31 (m, 1 H) 4.51 (d, J = 7.34 Hz, 1 H) 4.64 (t, J = 4.58 Hz, 1 H) 4.92-4.98 (m, 1 H) 5.04 (d, J = 4.13 Hz, 1 H) 6.85-6.93 (m, 2 H) 7.22-7.29 (m, 2 H) |
| 63 | 42 | | 880.5 | (600 MHz): 0.88 (d, J = 7.34 Hz, 3 H) 1.01 (d, J = 6.88 Hz, 3 H) 1.11 (d, J = 7.34 Hz, 3 H) 1.13 (s, 3 H) 1.15 (d, J = 6.42 Hz, 3 H) 1.18 (d, J = 5.96 Hz, 3 H) 1.21 (d, J = 11.92 Hz, 1 H) 1.24 (d, J = 7.34 Hz, 3 H) 1.35 (d, J = 13.75 Hz, 1 H) 1.38 (s, 3 H) 1.47 (s, 6 H) 1.58-1.64 (m, 1 H) 1.97-2.02 (m, 1 H) 2.03-2.07 (m, 1 H) 2.09-2.16 (m, 1 H) 2.26-2.29 (m, 1 H) 2.29 (br. s, 6 H) 2.40-2.48 (m, 3 H) 2.55-2.60 (m, 1 H) 2.62-2.66 (m, 2 H) 2.83-2.96 (m, 4 H) 2.99-3.04 (m, 1 H) 3.11-3.24 (m, 3 H) 3.29 (s, 3 H) 3.35 (s, 3 H) 3.37-3.42 (m, 1 H) 3.46-3.53 (m, 1 H) 3.55-3.62 (m, 1 H) 3.67-3.72 (m, 1 H) 3.90 (d, J = 6.42 Hz, 1 H) 4.26 (q, J = 6.11 Hz, 1 H) 4.47 (d, J = 7.34 Hz, 1 H) 4.63 (t, J = 4.58 Hz, 1 H) 5.01 (d, J = 4.13 Hz, 1 H) 7.21-7.25 (m, 1 H) 7.73-7.76 (m, 1 H) 8.47 (dd, J = 4.58, 1.83 Hz, 1 H) 8.69 (d, J = 2.29 Hz, 1 H) |
| 64 | 43 | | 916.4 | (600 MHz): 0.88 (d, J = 7.34 Hz, 3 H) 1.01 (d, J = 6.88 Hz, 3 H) 1.06-1.17 (m, 12 H) 1.19 (d, J = 12.84 Hz, 1 H) 1.24 (d, J = 7.34 Hz, 3 H) 1.35 (d, J = 14.67 Hz, 1 H) 1.37 (s, 3 H) 1.50 (d, J = 6.42 Hz, 3 H) 1.55-1.62 (m, 1 H) 1.93-2.01 (m, 1 H) 2.02-2.08 (m, 1 H) 2.09-2.17 (m, 1 H) 2.28 (s, 6 H) 2.28-2.33 (m, 1 H) 2.39-2.47 (m, 1 H) 2.51-2.75 (m, 5 H) 2.82-2.96 (m, 4 H) 2.99-3.04 (m, 1 H) 3.11-3.23 (m, 3 H) 3.24-3.31 (m, 3 H) 3.35 (s, 3 H) 3.37-3.43 (m, 1 H) 3.44-3.53 (m, 1 H) 3.55-3.62 (m, 1 H) 3.69 (d, J = 9.63 Hz, 1 H) 3.89 (d, J = 6.42 Hz, 1 H) 4.22-4.30 (m, 1 H) 4.45 (d, J = 7.34 Hz, 1 H) 4.51-4.58 (m, 1 H) 4.63 (t, J = 4.58 Hz, 1 H) 4.98-5.03 (m, 1 H) 7.38-7.42 (m, 1 H) 7.62-7.72 (m, 2 H) 8.01 (d, J = 7.79 Hz, 1 H) 8.63 (d, J = 8.71 Hz, 1 H) 8.88-8.94 (m, 1 H) |

TABLE 4-6

| Example | Reference Example | R | ESI MS (M + H) | ¹H-NMR, CDCl₃, δ (ppm) |
|---|---|---|---|---|
| 65 | 44 | | 924.5 | (600 MHz): 0.88 (d, J = 6.88 Hz, 3 H) 1.01 (d, J = 6.88 Hz, 3 H) 1.11 (d, J = 7.79 Hz, 3 H) 1.13-1.27 (m, 13 H) 1.32-1.37 (m, 1 H) 1.38 (s, 3 H) 1.46 (br. s., 6 H) 1.59-1.66 (m, 1 H) 1.99-2.17 (m, 4 H) 2.13 (s, 3 H) 2.20-2.34 (m, 4 H) 2.30 (br. s., 6 H) 2.41-2.65 (m, 3 H) 2.77-2.93 (m, 4 H) 2.99-3.04 (m, 1 H) 3.12-3.25 (m, 3 H) 3.29 (s, 3 H) 3.37 (s, 3 H) 3.38-3.49 (m, 2 H) 3.56-3.62 (m, 1 H) 3.68-3.73 (m, 1 H) 3.91 (d, J = 5.96 Hz, 1 H) 3.98 (s, 3 H) 4.14-4.19 (m, 1 H) 4.48 (d, J = 6.88 Hz, 1 H) 4.63 (t, J = 4.58 Hz, 1 H) 5.04 (d, J = 5.04 Hz, 1 H) 6.83-6.88 (m, 1 H) 7.48-7.53 (m, 1 H) 8.01-8.06 (m, 1 H) |
| 66 | 45 | | 923.6 | (600 MHz): 0.87 (d, J = 7.34 Hz, 3 H) 1.00 (d, J = 6.88 Hz, 3 H) 1.11 (d, J = 7.34 Hz, 3 H) 1.14-1.27 (m, 1 H) 1.16 (s, 3 H) 1.18-1.22 (m, 6 H) 1.25 (d, J = 7.34 Hz, 3 H) 1.35 (d, J = 14.21 Hz, 1 H) 1.38 (s, 3 H) 1.48 (br. s., 6 H) 1.62 (d, J = 14.21 Hz, 1 H) 1.99-2.18 (m, 4 H) 2.09 (s, 3 H) 2.24-2.66 (m, 6 H) 2.29 (s, 6 H) 2.77-2.93 (m, 4 H) 2.99-3.04 (m, 1 H) 3.11-3.23 (m, 3 H) 3.29 (s, 3 H) 3.37 (s, 3 H) 3.38-3.42 (m, 1 H) 3.42-3.50 (m, 1 H) 3.55-3.62 (m, 1 H) 3.67-3.73 (m, 1 H) 3.85 (s, 3 H) 3.91 (d, J = 6.42 Hz, 1 H) 4.16 (q, J = 5.96 Hz, 1 H) 4.47 (d, J = 7.34 Hz, 1 H) 4.62 (t, J = 4.58 Hz, 1 H) 5.04 (d, J = 4.13 Hz, 1 H) 6.85-6.95 (m, 2 H) 7.18-7.27 (m, 2 H) |
| 67 | 46 | | 951.5 | (600 MHz): 0.87 (d, J = 7.34 Hz, 3 H) 0.97-1.02 (m, 6 H) 1.08-1.12 (m, 1 H) 1.15 (d, J = 6.42 Hz, 3 H) 1.20-1.23 (m, 1 H) 1.21-1.27 (m, 6 H) 1.33-1.37 (m, 1 H) 1.37 (s, 3 H) 1.44 (s, 6 H) 1.61-1.67 (m, 1 H) 1.95-2.17 (m, 4 H) 2.26 (s, 3 H) 2.30 (br. s., 6 H) 2.41-2.69 (m, 8 H) 2.79-2.92 (m, 4 H) 2.98-3.04 (m, 1 H) 3.12-3.24 (m, 3 H) 3.28 (s, 3 H) 3.36 (s, 3 H) 3.37-3.42 (m, 1 H) 3.42-3.49 (m, 1 H) 3.56-3.62 (m, 1 H) 3.67-3.72 (m, 1 H) 3.78 (s, 3 H) 3.90 (d, J = 6.42 Hz, 1 H) 4.13-4.18 (m, 1 H) 4.47 (d, J = 7.34 Hz, 1 H) 4.62 (t, J = 4.81 Hz, 1 H) 5.02 (d, J = 5.50 Hz, 1 H) 6.83-6.90 (m, 2 H) 7.14-7.19 (m, 1 H) 7.48-7.52 (m, 1 H) |
| 68 | 47 | | 931.6 | (500 MHz): 0.88 (d, J = 7.26 Hz, 3 H) 1.01 (d, J = 6.88 Hz, 3 H) 1.06-1.31 (m, 16 H) 1.33-1.40 (m, 4 H) 1.58-1.69 (m, 2 H) 1.95-2.09 (m, 2 H) 2.09-2.17 (m, 1 H) 2.22-2.32 (m, 1 H) 2.30 (s, 6 H) 2.34-2.64 (m, 7 H) 2.81-2.96 (m, 5 H) 2.99-3.05 (m, 1 H) 3.13-3.25 (m, 3 H) 3.28 (s, 3 H) 3.34-3.38 (m, 3 H) 3.38-3.44 (m, 1 H) 3.46-3.53 (m, 1 H) 3.53-3.63 (m, 2 H) 3.67-3.72 (m, 1 H) 3.90 (d, J = 5.35 Hz, 1 H) 4.21-4.30 (m, 1 H) 4.46 (d, J = 7.26 Hz, 1 H) 4.63 (t, J = 4.40 Hz, 1 H) 5.01 (d, J = 4.59 Hz, 1 H) 7.04 (s, 1 H) 7.20 (s, 1 H) 7.22 (s, 1 H) 7.30-7.35 (m, 1 H) 7.45-7.51 (m, 1 H) 7.56 (s, 1 H) 7.59-7.65 (m, 1 H) |
| 69 | 48 | | 924.6 | (600 MHz): 0.89 (d, J = 7.34 Hz, 3 H) 1.02 (d, J = 6.42 Hz, 3 H) 1.07-1.23 (m, 10 H) 1.19 (d, J = 5.96 Hz, 3 H) 1.25 (d, J = 7.34 Hz, 3 H) 1.34-1.72 (m, 2 H) 1.38 (s, 3 H) 1.42 (t, J = 7.11 Hz, 3 H) 1.48 (s, 6 H) 1.97-2.07 (m, 2 H) 2.10-2.16 (m, 1 H) 2.21-2.68 (m, 6 H) 2.29-2.32 (m, 7 H) 2.84-2.99 (m, 4 H) 3.00-3.05 (m, 1 H) 3.13-3.26 (m, 3 H) 3.29 (s, 3 H) 3.35 (s, 3 H) 3.38-3.44 (m, 1 H) 3.46-3.54 (m, 1 H) 3.56-3.62 (m, 1 H) 3.70 (dd, J = 9.63, 1.83 Hz, 1 H) 3.91 (d, J = 6.42 Hz, 1 H) 4.21-4.27 (m, 1 H) 4.42-4.49 (m, 3 H) 4.62-4.65 (m, 1 H) 4.87-4.95 (m, 1 H) 5.00-5.03 (m, 1 H) 6.82-6.88 (m, 1 H) 7.47-7.52 (m, 1 H) 8.03 (br. s., 1 H) |
| 70 | 49 | | 932.6 | (600 MHz): 0.88 (d, J = 6.88 Hz, 3 H) 1.02 (d, J = 6.88 Hz, 3 H) 1.05-1.21 (m, 13 H) 1.25 (d, J = 6.88 Hz, 3 H) 1.33-1.37 (m, 1 H) 1.38 (s, 3 H) 1.51-1.59 (m, 1 H) 1.63 (br. s., 6 H) 1.95-2.07 (m, 2 H) 2.10-2.22 (m, 1 H) 2.30 (br. s., 6 H) 2.35-2.64 (m, 6 H) 2.81-2.94 (m, 4 H) 3.00-3.05 (m, 1 H) 3.13-3.25 (m, 3 H) 3.27 (s, 3 H) 3.36 (s, 3 H) 3.38-3.49 (m, 2 H) 3.57-3.62 (m, 1 H) 3.69 (dd, J = 9.63, 1.83 Hz, 1 H) 3.79 (s, 3 H) 3.90 (d, J = 5.96 Hz, 1 H) 4.18-4.24 (m, 1 H) 4.46 (d, J = 6.88 Hz, 1 H) 4.63 (t, J = 4.58 Hz, 1 H) 4.89-4.95 (m, 1 H) 5.01 (d, J = 4.58 Hz, 1 H) 6.81 (d, J = 2.75 Hz, 1 H) 7.01-7.06 (m, 2 H) 7.16 (t, J = 7.79 Hz, 1 H) 7.25 (d, J = 8.25 Hz, 1 H) |

TABLE 4-6-continued

| Example | Reference Example | R | ESI MS (M + H) | ¹H-NMR, CDCl₃, δ (ppm) |
|---|---|---|---|---|
| 71 | 50 | 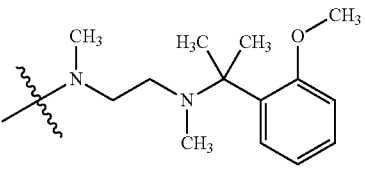 | 937.6 | (600 MHz): 0.88 (d, J = 7.34 Hz, 3 H) 1.01 (d, J = 6.42 Hz, 3 H) 1.10 (d, J = 7.79 Hz, 3 H) 1.13 (s, 3 H) 1.17 (d, J = 5.96 Hz, 3 H) 1.19-1.27 (m, 1 H) 1.23 (d, J = 6.42 Hz, 3 H) 1.24 (d, J = 6.88 Hz, 3 H) 1.35 (d, J = 16.05 Hz, 1 H) 1.38 (s, 3 H) 1.42 (d, J = 4.13 Hz, 6 H) 1.60-1.67 (m, 1 H) 1.97-2.09 (m, 3 H) 2.10-2.16 (m, 1 H) 2.18 (s, 3 H) 2.25 (s, 3 H) 2.29 (br. s., 6 H) 2.37-2.64 (m, 6 H) 2.78-2.92 (m, 4 H) 2.98-3.05 (m, 1 H) 3.11-3.24 (m, 3 H) 3.29 (s, 3 H) 3.36 (s, 3 H) 3.37-3.42 (m, 1 H) 3.42-3.49 (m, 1 H) 3.55-3.62 (m, 1 H) 3.67-3.71 (m, 1 H) 3.79 (s, 3 H) 3.91 (d, J = 5.96 Hz, 1 H) 4.12-4.17 (m, 1 H) 4.48 (d, J = 7.34 Hz, 1 H) 4.63 (t, J = 3.67 Hz, 1 H) 5.03 (d, J = 5.04 Hz, 1 H) 6.83-6.90 (m, 2 H) 7.16 (t, J = 7.34 Hz, 1 H) 7.61 (d, J = 7.79 Hz, 1 H) |

TABLE 4-7

| Example | Reference Example | R | ESI MS (M + H) | ¹H-NMR, CDCl₃, δ (ppm) |
|---|---|---|---|---|
| 72 | 51 | 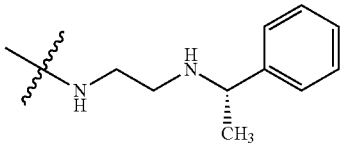 | 865.7 | (500 MHz): 0.88 (d, J = 7.40 Hz, 3 H) 1.01 (d, J = 6.86 Hz, 3 H) 1.08-1.26 (m, 16 H) 1.32-1.39 (m, 7 H) 1.58-1.63 (m, 1 H) 1.95-2.08 (m, 2 H) 2.09-2.16 (m, 1 H) 2.26-2.31 (m, 1 H) 2.29 (s, 6 H) 2.40-2.69 (m, 6 H) 2.82-2.93 (m, 4 H) 2.98-3.05 (m, 1 H) 3.12-3.24 (m, 3 H) 3.28 (s, 3 H) 3.35 (s, 3 H) 3.37-3.43 (m, 1 H) 3.45-3.53 (m, 1 H) 3.56-3.62 (m, 1 H) 3.67-3.77 (m, 2 H) 3.90 (d, J = 6.31 Hz, 1 H) 4.26 (q, J = 6.31 Hz, 1 H) 4.46 (d, J = 7.40 Hz, 1 H) 4.62 (t, J = 4.52 Hz, 1 H) 5.01 (d, J = 3.84 Hz, 1 H) 7.20-7.34 (m, 5 H) |
| 73 | 52 | 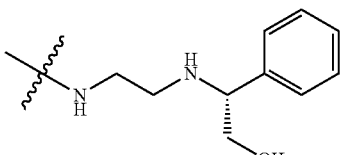 | 881.5 | (500 MHz): 0.88 (d, J = 7.13 Hz, 3 H) 1.01 (d, J = 6.86 Hz, 3 H) 1.07-1.27 (m, 16 H) 1.32-1.39 (m, 1 H) 1.38 (s, 3 H) 1.59-1.66 (m, 1 H) 1.94-2.08 (m, 2 H) 2.09-2.16 (m, 1 H) 2.30 (s, 6 H) 2.33 (d, J = 13.44 Hz, 1 H) 2.42-2.50 (m, 1 H) 2.55-2.75 (m, 5 H) 2.83-2.95 (m, 4 H) 2.99-3.05 (m, 1 H) 3.12-3.25 (m, 3 H) 3.29 (s, 3 H) 3.35 (s, 3 H) 3.37-3.44 (m, 1 H) 3.46-3.62 (m, 3 H) 3.67-3.77 (m, 3 H) 3.90 (d, J = 6.03 Hz, 1 H) 4.28 (q, J = 6.22 Hz, 1 H) 4.46 (d, J = 7.40 Hz, 1 H) 4.63 (t, J = 4.66 Hz, 1 H) 5.01 (d, J = 3.84 Hz, 1 H) 7.24-7.37 (m, 5 H) |
| 74 | 53 | 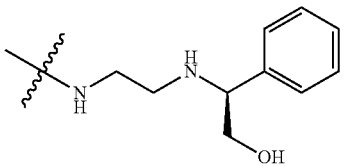 | 881.5 | (500 MHz): 0.88 (d, J = 7.13 Hz, 3 H) 1.01 (d, J = 6.58 Hz, 3 H) 1.09-1.26 (m, 16 H) 1.32-1.39 (m, 4 H) 1.60-1.66 (m, 1 H) 1.96-2.08 (m, 2 H) 2.09-2.15 (m, 1 H) 2.30 (s, 6 H) 2.33 (d, J = 13.16 Hz, 1 H) 2.43-2.51 (m, 1 H) 2.55-2.76 (m, 5 H) 2.83-2.98 (m, 4 H) 2.99-3.04 (m, 1 H) 3.13-3.25 (m, 3 H) 3.29 (s, 3 H) 3.35 (s, 3 H) 3.38-3.43 (m, 1 H) 3.49-3.62 (m, 3 H) 3.67-3.76 (m, 3 H) 3.90 (d, J = 6.31 Hz, 1 H) 4.28 (q, J = 6.49 Hz, 1 H) 4.47 (d, J = 7.13 Hz, 1 H) 4.63 (t, J = 4.66 Hz, 1 H) 4.99-5.03 (m, 1 H) 7.24-7.37 (m, 5 H) |
| 75 | 54 | 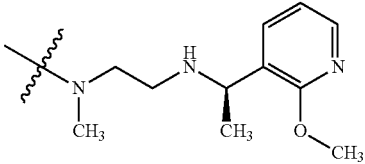 | 910.6 | (500 MHz): 0.89 (d, J = 7.13 Hz, 3 H) 1.02 (d, J = 6.86 Hz, 3 H) 1.12 (d, J = 7.68 Hz, 3 H) 1.18 (s, 3 H) 1.22 (dd, J = 9.05, 6.31 Hz, 10 H) 1.34 (d, J = 6.58 Hz, 3 H) 1.36-1.42 (m, 4 H) 1.59-1.69 (m, 1 H) 1.98-2.19 (m, 3 H) 2.24 (s, 3 H) 2.30 (s, 6 H) 2.27-2.35 (m, 1 H) 2.42-2.62 (m, 5 H) 2.64-2.73 (m, 1 H) 2.82-2.95 (m, 4 H) 2.99-3.06 (m, 1 H) 3.13-3.25 (m, 3 H) 3.30 (s, 3 H) 3.38 (s, 3 H) 3.38-3.51 (m, 2 H) 3.55-3.65 (m, 1 H) 3.71 (dd, J = 9.60, 1.92 Hz, 1 H) 3.90-3.98 (m, 2 H) 3.96 (s, 3 H) 4.19 (q, J = 6.03 Hz, 1 H) 4.49 (d, J = 7.13 Hz, 1 H) 4.63 (t, J = 4.66 Hz, 1 H) 5.04 (d, J = 4.94 Hz, 1 H) 6.86 (dd, J = 7.27, 5.07 Hz, 1 H) 7.60 (dd, J = 7.27, 1.78 Hz, 1 H) 8.04 (dd, J = 4.94, 1.92 Hz, 1 H) |

TABLE 4-7-continued

| Example | Reference Example | R | ESI MS (M + H) | ¹H-NMR, CDCl₃, δ (ppm) |
|---|---|---|---|---|
| 76 | 55 | | 910.5 | (500 MHz): 0.89 (d, J = 7.40 Hz, 3 H) 1.02 (d, J = 6.58 Hz, 3 H) 1.12 (d, J = 7.68 Hz, 3 H) 1.15-1.29 (m, 13 H) 1.31-1.41 (m, 7 H) 1.61-1.68 (m, 1 H) 1.99-2.17 (m, 3 H) 2.25 (s, 3 H) 2.27-2.33 (m, 1 H) 2.30 (s, 6 H) 2.42-2.67 (m, 6 H) 2.80-2.96 (m, 4 H) 2.99-3.07 (m, 1 H) 3.14-3.25 (m, 3 H) 3.30 (s, 3 H) 3.38 (s, 3 H) 3.38-3.51 (m, 2 H) 3.57-3.63 (m, 1 H) 3.69-3.73 (m, 1 H) 3.91-4.00 (m, 2 H) 3.96 (s, 3 H) 4.19 (q, J = 6.31 Hz, 1 H) 4.49 (d, 1 H) 4.64 (t, J = 4.52 Hz, 1 H) 5.03-5.07 (m, 1 H) 6.86 (dd, J = 7.27, 5.07 Hz, 1 H) 7.61 (dd, J = 7.27, 1.78 Hz, 1 H) 8.04 (dd, J = 4.94, 1.92 Hz, 1 H) |
| 77 | 56 | | 924.6 | (500 MHz): 0.89 (d, J = 7.13 Hz, 3 H) 0.95-1.05 (m, 6 H) 1.07-1.31 (m, 19 H) 1.32-1.41 (m, 4 H) 1.60-1.70 (m, 1 H) 1.96-2.18 (m, 3 H) 2.27-2.33 (m, 1 H) 2.30 (s, 6 H) 2.41-2.68 (m, 8 H) 2.84-2.97 (m, 4 H) 3.00-3.05 (m, 1 H) 3.13-3.26 (m, 4 H) 3.27-3.38 (m, 7 H) 3.38-3.44 (m, 1 H) 3.47-3.55 (m, 1 H) 3.57-3.63 (m, 1 H) 3.68-3.73 (m, 1 H) 3.89-3.94 (m, 1 H) 3.92 (s, 3 H) 4.23-4.34 (m, 2 H) 4.49 (d, J = 7.13 Hz, 1 H) 4.64 (t, J = 4.53 Hz, 1 H) 7.23-7.26 (m, 1 H) 8.20-8.25 (m, 2 H) |
| 78 | 57 | | 932.6 | (600 MHz): 0.88 (d, J = 7.34 Hz, 3 H) 1.01 (d, J = 6.88 Hz, 3 H) 1.06-1.21 (m, 13 H) 1.24 (d, J = 6.88 Hz, 3 H) 1.35 (d, J = 14.67 Hz, 1 H) 1.38 (s, 3 H) 1.53 (br. s., 6 H) 1.57-1.66 (m, 1 H) 1.93-2.08 (m, 2 H) 2.09-2.16 (m, 1 H) 2.23-2.34 (m, 1 H) 2.28 (br. s., 6 H) 2.37-2.50 (m, 3 H) 2.52-2.70 (m, 3 H) 2.81-2.95 (m, 4 H) 2.98-3.04 (m, 1 H) 3.12-3.24 (m, 3 H) 3.28 (s, 3 H) 3.35 (s, 3 H) 3.37-3.43 (m, 1 H) 3.43-3.52 (m, 1 H) 3.56-3.62 (m, 1 H) 3.67-3.71 (m, 1 H) 3.78 (s, 3 H) 3.89 (d, J = 5.96 Hz, 1 H) 4.20-4.28 (m, 1 H) 4.43-4.48 (m, 1 H) 4.63 (t, J = 4.81 Hz, 1 H) 4.98-5.03 (m, 1 H) 6.42-6.46 (m, 1 H) 7.01-7.06 (m, 1 H) 7.26-7.37 (m, 2 H) 7.62 (br. s., 1 H) |
| 79 | 58 | | 907.6 | (600 MHz): 0.87 (d, J = 6.88 Hz, 3 H) 1.00 (d, J = 6.42 Hz, 3 H) 1.03-1.08 (m, 3 H) 1.09-1.16 (m, 9 H) 1.18-1.21 (m, 3 H) 1.19-1.23 (m, 1 H) 1.24 (d, J = 6.88 Hz, 3 H) 1.32-1.37 (m, 1 H) 1.38 (d, J = 2.75 Hz, 3 H) 1.64 (br. s., 1 H) 1.95-2.08 (m, 2 H) 2.13 (br. s., 1 H) 2.22-2.27 (m, 1 H) 2.29 (br. s., 6 H) 2.37-2.68 (m, 8 H) 2.80 (d, J = 13.30 Hz, 1 H) 2.85-2.95 (m, 3 H) 2.99-3.04 (m, 1 H) 3.14-3.24 (m, 3 H) 3.29 (br. s., 3 H) 3.34-3.37 (m, 3 H) 3.38-3.41 (m, 1 H) 3.45-3.53 (m, 1 H) 3.57-3.61 (m, 1 H) 3.70 (d, J = 9.63 Hz, 1 H) 3.91 (d, J = 6.42 Hz, 1 H) 4.24 (dd, J = 6.42, 4.13 Hz, 1 H) 4.38-4.45 (m, 2 H) 4.45-4.49 (m, 1 H) 4.62 (t, J = 4.81 Hz, 1 H) 4.66 (dd, J = 8.48, 3.90 Hz, 1 H) 4.91 (d, J = 8.71 Hz, 1 H) 5.02 (d, J = 5.04 Hz, 1 H) 6.80 (dd, J = 8.02, 2.52 Hz, 1 H) 6.84-6.92 (m, 1 H) 7.18 (t, J = 7.79 Hz, 1 H) 7.25 (d, J = 16.05 Hz, 1 H) |

TABLE 4-8

| Example | Reference Example | R | ESI MS (M + H) | ¹H-NMR, CDCl₃, δ (ppm) |
|---|---|---|---|---|
| 80 | 59 | | 923.6 | (600 MHz): 0.87 (d, J = 7.34 Hz, 3 H) 0.91-0.97 (m, 3 H) 1.00 (d, J = 6.42 Hz, 3 H) 1.11 (d, J = 7.79 Hz, 12 H) 1.17 (d, J = 5.96 Hz, 3 H) 1.21 (d, J = 11.46 Hz, 3 H) 1.24 (d, J = 6.88 Hz, 3 H) 1.33-1.36 (m, 1 H) 1.37 (s, 3 H) 1.45-1.49 (m, 3 H) 1.53-1.59 (m, 1 H) 1.98-2.07 (m, 3 H) 2.09-2.17 (m, 2 H) 2.26-2.29 (m, 1 H) 2.30 (s, 6 H) 2.43-2.49 (m, 1 H) 2.54-2.59 (m, 2 H) 2.86-2.95 (m, 4 H) 2.98-3.03 (m, 1 H) 3.11-3.23 (m, 3 H) 3.30 (s, 3 H) 3.35 (s, 3 H) 3.38-3.41 (m, 1 H) 3.47-3.53 (m, 1 H) 3.56-3.62 (m, 1 H) 3.65-3.71 (m, 1 H) 3.82-3.89 (m, 1 H) 3.91 (d, J = 5.96 Hz, 1 H) 4.25 (q, J = 5.96 Hz, 1 H) 4.49 (d, J = 7.34 Hz, 1 H) 4.62 (t, J = 4.58 Hz, 1 H) 4.94 (d, J = 9.63 Hz, 1 H) 5.03 (d, J = 5.96 Hz, 1 H) 6.88-6.96 (m, 2 H) 7.19-7.24 (m, 2 H) |

TABLE 4-8-continued

| Example | Reference Example | R | ESI MS (M + H) | ¹H-NMR, CDCl₃, δ (ppm) |
|---|---|---|---|---|
| 81 | 60 | (structure: -NH-CH₂CH₂-NH- linked to 3,3-dimethyl-chroman-4-yl) | 921.6 | (600 MHz): 0.87 (d, J = 6.88 Hz, 3 H) 0.93 (s, 3 H) 0.98-1.02 (m, 6 H) 1.09-1.13 (m, 6 H) 1.15 (d, J = 6.42 Hz, 3 H) 1.19 (dd, J = 8.25, 6.42 Hz, 3 H) 1.20-1.23 (m, 1 H) 1.24 (d, J = 7.34 Hz, 3 H) 1.33-1.37 (m, 1 H) 1.37 (d, J = 2.29 Hz, 3 H) 1.60-1.64 (m, 1 H) 1.95-2.08 (m, 2 H) 2.10-2.16 (m, 1 H) 2.27-2.30 (m, 6 H) 2.35 (d, J = 13.30 Hz, 1 H) 2.42-2.48 (m, 1 H) 2.58 (q, J = 6.88 Hz, 1 H) 2.64-2.73 (m, 2 H) 2.79-2.93 (m, 4 H) 2.96 (d, J = 13.75 Hz, 1 H) 2.99-3.09 (m, 2 H) 3.14 (m, 4 H) 3.27-3.29 (m, 3 H) 3.34-3.36 (m, 3 H) 3.40 (br. s., 1 H) 3.48-3.55 (m, 1 H) 3.57-3.60 (m, 1 H) 3.68-3.71 (m, 2 H) 3.90 (d, J = 6.42 Hz, 1 H) 3.94 (dd, J = 10.55, 3.21 Hz, 1 H) 4.24-4.30 (m, 1 H) 4.47 (d, J = 6.88 Hz, 1 H) 4.62 (t, J = 4.58 Hz, 1 H) 4.92 (d, J = 10.09 Hz, 1 H) 5.01 (d, J = 4.59 Hz, 1 H) 6.79 (d, J = 8.25 Hz, 1 H) 6.83-6.88 (m, 1 H) 7.11-7.20 (m, 2 H) |
| 82 | 61 | (structure: chiral -NH-CH(CH₃)CH₂-N(CH₃)-C(CH₃)₂-(2-methoxyphenyl)) | 937.6 | (600 MHz): 0.87 (d, J = 7.34 Hz, 3 H) 0.89 (d, J = 5.96 Hz, 3 H) 1.00 (d, J = 6.88 Hz, 3 H) 1.11 (d, J = 7.79 Hz, 3 H) 1.12 (s, 3 H) 1.17-1.21 (m, 6 H) 1.22-1.24 (m, 1 H) 1.24 (d, J = 6.88 Hz, 3 H) 1.34 (d, J = 14.21 Hz, 1 H) 1.37 (s, 3 H) 1.43 (d, J = 3.67 Hz, 6 H) 1.60-1.66 (m, 1 H) 2.00-2.03 (m, 2 H) 2.12 (s, 3 H) 2.13-2.19 (m, 3 H) 2.29 (s, 6 H) 2.38-2.43 (m, 1 H) 2.45-2.51 (m, 1 H) 2.57 (q, J = 6.42 Hz, 1 H) 2.61-2.69 (m, 1 H) 2.85-2.93 (m, 3 H) 3.01 (dd, J = 10.32, 3.44 Hz, 1 H) 3.09-3.19 (m, 3 H) 3.19-3.23 (m, 1 H) 3.31 (s, 3 H) 3.36 (s, 3 H) 3.37-3.41 (m, 1 H) 3.47-3.54 (m, 1 H) 3.56-3.60 (m, 1 H) 3.65-3.69 (m, 1 H) 3.79 (s, 3 H) 3.94 (d, J = 5.96 Hz, 1 H) 4.22-4.27 (m, 1 H) 4.51 (d, J = 7.34 Hz, 1 H) 4.62 (t, J = 4.81 Hz, 1 H) 4.97 (d, J = 10.55 Hz, 1 H) 5.02 (t, J = 3.44 Hz, 1 H) 6.85-6.91 (m, 2 H) 7.16-7.22 (m, 1 H) 7.39-7.43 (m, 1 H) |
| 83 | 62 | (structure: chiral -N(CH₃)-CH(CH₃)CH₂-NH-C(CH₃)₂-(2-methoxyphenyl)) | 937.6 | (600 MHz): 0.81 (d, J = 6.88 Hz, 3 H) 0.87 (d, J = 6.88 Hz, 3 H) 1.00 (d, J = 6.88 Hz, 3 H) 1.11 (d, J = 7.79 Hz, 3 H) 1.18 (s, 3 H) 1.20-1.23 (m, 6 H) 1.23-1.24 (m, 1 H) 1.25 (d, J = 6.88 Hz, 3 H) 1.36 (d, J = 14.21 Hz, 1 H) 1.38 (s, 3 H) 1.49 (d, J = 6.88 Hz, 6 H) 1.58-1.64 (m, 1 H) 1.90 (s, 3 H) 1.95-2.00 (m, 1 H) 2.02-2.08 (m, 2 H) 2.10-2.15 (m, 1 H) 2.17-2.23 (m, 1 H) 2.29 (s, 6 H) 2.44-2.50 (m, 1 H) 2.57 (q, J = 6.72 Hz, 1 H) 2.84-2.94 (m, 6 H) 3.01 (dd, J = 10.32, 3.44 Hz, 1 H) 3.12-3.23 (m, 3 H) 3.29 (s, 3 H) 3.37 (s, 3 H) 3.38-3.41 (m, 1 H) 3.46-3.52 (m, 1 H) 3.55-3.60 (m, 1 H) 3.69-3.72 (m, 1 H) 3.85 (s, 3 H) 3.92 (d, J = 5.96 Hz, 1 H) 4.17-4.20 (m, 1 H) 4.49 (d, J = 7.34 Hz, 1 H) 4.62 (t, J = 4.81 Hz, 1 H) 4.96 (d, J = 10.55 Hz, 1 H) 5.04-5.07 (m, 1 H) 6.86-6.93 (m, 2 H) 7.19-7.25 (m, 2 H) |
| 84 | 63 | (structure: chiral -NH-CH(CH₃)CH₂-N(Et)-C(CH₃)₂-(2-methoxyphenyl)) | 951.6 | (600 MHz): 0.86 (d, J = 5.96 Hz, 3 H) 0.87 (d, J = 7.34 Hz, 3 H) 0.92 (t, J = 7.11 Hz, 3 H) 1.00 (d, J = 6.42 Hz, 3 H) 1.11 (d, J = 7.79 Hz, 3 H) 1.14 (s, 3 H) 1.19 (dd, J = 5.96, 3.21 Hz, 6 H) 1.22 (d, J = 11.46 Hz, 1 H) 1.25 (d, J = 6.88 Hz, 3 H) 1.34 (d, J = 14.67 Hz, 1 H) 1.37 (s, 3 H) 1.44 (s, 3 H) 1.48 (s, 3 H) 1.62 (d, J = 12.38 Hz, 1 H) 2.00-2.08 (m, 3 H) 2.09-2.16 (m, 1 H) 2.25-2.28 (m, 1 H) 2.29 (s, 6 H) 2.34-2.40 (m, 1 H) 2.40-2.60 (m, 5 H) 2.90 (d, J = 2.29 Hz, 3 H) 2.99-3.03 (m, 1 H) 3.08-3.24 (m, 4 H) 3.32 (s, 3 H) 3.36 (s, 3 H) 3.37-3.42 (m, 1 H) 3.48-3.54 (m, 1 H) 3.56-3.61 (m, 1 H) 3.63-3.69 (m, 1 H) 3.81 (s, 3 H) 3.94 (d, J = 5.96 Hz, 1 H) 4.24 (q, J = 6.11 Hz, 1 H) 4.54 (d, J = 6.88 Hz, 1 H) 4.62 (t, J = 4.81 Hz, 1 H) 4.97 (d, J = 10.55 Hz, 1 H) 5.03 (t, J = 3.44 Hz, 1 H) 6.83-6.92 (m, 2 H) 7.17-7.23 (m, 1 H) 7.37-7.42 (m, 1 H) |
| 85 | 64 | (structure: -N(CH₃)-CH₂CH₂-N(CH₃)-C(CH₃)₂-(2-methoxypyridin-3-yl)) | 938.6 | (600 MHz): 0.88 (d, J = 7.34 Hz, 3 H) 1.01 (d, J = 6.42 Hz, 3 H) 1.10 (d, J = 7.34 Hz, 3 H) 1.14 (s, 3 H) 1.19 (d, J = 6.42 Hz, 3 H) 1.20-1.27 (m, 1 H) 1.21-1.27 (m, 6 H) 1.32-1.37 (m, 1 H) 1.37-1.42 (m, 9 H) 1.61-1.68 (m, 1 H) 1.97-2.16 (m, 4 H) 2.18 (s, 3 H) 2.25 (s, 3 H) 2.30 (br. s., 6 H) 2.35-2.65 (m, 6 H) 2.79-2.92 (m, 4 H) 2.99-3.05 (m, 1 H) 3.10-3.26 (m, 3 H) 3.29 (s, 3 H) 3.36 (s, 3 H) 3.37-3.50 (m, 2 H) 3.55-3.63 (m, 1 H) 3.67-3.73 (m, 1 H) 3.88-3.91 (m, 1 H) 3.92 (s, 3 H) 4.16 (q, J = 5.66 Hz, 1 H) 4.48 (d, J = 6.88 Hz, 1 H) 4.63 (t, J = 4.36 Hz, 1 H) 5.04 (d, J = 5.04 Hz, 1 H) 6.81 (dd, J = 7.34, 5.04 Hz, 1 H) 7.96 (d, J = 7.34 Hz, 1 H) 8.00 (dd, J = 4.58, 1.83 Hz, 1 H) |

TABLE 4-9

| Example | Reference Example | R | ESI MS (M + H) | $^1$H-NMR, CDCl$_3$, δ (ppm) |
|---|---|---|---|---|
| 86 | 65 | | 932.5 | (600 MHz): 0.87 (d, J = 7.34 Hz, 3 H) 1.01 (d, J = 6.42 Hz, 3 H) 1.11 (d, J = 7.79 Hz, 3 H) 1.14 (s, 3 H) 1.18 (d, J = 6.42 Hz, 3 H) 1.19-1.28 (m, 1 H) 1.21 (d, J = 5.96 Hz, 3 H) 1.25 (d, J = 6.88 Hz, 3 H) 1.34-1.37 (m, 1 H) 1.38 (s, 3 H) 1.59-1.64 (m, 1 H) 1.97-2.17 (m, 4 H) 2.24 (s, 3 H) 2.27 (br. s., 3 H) 2.29 (s, 6 H) 2.41-2.71 (m, 6 H) 2.82 (d, J = 14.67 Hz, 1 H) 2.84-2.92 (m, 3 H) 2.99-3.05 (m, 1 H) 3.12-3.24 (m, 3 H) 3.28 (s, 3 H) 3.36 (s, 3 H) 3.37-3.42 (m, 1 H) 3.43-3.50 (m, 1 H) 3.56-3.62 (m, 1 H) 3.67-3.72 (m, 1 H) 3.70 (br. s., 3 H) 3.75 (s, 2 H) 3.92 (d, J = 5.96 Hz, 1 H) 4.16 (q, J = 6.27 Hz, 1 H) 4.48 (d, J = 6.88 Hz, 1 H) 4.59-4.66 (m, 1 H) 5.04 (d, J = 5.04 Hz, 1 H) 7.03 (s, 1 H) 7.08 (t, J = 7.57 Hz, 1 H) 7.20 (t, J = 7.11 Hz, 1 H) 7.28 (d, J = 8.25 Hz, 1 H) 7.66 (d, J = 7.79 Hz, 1 H) |
| 87 | 66 | | 937.6 | (600 MHz): 0.87 (d, J = 6.88 Hz, 3 H) 1.01 (d, J = 6.42 Hz, 3 H) 1.10 (d, J = 7.34 Hz, 3 H) 1.12 (s, 3 H) 1.17 (d, J = 6.42 Hz, 3 H) 1.19-1.27 (m, 1 H) 1.22 (d, J = 5.96 Hz, 3 H) 1.25 (d, J = 7.34 Hz, 3 H) 1.31 (s, 6 H) 1.35 (d, J = 15.13 Hz, 1 H) 1.38 (s, 3 H) 1.59-1.66 (m, 1 H) 1.97-2.10 (m, 3 H) 2.06 (s, 3 H) 2.10-2.15 (m, 1 H) 2.23 (s, 3 H) 2.25-2.35 (m, 2 H) 2.29 (br. s., 6 H) 2.38-2.62 (m, 4 H) 2.78 (d, J = 14.67 Hz, 1 H) 2.83-2.92 (m, 3 H) 2.97-3.05 (m, 1 H) 3.11-3.25 (m, 3 H) 3.28 (s, 3 H) 3.37 (s, 3 H) 3.35-3.49 (m, 2 H) 3.56-3.62 (m, 1 H) 3.67-3.72 (m, 1 H) 3.79 (s, 3 H) 3.91 (d, J = 5.96 Hz, 1 H) 4.14 (q, J = 6.42 Hz, 1 H) 4.47 (d, J = 7.34 Hz, 1 H) 4.62 (t, J = 4.58 Hz, 1 H) 5.03 (d, J = 5.04 Hz, 1 H) 6.69-6.74 (m, 1 H) 7.07-7.09 (m, 1 H) 7.12 (d, J = 7.79 Hz, 1 H) 7.18 (t, J = 7.79 Hz, 1 H) |
| 88 | 67 | | 951.6 | (600 MHz): 0.88 (d, J = 7.34 Hz, 6 H) 1.01 (d, J = 6.88 Hz, 3 H) 1.12 (d, J = 7.79 Hz, 3 H) 1.15 (s, 3 H) 1.18-1.29 (m, 10 H) 1.35-1.39 (m, 1 H) 1.39 (s, 3 H) 1.45 (d, J = 11.46 Hz, 3 H) 1.55 (br. s., 6 H) 1.60-1.66 (m, 1 H) 1.97-2.19 (m, 5 H) 2.21 (br. s., 3 H) 2.30 (s, 6 H) 2.43-2.51 (m, 2 H) 2.55-2.60 (m, 1 H) 2.77-2.97 (m, 5 H) 3.00-3.05 (m, 1 H) 3.13-3.25 (m, 3 H) 3.31 (s, 3 H) 3.39 (s, 3 H) 3.39-3.41 (m, 1 H) 3.46-3.53 (m, 1 H) 3.57-3.61 (m, 1 H) 3.72 (dd, J = 9.63, 1.83 Hz, 1 H) 3.79 (s, 3 H) 3.93 (d, J = 6.42 Hz, 1 H) 4.19 (q, J = 6.27 Hz, 1 H) 4.49 (d, J = 7.34 Hz, 1 H) 4.63 (t, J = 4.58 Hz, 1 H) 4.96 (d, J = 10.55 Hz, 1 H) 5.06 (d, J = 5.04 Hz, 1 H) 6.84-6.90 (m, 2 H) 7.15-7.20 (m, 1 H) 7.57-7.61 (m, 1 H) |
| 89 | | | 789 | (400 MHz): 0.89 (d, J = 7.33 Hz, 3 H) 1.10 (d, J = 6.83 Hz, 3 H) 1.12 (d, J = 7.56 Hz, 3 H) 1.14 (s, 3 H) 1.16 (d, J = 6.35 Hz, 3 H) 1.20-1.28 (m, 1 H) 1.22 (d, J = 6.10 Hz, 3 H) 1.22 (d, J = 6.10 Hz, 3 H) 1.25 (d, J = 7.08 Hz, 3 H) 1.33-1.39 (m, 1 H) 1.39 (s, 3 H) 1.60-1.69 (m, 1 H) 2.00 (dd, J = 14.9, 5.13 Hz, 1 H) 2.04-2.19 (m, 3 H) 2.22 (s, 3 H) 2.30 (s, 6 H) 2.33-2.41 (m, 3 H) 2.42-2.52 (m, 1 H) 2.59 (q, J = 6.59 Hz, 1 H) 2.64-2.76 (m, 2 H) 2.83-2.95 (m, 3 H) 2.95 (d, J = 13.7 Hz, 1 H) 2.99-3.06 (m, 1 H) 3.12-3.25 (m, 3 H) 3.28-3.44 (m, 2 H) 3.30 (s, 3 H) 3.36 (s, 3 H) 3.49-3.63 (m, 2 H) 3.71 (dd, J = 9.77, 1.96 Hz, 1 H) 3.92 (d, J = 6.35 Hz, 1 H) 4.28 (q, J = 6.35 Hz, 1 H) 4.49 (d, J = 7.08 Hz, 1 H) 4.63 (t, J = 4.63 Hz, 1 H) 4.93 (d, J = 10.3 Hz, 1 H) 5.03 (d, J = 3.91 Hz, 1 H) |
| 90 | 12 | | 923 FAB MASS | (400 MHz): 0.88 (d, J = 7.1 Hz, 3 H) 1.00 (t, J = 7.1 Hz, 3 H) 1.00-1.04 (m, 6 H) 1.08(s, 3 H) 1.11 (d, J = 5.6 Hz, 3 H) 1.12 (d, J = 8.1 Hz, 3 H) 1.20 (d, J = 6.1 Hz, 3 H) 1.25 (d, J = 7.1 Hz, 3 H) 1.29 (d, J = 6.91 Hz, 3 H) 1.38 (s, 3 H) 1.51-1.75 (m, 2 H) 1.95-2.08 (m, 2 H) 2.11-2.19 (m, 1 H) 2.29 (s, 6 H) 2.42-2.70 (m, 5 H) 2.83-2.94 (m, 3 H) 2.99-3.05 (m, 1 H) 3.13-3.24 (m, 3 H) 3.27-3.43 (m, 8 H) 3.45-3.55 (m, 1 H) 3.56-3.65 (m, 1 H) 3.67-3.72 (m, 1 H) 3.80 (s, 3 H) 3.92 (d, J = 6.1 Hz, 1 H) 4.22 (q, J = 6.6 Hz, 1 H) 4.37 (q, J = 6.9 Hz, 1 H) 4.50 (d, J = 7.1 Hz, 1 H) 4.63 (t, J = 4.7 Hz, 1 H) 4.97 (d, J = 10.2 Hz, 1 H) 5.03 (d, J = 3.9 Hz, 1 H) 6.86 (d, J = 8.3 Hz, 1 H) 6.92 (t, J = 7.5 Hz, 1 H) 7.18-7.24 (m, 1 H) 7.29-7.33 (m, 1 H) |

TABLE 4-9-continued

| Example | Reference Example | R | ESI MS (M + H) | ¹H-NMR, CDCl₃, δ (ppm) |
|---|---|---|---|---|
| 91 | 7 | [structure] | 937 | (400 MHz): 0.88 (t, J = 7.1 Hz, 3 H) 0.96-1.06 (m, 6 H) 1.07-1.46 (m, 20 H) 1.39 (3H, s) 1.55-1.70 (m, 3 H) 1.99 (dd, J = 14.9, 5.1 Hz, 1 H) 2.06 (d, J = 14.9 Hz, 1H) 2.10-2.18 (m, 1 H) 2.24 (d, J = 13.4 Hz, 1 H) 2.30 (s, 6 H) 2.42-2.77 (m, 8 H) 2.82-2.96 (m, 4 H) 2.98-3.05 (m, 1 H) 3.13-3.26 (m, 4 H) 3.29 (s, 3 H) 3.36 (s, 3 H) 3.37-3.44 (m, 1 H) 3.67-3.72 (m, 1 H) 3.82 (s, 3 H) 3.92 (d, J = 6.1 Hz, 1 H) 4.26 (q, J = 6.1 Hz, 1H) 4.30-4.40 (m, 1 H) 4.49 (d, J = 7.3 Hz, 1H) 4.64 (t, J = 4.6 Hz, 1 H) 4.01-5.00 (m, 1H) 5.02 (d, J = 3.7 Hz, 1 H) 6.86 (d, J = 8.1 Hz, 1H) 6.93 (t, J = 7.3 Hz, 1 H) 7.16-7.24 (m, 1 H) 7.39 (d, J = 7.3 Hz, 1 H) |
| 92 | 9 | [structure] | 951 | (400 MHz): 0.88 (t, J = 7.1 Hz, 3 H) 0.97-1.05 (m, 6 H) 1.09-1.35 (m, 20 H) 1.40 (s, 3 H) 1.40-1.50 (m, 4 H) 1.61-1.67 (m, 1 H) 1.99 (dd, J = 14.9, 5.1 Hz, 1 H) 2.07 (d, J = 14.9 Hz, 1H) 2.10-2.18 (m, 1 H) 2.30 (s, 6 H) 2.33 (d, J = 13.4 Hz, 1 H) 2.37-2.62 (m, 7 H) 2.62-2.73 (m, 1 H) 2.82-2.96 (m, 4 H) 2.99-3.07 (m, 1 H) 3.13-3.24 (m, 3 H) 3.30 (s, 3 H) 3.30-3.44 (m, 5 H) 3.51-3.63 (m, 2 H) 3.68-3.74 (m, 1 H) 3.82 (s, 3 H) 3.92 (d, J = 6.3 Hz, 1 H) 4.23-4.47 (m, 2 H) 4.48 (d, J = 7.3 Hz, 1 H) 4.63 (t, J = 4.6 Hz, 1 H) 4.93 (d, J = 10.5 Hz, 1 H) 5.02 (d, J = 4.4 Hz, 1 H) 6.86 (d, J = 8.3 Hz, 1H) 6.94 (t, J = 7.3 Hz, 1H) 7.15-7.23 (m, 1 H) 7.37-7.47 (m, 1 H) |

TABLE 4-10

| Example | Reference Example | R | ESI MS (M + H) | ¹H-NMR, CDCl₃, δ (ppm) |
|---|---|---|---|---|
| 93 | 13 | [structure] | 937 FAB MASS | (400 MHz): 0.74 (t, J = 6.8 Hz, 2.1 H) 0.81 (t, J = 7.1 Hz, 0.9 H) 0.90 (d, J = 7.1 Hz, 3 H) 1.08-1.44 (m, 20 H) 1.50-1.68 (m, 4 H) 2.02 (dd, J = 14.9, 5.6 Hz, 1 H) 2.10 (d, J = 14.9 Hz, 1 H) 2.10-2.18 (m, 1 H) 2.32 (s, 6 H) 2.43-2.57 (m, 2 H) 2.55-2.65 (m, 1 H), 2.79-3.95 (m, 27 H), 4.27-4.38 (m, 1H), 4.50 (d, J = 7.3 Hz, 1 H) 4.64 (t, J = 4.9 Hz, 1 H) 4.86-4.96 (m, 1 H) 5.00-5.09 (m, 1 H) 5.15 and 5.94 (each q, J = 7.3 Hz, 1 H) 6.83-6.91 (m, 1 H) 6.95-7.03 (m, 1 H) 7.28-7.38 (m, 2 H) |
| 94 | 14 | [structure] | 951 FAB MASS | (400 MHz): 0.89 (t, J = 7.1 Hz, 3 H) 0.96-1.06 (m, 6 H) 1.08-1.18 (m, 10 H) 1.20-1.36 (m, 10 H) 1.38 (s, 3 H) 1.60-1.68 (m, 1 H) 1.97-2.10 (m, 3 H) 2.10-2.17 (m, 1 H) 2.22 (s, 3 H) 2.31 (s, 6 H) 2.40-2.63 (m, 7 H) 2.65-2.76 (m, 1 H) 2.79-2.94 (m, 4 H) 2.99-3.06 (m, 1 H) 3.12-3.24 (m, 4 H) 3.30 (s, 3 H) 3.37 (s, 3 H) 3.38-3.52 (m, 2 H) 3.56-3.64 (m, 1 H) 3.70 (d, J = 9.5 Hz, 1H) 3.80 (s, 3 H), 3.93 (d, J = 6.1 Hz, 1 H) 4.15 (q, J = 6.3 Hz, 1 H) 4.30-4.39 (m, 1 H) 4.48 (d, J = 7.3 Hz, 1 H) 4.63 (t, J = 4.6 Hz, 1 H) 5.05 (d, J = 4.6 Hz, 1 H) 6.85 (d, J = 8.5 Hz, 1 H) 6.94 (t, J = 7.1 Hz, 1 H) 7.19 (t, J = 8.5 Hz, 1 H) 7.42 (d, J = 7.1 Hz, 1 H) |
| 95 | 10 | [structure] | 937 | (400 MHz): 0.88 (d, J = 7.57 Hz, 3 H) 0.90 (d, J = 7.08 Hz, 3 H) 0.94 (t, J = 7.08 Hz, 3 H) 0.99 (s, 3 H) 1.01 (d, J = 6.84 Hz, 3 H) 1.11 (d, J = 7.56 Hz, 3 H) 1.15-1.25 (m, 1 H) 1.16 (d, J = 6.40 Hz, 3 H) 1.18 (d, J = 6.35 Hz, 3 H) 1.24 (d, J = 7.57 Hz, 3 H) 1.26 (d, J = 7.08 Hz, 3 H) 1.32-1.39 (m, 1 H) 1.38 (s, 3 H) 1.56-1.65 (m, 1 H) 2.06-2.19 (m, 2 H) 2.24-2.62 (m, 7 H) 2.30 (s, 6 H) 2.62-2.72 (m, 1 H) 2.84-3.05 (m, 5 H) 3.12-3.43 (m, 6 H) 3.30 (s, 3 H) 3.36 (s, 3 H) 3.45-3.54 (m, 1 H) 3.56-3.63 (m, 1 H) 3.67 (dd, J = 9.77, 1.96 Hz, 1 H) 3.82 (s, 3 H) 3.93 (d, J = 6.11 Hz, 1 H) 4.23 (q, J = 6.34 Hz, 1 H) 4.34 (q, J = 6.59 Hz, 1 H) 4.52 (d, J = 7.08 Hz, 1 H) 4.63 (t, J = 4.63 Hz, 1 H) 4.97 (d, J = 10.3 Hz, 1 H) 4.99-5.04 (m, 1 H) 6.85 (d, J = 7.81 Hz, 1 H) 6.92 (t, J = 7.57 Hz, 1 H) 7.18-7.24 (m, 1 H) 7.31 (dd, J = 7.57, 1.46 Hz, 1 H) |

TABLE 4-10-continued

| Example | Reference Example | R | ESI MS (M + H) | ¹H-NMR, CDCl₃, δ (ppm) |
|---|---|---|---|---|
| 96 | 11 | (structure) | 937 | (400 MHz): 0.88 (d, J = 5.96 Hz, 3 H) 0.89 (d, J = 7.08 Hz, 3 H) 0.97 (t, J = 7.08 Hz, 3 H) 1.02 (d, J = 6.84 Hz, 3 H) 1.14 (d, J = 7.57 Hz, 3 H) 1.17-1.23 (m, 1 H) 1.19 (d, J = 6.11 Hz, 3 H) 1.20 (s, 3 H) 1.25 (d, J = 6.10 Hz, 3 H) 1.27 (d, J = 6.84 Hz, 3 H) 1.30 (d, J = 7.08 Hz, 3 H) 1.35-1.42 (m, 1 H) 1.41 (s, 3 H) 1.60-1.69 (m, 1 H) 2.02 (dd, J = 14.9, 5.13 Hz, 1 H) 2.10-2.37 (m, 6 H) 2.30 (s, 6 H) 2.42-2.53 (m, 2 H) 2.54-2.68 (m, 2 H) 2.74-2.96 (m, 5 H) 3.03 (dd, J = 10.0, 3.42 Hz, 1 H) 3.13-3.26 (m, 3 H) 3.28-3.44 (m, 2 H) 3.32 (s, 3 H) 3.40 (s, 3 H) 3.51-3.63 (m, 2 H) 3.67 (dd, J = 9.52, 1.95 Hz, 1 H) 3.80 (s, 3 H) 3.94 (d, J = 6.59 Hz, 1 H) 4.33 (q, J = 6.59 Hz, 1 H) 4.41 (q, J = 6.83 Hz, 1 H) 4.51 (d, J = 7.08 Hz, 1 H) 4.64 (t, J = 4.39 Hz, 1 H) 4.94 (d, J = 10.5 Hz, 1 H) 5.05 (d, J = 5.13 Hz, 1 H) 6.86 (d, J = 7.57 Hz, 1 H) 6.93 (dt, J = 7.56, 0.97 Hz, 1 H) 7.20 (dt, J = 8.30, 1.71 Hz, 1 H) 7.24-7.29 (m, 1 H) |
| 97 | 68 | (structure) | 909 FAB MASS | (400 MHz): 0.88 (d, J = 7.1 Hz, 3 H) 1.02 (d, J = 6.8 Hz, 3 H) 1.12 (d, J = 7.8 Hz, 3 H) 1.17 (s, 3 H) 1.18-1.29 (m, 10 H) 1.32-1.42 (m, 7 H) 1.60-1.68 (m, 1 H) 2.03 (dd, J = 14.9, 4.9 Hz, 1 H) 2.05-2.19 (m, 3 H) 2.22 (s, 3 H) 2.31 (s, 6 H) 2.42-2.66 (m, 6 H) 2.80-2.95 (m, 4 H) 3.00-3.07 (m, 1 H) 3.13-3.26 (m, 3 H) 3.30 (s, 3 H) 3.26-3.34 (m, 1 H) 3.37 (s, 3 H) 3.38-3.52 (m, 2 H) 3.55-3.64 (m, 1 H) 3.71 (dd, J = 9.8, 1.7 Hz, 1 H) 3.82 (s, 3 H) 3.96 (d, J = 6.3 Hz, 1 H) 4.06-4.13 (m, 1 H) 4.18 (q, J = 6.6 Hz, 1 H) 4.48 (d, J = 7.3 Hz, 1 H) 4.63 (t, J = 4.4 Hz, 1 H) 4.95 (d, J = 10.5 Hz, 1 H) 5.04 (d, J = 4.6 Hz, 1 H), 6.87 (d, J = 8.1 Hz, 1 H) 6.94 (t, J = 7.3 Hz, 1 H) 7.18-7.24 (m, 1 H) 7.27-7.32 (1H, m) |
| 98 | 69 | (structure) | 909 FAB MASS | (400 MHz): 0.88 (d, J = 6.83 Hz, 3 H) 0.98 (d, J = 6.11 Hz, 3 H) 1.01 (d, J = 6.59 Hz, 3 H) 1.09-1.37 (m, 5 H) 1.13 (s, 3 H) 1.16 (d, J = 5.38 Hz, 3 H) 1.17 (d, J = 5.37 Hz, 3 H) 1.25 (d, J = 6.60 Hz, 3 H) 1.34 (d, J = 6.60 Hz, 3 H) 1.38 (s, 3 H) 1.55-1.67 (m, 2 H) 1.97-2.19 (m, 2 H) 2.33-2.51 (m, 4 H) 2.30 (s, 6 H) 2.54-2.64 (m, 2 H) 2.85-2.95 (m, 4 H) 2.99-3.05 (m, 1 H) 3.12-3.25 (m, 3 H) 3.28-3.44 (m, 2 H) 3.31 (s, 3 H) 3.37 (s, 3 H) 3.46-3.63 (m, 2 H) 3.70 (d, J = 9.77 Hz, 1 H) 3.83 (s, 3 H) 3.92 (d, J = 5.86 Hz, 1 H) 4.05 (q, J = 6.34 Hz, 1 H) 4.27 (q, J = 6.34 Hz, 1 H) 4.49 (d, J = 7.08 Hz, 1 H) 4.63 (t, J = 4.64 Hz, 1 H) 4.95 (d, J = 10.3 Hz, 1 H) 5.03 (d, J = 2.93 Hz, 1 H) 6.87 (d, J = 8.30 Hz, 1 H) 6.94 (t, J = 7.32 Hz, 1 H) 7.18-7.30 (m, 2 H) |
| 99 | 70 | (structure) | 965 FAB MASS | (400 MHz): 0.81 (d, J = 6.83 Hz, 3 H) 0.83 (d, J = 5.37 Hz, 3 H) 0.88 (d, J = 7.33 Hz, 3 H) 0.97 (t, J = 6.84 Hz, 3 H) 1.01 (s, 3 H) 1.02 (d, J = 5.37 Hz, 3 H) 1.11 (d, J = 7.81 Hz, 3 H) 1.13-1.21 (m, 1 H) 1.14 (d, J = 6.35 Hz, 3 H) 1.17 (d, J = 6.10 Hz, 3 H) 1.25 (d, J = 8.30 Hz, 3 H) 1.27 (d, J = 7.08 Hz, 3 H) 1.32-1.37 (m, 1 H) 1.37 (s, 3 H) 1.54-1.67 (m, 1 H) 1.75-1.86 (m, 1 H) 1.95-2.18 (m, 2 H) 2.24-2.64 (m, 7 H) 2.29 (s, 6 H) 2.84-3.06 (m, 5 H) 3.11-3.52 (m, 7 H) 3.30 (s, 3 H) 3.36 (s, 3 H) 3.56-3.63 (m, 1 H) 3.67 (dd, J = 9.52, 1.96 Hz, 1 H) 3.82 (s, 3 H) 3.93 (d, J = 5.86 Hz, 1 H) 4.21 (q, J = 6.35 Hz, 1 H) 4.35 (q, J = 6.84 Hz, 1 H) 4.52 (d, J = 7.32 Hz, 1 H) 4.63 (t, J = 4.39 Hz, 1 H) 4.97 (d, J = 10.3 Hz, 1 H) 4.97-5.04 (m, 1 H) 6.85 (d, J = 8.3 Hz, 1 H) 6.92 (t, J = 7.33 Hz, 1 H) 7.18-7.24 (m, 1 H) 7.32 (dd, J = 7.57, 1.57 Hz, 1 H) |

TABLE 4-11

| Example | Reference Example | R | ESI MS (M + H) | ¹H-NMR, CDCl₃, δ (ppm) |
|---|---|---|---|---|
| 100 | 71 | (structure) | 975 | (400 MHz): 0.88 (d, J = 7.08 Hz, 3 H) 1.01 (d, J = 6.84 Hz, 3 H) 1.11-1.18 (m, 18 H) 1.21-1.25 (m, 7 H) 1.35-1.41 (m, 9 H) 1.59-1.65 (m, 1 H) 1.97-2.19 (m, 3 H) 2.35-2.74 (m, 9 H) 2.79-2.94 (m, 3 H) 2.99-3.04 (m, 1 H) 3.15-3.55 (m, 3 H) 3.27 (s, 3 H) 3.38 (s, 3 H) 3.42 (m, 1 H) 3.50 (m, 1 H) 3.58-3.66 (m, 1 H) 3.70 (d, J = 9.52 Hz, 1 H) 3.83 (s, 3 H) 3.93 (d, J = 6.35 Hz, 1 H) 4.10 (q, J = 7.30 Hz, 1 H) 4.39 (m, 1 H) 4.49 (d, J = 7.11 Hz, 1 H) 4.63 (t, J = 7.3 Hz, 1 H) 4.90-4.96 (m, 1 H) 5.00 (d, J = 7.2 Hz, 1 H) 6.76 (s, 1 H) 6.87 (d, J = 8.3 Hz, 1 H) 6.94 (t, J = 7.57 Hz, 1 H) 7.24 (m, 1 H) 7.27-7.29 (m, 1 H) 7.50 (s, 1 H) |

TABLE 4-11-continued

| Example | Reference Example | R | ESI MS (M + H) | 1H-NMR, CDCl3, δ (ppm) |
|---|---|---|---|---|
| 101 | 72 | (structure) | 923 FAB MASS | (400 MHz): 0.90 (d, J = 7.1 Hz, 3 H) 0.94 (t, J = 7.1 Hz, 3 H) 1.02 (d, J = 6.6 Hz, 3 H) 1.12 (d, J = 7.6 Hz, 3 H) 1.17 (s, 3 H) 1.19-1.30 (m, 10 H) 1.32-1.44 (m, 7 H) 1.60-1.68 (m, 1 H) 1.96-2.20 (m, 4 H) 2.31 (s, 6 H) 2.44-2.74 (m, 8 H) 2.81-2.95 (m, 4 H) 2.99-3.07 (m, 1 H) 3.14-3.27 (m, 3 H) 3.30 (s, 3 H) 3.30-3.37 (m, 1 H) 3.37 (s, 3 H) 3.39-3.56 (m, 2 H) 3.55-3.64 (m, 1 H) 3.70 (d, J = 9.5 Hz, 1 H) 3.84 (s, 3 H) 3.92 (d, J = 6.3 Hz, 1 H) 4.08-4.15 (m, 1 H) 4.18 (q, J = 6.1 Hz, 1 H) 4.50 (d, J = 7.1 Hz, 1 H) 4.64 (t, J = 4.4 Hz, 1 H) 4.92-5.01 (m, 1 H) 5.04 (d, J = 3.7 Hz, 1 H), 6.87 (d, J = 8.1 Hz, 1 H) 6.95 (t, J = 7.6 Hz, 1 H) 7.23 (t, J = 8.1 Hz, 1 H) 7.27-7.34 (1H, m) |
| 102 | 73 | (structure) | 975 | (400 MHz): 0.89 (d, J = 7.08 Hz, 3 H) 1.02 (d, J = 6.59 Hz, 3 H) 1.12 (s, 3 H) 1.11-1.18 (m, 15 H) 132-1.42 (m, 7 H) 163-1.67 (m, 1 H) 1.97-2.19 (m, 6 H) 2.31 (s, 6 H), 2.26-2.77 (m, 10 H) 2.82-3.04 (m, 4 H) 3.15-3.44 (m, 3 H) 3.29 (s, 3 H) 3.38 (s, 3 H) 3.53 (m, 1 H) 3.61 (m, 1 H) 3.70 (d, J = 9.52 Hz, 1 H) 3.83 (s, 3 H) 3.93 (d, J = 6.35 Hz, 1 H) 4.05 (q, J = 7.30 Hz, 1 H) 4.30 (m, 1 H) 4.49 (d, J = 7.32 Hz, 1 H) 4.65 (t, J = 3.30 Hz, 1 H) 4.89-4.96 (m, 1 H) 5.03 (d, J = 3.20 Hz, 1 H) 6.74 (s, 1 H) 6.87 (d, J = 8.30 Hz, 1 H) 6.94 (t, J = 7.57 Hz, 1 H) 7.20-7.27 (m, 2 H) 7.50 (s, 1 H) |
| 103 | | (structure) | 923 FAB MASS | (400 MHz): 0.88 (d, J = 7.1 Hz, 3 H) 1.02 (d, J = 6.6 Hz, 3 H) 1.12 (d, J = 7.8 Hz, 3 H) 1.14-1.35 (m, 17 H) 1.38 (s, 3 H), 1.57-1.70 (m, 1 H) 1.98-2.17 (m, 4 H) 2.20 (s, 3 H) 2.25 (s, 3 H) 2.32 (s, 6 H), 2.42-2.64 (m, 5 H) 2.80-2.94 (m, 4 H) 3.99-3.06 (m, 1 H) 3.12-3.26 (m, 3 H) 3.30 (s, 3 H), 3.38 (s, 3 H) 3.38-3.43 (m, 1 H) 3.44-3.52 (m, 1 H) 3.57-3.64 (m, 1 H) 3.71 (dd, J = 10.0, 2.0 Hz, 1 H) 3.81 (s, 3 H) 3.92 (d, J = 6.3 Hz, 1 H) 4.04-4.14 (m, 1 H) 4.15 (q, J = 6.3 Hz, 1H) 4.49 (d, J = 7.3 Hz, 1 H) 4.64 (t, J = 4.6 Hz, 1H) 4.92-4.97 (m, 1H) 5.05 (d, J = 3.9 Hz, 1 H) 6.86 (d, J = 7.6 Hz, 1 H) 6.93 (t, J = 7.6 Hz, 1 H) 7.15-7.21 (m, 1 H) 7.40-7.47 (m, 1 H) |
| 104 | | (structure) | 952.6 | (600 MHz): 0.89 (d, 3 H) 0.96-1.30 (m, 22 H) 1.33-1.41 (m, 4 H) 1.43 (s, 3 H) 1.43 (s, 3 H) 1.53-1.68 (m, 1 H) 1.95-2.17 (m, 4 H) 2.28 (s, 3 H) 2.31 (br. s., 6 H) 2.42-2.67 (m, 8 H) 2.80-2.94 (m, 4 H) 3.00-3.05 (m, 1 H) 3.12-3.26 (m, 3 H) 3.29 (s, 3 H) 3.37 (s, 3 H) 3.39-3.50 (m, 2 H) 3.58-3.62 (m, 1 H) 3.69-3.72 (m, 1 H) 3.90-3.92 (m, 1 H) 3.92 (s, 3 H) 4.13-4.19 (m, 1 H) 4.48 (d, J = 6.88 Hz, 1 H) 4.62-4.66 (m, 1 H) 4.88-4.99 (m, 1 H) 5.04 (d, J = 5.50 Hz, 1 H) 6.83 (dd, J = 7.57, 4.81 Hz, 1 H) 7.80 (dd, J = 7.34, 1.83 Hz, 1 H) 8.01 (dd, J = 5.04, 1.83 Hz, 1 H) |
| 105 | | (structure) | 924.6 | (500 MHz): 0.89 (d, J = 7.13 Hz, 3 H) 1.02 (d, J = 6.58 Hz, 3 H) 1.12 (d, J = 7.68 Hz, 3 H) 1.17 (s, 3 H) 1.19-1.30 (m, 13 H) 1.33-1.44 (m, 4 H) 1.61-1.70 (m, 1 H) 1.97-2.18 (m, 3 H) 2.16 (s, 3 H) 2.25 (s, 3 H) 2.27-2.51 (m, 5 H) 2.30 (s, 6 H) 2.55-2.70 (m, 2 H) 2.79-2.94 (m, 4 H) 3.00-3.06 (m, 1 H) 3.13-3.25 (m, 3 H) 3.30 (s, 3 H) 3.37-3.52 (m, 2 H) 3.38 (s, 3 H) 3.57-3.63 (m, 1 H) 3.72 (dd, J = 9.60, 1.92 Hz, 1 H) 3.88-3.97 (m, 2 H) 3.94 (s, 3 H) 4.18 (q, J = 6.31 Hz, 1 H) 4.49 (d, J = 7.40 Hz, 1 H) 4.64 (t, J = 4.52 Hz, 1 H) 5.06 (d, J = 4.94 Hz, 1 H) 6.85 (dd, J = 7.40, 4.94 Hz, 1 H) 7.76 (d, J = 6.86 Hz, 1 H) 8.03 (dd, J = 4.94, 1.92 Hz, 1 H) |
| 106 | | (structure) | 924.6 | (500 MHz): 0.89 (d, J = 7.13 Hz, 3 H) 1.02 (d, J = 6.86 Hz, 3 H) 1.12 (d, J = 7.68 Hz, 3 H) 1.15 (s, 3 H) 1.18-1.30 (m, 13 H) 1.34-1.40 (m, 4 H) 1.62-1.70 (m, 1 H) 1.99-2.17 (m, 3 H) 2.22 (s, 3 H) 2.25 (s, 3 H) 2.31 (s, 6 H) 2.33-2.38 (m, 1 H) 2.41-2.64 (m, 6 H) 2.81-2.93 (m, 4 H) 3.00-3.06 (m, 1 H) 3.13-3.26 (m, 3 H) 3.30 (s, 3 H) 3.37 (s, 3 H) 3.39-3.51 (m, 2 H) 3.57-3.64 (m, 1 H) 3.70 (dd, J = 9.60, 1.92 Hz, 1 H) 3.90-3.94 (m, 2 H) 3.94 (s, 3 H) 4.16 (q, J = 6.31 Hz, 1 H) 4.49 (d, J = 7.13 Hz, 1 H) 4.63 (t, J = 4.66 Hz, 1 H) 5.05 (d, J = 4.39 Hz, 1 H) 6.85 (dd, J = 7.40, 4.94 Hz, 1 H) 7.74 (dd, J = 7.40, 1.92 Hz, 1 H) 8.04 (dd, J = 4.94, 1.92 Hz, 1 H) |

In Examples 31 to 88, by using the compound obtained in Example 3, (3) and corresponding amine reagents, the compounds shown in Table 4 were synthesized in the same manner as that of Example 13, (2). In Examples 46 and 47, the compounds were synthesized by separation of diastereomers.

In Examples 89 to 102, by using the compound obtained in Example 3, (3) and corresponding amine reagents, the compounds shown in Table 4 were synthesized in the same manner as that of Example 3, (4).

Example 103

The compound obtained in Example 97 (37.0 mg) was dissolved in a mixed solvent of chloroform and ethanol (3:1, 0.8 ml), 36% aqueous formaldehyde (17 μl), and sodium triacetoxyborohydride (43 mg) were added to the solution, and the resulting mixture was stirred at room temperature for 45 minutes. Saturated aqueous sodium hydrogencarbonate and chloroform were added to the reaction mixture, the layers were separated, and then the organic layer was dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 4 (35.4 mg).

Example 104

The compound obtained in Example 65 (15.9 mg) was dissolved in chloroform (1 ml), acetaldehyde (8.4 mg), and sodium triacetoxyborohydride (11 mg) were added to the solution, and the resulting mixture was stirred at room temperature for 1 hour. Saturated aqueous sodium hydrogencarbonate and chloroform were added to the reaction mixture, the layers were separated, and then the organic layer was dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 4 (8.6 mg).

Example 105

The compound obtained in Example 75 (35 mg) was dissolved in chloroform (1 ml), 37% aqueous formaldehyde (16 μl), and sodium triacetoxyborohydride (11.5 mg) were added to the solution, and the resulting mixture was stirred at room temperature for 2 hours. Saturated aqueous sodium hydrogencarbonate and chloroform were added to the reaction mixture, the layers were separated, and then the organic layer was dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 4 (30.6 mg).

Example 106

By using the compound obtained in Example 76 (20 mg) as a starting material, the compound shown in Table 4 (18.3 mg) was obtained in the same manner as that of Example 105.

Examples 107 to 186

Preparation methods of the compounds represented by the formula (G) having R defined in Tables 5-1 to 5-11 are shown below.

TABLE 5-1

| Example | Reference Example | R | ESI MS (M + H) | $^1$H-NMR, CDCl$_3$, δ (ppm) |
|---|---|---|---|---|
| 107 | 74 | (structure) | 953 FAB MASS | (400 MHz): 0.89 (d, J = 7.1 Hz, 3 H) 1.02 (d, J = 6.8 Hz, 1 H) 1.05-1.28 (m, 19 H) 1.30-1.44 (m, 7 H) 1.58-1.68 (m, 1 H) 1.97 (dd, J = 15.1, 5.4 Hz, 1 H) 2.05 (d, J = 14.9 Hz, 1 H) 2.10-2.19 (m, 1 H) 2.31 (s, 3 H) 2.37-2.52 (m, 4 H) 2.55-2.78 (m, 4 H) 2.80-2.96 (m, 4 H) 2.99-3.07 (m, 1 H) 3.12-3.54 (m, 12 H) 3.55-3.64 (m, 2 H) 3.67-3.73 (m, 1 H) 3.84 (s, 3 H) 3.88 (d, J = 6.1 Hz, 1 H) 4.27 (q, J = 6.1 Hz, 1 H) 4.40-4.50 (m, 2 H) 4.64 (t, J = 4.4 Hz, 1 H) 4.85-4.96 (m, 1 H) 5.00 (d, J = 4.9 Hz, 1 H) 6.89 (d, J = 8.3 Hz, 1 H) 6.95 (t, J = 7.3 Hz, 1 H) 7.20-7.33 (m, 2 H) |
| 108 | 75 | (structure) | 953 FAB MASS | (400 MHz): 0.89 (d, J = 7.1 Hz, 3 H) 1.02 (d, J = 6.8 Hz, 3 H) 1.05-1.29 (m, 23 H) 1.35 (d, J = 7.1 Hz, 3 H) 1.38 (s, 3 H) 1.58-1.68 (m, 1 H) 1.97 (dd, J = 14.6, 7.1 Hz, 1 H) 2.05 (d, J = 14.6 Hz, 1 H) 2.10-2.19 (m, 1 H) 2.31 (s, 3 H) 2.37-2.52 (m, 4 H) 2.55-2.79 (m, 4 H) 2.80-2.97 (m, 4 H) 2.99-3.08 (m, 1 H) 3.12-3.26 (m, 4 H) 3.28 (s, 3 H) 3.35 (s, 3 H) 3.37-3.55 (m, 3 H) 3.56-3.65 (m, 2 H) 3.70 (d, J = 9.5 Hz, 1 H) 3.84 (s, 3 H) 3.89 (d, J = 6.3 Hz, 1 H) 4.27 (q, J = 6.6 Hz, 1 H) 4.40-4.50 (m, 1 H) 4.63 (t, J = 4.9 Hz, 1 H) 4.85-4.97 (m, 1 H) 5.00 (d, J = 4.2 Hz, 1 H) 7.90 (d, J = 8.3 Hz, 1 H) 6.96 (t, J = 7.6 Hz, 1 H) 7.21-7.32 (m, 2 H) |
| 109 | 76 | (structure) | 967 FAB MASS | (400 MHz): 0.88 (d, J = 7.1 Hz, 3 H) 0.96 (t, J = 7.1 Hz, 3 H) 0.99-1.05 (m, 6 H) 1.11 (d, J = 7.6 Hz, 3 H) 1.16 (d, J = 6.3 Hz 3 H) 1.19 (d, J = 6.1 Hz, 3 H) 1.20-1.35 (m, 8 H) 1.38 (s, 3 H) 1.57-1.65 (m, 1 H) 1.94-2.05 (m, 2 H) 2.08-2.20 (m, 1 H) 2.30 (s, 3 H) 2.31-2.64 (m, 7 H) 2.67-2.77 (m, 1 H) 2.83-2.95 (m, 3 H) 2.97-3.07 (m, 2H) 3.12-3.38 (m, 15 H) 3.39-3.45 (m, 1 H) 3.46-3.55 (m, 1 H) 3.56-3.64 (m, 1 H) 3.65-3.72 (m, 1 H) 3.82 (s, 3 H) 3.93 (d, J = 6.1 Hz, 1 H) 4.24 (q, J = 6.1 Hz, 1 H) 4.37 (q, J = 6.8 Hz, 1 H) 4.51 (d, J = 7.1 Hz, 1 H) 4.64 (t, J = 4.6 Hz, 1 H) 4.92-5.07 (m, 2 H) 6.86 (d, J = 8.3 Hz, 1 H) 6.93 (t, J = 7.3 Hz, 1 H) 7.17-7.24 (m, 1 H) 7.29-7.36 (m, 1 H) |

TABLE 5-1-continued

| Example | Reference Example | R | ESI MS (M + H) | ¹H-NMR, CDCl₃, δ (ppm) |
|---|---|---|---|---|
| 110 | 77 | | 921 | (400 MHz): 0.88 (d, J = 7.08 Hz, 3 H) 1.01 (d, J = 6.60 Hz, 3 H) 1.04 (s, 3 H) 1.06 (d, J = 6.10 Hz, 3 H) 1.10 (d, J = 7.82 Hz, 3 H) 1.17-1.37 (m, 2 H) 1.21 (d, J = 6.10 Hz, 3 H) 1.24 (d, J = 7.08 Hz, 3 H) 1.34 (d, J = 6.84 Hz, 3 H) 1.37 (s, 3 H) 1.55-1.77 (m, 1 H) 1.94 (dd, J = 14.9, 5.37 Hz, 1 H) 2.03-2.18 (m, 3 H) 2.30 (s, 6 H) 2.41-2.70 (m, 5 H) 2.82-2.93 (m, 4 H) 2.98-3.08 (m, 3 H) 3.11-3.62 (m, 9 H) 3.27 (s, 3 H) 3.36 (s, 3 H) 3.69 (dd, J = 9.76, 1.70 Hz, 1 H) 3.83 (s, 3 H) 3.89 (d, J = 6.10 Hz, 1 H) 4.05 (q, J = 6.83 Hz, 1 H) 4.12 (q, J = 6.60 Hz, 1 H) 4.46 (d, J = 7.08 Hz, 1 H) 4.63 (t, J = 4.88 Hz, 1 H) 4.97 (d, J = 10.5 Hz, 1 H) 5.01 (d, J = 4.89 Hz, 1 H) 6.88 (d, J = 8.06 Hz, 1 H) 6.95 (t, J = 6.59 Hz, 1 H) 7.20-7.31 (m, 1 H) |
| 111 | 78 | | 967 | (400 MHz): 0.88 (d, J = 7.32 Hz, 3 H) 1.01 (d, J = 6.84 Hz, 3 H) 1.09 (s, 3 H) 1.11 (d, J = 7.57 Hz, 3 H) 1.16 (d, J = 6.34 Hz, 3 H) 1.17-1.37 (m, 2 H) 1.22 (d, J = 6.10 Hz, 3 H) 1.25 (d, J = 7.08 Hz, 3 H) 1.37 (s, 3 H) 1.45 (s, 3 H) 1.55 (s, 3 H) 1.62-1.69 (m, 1 H) 1.96-2.41 (m, 5 H) 2.04 (s, 3 H) 2.20 (s, 3 H) 2.31 (s, 6 H) 2.43-2.51 (m, 1 H) 2.55-2.61 (m, 1 H) 2.82-3.49 (m, 13 H) 3.29 (s, 3 H) 3.37 (s, 3 H) 3.56-3.63 (m, 1 H) 3.66-3.83 (m, 3 H) 3.82 (s, 3 H) 3.90 (d, J = 6.10 Hz, 1 H) 4.19 (q, J = 6.10 Hz, 1 H) 4.48 (d, J = 7.33 Hz, 1 H) 4.63 (t, J = 4.64 Hz, 1 H) 4.91-5.15 (m, 1 H) 5.03 (d, J = 4.88 Hz, 1 H) 6.88-6.94 (m, 2 H) 7.22-7.31 (m, 2 H) |
| 112 | 79 | | 981 | (400 MHz): 0.82 (d, J = 7.08 Hz, 3 H) 0.89 (d, J = 7.32 Hz, 3 H) 1.02 (d, J = 6.59 Hz, 3 H) 1.10 (s, 3 H) 1.12 (d, J = 7.82 Hz, 3 H) 1.17 (d, J = 6.35 Hz, 3 H) 1.17-1.37 (m, 2 H) 1.22 (d, J = 6.10 Hz, 3 H) 1.25 (d, J = 7.08 Hz, 3 H) 1.38 (s, 3 H) 1.49 (s, 3 H) 1.58 (s, 3 H) 1.65-1.73 (m, 1 H) 2.00 (dd, J = 14.89, 5.12 Hz, 1 H) 2.03-2.18 (m, 3 H) 2.24 (s, 3 H) 2.26-2.32 (m, 1 H) 2.33 (s, 6 H) 2.43-2.53 (m, 1 H) 2.55-2.72 (m, 3 H) 2.81-2.94 (m, 4 H) 2.99-3.05 (m, 1 H) 3.08-3.51 (m, 6 H) 3.29 (s, 3 H) 3.37 (s, 3 H) 3.56-3.65 (m, 1 H) 3.71 (d, J = 8.54 Hz, 1 H) 3.78-3.93 (m, 2 H) 3.82 (s, 3 H) 4.20 (q, J = 6.35 Hz, 1 H) 4.48 (d, J = 7.32 Hz, 1 H) 4.64 (t, J = 4.64 Hz, 1 H) 4.90-5.07 (m, 1 H) 5.04 (d, J = 5.13 Hz, 1 H) 6.86-6.95 (m, 2 H) 7.22-7.34 (m, 2 H) |
| 113 | 80 | | 953.6 | (400 MHz): 0.88 (d, J = 7.1 Hz, 3 H) 1.02 (d, J = 6.6 Hz, 3 H) 1.10 (s, 3 H) 1.12 (d, J = 7.6 Hz, 3 H) 1.15 (d, J = 6.3 Hz, 3 H) 1.17-1.29 (m, 7 H) 1.31-1.43 (m, 7 H) 1.62-1.70 (m, 1 H) 2.00 (dd, J = 15.1, 5.4 Hz, 1 H) 2.04-2.16 (m, 2 H) 2.18 (s, 3 H) 2.20 (m, 3 H) 2.22-2.30 (m, 1 H) 2.32 (s, 6 H) 2.42-2.53 (m, 2 H) 2.56-2.65 (m, 1 H) 2.80-2.97 (m, 5 H) 2.99-3.13 (m, 2 H) 3.14-3.26 (m, 3 H) 3.30 (s, 3 H) 3.32-3.48 (m, 7 H) 3.55-3.65 (m, 1 H) 3.67-3.77 (m, 2 H) 3.84 (s, 3 H) 3.89 (d, J = 6.3 Hz, 1 H) 4.13-4.22 (m, 2 H) 4.47 (d, J = 7.3 Hz, 1 H) 4.63 (t, J = 4.4 Hz, 1 H) 4.88-5.00 (m, 1 H) 5.03 (d, J = 4.9 Hz, 1 H) 6.90 (d, J = 8.1 Hz, 1 H) 6.97 (t, J = 7.6 Hz, 1 H) 7.22-7.31 (m, 2 H) |
| 114 | 81 | | 967 FAB MASS | (400 MHz): 0.88 (d, J = 7.1 Hz, 3 H) 1.02 (d, J = 6.6 Hz, 3 H) 1.06 (d, J = 8.1 Hz, 3 H) 1.08 (d, J = 6.1 Hz, 3 H) 1.11 (d, J = 7.6 Hz, 3 H) 1.15 (d, J = 6.1 Hz, 3 H) 1.20 (d, J = 5.9 Hz, 3 H) 1.22-1.27 (m, 4 H) 1.33-1.44 (m, 7 H) 1.62-1.69 (m, 1 H) 1.98 (dd, J = 14.6, 5.1 Hz, 1 H) 2.06 (d, J = 14.6 Hz, 1 H) 209-2.17 (m, 2 H) 2.19 (s, 3 H) 2.30 (s, 6 H) 2.37-2.52 (m, 2 H) 2.54-2.73 (m, 3 H) 2.77-2.95 (5H, m) 2.99-3.06 (m, 1 H) 3.07-3.26 (m, 4 H) 3.28 (s, 3 H) 3.36 (s, 3 H) 3.37-3.49 (m, 3 H) 3.55-3.64 (m, 1 H) 3.67-3.82 (m, 2 H) 3.83 (s, 3 H) 3.89 (d, J = 6.3 Hz, 1 H) 4.18 (q, J = 6.3 Hz, 1 H) 4.42 (q, J = 7.1 Hz, 1 H) 4.47 (d, J = 7.1 Hz, 1 H) 4.63 (t, J = 4.6 Hz, 1 H) 5.02 (d, J = 4.6 Hz, 1 H) 6.90 (d, J = 8.1 Hz, 1 H) 6.98 (t, J = 7.6 Hz, 1 H) 7.21-7.31 (m, 2 H) |

TABLE 5-2

| Example | Reference Example | R | ESI MS (M + H) | ¹H-NMR CDCl₃, δ (ppm) |
|---|---|---|---|---|
| 115 | 82 | (structure: OH, N-Me, NH-C(Me)₂-(2-methoxyphenyl)) | 953 | (400 MHz): 0.88 (d, J = 7.33 Hz, 3 H) 1.01 (d, J = 6.59 Hz, 3 H) 1.09-1.15 (m, 9 H) 1.17-1.37 (m, 2 H) 1.19 (d, J = 6.11 Hz, 3 H) 1.25 (d, J = 7.08 Hz, 3 H) 1.37 (s, 3 H) 1.49 (s, 3 H) 1.54 (s, 3 H) 1.62-1.69 (m, 1 H) 1.99 (dd, J = 14.65, 5.13 Hz, 1 H) 2.03-2.18 (m, 3 H) 2.14 (s, 3 H) 2.31 (s, 6 H) 2.32-2.37 (m, 1 H) 2.42-2.61 (m, 3 H) 2.65-2.75 (m, 1 H) 2.84-2.93 (m, 3 H) 3.02 (dd, J = 10.50, 3.42 Hz, 1 H) 3.07-3.48 (m, 8 H) 3.30 (s, 3 H) 3.37 (s, 3 H) 3.56-3.62 (m, 1 H) 3.69 (dd, J = 10.01, 1.95 Hz, 1 H) 3.76-3.92 (m, 3 H) 3.86 (s, 3 H) 4.16 (q, J = 6.35 Hz, 1 H) 4.47 (q, J = 7.08 Hz, 1 H) 4.63 (t, J = 4.39 Hz, 1 H) 4.97 (d, J = 10.50 Hz, 1 H) 5.02 (d, J = 4.64 Hz, 1 H) 6.89-6.98 (m, 2 H) 7.20-7.30 (m, 2 H) |
| 116 | 83 | (structure: HO, Me, Me, NH, N-Et, CH(Me)-(2-methoxyphenyl)) | 967 FAB MASS | (400 MHz): 0.89 (d, J = 7.1 Hz, 3 H) 1.02 (d, J = 6.6 Hz, 3 H) 1.04-1.29 (m, 16 H) 1.33 (d, J = 7.1 Hz, 3 H) 1.38 (s, 3 H) 1.58-1.66 (m, 1 H) 1.99 (dd, J = 14.6, 4.6 Hz, 1 H) 2.02-2.18 (m, 2 H) 2.30 (s, 6 H) 2.34-2.74 (m, 7 H) 2.80-2.99 (m, 4 H) 3.00-3.07 (m, 1 H) 3.13-3.26 (m, 3 H) 3.30-3.38 (m, 4 H) 3.39-3.54 (m, 2 H) 3.56-3.74 (m, 3 H) 3.82 (s, 3 H) 3.90 (d, J = 6.3 Hz, 1 H) 4.24 (q, J = 6.3 Hz, 1 H) 4.42-4.51 (m, 2 H) 4.63 (t, J = 4.6 Hz, 1 H) 4.86-4.99 (m, 1 H) 5.01 (d, J = 3.9 Hz, 1 H) 6.89 (d, J = 8.3 Hz, 1 H) 6.95 (t, J = 7.3 Hz, 1 H) 7.22-7.34 (m, 2 H) |
| 117 | 84 | (structure: OH, NH, N-Me, N-Et, CH(Me)-(2-methoxyphenyl)) | 967 | (400 MHz): 0.88 (d, J = 7.08 Hz, 3 H) 1.01 (d, J = 6.59 Hz, 3 H) 1.03-1.17 (m, 15 H) 1.17-1.37 (m, 2 H) 1.24 (d, J = 6.84 Hz, 3 H) 1.36 (d, J = 7.32 Hz, 3 H) 1.38 (s, 3 H) 1.52-1.76 (m, 3 H) 1.95 (dd, J = 15.7, 4.88 Hz, 1 H) 2.06 (d, J = 15.7 Hz, 1 H) 2.09-2.18 (m, 1 H) 2.29 (s, 6 H) 2.31-2.48 (m, 5 H) 2.59 (q, J = 6.84 Hz, 1 H) 2.67-2.78 (m, 2 H) 2.82-2.96 (m, 4 H) 2.99-3.06 (m, 1 H) 3.12-3.44 (m, 5 H) 3.29 (s, 3 H) 3.35 (s, 3 H) 3.48-3.74 (m, 5 H) 3.82 (s, 3 H) 3.89 (d, J = 6.34 Hz, 1 H) 4.30 (q, J = 6.34 Hz, 1 H) 4.43-4.53 (m, 2 H) 4.63 (t, J = 4.39 Hz, 1 H) 4.92 (d, J = 10.7 Hz, 1 H) 4.99 (d, J = 4.64 Hz, 1 H) 6.88 (d, J = 8.30 Hz, 1 H) 6.95 (t, J = 7.57 Hz, 1 H) 7.21-7.35 (m, 2 H) |
| 118 | 85 | (structure: azetidine N, NH-C(Me)₂-(2-methoxyphenyl)) | 921 | (400 MHz): 0.88 (d, J = 7.08 Hz, 3 H) 0.98-1.03 (m, 6 H) 0.99 (s, 3 H) 1.09 (d, J = 7.57 Hz, 3 H) 1.17-1.37 (m, 2 H) 1.20 (d, J = 6.10 Hz, 3 H) 1.22 (d, J = 7.08 Hz, 3 H) 1.36 (s, 3 H) 1.46 (s, 6 H) 1.55-1.75 (m, 1 H) 1.90 (dd, J = 14.7, 5.13 Hz, 1 H) 2.00-2.18 (m, 3 H) 2.32 (s, 6 H) 2.40-2.49 (m, 1 H) 2.50 (q, J = 6.59 Hz, 1 H) 2.75-2.93 (m, 6 H) 3.01 (dd, J = 10.0, 3.42 Hz, 1 H) 3.10-3.47 (m, 9 H) 3.25 (s, 3 H) 3.34 (s, 3 H) 3.58 (dd, J = 8.55, 4.89 Hz, 1 H) 3.67 (d, J = 10.0 Hz, 1 H) 3.84-3.89 (m, 1 H) 3.87 (s, 3 H) 4.09 (q, J = 6.35 Hz, 1 H) 4.45 (d, J = 7.32 Hz, 1 H) 4.62 (t, J = 4.40 Hz, 1 H) 4.92-5.02 (m, 2 H) 6.87 (d, J = 8.06 Hz, 1 H) 6.92 (t, J = 7.32 Hz, 1 H) 7.20-7.29 (m, 1 H) |
| 119 | 86 | (structure: Me, N-Me, Me-N, NH, N-Et, CH(Me)-(2-methoxyphenyl)) | 980 FAB MASS | (400 MHz): 0.88 (d, J = 7.1 Hz, 3 H) 0.97 (t, J = 7.1 Hz, 3 H) 1.02 (d, J = 6.8 Hz, 3 H) 1.04 (s, 3 H) 1.12 (d, J = 7.6 Hz, 3 H) 1.13-1.30 (m, 13 H) 1.32-1.40 (m, 4 H) 1.55-1.64 (m, 1 H) 1.95-2.03 (m, 2 H) 2.09-2.20 (m, 9 H) 2.26-2.38 (m, 8 H) 2.39-2.67 (m, 6 H) 2.83-2.97 (m, 4 H) 2.99-3.07 (m, 1 H) 3.12-3.26 (m, 3 H) 3.30 (s, 3 H) 3.37 (s, 3 H) 3.38-3.44 (m, 1 H) 3.46-3.63 (m, 3 H) 3.65-3.71 (m, 1 H) 3.81 (s, 3 H) 3.92 (d, J = 6.1 Hz, 1 H) 4.24 (q, J = 6.3 Hz, 1 H) 4.33 (q, J = 6.8 Hz, 1 H) 4.51 (d, J = 7.3 Hz, 1 H) 4.63 (t, J = 4.6 Hz, 1 H) 4.94-5.04 (m, 2 H) 6.94 (d, J = 8.1 Hz, 1 H) 6.92 (t, J = 7.3 Hz, 1 H) 7.17-7.23 (m, 1H) 7.30-7.34 (m, 1H) |

TABLE 5-2-continued

| Example | Reference Example | R | ESI MS (M + H) | ¹H-NMR CDCl₃, δ (ppm) |
|---|---|---|---|---|
| 120 | 87 | (structure) | 923 FAB MASS | (400 MHz): 0.89 (d, J = 7.1 Hz, 3 H) 1.02 (d, J = 6.8 Hz, 3 H) 1.11 (d, J = 7.8 Hz, 3 H) 1.14 (s, 3 H) 1.17-1.30 (m, 10 H) 1.32 (s, 6 H) 1.33-1.42 (m, 4 H) 1.62-1.72 (m, 1 H) 1.95-2.05 (m, 2 H) 2.08 (s, 3 H) 2.09-2.19 (m, 2 H) 2.22 (s, 3 H) 2.24-2.42 (m, 8 H) 2.43-2.66 (m, 4 H) 2.76 (d, J = 14.6 Hz, 1 H) 2.82-2.96 (m, 3 H) 3.00-3.08 (m, 1 H) 3.13-3.23 (m, 3 H) 3.24-3.32 (m, 4 H) 3.37 (s, 3 H) 3.38-3.47 (m, 2 H) 3.57-3.66 (m, 1 H) 3.68-3.75 (m, 1 H) 3.90 (d, J = 6.1 Hz, 1 H) 4.16 (q, J = 6.1 Hz, 1 H) 4.47 (d, J = 7.1 Hz, 1 H) 4.64 (t, J = 4.6 Hz, 1 H) 4.94-5.03 (m, 1 H) 5.05 (d, J = 4.6 Hz, 1 H) 6.69 (dd, J = 7.8, 1.7 Hz, 1 H) 6.99 (d, J = 7.8 Hz, 1 H) 7.09-7.27 (m, 2 H) |
| 121 | 88 | (structure) | 1013 FAB MASS | (400 MHz): 0.88 (d, J = 7.3 Hz, 3 H) 1.02 (d, J = 6.8 Hz, 3 H) 1.06-1.28 (m, 16 H) 1.33-1.41 (m, 4 H) 1.45 (s, 3 H) 1.46 (s, 3 H) 1.58-1.70 (m, 1 H) 2.00 (dd, J = 15.1, 5.4 Hz, 1 H) 2.06 (d, J = 15.1 Hz, 1 H) 2.08-2.16 (m, 1 H) 2.17 (s, 3 H) 2.27 (s, 3 H) 2.30 (s, 6 H) 2.38-2.65 (m, 6 H) 2.76-2.94 (m, 4 H) 2.98-3.07 (m, 1 H) 3.28 (s, 3 H) 3.29-3.49 (m, 6 H) 3.57-3.64 (m, 1 H) 3.69-3.73 (m, 1 H) 3.90 (d, J = 6.3 Hz, 1 H) 4.15 (q, J = 6.6 Hz, 1 H) 4.48 (d, J = 7.3 Hz, 1 H) 4.63 (t, J = 4.9 Hz, 1 H) 4.91-5.02 (m, 1 H) 5.04 (d, J = 4.9 Hz, 1 H) 5.08 (s, 2 H) 6.86-6.96 (m, 2 H) 7.13-7.19 (m, 1 H) 7.29-7.36 (m, 1 H) 7.38 (t, J = 7.1 Hz, 1 H) 7.47 (d, J = 7.6 Hz, 1 H) 7.66 (d, J = 7.8 Hz, 1 Hz) |
| 122 | 89 | (structure) | 938.6 | (600 MHz): 0.88 (d, J = 6.88 Hz, 3 H) 0.99-1.04 (m, 6 H) 1.10-1.16 (m, 6 H) 1.17-1.31 (m, 13 H) 1.34-1.40 (m, 4 H) 1.61-1.67 (m, 1 H) 1.99-2.17 (m, 3 H) 2.20 (s, 3 H) 2.30 (s, 6 H) 2.42-2.63 (m, 7 H) 2.66-2.73 (m, 1 H) 2.79-2.93 (m, 5 H) 3.00-3.05 (m, 1 H) 3.13-3.25 (m, 4 H) 3.30 (s, 3 H) 3.38 (s, 3 H) 3.39-3.43 (m, 1 H) 3.45-3.51 (m, 1 H) 3.57-3.62 (m, 1 H) 3.69-3.73 (m, 1 H) 3.93 (s, 3 H) 4.14-4.24 (m, 2 H) 4.49 (d, J = 7.34 Hz, 1 H) 4.61-4.66 (m, 1 H) 5.03-5.08 (m, 1 H) 6.83-6.87 (m, 1 H) 7.69-7.72 (m, 1 H) 8.01-8.05 (m, 1 H) |

TABLE 5-3

| Example | Reference Example | R | ESI MS (M + H) | ¹H-NMR, CDCl₃, δ (ppm) |
|---|---|---|---|---|
| 123 | 90 | (structure) | 938.6 | (600 MHz): 0.88 (d, J = 6.88 Hz, 3 H) 0.99-1.04 (m, 6 H) 1.09-1.13 (m, 6 H) 1.17 (d, J = 6.42 Hz, 3 H) 1.19-1.30 (m, 10 H) 1.34-1.40 (m, 4 H) 1.61-1.66 (m, 1 H) 1.97-2.17 (m, 3 H) 2.23 (s, 3 H) 2.30 (s, 6 H) 2.43-2.61 (m, 7 H) 2.66-2.73 (m, 1 H) 2.80-2.94 (m, 5 H) 2.99-3.05 (m, 1 H) 3.13-3.24 (m, 4 H) 3.29 (s, 3 H) 3.37 (s, 3 H) 3.38-3.42 (m, 1 H) 3.45-3.50 (m, 1 H) 3.57-3.62 (m, 1 H) 3.68-3.72 (m, 1 H) 3.94 (s, 3 H) 4.12-4.23 (m, 2 H) 4.49 (d, J = 7.34 Hz, 1 H) 4.62-4.65 (m, 1 H) 5.03-5.07 (m, 1 H) 6.83-6.88 (m, 1 H) 7.69-7.73 (m, 1 H) 8.02-8.06 (m, 1 H) |
| 124 | 91 | (structure) | 932.6 | (600 MHz): 0.89 (d, J = 6.88 Hz, 3 H) 1.02 (d, J = 6.42 Hz, 3 H) 1.12 (d, J = 7.79 Hz, 3 H) 1.14-1.29 (m, 13 H) 1.33-1.41 (m, 4 H) 1.48 (dd, J = 6.88, 2.29 Hz, 3 H) 1.58-1.66 (m, 1 H) 1.99-2.17 (m, 4 H) 2.20 (d, J = 8.25 Hz, 3 H) 2.29 (s, 6 H) 2.42-2.49 (m, 1 H) 1.99-2.71 (m, 5 H) 2.78-2.93 (m, 4 H) 3.00-3.05 (m, 1 H) 3.13-3.24 (m, 3 H) 3.30 (s, 3 H) 3.34-3.50 (m, 5 H) 3.57-3.62 (m, 1 H) 3.71 (d, J = 9.63 Hz, 1 H) 3.79 (s, 3 H) 3.92 (d, J = 5.96 Hz, 1 H) 4.14-4.24 (m, 2 H) 4.46-4.50 (m, 1 H) 4.63 (t, J = 4.81 Hz, 1 H) 5.05 (d, J = 4.58 Hz, 1 H) 6.58-6.62 (m, 1 H) 7.03-7.11 (m, 2 H) 7.18-7.24 (m, 2 H) |

TABLE 5-3-continued

| Example | Reference Example | R | ESI MS (M + H) | ¹H-NMR, CDCl$_3$, δ (ppm) |
|---|---|---|---|---|
| 125 | 92 | | 955.7 | (600 MHz): 0.88 (d, J = 7.34 Hz, 3 H) 1.01 (d, J = 6.88 Hz, 3 H) 1.07-1.16 (m, 6 H) 1.16-1.41 (m, 16 H) 1.60-1.64 (m, 1 H) 1.97-2.17 (m, 8 H) 2.28-2.31 (m, 6 H) 2.37-2.53 (m, 4 H) 2.58 (d, J = 6.88 Hz, 1 H) 2.78 (d, J = 14.67 Hz, 1 H) 2.82-2.93 (m, 3 H) 3.00-3.05 (m, 1 H) 3.13-3.24 (m, 3 H) 3.27-3.34 (m, 4 H) 3.36-3.48 (m, 5 H) 3.57-3.62 (m, 1 H) 3.68-3.73 (m, 1 H) 3.86-3.94 (m, 2 H) 4.13-4.18 (m, 1 H) 4.46-4.50 (m, 1 H) 4.63 (t, J = 4.81 Hz, 1 H) 5.02-5.06 (m, 1 H) 7.16-7.19 (m, 1 H) 7.23-7.28 (m, 3 H) 7.32-7.42 (m, 4 H) 7.55-7.59 (m, 1 H) |
| 126 | 93 | | 956.6 | (600 MHz): 0.89 (d, J = 6.88 Hz, 3 H) 1.02 (d, J = 6.88 Hz, 3 H) 1.08-1.30 (m, 19 H) 1.33-1.41 (m, 4 H) 1.61-1.66 (m, 1 H) 1.96-2.20 (m, 7 H) 2.30 (s, 6 H) 2.35-2.63 (m, 6 H) 2.76-2.94 (m, 4 H) 2.99-3.05 (m, 1 H) 3.14-3.26 (m, 3 H) 3.26-3.31 (m, 3 H) 3.35-3.39 (m, 3 H) 3.39-3.49 (m, 2 H) 3.58-3.64 (m, 1 H) 3.68-3.73 (m, 1 H) 3.79-3.85 (m, 1 H) 3.88-3.93 (m, 1 H) 4.13-4.20 (m, 1 H) 4.47 (d, J = 6.88 Hz, 1 H) 4.61-4.66 (m, 1 H) 5.01-5.06 (m, 1 H) 7.14-7.18 (m, 1 H) 7.28-7.32 (m, 1 H) 7.33-7.37 (m, 1 H) 7.41-7.46 (m, 1 H) 7.57-7.67 (m, 2 H) 8.53-8.57 (m, 1 H) 8.59-8.63 (m, 1 H) |
| 127 | 94 | | 956.6 | (600 MHz): 0.88 (d, J = 6.88 Hz, 3 H) 1.01 (d, J = 6.88 Hz, 3 H) 1.09-1.16 (m, 6 H) 1.18-1.27 (m, 10 H) 1.30 (d, J = 6.42 Hz, 3 H) 1.34-1.40 (m, 4 H) 1.60-1.65 (m, 1 H) 1.96-2.20 (m, 6 H) 2.29 (s, 6 H) 2.41-2.61 (m, 6 H) 2.77-2.83 (m, 1 H) 2.84-2.93 (m, 4 H) 3.00-3.04 (m, 1 H) 3.13-3.24 (m, 3 H) 3.27-3.30 (m, 3 H) 3.35-3.49 (m, 5 H) 3.57-3.62 (m, 1 H) 3.68-3.73 (m, 1 H) 3.89-4.00 (m, 2 H) 4.12-4.19 (m, 1 H) 4.48 (d, J = 7.34 Hz, 1 H) 4.61-4.65 (m, 1 H) 5.02-5.06 (m, 1H) 7.25-7.33 (m, 3 H) 7.35 (d, J = 7.79 Hz, 1 H) 7.39-7.44 (m, 1 H) 7.56-7.60 (m, 1 H) 7.72-7.78 (m, 1 H) 8.65-8.70 (m, 1 H) |
| 128 | 95 | | 921.7 | (600 MHz): 0.87 (d, J = 6.88 Hz, 3 H) 1.00 (d, J = 6.88 Hz, 3 H) 1.08-1.13 (m, 3 H) 1.15-1.28 (m, 13 H) 1.33-1.37 (m, 1 H) 1.37-1.40 (m, 3 H) 1.59-1.66 (m, 1 H) 1.96-2.27 (m, 10 H) 2.28 (s, 6 H) 2.37 (s, 3 H) 2.41-2.48 (m, 1 H) 2.49-2.61 (m, 3 H) 2.80-2.92 (m, 4 H) 2.98-3.04 (m, 1 H) 3.12-3.24 (m, 3 H) 3.28-3.31 (m, 3 H) 3.29-3.33 (m, 1 H) 3.35-3.39 (m, 3 H) 3.37-3.41 (m, 1 H) 3.42-3.50 (m, 1 H) 3.55-3.60 (m, 1 H) 3.67-3.73 (m, 1 H) 3.91 (t, J = 5.73 Hz, 1 H) 3.96 (t, J = 7.79 Hz, 1 H) 4.04-4.11 (m, 1 H) 4.14-4.21 (m, 1 H) 4.29-4.36 (m, 1 H) 4.47 (d, J = 7.34 Hz, 1 H) 4.62 (t, J = 4.58 Hz, 1 H) 4.94 (d, J = 10.55 Hz, 1 H) 5.05 (d, J = 5.04 Hz, 1 H) 6.70-6.78 (m, 1 H) 6.81-6.86 (m, 1 H) 7.05-7.11 (m, 1 H) 7.55-7.59 (m, 1 H) |
| 129 | 96 | | 946.7 | (600 MHz): 0.89 (d, J = 7.34 Hz, 3 H) 1.00-1.04 (m, 3 H) 1.11 (d, J = 7.79 Hz, 3 H) 1.14-1.29 (m, 13 H) 1.39 (s, 4 H) 1.52-1.67 (m, 7 H) 1.96-2.17 (m, 7 H) 2.25-2.38 (m, 7 H) 2.42-2.51 (m, 2 H) 2.53-2.63 (m, 2 H) 2.75-2.81 (m, 1 H) 2.84-2.93 (m, 3 H) 3.01-3.05 (m, 1 H) 3.13-3.25 (m, 3 H) 3.29 (s, 3 H) 3.37-3.47 (m, 5 H) 3.58-3.63 (m, 2 H) 3.69-3.74 (m, 2 H) 3.79 (s, 3 H) 3.89-3.93 (m, 1 H) 4.13-4.19 (m, 1 H) 4.48 (d, J = 7.34 Hz, 1 H) 4.62-4.66 (m, 1 H) 5.04-5.07 (m, 1 H) 6.83-6.85 (m, 1 H) 7.02-7.07 (m, 2 H) 7.14-7.18 (m, 1 H) 7.22-7.25 (m, 1 H) |
| 130 | 97 | | 946.6 | (600 MHz): 0.88 (d, J = 7.34 Hz, 3 H) 1.01 (d, J = 6.42 Hz, 3 H) 1.11 (d, J = 7.79 Hz, 3 H) 1.14-1.30 (m, 13 H) 1.36 (d, J = 14.67 Hz, 1 H) 1.39 (s, 3 H) 1.50 (br s, 6 H) 1.58-1.65 (m, 1 H) 2.00-2.11 (m, 4 H) 2.15 (br s, 3 H) 2.28 (br s, 6 H) 2.36-2.63 (m, 6 H) 2.77-2.93 (m, 4 H) 2.98-3.05 (m, 1 H) 3.10-3.25 (m, 3 H) 3.29 (s, 3 H) 3.37 (s, 3 H) 3.35-3.50 (m, 2 H) 3.56-3.62 (m, 1 H) 3.71 (d, J = 9.17 Hz, 1 H) 3.77 (br s, 3 H) 3.87-3.95 (m, 1 H) 4.12-4.22 (m, 1 H) 4.47 (d, J = 6.88 Hz, 1 H) 4.58-4.67 (m, 1 H) 5.01-5.09 (m, 1 H) 6.39-6.48 (m, 1 H) 6.99-7.06 (m, 1 H) 7.21-7.30 (m, 1 H) 7.33-7.39 (m, 1 H) 7.62-7.69 (m, 1 H) |

TABLE 5-3-continued

| Example | Reference Example | R | ESI MS (M + H) | $^1$H-NMR, CDCl$_3$, δ (ppm) |
|---|---|---|---|---|
| 131 | 98 | *structure: N(Me)-CH$_2$CH$_2$-NH-CH(Me)-quinolin-5-yl* | 930.4 | (600 MHz): 0.82-0.95 (m, 3 H) 0.96-1.31 (m, 19 H) 1.32-1.52 (m, 7 H) 1.57-1.66 (m, 1 H) 1.96-2.17 (m, 4 H) 2.17-2.25 (m, 3 H) 2.30 (s, 6 H) 2.49-2.72 (m, 6 H) 2.80-2.95 (m, 4 H) 2.98-3.08 (m, 1 H) 3.09-3.51 (m, 5 H) 3.29 (s, 3 H) 3.36 (br s, 3 H) 3.54-3.65 (m, 1 H) 3.65-335 (m, 1 H) 3.85-3.94 (m, 1 H) 4.11-4.22 (m, 1 H) 4.41-4.70 (m, 3 H) 5.00-5.08 (m, 1 H) 7.35-7.42 (m, 1 H) 7.62-7.75 (m, 2 H) 7.96-8.03 (m, 1 H) 8.60-8.68 (m, 1 H) 8.87-8.95 (m, 1 H) |

TABLE 5-4

| Example | Reference Example | R | ESI MS (M + H) | $^1$H-NMR, CDCl$_3$, δ (ppm) |
|---|---|---|---|---|
| 132 | 99 | *structure: N(Me)-CH$_2$CH$_2$-(8-methoxy-1,2,3,4-tetrahydroisoquinolin-2-yl)* | 921.6 | (600 MHz): 0.87 (d, J = 7.34 Hz, 3 H) 1.00 (d, J = 6.42 Hz, 3 H) 1.10 (d, J = 7.79 Hz, 3 H) 1.14 (d, 3 H) 1.17 (d, J = 6.42 Hz, 3 H) 1.21-1.24 (m, 7 H) 1.32-1.36 (m, 1 H) 1.37 (s, 3 H) 1.62-1.72 (m, 1 H) 1.91-2.00 (m, 1 H) 2.00-2.06 (m, 1 H) 2.08-2.18 (m, 2 H) 2.30 (s, 6 H) 2.39 (s, 3 H) 2.43-2.51 (m, 1 H) 2.54-2.72 (m, 5 H) 2.76-2.92 (m, 6 H) 2.97-3.05 (m, 1 H) 3.11-3.23 (m, 3 H) 3.28 (s, 3 H) 3.35 (s, 3 H) 3.37-3.42 (m, 1 H) 3.44-3.53 (m, 1 H) 3.53-3.63 (m, 5 H) 3.67 (dd, J = 9.63, 1.83 Hz, 1 H) 3.78 (s, 3 H) 3.91 (d, J = 6.42 Hz, 1 H) 4.14-4.18 (m, 1 H) 4.48 (d, J = 6.88 Hz, 1 H) 4.62 (t, J = 4.59 Hz, 1 H) 4.90-4.98 (m, 1 H) 5.00 (d, J = 5.04 Hz, 1 H) 6.63 (d, J = 8.25 Hz, 1 H) 6.70 (d, J = 7.79 Hz, 1 H) 7.09 (t, J = 8.02 Hz, 1 H) |
| 133 | 100 | *structure: N(Me)-CH$_2$CH$_2$-N(Me)-(5-methoxy-1,2,3,4-tetrahydronaphthalen-1-yl)* | 949.7 | (600 MHz): 0.87 (d, J = 6.88 Hz, 3 H) 1.00 (d, J = 6.42 Hz, 3 H) 1.08-1.13 (m, 3 H) 1.14-1.27 (m, 13 H) 1.33-1.37 (m, 1 H) 1.37-1.40 (m, 3 H) 1.50-1.68 (m, 4 H) 1.94-2.26 (m, 8 H) 2.29 (s, 6 H) 2.32 (s, 3 H) 2.34-2.70 (m, 7 H) 2.73-2.92 (m, 5 H) 2.98-3.04 (m, 1 H) 3.11-3.24 (m, 3 H) 3.29 (s, 3 H) 3.35-3.39 (m, 3 H) 3.38-3.42 (m, 1 H) 3.43-3.50 (m, 1 H) 3.56-3.61 (m, 1 H) 3.67-3.73 (m, 1 H) 3.79 (s, 3 H) 3.81-3.86 (m, 1 H) 3.88-3.95 (m, 1 H) 4.14-4.22 (m, 1 H) 4.48 (d, J = 6.88 Hz, 1 H) 4.62 (t, J = 4.81 Hz, 1 H) 4.88-4.97 (m, 1 H) 5.04 (t, J = 4.13 Hz, 1 H) 6.65 (dd, J = 8.02, 4.36 Hz, 1 H) 7.04-7.11 (m, 1 H) 7.36 (d, J = 7.79 Hz, 1 H) |
| 134 | | *structure: N(Me)-CH$_2$CH$_2$-NH-Me* | 789.7 | (600 MHz): 0.89 (d, J = 7.34 Hz, 3 H) 1.02 (d, J = 6.42 Hz, 3 H) 1.12 (d, J = 7.79 Hz, 3 H) 1.16-1.21 (m, 7 H) 1.22-1.28 (m, 6 H) 1.36 (d, J = 13.76 Hz, 1 H) 1.39 (s, 3 H) 1.63-1.71 (m, 1 H) 1.95-2.02 (m, 1 H) 2.05-2.17 (m, 3 H) 2.32 (s, 6 H) 2.35 (s, 3 H) 2.44-2.52 (m, 4 H) 2.57-2.94 (m, 9 H) 3.00-3.05 (m, 1 H) 3.14-3.21 (m, 2 H) 3.23 (dd, J = 10.09, 7.34 Hz, 1 H) 3.30 (s, 3 H) 3.36 (s, 3 H) 3.40-3.45 (m, 1 H) 3.45-3.52 (m, 1 H) 3.58-3.64 (m, 1 H) 3.70 (dd, J = 9.86, 2.06 Hz, 1 H) 3.91 (d, J = 6.42 Hz, 1 H) 4.20 (d, J = 6.42 Hz, 1 H) 448 (d, J = 7.34 Hz, 1 H) 4.64 (t, J = 4.59 Hz, 1 H) 4.88-4.96 (m, 1 H) 5.02 (d, J = 5.04 Hz, 1 H) |
| 135 | 101 | *structure: N(Me)-CH$_2$CH$_2$-NH-CH(Me)-quinolin-3-yl* | 930.6 | (600 MHz): 0.89 (d, J = 6.88 Hz, 3 H) 1.02 (d, J = 6.42 Hz, 3 H) 1.10 (d, J = 6.88 Hz, 3 H) 1.13-1.28 (m, 13 H) 1.34 (d, J = 14.67 Hz, 1 H) 1.38 (s, 3 H) 1.46 (d, J = 6.88 Hz, 3 H) 1.62-1.70 (m, 1 H) 1.97-2.17 (m, 4 H) 2.21-2.27 (m, 3 H) 2.27-2.39 (m, 6 H) 2.48-2.72 (m, 6 H) 2.79-2.93 (m, 4 H) 2.99-3.05 (m, 1 H) 3.12-3.26 (m, 3 H) 3.26-3.31 (m, 3 H) 3.36 (s, 3 H) 3.39-3.49 (m, 2 H) 3.57-3.65 (m, 1 H) 3.70 (d, J = 9.17 Hz, 1 H) 3.90 (d, J = 5.96 Hz, 1 H) 3.96-4.03 (m, 1 H) 4.13-4.19 (m, 1 H) 4.44-4.51 (m, 1 H) 4.60-4.66 (m, 1 H) 5.01-5.06 (m, 1 H) 7.50-7.56 (m, 1 H) 7.64-7.70 (m, 1 H) 7.76-7.81 (m, 1 H) 8.05-8.12 (m, 2 H) 8.88 (dd, J = 6.42, 2.29 Hz, 1 H) |

TABLE 5-4-continued

| Example | Reference Example | R | ESI MS (M + H) | ¹H-NMR, CDCl₃, δ (ppm) |
|---|---|---|---|---|
| 136 | 102 | 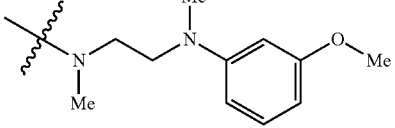 | 895.6 | (600 MHz): 0.88 (d, J = 7.34 Hz, 3 H) 1.01 (d, J = 6.88 Hz, 3 H) 1.06-1.27 (m, 16 H) 1.33-1.40 (m, 4 H) 1.61-1.66 (m, 1 H) 1.95-2.16 (m, 3 H) 2.29 (s, 6 H) 2.40-2.48 (m, 4 H) 2.54-261 (m, 1 H) 2.66-2.82 (m, 2 H) 2.84-2.94 (m, 7 H) 3.00-3.05 (m, 1 H) 3.12-3.48 (m, 8 H) 3.28 (s, 3 H) 3.36 (s, 3 H) 3.57-3.61 (m, 1 H) 3.68-3.72 (m, 1 H) 3.78 (s, 3 H) 3.89 (d, J = 6.42 Hz, 1 H) 4.14-4.20 (m, 1 H) 4.46 (d, J = 7.34 Hz, 1 H) 4.61-4.65 (m, 1 H) 5.02 (d, J = 5.04 Hz, 1 H) 6.21-6.34 (m, 3 H) 7.12 (t, J = 8.02 Hz, 1 H) |
| 137 | 103 | 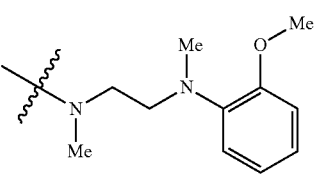 | 895.6 | (600 MHz): 0.88 (d, J = 7.34 Hz, 3 H) 1.02 (d, J = 6.88 Hz, 3 H) 1.07-1.13 (m, 6 H) 1.16 (d, J = 6.42 Hz, 3 H) 1.18-1.28 (m, 7 H) 1.33-1.40 (m, 4 H) 1.61-1.67 (m, 1H) 1.96-2.17 (m, 4 H) 2.30 (s, 6 H) 2.35 (s, 3 H) 2.41-2.49 (m, 1 H) 2.54-2.62 (m, 1 H) 2.68-2.83 (m, 2 H) 2.80 (s, 3 H) 2.83-2.93 (m, 4 H) 3.00-3.06 (m, 1 H) 3.13-3.24 (m, 5 H) 3.29 (s, 3 H) 3.37 (s, 3 H) 3.38-3.48 (m, 2 H) 3.57-3.63 (m, 1 H) 3.68-3.72 (m, 1 H) 3.86 (s, 3 H) 3.90 (d, J = 6.42 Hz, 1 H) 4.13-4.20 (m, 1 H) 4.47 (d, J = 6.88 Hz, 1 H) 4.61-4.66 (m, 1 H) 5.03 (d, J = 5.04 Hz, 1 H) 6.83-6.99 (m, 4 H) |
| 138 | 150 | 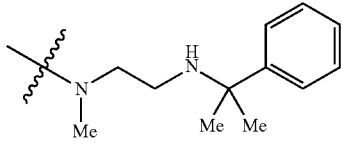 | 893 FAB MASS | (400 MHz): 0.90 (d, J = 7.08 Hz, 3 H) 1.01 (d, J = 6.59 Hz, 3 H) 1.12 (d, J = 7.81 Hz, 3 H) 1.19 (s, 3 H) 1.22 (d, J = 6.35 Hz, 3 H) 1.23 (d, J = 6.10 Hz, 3 H) 1.27 (d, J = 7.08 Hz, 3 H) 1.40 (s, 3 H) 1.46 (s, 6 H) 1.50-1.72 (m, 2 H) 2.03 (dd, J = 14.9, 5.13 Hz, 1 H) 2.09 (d, J = 14.9 Hz, 1 H) 2.17 (s, 3 H) 2.30 (s, 6 H) 2.37-2.52 (m, 6 H) 2.83 (d, J = 14.9 Hz, 1 H) 2.83-2.93 (m, 2 H) 3.00-3.06 (m, 1 H) 3.13-3.26 (m, 4 H) 3.31 (s, 3 H) 3.31-3.44 (m, 5 H) 3.44-3.52 (m, 1 H) 3.57-3.63 (m, 1 H) 3.69-3.74 (m, 1 H) 3.92 (d, J = 6.35 Hz, 1 H) 4.20 (q, J = 6.35 Hz, 1 H) 4.50 (d, J = 7.32 Hz, 1 H) 4.64 (t, J = 4.64 Hz, 1 H) 4.98 (d, J = 10.2 Hz, 1 H) 5.06 (d, J = 3.91 Hz, 1 H) 7.19-7.23 (m, 1 H) 7.28-7.35 (m, 2 H) 7.43-7.48 (m, 2 H) |
| 139 | 104 | 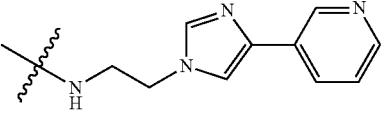 | 889.6 | (600 MHz): 0.90 (d, J = 7.34 Hz, 3 H) 1.02 (d, J = 6.88 Hz, 3 H) 1.11-1.16 (m, 6 H) 1.17-1.30 (m, 10 H) 1.35-1.41 (m, 4 H) 1.63-1.67 (m, 1 H) 1.90-1.95 (m, 1 H) 2.03-2.08 (m, 1 H) 2.11-2.17 (m, 1 H) 2.29 (s, 6 H) 2.42-2.49 (m, 1 H) 2.51 (d, J = 12.84 Hz, 1 H) 2.62-2.67 (m, 1 H) 2.77-3.07 (m, 7 H) 3.16-3.25 (m, 6 H) 3.33 (s, 3 H) 3.41-3.66 (m, 3 H) 3.69-3.72 (m, 1 H) 3.87 (d, J = 6.88 Hz, 1 H) 4.05-4.15 (m, 2 H) 4.38-4.46 (m, 2 H) 4.62-4.66 (m, 1 H) 4.95-4.98 (m, 1 H) 7.29-7.33 (m, 2 H) 7.56-7.58 (m, 1 H) 8.07-8.11 (m, 1 H) 8.47-8.50 (m, 1 H) 8.95-8.97 (m, 1 H) |

TABLE 5-5

| Example | Reference Example | R | ESI MS (M + H) | ¹H-NMR, CDCl₃, δ (ppm) |
|---|---|---|---|---|
| 140 | 105 | 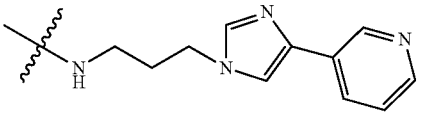 | 903.6 | (600 MHz): 0.89 (d, J = 7.34 Hz, 3 H) 1.02 (d, J = 6.42 Hz, 3 H) 1.09-1.27 (m, 16 H) 1.33-1.40 (m, 4 H) 1.59-1.64 (m, 1 H) 1.95-2.17 (m, 4 H) 2.27 (s, 6 H) 2.37-2.48 (m, 2 H) 2.58-2.71 (m, 3 H) 2.81-2.95 (m, 4 H) 3.00-3.06 (m, 1 H) 3.15-3.25 (m, 4 H) 3.29 (s, 3 H) 3.35 (s, 3 H) 3.40-3.46 (m, 1 H) 3.49-3.56 (m, 1 H) 3.58-3.64 (m, 1 H) 3.71 (d, J = 6.88 Hz, 1 H) 3.89 (d, J = 6.42 Hz, 1 H) 4.09 (t, J = 7.11 Hz, 2 H) 4.30-4.36 (m, 1 H) 4.45 (d, J = 7.34 Hz, 1 H) 4.64 (t, J = 4.58 Hz, 1 H) 5.00 (d, J = 4.13 Hz, 1 H) 7.27-7.32 (m, 2 H) 7.52-7.55 (m, 1 H) 8.07-8.10 (m, 1 H) 8.45-8.49 (m, 1 H) 8.94-8.97 (m, 1 H) |

| Example | Reference Example | R | ESI MS (M + H) | $^1$H-NMR, CDCl$_3$, δ (ppm) |
|---|---|---|---|---|
| 141 | 106 | 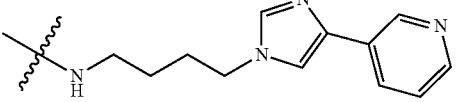 | 917.6 | (600 MHz): 0.89 (d, J = 6.88 Hz, 3 H) 1.01 (d, J = 6.88 Hz, 3 H) 1.09-1.26 (m, 16 H) 1.33-1.39 (m, 4 H) 1.47-1.54 (m, 1 H) 1.57-1.63 (m, 1 H) 1.84-2.17 (m, 5 H) 2.29 (s, 6 H) 2.35 (d, J = 13.30 Hz, 1 H) 2.41-2.47 (m, 1 H) 2.56-2.70 (m, 3 H) 2.83-2.95 (m, 4 H) 3.00-3.05 (m, 1 H) 3.14-3.24 (m, 4 H) 3.28 (s, 3 H) 3.35 (s, 3 H) 3.39-3.44 (m, 1 H) 3.49-3.55 (m, 1 H) 3.58-3.62 (m, 1 H) 3.68-3.72 (m, 1 H) 3.90 (d, J = 6.42 Hz, 1 H) 4.01 (t, J = 7.11 Hz, 2 H) 4.27-4.32 (m, 1 H) 4.46 (d, J = 6.88 Hz, 1 H) 4.61-4.66 (m, 1 H) 5.01 (d, J = 5.04 Hz, 1 H) 7.27-7.32 (m, 2 H) 7.52-7.56 (m, 1 H) 8.06-8.12 (m, 1 H) 8.44-8.51 (m, 1 H) 8.93-8.98 (m, 1 H) |
| 142 | 107 | 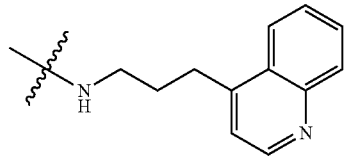 | 887.6 | (600 MHz): 0.89 (d, J = 7.34 Hz, 3 H) 1.01 (d, J = 6.88 Hz, 3 H) 1.09-1.22 (m, 13 H) 1.25 (d, J = 7.34 Hz, 3 H) 1.34-1.40 (m, 4 H) 1.51-1.56 (m, 1 H) 1.91-2.17 (m, 4 H) 2.23 (s, 6 H) 2.38-2.45 (m, 2 H) 2.57-2.63 (m, 1 H) 2.71-2.76 (m, 2 H) 2.83-2.96 (m, 4 H) 2.99-3.05 (m, 1 H) 3.11-3.22 (m, 6 H) 3.29 (s, 3 H) 3.36 (s, 3 H) 3.39-3.44 (m, 1 H) 3.50-3.62 (m, 2 H) 3.69-3.73 (m, 1 H) 3.90 (d, J = 6.42 Hz, 1 H) 4.30-4.36 (m, 1 H) 4.46 (d, J = 6.88 Hz, 1 H) 4.61-4.65 (m, 1 H) 5.01 (d, J = 4.13 Hz, 1 H) 7.23 (d, J = 4.58 Hz, 1 H) 7.55-7.59 (m, 1 H) 7.70-7.74 (m, 1 H) 8.02 (d, J = 7.79 Hz, 1 H) 8.13 (d, J = 8.25 Hz, 1 H) 8.81 (d, J = 4.13 Hz, 1 H) |
| 143 | 108 | 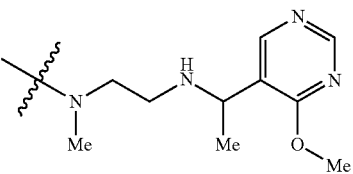 | 911.6 | (600 MHz): 0.87 (d, J = 6.88 Hz, 3 H) 1.00 (d, J = 6.88 Hz, 3 H) 1.10 (d, J = 7.79 Hz, 3 H) 1.13-1.27 (m, 13 H) 1.31-1.37 (m, 4 H) 1.37 (s, 3 H) 1.60-1.67 (m, 1 H) 1.95-2.17 (m, 4 H) 2.21-2.26 (m, 3 H) 2.29 (s, 6 H) 2.57 (br s, 6 H) 2.79-2.92 (m, 4 H) 2.98-3.04 (m, 1 H) 3.11-3.24 (m, 3 H) 3.29 (s, 3 H) 3.36 (s, 3 H) 3.37-3.42 (m, 1 H) 3.42-3.49 (m, 1 H) 3.55-3.61 (m, 1 H) 3.69 (d, J = 10.09 Hz, 1 H) 3.86-3.94 (m, 2 H) 4.00 (s, 3 H) 4.18 (q, J = 6.42 Hz, 1 H) 4.44-4.49 (m, 1 H) 4.62 (t, J = 4.81 Hz, 1 H) 5.03 (d, J = 5.04 Hz, 1 H) 8.40-8.46 (m, 1 H) 8.66 (s, 1 H) |
| 144 | 109 | 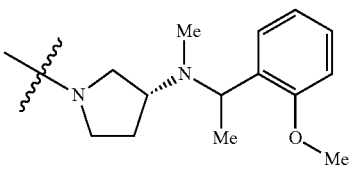 | 935.6 | (600 MHz): 0.88 (d, J = 6.88 Hz, 3 H) 1.01 (d, J = 6.42 Hz, 3 H) 1.08-1.14 (m, 9 H) 1.15-1.27 (m, 7 H) 1.29-1.40 (m, 7 H) 1.59-1.65 (m, 1 H) 1.83-2.21 (m, 10 H) 2.28-2.32 (m, 6 H) 2.42-2.49 (m, 1 H) 2.54-2.61 (m, 1 H) 2.84-2.94 (m, 5 H) 3.00-3.05 (m, 1 H) 3.11-3.24 (m, 4 H) 3.25-3.47 (m, 10 H) 3.57-3.62 (m, 1 H) 3.68-3.73 (m, 1 H) 3.80-3.84 (m, 3 H) 3.90 (t, J = 6.65 Hz, 1 H) 4.12-4.20 (m, 1 H) 4.24-4.31 (m, 1 H) 4.46-4.50 (m, 1 H) 4.61-4.65 (m, 1 H) 5.01-5.05 (m, 1 H) 6.85-6.89 (m, 1 H) 6.92-6.97 (m, 1 H) 7.19-7.24 (m, 1 H) 7.30-7.36 (m, 1 H) |
| 145 | 110 | 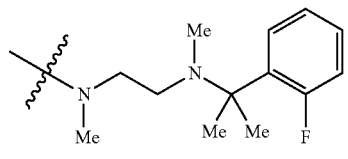 | 925.6 | (600 MHz): 0.88 (d, J = 6.88 Hz, 3 H) 1.01 (d, J = 6.42 Hz, 3 H) 1.09-1.14 (m, 6 H) 1.16-1.27 (m, 10 H) 1.34-1.40 (m, 4 H) 1.42-1.46 (m, 6 H) 1.61-1.65 (m, 1 H) 1.97-2.10 (m, 7 H) 2.11-2.17 (m, 1 H) 2.27 (s, 3 H) 2.29 (s, 6 H) 2.42-2.49 (m, 1 H) 2.55-2.61 (m, 1 H) 2.78 (d, J = 14.67 Hz, 1 H) 2.84-2.92 (m, 4 H) 3.00-3.05 (m, 1 H) 3.13-3.24 (m, 4 H) 3.29 (s, 3 H) 3.36-3.48 (m, 6 H) 3.57-3.62 (m, 1 H) 3.69-3.73 (m, 1 H) 3.89-3.93 (m, 1 H) 4.12-4.18 (m, 1 H) 4.48 (d, J = 7.34 Hz, 1 H) 4.63 (d, J = 9.17 Hz, 1 H) 5.05 (d, J = 5.04 Hz, 1 H) 6.93-6.99 (m, 1 H) 7.02-7.06 (m, 1 H) 7.14-7.20 (m, 1 H) 7.50-7.55 (m, 1 H) |

TABLE 5-5-continued

| Example | Reference Example | R | ESI MS (M + H) | ¹H-NMR, CDCl₃, δ (ppm) |
|---|---|---|---|---|
| 146 | 111 | *structure: ~N(Me)CH₂CH₂N(Me)C(Me)₂-(2-Br-phenyl)* | 985.6 | (600 MHz): 0.89 (d, J = 6.88 Hz, 3 H) 1.02 (d, J = 6.88 Hz, 3 H) 1.05-1.28 (m, 16 H) 1.33-1.40 (m, 4 H) 1.49 (s, 6 H) 1.57-1.64 (m, 1 H) 1.93-2.16 (m, 7 H) 2.20 (s, 3 H) 2.31 (s, 6 H) 2.33-2.40 (m, 1 H) 2.43-2.50 (m, 1 H) 2.57-2.62 (m, 1 H) 2.74-2.93 (m, 5 H) 3.00-3.05 (m, 1 H) 3.14-3.24 (m, 4 H) 3.28 (s, 3 H) 3.34-3.47 (m, 6 H) 3.58-3.63 (m, 1 H) 3.67-3.72 (m, 1 H) 3.89 (d, J = 6.42 Hz, 1 H) 4.11-4.17 (m, 1 H) 4.47 (d, J = 7.34 Hz, 1 H) 4.61-4.66 (m, 1 H) 5.02 (d, J = 5.04 Hz, 1 H) 7.01-7.05 (m, 1 H) 7.19-7.24 (m, 1 H) 7.43-7.47 (m, 1 H) 7.55-7.60 (m, 1 H) |
| 147 | 112 | *structure: ~N(Me)CH₂CH₂OC(Me)₂-(2-OMe-phenyl)* | 910.6 | (600 MHz): 0.87 (d, J = 7.34 Hz, 3 H) 1.00 (d, J = 6.42 Hz, 3 H) 1.08-1.13 (m, 6 H) 1.14 (d, J = 6.42 Hz, 3 H) 1.17-1.23 (m, 1 H) 1.20 (d, J = 5.96 Hz, 3 H) 1.24 (d, J = 6.88 Hz, 3 H) 1.33-1.37 (m, 1 H) 1.37 (s, 3 H) 1.59 (d, J = 2.29 Hz, 6 H) 1.60-1.65 (m, 1 H) 1.96-2.02 (m, 1 H) 2.03-2.08 (m, 1 H) 2.08-2.17 (m, 1 H) 2.29 (s, 6 H) 2.32 (d, J = 13.75 Hz, 1 H) 2.42-2.49 (m, 1 H) 2.54-2.60 (m, 1 H) 2.78 (t, J = 5.04 Hz, 2 H) 2.82-2.93 (m, 3 H) 2.98 (d, J = 13.76 Hz, 1 H) 2.99-3.04 (m, 1 H) 3.11-3.23 (m, 3 H) 3.29 (s, 3 H) 3.30-3.42 (m, 3 H) 3.35 (s, 3 H) 3.47-3.54 (m, 1 H) 3.55-3.60 (m, 1 H) 3.67-3.71 (m, 1 H) 3.82 (s, 3 H) 3.91 (d, J = 6.42 Hz, 1 H) 4.23-4.29 (m, 1 H) 4.49 (d, J = 7.34 Hz, 1 H) 4.62 (t, J = 4.58 Hz, 1 H) 5.02 (d, J = 4.58 Hz, 1 H) 6.87-6.94 (m, 2 H) 7.21-7.25 (m, 1 H) 7.34-7.39 (m, 1 H) |

TABLE 5-6

| Example | Reference Example | R | ESI MS (M + H) | ¹H-NMR, CDCl₃, δ (ppm) |
|---|---|---|---|---|
| 148 | 113 | *structure: ~N(Me)CH₂CH₂N(Me)C(Me)₂-(2-Me-phenyl)* | 921.6 | (600 MHz): 0.87 (d, J = 7.34 Hz, 3 H) 1.00 (d, J = 6.88 Hz, 3 H) 1.04-1.12 (m, 9 H) 1.17-1.26 (m, 1 H) 1.21 (d, J = 5.96 Hz, 3 H) 1.24 (d, J = 6.88 Hz, 3 H) 1.35 (d, J = 14.67 Hz, 1 H) 1.37 (s, 3 H) 1.40 (s, 6 H) 1.60-1.66 (m, 1 H) 1.93-2.03 (m, 2 H) 2.03-2.15 (m, 2 H) 2.08 (s, 3 H) 2.17 (s, 3 H) 2.29 (s, 6 H) 2.32-2.60 (m, 6 H) 2.66 (s, 3 H) 2.71-2.78 (m, 1 H) 2.82-2.92 (m, 3 H) 2.98-3.04 (m, 1 H) 3.10-3.23 (m, 3 H) 3.27 (s, 3 H) 3.36 (s, 3 H) 3.37-3.46 (m, 2 H) 3.55-3.61 (m, 1 H) 3.66-3.71 (m, 1 H) 3.89 (d, J = 6.42 Hz, 1 H) 4.10-4.16 (m, 1 H) 4.46 (d, J = 7.34 Hz, 1 H) 4.62 (t, J = 4.81 Hz, 1 H) 5.02 (d, J = 5.04 Hz, 1 H) 7.04-7.10 (m, 3 H) 7.27-7.31 (m, 1 H) |
| 149 | 114 | *structure: ~N(Me)CH₂CH₂N(Me)C(Me)₂-(2-Cl-phenyl)* | 941.6 | (600 MHz): 0.87 (d, J = 7.34 Hz, 3 H) 1.00 (d, J = 6.88 Hz, 3 H) 1.05-1.15 (m, 9 H) 1.17-1.27 (m, 7 H) 1.35 (d, J = 14.67 Hz, 1 H) 1.37 (s, 3 H) 1.48 (s, 6 H) 1.61-1.67 (m, 1 H) 1.93-1.99 (m, 1 H) 1.96-2.03 (m, 1 H) 2.06 (d, J = 14.67 Hz, 1 H) 2.06-2.16 (m, 1 H) 2.10 (s, 3 H) 2.21 (s, 3 H) 2.29 (s, 6 H) 2.30-2.39 (m, 2 H) 2.41-2.61 (m, 4 H) 2.72-2.81 (m, 1 H) 2.82-2.92 (m, 3 H) 2.98-3.04 (m, 1 H) 3.10-3.25 (m, 3 H) 3.27 (s, 3 H) 3.36 (s, 3 H) 3.36-3.47 (m, 2 H) 3.55-3.61 (m, 1 H) 3.66-3.71 (m, 1 H) 3.89 (d, J = 6.42 Hz, 1 H) 4.13 (q, J = 6.27 Hz, 1 H) 4.46 (d, J = 7.34 Hz, 1 H) 4.62 (t, J = 4.59 Hz, 1 H) 5.02 (d, J = 5.04 Hz, 1 H) 7.08-7.13 (m, 1 H) 7.13-7.18 (m, 1 H) 7.28-7.33 (m, 1 H) 7.47-7.53 (m, 1 H) |

TABLE 5-6-continued

| Example | Reference Example | R | ESI MS (M + H) | ¹H-NMR, CDCl$_3$, δ (ppm) |
|---|---|---|---|---|
| 150 | 115 | (structure) | 909.6 | (600 MHz): 0.88 (d, J = 6.88 Hz, 3 H) 1.01 (d, J = 6.88 Hz, 3 H) 1.07-1.27 (m, 16 H) 1.33-1.40 (m, 4 H) 1.60-1.65 (m, 1 H) 1.69-1.79 (m, 2 H) 1.95-2.17 (m, 4 H) 2.30 (s, 6 H) 2.31 (s, 3 H) 2.42-2.49 (m, 1 H) 2.53-2.61 (m, 3 H) 2.77 (s, 3 H) 2.78-2.92 (m, 3 H) 3.00-3.09 (m, 3 H) 3.13-3.28 (m, 4 H) 3.29 (s, 3 H) 3.37 (s, 3 H) 3.38-3.47 (m, 2 H) 3.57-3.62 (m, 1 H) 3.68-3.72 (m, 1 H) 3.86 (s, 3 H) 3.90 (d, J = 6.42 Hz, 1 H) 4.14-4.20 (m, 1 H) 4.47 (d, J = 7.34 Hz, 1 H) 4.62-4.65 (m, 1 H) 5.03 (d, J = 5.04 Hz, 1 H) 6.83-7.00 (m, 4 H) |
| 151 | 116 | (structure) | 932.6 | (600 MHz): 0.87 (d, J = 7.34 Hz, 3 H) 1.00 (d, J = 6.88 Hz, 3 H) 1.11 (d, J = 7.34 Hz, 3 H) 1.12-1.28 (m, 13 H) 1.33-1.37 (m, 1 H) 1.37-1.39 (m, 3 H) 1.45-1.50 (m, 3 H) 1.58-1.65 (m, 1 H) 1.96-2.15 (m, 4 H) 2.20-2.25 (m, 3 H) 2.28 (s, 6 H) 2.41-2.48 (m, 1 H) 2.50-2.70 (m, 5 H) 2.79-2.92 (m, 4 H) 2.98-3.05 (m, 1 H) 3.12-3.24 (m, 3 H) 3.26-3.31 (m, 3 H) 3.35-3.39 (m, 3 H) 3.37-3.42 (m, 1 H) 3.42-3.48 (m, 1 H) 3.55-3.62 (m, 1 H) 3.67-3.73 (m, 1 H) 3.87-3.95 (m, 1 H) 4.04 (s, 3 H) 4.13-4.20 (m, 1 H) 4.47 (dd, J = 7.11, 2.06 Hz, 1 H) 4.62 (t, J = 4.58 Hz, 1 H) 4.66-4.73 (m, 1 H) 4.92-4.99 (m, 1 H) 5.03 (d, J = 5.50 Hz, 1 H) 6.45 (d, J = 3.21 Hz, 1 H) 6.93 (d, J = 3.21 Hz, 1 H) 7.06 (t, J = 7.57 Hz, 1 H) 7.28 (t, J = 6.88 Hz, 1 H) 7.48 (d, J = 8.71 Hz, 1 H) |
| 152 | 117 | (structure) | 939.7 | (600 MHz): 0.87 (d, J = 7.34 Hz, 3 H) 1.00 (d, J = 6.88 Hz, 3 H) 1.08 (s, 3 H) 1.10 (d, J = 7.79 Hz, 3 H) 1.14 (d, J = 6.42 Hz, 3 H) 1.18 (d, J = 6.42 Hz, 3 H) 1.20-1.23 (m, 1 H) 1.23 (d, J = 6.88 Hz, 3 H) 1.33-1.37 (m, 1 H) 1.37 (s, 3 H) 1.47-1.54 (m, 6 H) 1.59-1.64 (m, 1 H) 1.95 (dd, J = 14.90, 5.27 Hz, 1 H) 2.03-2.07 (m, 1 H) 2.10-2.15 (m, 1 H) 2.29 (s, 6 H) 2.31-2.35 (m, 1 H) 2.40-2.52 (m, 4 H) 2.55-2.60 (m, 1 H) 2.80 (d, J = 13.76 Hz, 1 H) 2.82-2.91 (m, 3 H) 2.99-3.04 (m, 1 H) 3.12-3.22 (m, 3 H) 3.27 (s, 3 H) 3.34 (s, 3 H) 3.37-3.42 (m, 1 H) 3.44-3.51 (m, 1 H) 3.56-3.64 (m, 2 H) 3.67-3.71 (m, 1 H) 3.72-3.76 (m, 1 H) 3.88 (s, 3 H) 3.88-3.89 (m, 1 H) 4.26 (q, J = 6.11 Hz, 1 H) 4.44 (d, J = 7.34 Hz, 1 H) 4.62 (t, J = 4.81 Hz, 1 H) 4.89-4.93 (m, 1 H) 5.00 (d, J = 4.58 Hz, 1 H) 6.89-6.95 (m, 2 H) 7.17-7.21 (m, 1 H) 7.23-7.26 (m, 1 H) |
| 153 | 118 | (structure) | 953.7 | (600 MHz): 0.87 (d, J = 7.34 Hz, 3 H) 1.00 (d, J = 6.42 Hz, 3 H) 1.08-1.15 (m, 9 H) 1.17-1.25 (m, 7 H) 1.34-1.37 (m, 1 H) 1.37 (s, 3 H) 1.43 (s, 3 H) 1.51 (s, 3 H) 1.60-1.64 (m, 1 H) 1.94-1.99 (m, 1 H) 2.03-2.07 (m, 1 H) 2.08 (s, 3 H) 2.10-2.15 (m, 1 H) 2.29 (s, 6 H) 2.39-2.47 (m, 2 H) 2.51-2.67 (m, 3 H) 2.72-2.79 (m, 1 H) 2.82-2.95 (m, 4 H) 2.98-3.05 (m, 1 H) 3.11-3.23 (m, 3 H) 3.28 (s, 3 H) 3.34 (s, 3 H) 3.35-3.43 (m, 2 H) 3.47-3.54 (m, 1 H) 3.56-3.61 (m, 1 H) 3.67-3.75 (m, 2 H) 3.81 (s, 3 H) 3.88 (d, J = 6.42 Hz, 1 H) 424-4.28 (m, 1 H) 4.45 (d, J = 6.88 Hz, 1 H) 4.59-4.64 (m, 1 H) 4.89-4.97 (m, 1 H) 5.00 (d, J = 4.13 Hz, 1 H) 6.86-8.93 (m, 2 H) 7.22-7.30 (m, 2 H) |
| 154 | 119 | (structure) | 964.7 | (600 MHz): 0.88 (d, J = 7.34 Hz, 3 H) 1.01 (d, J = 6.42 Hz, 3 H) 1.08-1.15 (m, 9 H) 1.19-1.28 (m, 7 H) 1.34-1.45 (m, 10 H) 1.62-1.67 (m, 1 H) 2.11 (s, 7 H) 2.22 (s, 3 H) 2.25 (s, 6 H) 2.30 (s, 6 H) 242-2.65 (m, 6 H) 2.77-2.92 (m, 4 H) 3.00-3.05 (m, 1 H) 3.13-3.25 (m, 3 H) 3.29 (s, 3 H) 3.37 (s, 3 H) 3.38-3.48 (m, 2 H) 3.57-3.62 (m, 1 H) 3.67-3.72 (m, 1 H) 3.87-3.99 (m, 3 H) 4.14-4.19 (m, 1 H) 4.47 (d, J = 7.34 Hz, 1 H) 4.61-4.65 (m, 1 H) 5.01-5.05 (m, 1 H) 7.12-7.22 (m, 2 H) 7.33 (d, J = 7.79 Hz, 1 H) 7.65 (d, J = 7.34 Hz, 1 H) |

TABLE 5-6-continued

| Example | Reference Example | R | ESI MS (M + H) | ¹H-NMR, CDCl₃, δ (ppm) |
|---|---|---|---|---|
| 155 | 120 | 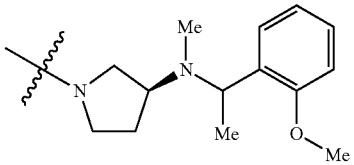 | 935.6 | (600 MHz): 0.88 (d, J = 7.34 Hz, 3 H) 1.01 (d, J = 6.88 Hz, 3 H) 1.07-1.17 (m, 9 H) 1.18-1.27 (m, 7 H) 1.29-1.41 (m, 7 H) 1.59-1.66 (m, 1 H) 1.81-1.92 (m, 2 H) 1.94-2.03 (m, 1 H) 2.05-2.21 (m, 7 H) 2.27-2.33 (m, 6 H) 2.41-2.49 (m, 1 H) 2.54-2.61 (m, 1 H) 2.84-2.97 (m, 5 H) 2.99-3.05 (m, 1 H) 3.12-3.24 (m, 4 H) 3.25-3.48 (m, 10 H) 3.57-3.63 (m, 1 H) 3.68-3.74 (m, 1 H) 3.79-3.83 (m, 3 H) 3.90 (t, J = 5.96 Hz, 1 H) 4.13-4.31 (m, 2 H) 4.47 (t, J = 7.57 Hz, 1 H) 4.61-4.65 (m, 1 H) 5.01-5.05 (m, 1 H) 6.85-6.89 (m, 1 H) 6.92-6.97 (m, 1 H) 7.19-7.24 (m, 1 H) 7.31-7.36 (m, 1 H) |

TABLE 5-7

| Example | Reference Example | R | ESI MS (M + H) | ¹H-NMR, CDCl₃, δ (ppm) |
|---|---|---|---|---|
| 156 | 121 | 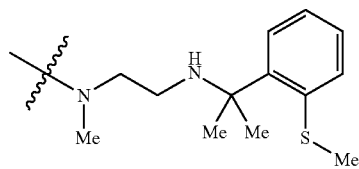 | 939.6 | (600 MHz): 0.88 (d, J = 6.88 Hz, 3 H) 1.01 (d, J = 6.42 Hz, 3 H) 1.11 (d, J = 7.79 Hz, 3 H) 1.16 (s, 3 H) 1.18-1.28 (m, 10 H) 1.34-1.40 (m, 4 H) 1.58 (s, 6 H) 1.61-1.66 (m, 1 H) 1.99-2.17 (m, 4 H) 2.19 (s, 3 H) 2.24-2.33 (m, 8 H) 2.43-2.49 (m, 1 H) 2.49 (s, 3 H) 2.52-2.67 (m, 3 H) 2.80-2.93 (m, 4 H) 3.00-3.05 (m, 1 H) 3.13-3.24 (m, 3 H) 3.29 (s, 3 H) 3.38 (s, 3 H) 3.39-3.49 (m, 2 H) 3.58-3.62 (m, 1 H) 3.69-3.73 (m, 1 H) 3.92 (d, J = 6.42 Hz, 1 H) 4.14-4.19 (m, 1 H) 4.48 (d, J = 7.34 Hz, 1 H) 4.62-4.66 (m, 1 H) 5.03-5.06 (m, 1 H) 7.09-7.13 (m, 1 H) 7.18-7.23 (m, 1 H) 7.27-7.32 (m, 2 H) |
| 157 | 122 | 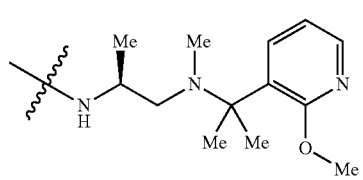 | 938.7 | (600 MHz): 0.87 (d, J = 6.88 Hz, 3 H) 0.92 (d, J = 5.96 Hz, 3 H) 1.00 (d, J = 6.42 Hz, 3 H) 1.11 (d, J = 7.34 Hz, 3 H) 1.10-1.13 (m, 1 H) 1.13 (s, 3 H) 1.18-1.21 (m, 6 H) 1.22-1.26 (m, 6 H) 1.34 (d, J = 13.75 Hz, 1 H) 1.37 (s, 3 H) 1.41 (d, J = 8.25 Hz, 3 H) 1.58-1.66 (m, 1 H) 2.00-2.03 (m, 2 H) 2.11 (s, 3 H) 2.15-2.22 (m, 2 H) 2.29 (s, 6 H) 2.36-2.44 (m, 1 H) 2.44-2.50 (m, 1 H) 2.54-2.61 (m, 1 H) 2.61-2.68 (m, 1 H) 2.84-2.93 (m, 3 H) 2.98-3.04 (m, 1 H) 3.10 (d, J = 13.30 Hz, 1 H) 3.13-3.19 (m, 2 H) 3.19-3.24 (m, 1 H) 3.31 (s, 3 H) 3.35 (s, 3 H) 3.37-3.42 (m, 1 H) 3.47-3.53 (m, 1 H) 3.54-3.56 (m, 1 H) 3.56-3.61 (m, 1 H) 3.65-3.69 (m, 1 H) 3.92 (s, 3 H) 3.93-3.95 (m, 1 H) 4.20-4.28 (m, 1 H) 4.50 (d, J = 7.34 Hz, 1 H) 4.62 (t, J = 4.81 Hz, 1 H) 4.92-4.99 (m, 1 H) 5.00-5.03 (m, 1 H) 6.82 (dd, J = 7.57, 4.81 Hz, 1 H) 7.69 (dd, J = 7.79, 1.83 Hz, 1 H) 8.03 (dd, J = 4.59, 1.83 Hz, 1 H) |
| 158 | 123 | 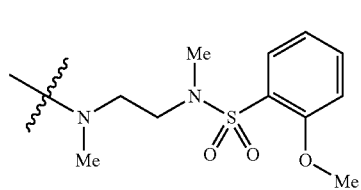 | 959.6 | (600 MHz): 0.87 (d, J = 6.88 Hz, 3 H) 1.00 (d, J = 6.42 Hz, 3 H) 1.11 (d, J = 7.34 Hz, 3 H) 1.13 (s, 3 H) 1.18 (d, J = 6.42 Hz, 3 H) 1.19-1.23 (m, 1 H) 1.23-1.26 (m, 6 H) 1.33-1.37 (m, 1 H) 1.37 (s, 3 H) 1.64-1.70 (m, 1 H) 1.96-2.02 (m, 1 H) 2.05-2.17 (m, 3 H) 2.29 (s, 6 H) 2.39 (s, 3 H) 2.42-2.50 (m, 1 H) 2.54-2.60 (m, 1 H) 2.69-2.79 (m, 2 H) 2.82 (s, 3 H) 2.84-2.96 (m, 4 H) 2.98-3.04 (m, 1 H) 3.10-3.37 (m, 5 H) 3.29 (s, 3 H) 3.36 (s, 3 H) 3.37-3.42 (m, 1 H) 3.43-3.49 (m, 1 H) 3.55-3.61 (m, 1 H) 3.67-3.71 (m, 1 H) 3.89 (d, J = 6.42 Hz, 1 H) 3.92 (s, 3 H) 4.15-4.21 (m, 1 H) 4.47 (d, J = 7.34 Hz, 1 H) 4.62 (t, J = 4.81 Hz, 1 H) 5.02 (d, J = 5.04 Hz, 1 H) 7.00 (d, J = 8.25 Hz, 1 H) 7.03 (t, J = 7.79 Hz, 1 H) 7.49-7.53 (m, 1 H) 7.89-7.92 (m, 1 H) |

TABLE 5-7-continued

| Example | Reference Example | R | ESI MS (M + H) | $^1$H-NMR, CDCl$_3$, δ (ppm) |
|---|---|---|---|---|
| 159 | 124 | (structure: N-Me linked ethyl to tetrahydroisoquinoline with 1-Me and 8-OMe) | 935.7 | (600 MHz): 0.87 (d, J = 6.88 Hz, 3 H) 1.00 (d, J = 6.88 Hz, 3 H) 1.07-1.12 (m, 3 H) 1.14-1.17 (m, 6 H) 1.18-1.20 (m, 1 H) 1.20-1.25 (m, 6 H) 1.25-1.29 (m, 3 H) 1.35 (d, J = 14.67 Hz, 1 H) 1.37 (s, 3 H) 1.60-1.67 (m, 1 H) 1.91-2.07 (m, 2 H) 2.13 (d, J = 14.67 Hz, 1 H) 2.29 (s, 6 H) 2.33-2.37 (m, 3 H) 2.41-2.50 (m, 1 H) 2.52-2.62 (m, 3 H) 2.64-2.73 (m, 3 H) 2.73-2.80 (m, 1 H) 2.81-2.91 (m, 4 H) 2.91-2.98 (m, 1 H) 2.99-3.04 (m, 1 H) 3.05-3.23 (m, 5 H) 3.26-3.29 (m, 3 H) 3.33-3.36 (m, 3 H) 3.37-3.42 (m, 1 H) 3.45-3.52 (m, 1 H) 3.56-3.61 (m, 1 H) 3.64-3.69 (m, 1 H) 3.79 (s, 3 H) 3.90-3.94 (m, 1 H) 3.99-4.06 (m, 1 H) 4.11-4.18 (m, 1 H) 4.48 (d, J = 7.34 Hz, 1 H) 4.62 (t, J = 4.58 Hz, 1 H) 4.92-4.98 (m, 1 H) 4.99-5.03 (m, 1 H) 6.65 (d, J = 8.25 Hz, 1 H) 6.68 (d, J = 7.79 Hz, 1 H) 7.05-7.10 (m, 1 H) |
| 160 | 125 | (structure: NH-ethyl-N(Me)-C(Me)$_2$-(2-OMe-phenyl)) | 923.7 | (600 MHz): 0.88 (d, J = 6.88 Hz, 3 H) 1.01 (d, J = 6.88 Hz, 3 H) 1.08-1.17 (m, 9 H) 1.17-1.25 (m, 1 H) 1.20 (d, J = 6.42 Hz, 3 H) 1.25 (d, J = 6.88 Hz, 3 H) 1.34-1.40 (m, 4 H) 1.42-1.47 (m, 6 H) 1.59-1.65 (m, 1 H) 1.97-2.03 (m, 1 H) 2.05-2.09 (m, 1 H) 2.12-2.17 (m, 4 H) 2.22 (d, J = 14.67 Hz, 1 H) 2.29 (s, 6 H) 2.43-2.52 (m, 3 H) 2.55-2.65 (m, 2 H) 2.85-2.96 (m, 5 H) 3.02 (dd, J = 9.63, 3.21 Hz, 1 H) 3.13-3.25 (m, 3 H) 3.30 (s, 3 H) 3.37 (s, 3 H) 3.38-3.42 (m, 1 H) 3.47-3.53 (m, 1 H) 3.57-3.62 (m, 1 H) 3.70 (dd, J = 9.63, 1.83 Hz, 1 H) 3.80 (s, 3 H) 3.92 (d, J = 5.96 Hz, 1 H) 4.20-4.25 (m, 1 H) 4.50 (d, J = 7.34 Hz, 1 H) 4.63 (t, J = 4.59 Hz, 1 H) 4.94 (d, J = 10.09 Hz, 1 H) 5.03 (d, J = 5.04 Hz, 1 H) 6.87-6.92 (m, 2 H) 7.18-7.22 (m, 1 H) 7.39-7.43 (m, 1 H) |
| 161 | 126 | (structure: azetidine-CH$_2$-NH-C(Me)$_2$-(2-OMe-phenyl)) | 935.6 | (600 MHz): 0.86 (d, J = 7.34 Hz, 3 H) 0.96-1.00 (m, 6 H) 1.02 (d, J = 6.42 Hz, 3 H) 1.08 (d, J = 7.34 Hz, 3 H) 1.15-1.26 (m, 4 H) 1.18 (d, J = 5.96 Hz, 3 H) 1.30-1.35 (m, 1 H) 1.35 (s, 4 H) 1.48 (s, 6 H) 1.59-1.66 (m, 1 H) 1.91 (dd, J = 15.13, 5.50 Hz, 1 H) 2.00-2.14 (m, 3 H) 228 (s, 6 H) 2.33-2.52 (m, 4 H) 2.52-2.59 (m, 1 H) 2.80 (d, J = 14.67 Hz, 1 H) 2.81-3.03 (m, 5 H) 3.09-3.22 (m, 3 H) 3.24 (s, 3 H) 3.33 (s, 3 H) 3.35-3.51 (m, 4 H) 3.54-3.59 (m, 1 H) 3.66 (d, J = 1.83 Hz, 1 H) 3.83 (s, 3 H) 3.86 (d, J = 6.42 Hz, 1 H) 4.09 (q, J = 6.42 Hz, 1 H) 4.43 (d, J = 6.88 Hz, 1 H) 4.60 (t, J = 4.58 Hz, 1 H) 4.98 (d, J = 5.04 Hz, 1 H) 6.88 (d, J = 7.79 Hz, 1 H) 6.92 (t, J = 7.57 Hz, 1 H) 7.19-7.26 (m, 2 H) |
| 162 | 127 | (structure: azetidine-CH$_2$-N(Me)-C(Me)$_2$-(2-OMe-phenyl)) | 949.7 | (600 MHz): 0.88 (d, J = 7.34 Hz, 3 H) 1.01 (d, J = 6.42 Hz, 3 H) 1.02 (s, 3 H) 1.05 (d, J = 5.96 Hz, 3 H) 1.10 (d, J = 7.79 Hz, 3 H) 1.15-1.27 (m, 1 H) 1.21 (d, J = 5.96 Hz, 3 H) 1.23 (d, J = 6.88 Hz, 3 H) 1.31-1.36 (m, 1 H) 1.37 (s, 3 H) 1.41 (s, 6 H) 1.61-1.68 (m, 1 H) 1.94 (dd, J = 14.90, 5.27 Hz, 1 H) 2.02-2.18 (m, 3 H) 2.13 (s, 3 H) 2.30 (s, 6 H) 2.39-2.66 (m, 5 H) 2.80 (d, J = 14.67 Hz, 1 H) 2.83-2.97 (m, 5 H) 2.97-3.05 (m, 1 H) 3.10-3.24 (m, 3 H) 3.26 (s, 3 H) 3.35 (s, 3 H) 327-3.55 (m, 4 H) 3.55-3.62 (m, 1 H) 3.69 (d, J = 10.55 Hz, 1 H) 3.78 (s, 3 H) 3.89 (d, J = 5.96 Hz, 1 H) 4.07-4.14 (m, 1 H) 4.46 (d, J = 7.34 Hz, 1 H) 4.62 (t, J = 4.36 Hz, 1 H) 5.00 (d, J = 5.04 Hz, 1 H) 6.82-6.92 (m, 2 H) 7.19 (t, J = 7.79 Hz, 1 H) 7.51 (d, J = 7.34 Hz, 1 H) |

TABLE 5-8

| Example | Reference Example | R | ESI MS (M + H) | $^1$H-NMR, CDCl$_3$, δ (ppm) |
|---|---|---|---|---|
| 163 | 128 | | 935.7 | (600 MHz): 0.87 (d, J = 7.34 Hz, 3 H) 1.00 (d, J = 6.42 Hz, 3 H) 1.02-1.05 (m, 3 H) 1.05-1.12 (m, 6 H) 1.13-1.21 (m, 4 H) 1.23 (d, J = 7.34 Hz, 3 H) 1.30-1.39 (m, 4 H) 1.40-1.51 (m, 7 H) 1.59-1.64 (m, 1 H) 1.79-1.98 (m, 2 H) 2.01-2.17 (m, 3 H) 2.24-2.33 (m, 6 H) 2.37-2.47 (m, 1 H) 2.52-2.77 (m, 5 H) 2.81-2.91 (m, 4 H) 2.91-3.05 (m, 2 H) 3.09-3.23 (m, 3 H) 3.24-3.28 (m, 3 H) 3.35 (s, 3 H) 3.37-3.44 (m, 2 H) 3.54-3.61 (m, 1 H) 3.68 (d, J = 9.63 Hz, 1 H) 3.85 (br s, 3 H) 3.88 (d, J = 6.42 Hz, 1 H) 4.11 (d, J = 6.72 Hz, 1 H) 4.42-4.47 (m, 1 H) 4.62 (t, J = 4.81 Hz, 1 H) 4.97-5.03 (m, 1 H) 6.83-6.96 (m, 2 H) 7.19-7.26 (m, 2 H) |
| 164 | 129 | | 921.7 | (600 MHz): 0.87 (d, J = 6.88 Hz, 3 H) 1.00 (d, J = 6.88 Hz, 3 H) 1.08-1.20 (m, 13 H) 1.24 (d, J = 6.88 Hz, 3 H) 1.29 (d, J = 6.42 Hz, 3 H) 1.33-1.39 (m, 1 H) 1.37 (s, 3 H) 1.49-1.60 (m, 2 H) 1.94-2.00 (m, 1 H) 2.02-2.17 (m, 3 H) 2.26-2.31 (m, 1 H) 2.27 (s, 6 H) 2.32-2.47 (m, 3 H) 2.54-2.63 (m, 2 H) 2.70-2.77 (m, 1 H) 2.81-2.94 (m, 4 H) 2.98-3.04 (m, 1 H) 3.11-3.22 (m, 4 H) 3.29 (s, 3 H) 3.35 (s, 3 H) 3.37-3.42 (m, 1 H) 3.46-3.54 (m, 1 H) 3.55-3.61 (m, 1 H) 3.67-3.72 (m, 1 H) 3.75-3.80 (m, 1 H) 3.81 (s, 3 H) 3.90 (d, J = 6.42 Hz, 1 H) 4.26 (q, J = 5.96 Hz, 1 H) 4.46 (d, J = 7.34 Hz, 1 H) 4.62 (t, J = 4.58 Hz, 1 H) 5.00 (d, J = 3.67 Hz, 1 H) 6.85 (d, J = 7.79 Hz, 1 H) 6.93 (t, J = 7.57 Hz, 1 H) 7.15-7.21 (m, 1 H) 7.43-7.47 (m, 1 H) |
| 165 | 130 | | 963.7 | (600 MHz): 0.87 (d, J = 7.34 Hz, 3 H) 0.93 (t, J = 7.11 Hz, 3 H) 1.00 (d, J = 6.88 Hz, 3 H) 1.03 (s, 3 H) 1.06 (d, J = 6.42 Hz, 3 H) 1.10 (d, J = 7.79 Hz, 3 H) 1.18-1.26 (m, 1 H) 1.22 (d, J = 6.42 Hz, 3 H) 1.23 (d, J = 6.88 Hz, 3 H) 1.35 (d, J = 14.21 Hz, 1 H) 1.37 (s, 3 H) 1.43 (s, 6 H) 1.62-1.67 (m, 1 H) 1.94 (dd, J = 14.67, 5.04 Hz, 1 H) 2.03-2.17 (m, 3 H) 2.30 (s, 6 H) 2.41-2.66 (m, 7 H) 2.81 (d, J = 15.13 Hz, 1 H) 2.83-2.92 (m, 4 H) 2.92-2.98 (m, 1 H) 2.98-3.04 (m, 1 H) 3.10-3.23 (m, 3 H) 3.27 (s, 3 H) 3.36 (s, 3 H) 3.37-3.41 (m, 1 H) 3.41-3.52 (m, 3 H), 3.55-3.61 (m, 1 H) 3.66-3.71 (m, 1 H) 3.77 (s, 3 H) 3.89 (d, J = 6.42 Hz, 1 H) 4.11 (q, J = 6.11 Hz, 1 H) 4.46 (d, J = 7.34 Hz, 1 H) 4.62 (t, J = 4.81 Hz, 1 H) 5.01 (d, J = 5.50 Hz, 1 H) 6.82-6.90 (m, 2 H) 7.14-7.20 (m, 1 H) 7.44-7.49 (m, 1 H) |
| 166 | 131 | | 949.7 | (600 MHz): 0.87 (d, J = 7.34 Hz, 3 H) 1.00 (d, J = 6.88 Hz, 3 H) 1.03 (s, 3 H) 1.07 (d, J = 5.96 Hz, 3 H) 1.09 (d, J = 7.79 Hz, 3 H) 1.17-1.18 (m, 1 H) 1.18 (d, J = 5.96 Hz, 3 H) 1.22 (d, J = 7.34 Hz, 3 H) 1.32-1.36 (m, 1 H) 1.36 (s, 3 H) 1.64-1.70 (m, 1 H) 1.75 (d, J = 4.13 Hz, 6 H) 1.92 (dd, J = 14.90, 5.27 Hz, 1 H) 2.05 (d, J = 14.67 Hz, 1 H) 2.09-2.15 (m, 1 H) 2.16 (d, J = 14.67 Hz, 1 H) 2.29 (s, 6 H) 2.38-2.45 (m, 1 H) 2.54-2.60 (m, 1 H) 2.80-2.92 (m, 4 H) 2.98-3.03 (m, 1 H) 3.03-3.09 (m, 1 H) 3.11-3.22 (m, 3 H) 3.25 (s, 3 H) 3.34 (s, 3 H) 3.36-3.48 (m, 4 H) 3.54-3.61 (m, 3 H) 3.66-3.70 (m, 1 H) 3.81 (s, 3 H) 3.86 (d, J = 5.96 Hz, 1 H) 4.14 (q, J = 6.42 Hz, 1 H) 4.44 (d, J = 6.88 Hz, 1 H) 4.61 (t, J = 4.81 Hz, 1 H) 5.00 (d, J = 5.04 Hz, 1 H) 6.86-6.90 (m, 1 H) 6.92-6.96 (m, 1 H) 7.21-7.25 (m, 1 H) 7.33-7.37 (m, 1 H) |

TABLE 5-8-continued

| Example | Reference Example | R | ESI MS (M + H) | ¹H-NMR, CDCl₃, δ (ppm) |
|---|---|---|---|---|
| 167 | 132 | (pyrrolidine with CH₂-NH-C(Me)₂-(2-methoxyphenyl)) | 949.8 | (600 MHz): 0.87 (d, J = 7.34 Hz, 3 H) 1.00 (d, J = 6.88 Hz, 3 H) 1.06-1.15 (m, 9 H) 1.16-1.22 (m, 4 H) 1.24 (d, J = 7.34 Hz, 3 H) 128-1.39 (m, 5 H) 1.47 (s, 6 H) 1.60-1.64 (m, 1 H) 1.88-2.00 (m, 2 H) 2.04-2.24 (m, 7 H) 2.29 (s, 6 H) 2.39-2.47 (m, 1 H) 2.53-2.75 (m, 3 H) 2.83-2.95 (m, 5 H) 2.98-3.04 (m, 1 H) 3.10-3.23 (m, 3 H) 3.28 (s, 3 H) 3.34-3.37 (m, 3 H) 3.37-3.46 (m, 2 H) 3.55-3.61 (m, 1 H) 3.66-3.72 (m, 1 H) 3.85 (s, 3 H) 3.90 (d, J = 6.42 Hz, 1 H) 4.10-4.18 (m, 1 H) 4.47 (d, J = 7.34 Hz, 1 H) 4.62 (t, J = 4.81 Hz, 1 H) 5.02 (d, J = 5.04 Hz, 1 H) 6.84-6.95 (m, 2 H) 7.18-7.28 (m, 2 H) |
| 168 | 133 | (HN-pyrrolidine-CH(Me)-(2-methoxyphenyl)) | 921.8 | (600 MHz): 0.87 (d, J = 7.34 Hz, 3 H) 1.00 (d, J = 6.88 Hz, 3 H) 1.11 (d, J = 7.79 Hz, 3 H) 1.12-1.15 (m, 6 H) 1.17 (d, J = 6.42 Hz, 3 H) 1.19-1.22 (m, 1 H) 1.24 (d, J = 6.88 Hz, 3 H) 128 (d, J = 6.42 Hz, 3 H) 1.33-1.37 (m, 1 H) 1.37 (s, 3 H) 1.47-1.60 (m, 2 H) 1.94-2.00 (m, 1 H) 2.06 (d, J = 15.13 Hz, 1 H) 2.05-2.17 (m, 2 H) 2.27 (s, 6 H) 2.33 (d, J = 13.30 Hz, 1 H) 2.35-2.40 (m, 1 H) 2.40-2.46 (m, 1 H) 2.48-2.61 (m, 3 H) 2.61-2.66 (m, 1 H) 2.81-2.94 (m, 4 H) 2.98-3.04 (m, 1 H) 3.10-3.22 (m, 4 H) 3.28 (s, 3 H) 3.35 (s, 3 H) 3.37-3.41 (m, 1 H) 3.47-3.55 (m, 1 H) 3.55-3.61 (m, 1 H) 3.67-3.72 (m, 1 H) 3.76-3.80 (m, 1 H) 3.80 (s, 3 H) 3.89 (d, J = 6.42 Hz, 1 H) 4.27 (q, J = 6.42 Hz, 1 H) 4.46 (d, J = 6.88 Hz, 1 H) 4.62 (t, J = 4.58 Hz, 1 H) 5.01 (d, J = 4.13 Hz, 1 H) 6.85 (d, J = 8.25 Hz, 1 H) 6.94 (t, J = 7.34 Hz, 1 H) 7.16-7.21 (m, 1 H) 7.42-7.46 (m, 1 H) |
| 169 | | (N(Me)₂) | 746.6 | (600 MHz): 0.88 (d, J = 7.34 Hz, 3 H) 1.01 (d, J = 6.42 Hz, 3 H) 1.09-1.15 (m, 6 H) 1.17 (d, J = 5.96 Hz, 3 H) 1.19-127 (m, 7 H) 1.34-1.40 (m, 4 H) 1.62-1.67 (m, 1 H) 1.97-2.02 (m, 2 H) 2.07-2.17 (m, 2 H) 2.30 (s, 6 H) 2.38 (s, 6 H) 2.43-2.49 (m, 1 H) 2.58 (q, J = 6.57 Hz, 1 H) 2.75 (d, J = 14.67 Hz, 1 H) 2.85-2.93 (m, 3 H) 3.00-3.04 (m, 1 H) 3.13-324 (m, 3 H) 3.30 (s, 3 H) 3.38 (s, 3 H) 3.38-3.49 (m, 2 H) 3.57-3.61 (m, 1 H) 3.70-3.73 (m, 1 H) 3.91 (d, J = 5.96 Hz, 1 H) 4.18 (q, J = 6.11 Hz, 1 H) 4.48 (d, J = 7.34 Hz, 1 H) 4.63 (t, J = 4.81 Hz, 1 H) 5.04 (d, J = 5.04 Hz, 1 H) |

TABLE 5-9

| Example | Reference Example | R | ESI MS (M + H) | ¹H-NMR, CDCl₃, δ (ppm) |
|---|---|---|---|---|
| 170 | 134 | (azetidine-OH-CH₂-N(Me)-C(Me)₂-(2-methoxyphenyl)) | 965.9 | (600 MHz): 0.88 (d, J = 7.34 Hz, 3 H) 1.01 (d, J = 6.42 Hz, 3 H) 1.04 (s, 3 H) 1.07 (d, J = 6.42 Hz, 3 H) 1.11 (d, J = 7.34 Hz, 3 H) 1.22 (d, J = 6.42 Hz, 3 H) 1.22-1.24 (m, 1 H) 1.24 (d, J = 6.88 Hz, 3 H) 1.30-1.35 (m, 1 H) 1.37 (s, 3 H) 1.47 (s, 6 H) 1.63-1.67 (m, 1 H) 1.95 (dd, J = 14.67, 5.50 Hz, 1 H) 2.06 (s, 3 H) 2.06-2.09 (m, 1 H) 2.10-2.16 (m, 1 H) 2.21 (d, J = 14.67 Hz, 1 H) 2.31 (s, 6 H) 2.41-2.47 (m, 1 H) 2.56-2.60 (m, 1 H) 2.78 (s, 2 H) 2.84-2.92 (m, 3 H) 2.96 (d, J = 14.67 Hz, 1 H) 3.00-3.04 (m, 1 H) 3.12-3.23 (m, 3 H) 3.28 (s, 3 H) 3.35 (s, 3 H) 3.37-3.47 (m, 6 H) 3.56-3.61 (m, 1 H) 3.67-3.71 (m, 1 H) 3.83 (s, 3 H) 3.87-3.90 (m, 1 H) 4.11-4.15 (m, 1 H) 4.47 (d, J = 7.34 Hz, 1 H) 4.63 (t, J = 4.58 Hz, 1 H) 4.91-4.99 (m, 1 H) 5.01 (d, J = 5.04 Hz, 1 H) 6.88-6.93 (m, 2 H) 7.21-7.26 (m, 2 H) |

TABLE 5-9-continued

| Example | Reference Example | R | ESI MS (M + H) | ¹H-NMR, CDCl₃, δ (ppm) |
|---|---|---|---|---|
| 171 | 135 | (imidazolylmethyl-NH-C(Me)₂-(2-methoxyphenyl)) | 946.8 | (600 MHz): 0.63 (br s, 3 H) 0.90 (d, J = 7.34 Hz, 3 H) 1.02 (d, J = 6.88 Hz, 3 H) 1.14-1.31 (m, 13 H) 1.37-1.44 (m, 4 H) 1.59-1.70 (m, 7 H) 1.95-2.05 (m, 2 H) 2.13-2.20 (m, 1 H) 2.30 (s, 6 H) 2.46-2.53 (m, 1 H) 2.59-2.65 (m, 1 H) 2.78-3.06 (m, 4 H) 3.15-3.45 (m, 12 H) 3.55-3.63 (m, 2 H) 3.68-3.73 (m, 1 H) 3.87 (s, 3 H) 3.88-3.93 (m, 1 H) 3.98 (d, J = 6.42 Hz, 1 H) 4.15 (d, J = 14.67 Hz, 1 H) 4.41-4.47 (m, 1 H) 4.55 (d, J = 7.34 Hz, 1 H) 4.61-4.66 (m, 1 H) 5.00-5.05 (m, 1 H) 6.70 (s, 1 H) 6.97-7.02 (m, 2 H) 7.27-7.34 (m, 2 H) 7.48 (s, 1 H) |
| 172 | 135 | (imidazolylmethyl-NH-C(Me)₂-(2-methoxyphenyl)) | 946.8 | (600 MHz): 0.87 (s, 3 H) 0.90 (d, J = 6.88 Hz, 3 H) 1.01 (d, J = 6.42 Hz, 3 H) 1.05 (d, J = 6.42 Hz, 3 H) 1.15 (d, J = 7.79 Hz, 3 H) 1.20-1.29 (m, 7 H) 1.37-1.43 (m, 4 H) 1.56 (s, 6 H) 1.67-1.72 (m, 1 H) 1.77-1.83 (m, 1 H) 2.07-2.18 (m, 2 H) 2.31 (s, 6 H) 2.44-2.51 (m, 1 H) 2.60-2.66 (m, 1 H) 2.78-2.85 (m, 1 H) 2.89-2.99 (m, 2 H) 3.01-3.07 (m, 1 H) 3.14-3.27 (m, 4 H) 3.27-3.32 (m, 6 H) 3.38-3.50 (m, 3 H) 3.56-3.62 (m, 1 H) 3.70-3.75 (m, 1 H) 3.78-3.88 (m, 5 H) 4.14 (d, J = 14.67 Hz, 1 H) 4.45 (d, J = 7.34 Hz, 1 H) 4.52-4.59 (m, 1 H) 4.62-4.66 (m, 1 H) 4.94 (d, J = 5.04 Hz, 1 H) 6.83-6.86 (m, 1 H) 6.89-6.94 (m, 2 H) 7.20-7.24 (m, 1 H) 7.29-7.32 (m, 1 H) 7.37-7.41 (m, 1 H) |
| 173 | 136 | (HN-pyrrolidinyl-C(Me)₂-(2-methoxyphenyl)) | 935.8 | (600 MHz): 0.85 (d, J = 6.88 Hz, 3 H) 0.98 (d, J = 6.88 Hz, 3 H) 1.09 (d, J = 7.79 Hz, 3 H) 1.10 (s, 3 H) 1.12 (d, J = 6.42 Hz, 3 H) 1.16 (d, J = 5.96 Hz, 3 H) 1.18 (d, J = 11.46 Hz, 1 H) 1.22 (d, J = 7.34 Hz, 3 H) 1.31-1.35 (m, 1 H) 1.35 (s, 3 H) 1.43 (s, 6 H) 1.47-1.62 (m, 2 H) 1.92-2.15 (m, 4 H) 2.26 (s, 6 H) 2.31 (d, J = 13.30 Hz, 1 H) 2.38-2.60 (m, 4 H) 2.66-2.76 (m, 2 H) 2.79-2.91 (m, 4 H) 2.95-3.04 (m, 1 H) 3.07-3.22 (m, 4 H) 3.27 (s, 3 H) 3.33 (s, 3 H) 3.35-3.40 (m, 1 H) 3.45-3.53 (m, 1 H) 3.53-3.60 (m, 1 H) 3.65-3.70 (m, 1 H) 3.77 (s, 3 H) 3.88 (d, J = 6.42 Hz, 1 H) 4.22-4.28 (m, 1 H) 4.45 (d, J = 7.34 Hz, 1 H) 4.60 (t, J = 4.81 Hz, 1 H) 4.99 (d, J = 5.04 Hz, 1 H) 6.82-6.91 (m, 2 H) 7.14-7.20 (m, 1 H) 7.45-7.52 (m, 1 H) |
| 174 | 137 | (NH-C(Me)₂-CH₂-N(CH₂Me)-CH(Me)-(2-methoxyphenyl)) | 951 FAB MASS | (400 MHz): 0.88 (d, J = 7.08 Hz, 3 H) 0.93-0.98 (m, 6 H) 1.01 (d, J = 6.84 Hz, 3 H) 1.02 (d, J = 6.59 Hz, 3 H) 1.08 (s, 3 H) 1.11 (d, J = 7.57 Hz, 3 H) 1.13 (d, J = 6.35 Hz, 3 H) 1.22 (d, J = 5.86 Hz, 3 H) 1.24 (d, J = 6.59 Hz, 3 H) 1.31 (d, J = 6.84 Hz, 3 H) 1.39 (s, 3 H) 1.59-1.66 (m, 1 H) 2.00 (dd, J = 14.9, 4.88 Hz, 1 H) 2.05 (d, J = 14.9 Hz, 1 H) 2.09-2.17 (m, 1 H) 2.21 (d, J = 13.4 Hz, 1 H) 2.29 (s, 6 H) 2.36-2.63 (m, 7 H) 2.82-2.95 (m, 4 H) 2.99-3.05 (m, 1 H) 3.12-3.25 (m, 4 H) 3.31 (s, 3 H) 3.32-3.42 (m, 3 H) 3.38 (s, 3 H) 3.52-3.62 (m, 2 H) 3.70 (dd, J = 9.77, 1.71 Hz, 1 H) 3.80 (s, 3 H) 3.93 (d, J = 6.11 Hz, 1 H) 4.27 (dd, J = 12.2, 5.86 Hz, 1 H) 4.47 (dd, J = 13.9, 6.84 Hz, 1 H) 4.52 (d, J = 7.32 Hz, 1 H) 4.63 (t, J = 7.64 Hz, 1 H) 4.99 (d, J = 9.52 Hz, 1 H) 5.04 (d, J = 4.40 Hz, 1 H) 6.86 (d, J = 8.30 Hz, 1 H) 6.93 (dt, J = 7.57, 0.98 Hz, 1 H) 7.22 (dt, J = 8.06, 1.71 Hz, 1 H) 7.27 (dd, J = 8.06, 1.47 Hz, 1 H) |

TABLE 5-9-continued

| Example | Reference Example | R | ESI MS (M + H) | ¹H-NMR, CDCl₃, δ (ppm) |
|---|---|---|---|---|
| 175 | 138 | [structure] | 967 | (400 MHz): 0.87 (d, J = 7.08 Hz, 3 H) 0.89 (d, J = 7.08 Hz, 3 H) 1.02 (d, J = 6.59 Hz, 3 H) 1.03 (d, J = 6.59 Hz, 3 H) 1.04-1.13 (m, 9 H) 1.15-1.29 (m, 16 H) 1.31 (d, J = 6.84 Hz, 3 H) 1.38 (d, J = 6.10 Hz, 3 H) 1.39 (s, 3 H) 1.62-1.68 (m, 1 H) 1.90-2.17 (m, 7 H) 2.23 (s, 3 H) 2.30 (s, 6 H) 2.42-2.52 (m, 1 H) 2.53-2.66 (m, 8 H) 2.79-3.05 (m, 9 H) 3.13-3.26 (m, 4 H) 3.28 (s, 3 H) 3.31 (s, 3 H) 3.33 (d, J = 6.97 Hz, 3 H) 3.38 (s, 3 H) 3.39-3.51 (m, 8 H) 3.57-3.62 (m, 1 H) 3.67-3.73 (m, 1 H) 3.80 (s, 3 H) 3.91 (d, J = 6.10 Hz, 1 H) 3.98 (d, J = 5.37 Hz, 1 H) 4.11-4.17 (m, 1 H) 4.31-4.41 (m, 1 H) 4.48 (d, J = 7.32 Hz, 1 H) 4.60-4.67 (m, 1 H) 4.79-4.83 (m, 1 H) 4.94-5.01 (m, 1 H) 5.03 (d, J = 4.64 Hz, 1 H) 5.08-5.11 (m, 1 H) 6.85 (d, J = 1.30 Hz, 1 H) 6.92 (t, J = 7.57 Hz, 1 H) 7.16-7.22 (m, 1 H) 7.36 (dd, J = 7.57, 1.47 Hz, 1 H) |
| 176 | 139 | [structure] | 909.6 | (400 MHz): 0.88 (d, J = 7.1 Hz, 3 H) 1.00 (d, J = 6.6 Hz, 3 H) 1.02 (d, J = 6.8 Hz, 3 H) 1.08-1.14 (m, 7 H) 1.15-1.22 (m, 6 H) 1.22-1.27 (m, 3 H) 1.29-1.37 (m, 4 H) 1.39 (s, 3 H) 1.50-1.65 (m, 2 H) 1.97-2.20 (m, 2 H) 2.29 (s, 6 H) 2.35 (d, J = 14.1 Hz, 1 H) 2.40-2.70 (m, 5 H) 2.83-2.95 (m, 3 H) 2.99-3.05 (m, 1 H) 3.13-3.24 (m, 3 H) 3.27-3.43 (m, 8 H) 3.47-3.62 (m, 1 H) 3.67-3.73 (m, 1 H) 3.83 (s, 3 H) 3.89-3.93 (m, 1 H) 4.15 (q, J = 6.9 Hz, 1 H) 4.19-4.31 (m, 1 H) 4.45-4.11 (m, 1 H) 4.60-4.65 (m, 1 H) 4.90-4.99 (m, 1 H) 4.99-5.05 (m, 1 H) 6.83-6.89 (m, 1 H) 6.90-6.96 (m, 1 H) 7.18-7.26 (m, 2 H) |
| 177 | 140 | [structure] | 937 FAB MASS | (400 MHz): 0.87 (d, J = 7.0 Hz, 3 H) 0.93-1.00 (m, 9 H) 1.01 (d, J = 6.8 Hz, 3 H) 1.06 (d, J = 6.4 Hz, 3 H) 1.10 (d, J = 7.5 Hz, 3 H) 1.15 (d, J = 5.9 Hz, 3 H) 1.24 (d, J = 7.1 Hz, 3 H) 1.30 (d, J = 6.9 Hz, 3 H) 1.37 (s, 3 H) 1.51-1.70 (m, 2 H) 1.92-2.05 (m, 2 H) 2.08-2.23 (m, 2 H) 2.29 (s, 6 H) 2.40-2.62 (m, 1 H) 2.77-2.93 (m, 2 H) 2.99-3.23 (m, 3 H) 3.27 (s, 3 H) 3.34 (s, 3 H) 3.37-3.47 (m, 1 H) 3.56-3.62 (m, 1 H) 3.65-3.70 (m, 1 H) 3.81 (s, 3 H) 3.90 (d, J = 6.1 Hz, 1 H) 4.14 (q, J = 6.2 Hz, 1 H) 4.39-4.51 (m, 2 H) 4.63 (t, J = 4.4 Hz, 1 H) 4.92-5.03 (m, 2 H) 6.79-6.86 (m, 1 H) 6.87-6.94 (m, 1 H) 7.16-7.22 (m, 1 H) 7.33-7.36 (m, 1 H) |

TABLE 5-10

| Example | Reference Example | R | ESI MS (M + H) | ¹H-NMR CDCl₃, δ (ppm) |
|---|---|---|---|---|
| 178 | 141 | [structure] | 925.7 | (400 MHz): 0.89 (d, J = 7.1 Hz, 3 H) 1.01 (d, J = 6.8 Hz, 3 H) 1.11 (s, 3 H) 1.10-1.22 (m, 10 H) 1.24 (d, J = 7.0 Hz, 3 H) 1.34-1.40 (m, 6 H) 1.50-1.75 (m, 2 H) 1.97 (dd, J = 14.9, 5.4 Hz, 1 H) 2.07 (d, J = 14.9 Hz, 3 H) 2.10-2.19 (m, 1 H) 2.30 (s, 6 H) 2.40-2.52 (m, 2 H) 2.64-2.72 (m, 2 H) 2.80-2.95 (m, 4 H) 2.99-3.07 (m, 1 H) 3.13-3.24 (m, 3 H) 3.27-3.43 (m, 8 H) 3.45-3.54 (m, 1 H) 3.57-3.66 (m, 1 H) 3.68-3.78 (m, 2 H) 3.83 (s, 3 H) 3.90 (d, J = 6.3 Hz, 1 H) 4.03 (q, J = 6.7 Hz, 1 H) 4.30 (q, J = 6.4 Hz, 1 H) 4.45 (d, J = 7.3 Hz, 1 H) 4.63 (t, J = 4.4 Hz, 1 H) 4.91 (d, J = 9.8 Hz, 1 H) 5.01 (d, J = 5.1 Hz, 1 H) 6.88 (d, J = 8.1 Hz, 1 H), 6.95 (t, J = 7.6 Hz, 1 H) 7.18-7.27 (m, 2 H) |

TABLE 5-10-continued

| Example | Reference Example | R | ESI MS (M + H) | ¹H-NMR CDCl₃, δ (ppm) |
|---|---|---|---|---|
| 179 | 142 | (structure) | 939.7 | (400 MHz): 0.82 (d, J = 7.3 Hz, 3 H) 1.07 (t, J = 7.5 Hz, 3 H) 1.09-1.44 (m, 10 H) 1.17 (d, J = 6.1 Hz, 3 H) 1.24 (d, J = 7.1 Hz, 3 H) 1.33 (d, J = 7.1 Hz, 3 H) 1.38 (s, 3 H) 1.51-1.73 (m, 2 H) 1.96 (dd, J = 14.9, 5.1 Hz, 3 H) 2.06 (d, J = 14.9, 2 H) 2.09-2.20 (m, 1 H) 2.23 (s, 6 H) 2.30 (s, 6 H) 2.39-2.49 (m, 4 H) 2.55-2.63 (m, 2 H) 2.68-2.79 (m, 1 H) 2.81-2.97 (m, 4 H) 2.98-3.06 (m, 1 H) 3.13-3.24 (m, 2 H) 3.27-3.54 (m, 9 H) 3.56-3.63 (m, 1 H) 3.63-3.72 (m, 2 H) 3.83 (s, 3 H) 3.86-3.91 (m, 1 H) 4.15 (q, J = 6.8 Hz, 1 H) 4.28 (q, J = 6.6 Hz, 1 H) 4.45 (d, J = 7.1 Hz, 1 H) 4.63 (t, J = 4.7 Hz, 1 H) 4.85-4.95 (m, 1 H) 5.00 (d, J = 42 Hz, 1 H) 6.89 (d, J = 8.3 Hz, 1 H) 6.96 (t, J = 7.5 Hz, 1 H) 7.22-7.26 (m, 1 H) 7.27-7.32 (m, 1 H) |
| 180 | 143 | (structure) | 939 | (400 MHz): 0.88 (d, J = 7.08 Hz, 3 H) 1.02 (d, J = 6.59 Hz, 3 H) 1.12 (d, J = 5.37 Hz, 3 H) 1.13 (s, 3 H) 1.18 (d, J = 6.35 Hz, 3 H) 1.18-1.22 (m, 1 H) 1.25 (d, J = 5.86 Hz, 3 H) 1.26 (d, J = 7.08 Hz, 3 H) 1.33-1.36 (m, 1 H) 1.38 (d, J = 6.10 Hz, 3 H) 1.39 (s, 3 H) 1.62-1.66 (m, 1 H) 1.98 (dd, J = 14.9, 5.37 Hz, 1 H) 2.10 (d, J = 14.9 Hz, 1 H) 2.10-2.17 (m, 1 H) 2.20 (s, 3 H) 2.30 (s, 6 H) 2.31-2.35 (m, 1 H) 2.42-2.50 (m, 1 H) 2.55-2.67 (m, 2 H) 2.69-2.76 (m, 2 H) 2.83-2.94 (m, 4 H) 3.00-3.06 (m, 1 H) 3.13-3.24 (m, 3 H) 3.30 (s, 3 H) 3.32-3.52 (m, 3 H) 3.36 (s, 3 H) 3.60 (dd, J = 9.03, 4.88 Hz, 1 H) 3.70 (dd, J = 9.77, 1.95 Hz, 1 H) 3.71-3.81 (m, 3 H) 3.83 (s, 3 H) 3.91 (d, J = 6.59 Hz, 1 H) 3.97-4.01 (m, 1 H) 4.16-4.21 (m, 1 H) 4.48 (d, J = 7.32 Hz, 1 H) 4.63 (t, J = 4.64 Hz, 1 H) 4.91 (d, J = 10.5 Hz, 1 H) 5.02 (d, J = 4.88 Hz, 1 H) 6.85 (dd, J = 8.30, 0.73 Hz, 1 H) 6.94 (dt, J = 7.32, 0.98 Hz, 1 H) 7.17 (dd, J = 7.57, 1.71 Hz, 1 H) 7.22-7.26 (m, 1 H) |
| 181 | 144 | (structure) | 925 FAB MASS | (400 MHz): 0.89 (d, J = 7.1 Hz, 3 H) 1.01 (d, J = 6.8 Hz, 3 H) 1.11 (d, J = 8.1 Hz, 3 H) 1.13 (s, 3 H) 1.16 (d, J = 6.1 Hz, 3 H) 1.20 (d, J = 6.1 Hz, 3 H) 1.24 (d, J = 7.1 Hz, 3 H) 1.37 (d, J = 6.6 Hz, 3 H) 1.39 (s, 3 H) 1.50-1.68 (m, 2 H) 1.98 (dd, J = 14.9, 5.3 Hz, 1 H) 2.07 (d, J = 14.9 Hz, 1 H) 2.10-2.22 (m, 1 H) 2.30 (s, 6 H) 2.35 (d, J = 13.4 Hz, 1 H) 2.41-2.52 (m, 1 H) 2.52-2.70 (m, 4 H) 2.78-2.96 (m, 2 H) 2.99-3.08 (m, 1 H) 3.10-3.26 (m, 3 H) 3.28 (s, 3 H) 3.36 (s, 3 H) 3.37-3.44 (m, 1 H) 3.47-3.56 (m, 1 H) 3.56-3.75 (m, 3 H) 3.83 (s, 3 H) 3.90 (d, J = 6.4 Hz, 1 H) 4.05 (q, J = 6.8 Hz, 1 H) 4.32 (q, J = 6.4 Hz, 1 H) 4.47 (d, J = 7.3 Hz, 1 H) 4.63 (t, J = 4.7 Hz, 1 H) 4.91 (d, J = 9.2 Hz, 1 H) 5.01 (d, J = 3.7 Hz, 1 H) 6.88 (d, J = 8.1 Hz, 1 H) 6.94 (t, J = 7.3 Hz, 1 H) 7.18-7.26 (m, 2 H) |
| 182 | 145 | (structure) | 939 FAB MASS | (400 MHz): 0.89 (d, J = 7.1 Hz, 3 H) 1.01 (d, J = 6.8 Hz, 3 H) 1.10-1.14 (m, 6 H) 1.16 (d, J = 6.1 Hz, 3 H) 1.20 (d, J = 6.1 Hz, 3 H) 1.24 (d, J = 7.1 Hz, 3 H) 1.32 (d, J = 6.8 Hz, 3 H) 1.39 (s, 3 H) 1.50-1.75 (m, 2 H) 1.98 (dd, J = 14.9, 4.9 Hz, 1 H) 2.07 (d, J = 14.9 Hz, 1 H) 2.10-2.20 (m, 1 H) 2.28 (s, 3 H) 2.30 (s, 6 H) 2.37 (d, J = 13.4 Hz, 1 H) 2.40-2.63 (m, 4 H) 2.67-2.75 (m, 1 H) 2.80-3.06 (m, 4 H) 3.13-3.25 (m, 3 H) 3.28 (s, 3 H) 3.36 (s, 3 H) 3.37-3.45 (m, 1 H) 3.45-3.65 (m, 2 H) 3.65-3.74 (m, 1 H) 3.82 (s, 3 H) 3.90 (d, J = 6.3 Hz, 1 H) 4.17 (q, J = 7.1 Hz, 1 H) 4.30 (q, J = 6.4 Hz, 1 H) 4.46 (d, J = 7.1 Hz, 1 H) 4.63 (t, J = 4.4 Hz, 1 H) 4.91 (d, J = 10.8 Hz, 1 H) 5.01 (d, J = 4.4 Hz, 1 H) 6.88 (d, J = 8.5 Hz, 1 H) 6.94 (t, J = 7.3 Hz, 1 H) 7.22-7.27 (m, 2 H) |

TABLE 5-10-continued

| Example | Reference Example | R | ESI MS (M + H) | ¹H-NMR CDCl₃, δ (ppm) |
|---|---|---|---|---|
| 183 | 146 | [structure with OH, Me, N-ethyl, 2-methoxybenzyl] | 939 FAB MASS | (400 MHz): 0.88 (d, J = 7.1 Hz, 3 H) 1.01 (d, J = 6.8 Hz, 3 H) 1.07-1.15 (m, 13 H) 1.18 (d, J = 6.1 Hz, 3 H) 1.24 (d, J = 7.1 Hz, 3 H) 1.38 (s, 3 H) 1.50-1.72 (m, 2 H) 1.95 (dd, J = 14.9, 5.1 Hz, 1 H) 2.06 (d, J = 14.9 Hz, 1 H) 2.10-2.19 (m, 1 H) 2.29 (s, 6 H) 2.38-2.52 (m, 4 H) 2.54-2.73 (m, 4 H) 2.81-2.92 (m, 4 H) 2.92-3.06 (m, 1 H) 3.10-3.25 (m, 3 H) 3.28 (s, 3 H) 3.33-3.43 (m, 5 H) 3.43-3.55 (m, 2 H) 3.55-3.61 (m, 2 H) 3.61-3.75 (m, 2 H) 3.82 (s, 3 H) 3.88 (d, J = 6.8 Hz, 1 H) 4.28 (q, J = 6.4 Hz, 1 H) 4.45 (d, J = 7.1 Hz, 1 H) 4.63 (t, J = 4.7 Hz, 1 H) 4.92 (d, J = 10.1 Hz, 1 H) 5.00 (d, J = 3.9 Hz, 1 H) 6.88 (d, J = 8.3 Hz, 1 H) 6.92 (t, J = 7.3 Hz, 1 H) 7.21-7.27 (m, 2 H) |
| 184 | 147 | [structure with OH, Me, N-ethyl, 2-methoxypyridine, chiral Me] | 954 FAB MASS | (400 MHz): 0.89 (d, J = 7.1 Hz, 3 H) 1.01 (d, J = 6.6 Hz, 3 H) 1.07 (t, J = 7.0 Hz, 3 H) 1.09 (s, 3 H) 1.11 (d, J = 7.8 Hz, 3 H) 1.13 (d, J = 6.3 Hz, 3 H) 1.20 (d, J = 6.1 Hz, 3 H) 1.24 (d, J = 7.1 Hz, 3 H) 1.33 (d, J = 6.9 Hz, 3 H) 1.39 (s, 3 H) 1.50-1.72 (m, 2 H) 1.96 (dd, J = 14.9, 5.4 Hz, 1 H) 2.07 (d, J = 14.9 Hz, 1 H) 2.09-2.18 (m, 1 H) 2.30 (s, 6 H) 2.48-2.50 (m, 3 H) 2.54-2.73 (m, 4 H) 2.80-2.95 (m, 4 H) 2.95-3.05 (m, 1 H) 3.18-3.24 (m, 3 H) 3.29 (s, 3 H) 3.55 (s, 3 H) 3.37-3.44 (m, 1 H) 3.46-3.54 (m, 1 H) 3.56-3.62 (m, 1 H) 3.67-3.72 (m, 1 H) 3.88 (d, J.4 Hz, 1 H) 3.95 (s, 3 H) 4.24-4.35 (m, 2 H) 4.46 (d, J = 7.1 Hz, 1 H) 4.63 (t, J = 4.7 Hz, 1 H) 4.92 (d, J = 10.5 Hz, 1 H) 5.00 (d, J = 4.2 Hz, 1 H) 6.89 (dd, J = 7.3, 4.9 Hz, 1 H) 7.55 (dd, J = 7.3, 1.7 Hz, 1 H) 8.09 (dd, J = 4.9, 1.7 Hz, 1 H) |

TABLE 5-11

| Example | Reference Example | R | ESI MS (M + H) | ¹H-NMR, CDCl₃, δ (ppm) |
|---|---|---|---|---|
| 185 | 148 | [structure with OH, Me, N-ethyl, gem-dimethyl, 2-methoxypyridine] | 968 FAB MASS | (400 MHz): 0.93-0.91 (m, 6 H) 1.01 (d, J = 6.59 Hz, 3 H) 1.09-1.19 (m, 10 H) 1.22 (d, J = 6.11 Hz, 3 H) 1.25 (d, J = 6.84 Hz, 3 H) 1.39 (s, 3 H) 1.47 (s, 3 H) 1.52 (s, 3 H) 1.53-1.72 (m, 2 H) 1.98 (dd, J = 14.6, 5.13 Hz, 1 H) 2.07 (d, J = 14.6 Hz, 1 H) 2.04-2.19 (m, 2 H) 2.30 (s, 6 H) 2.32-2.81 (m, 8 H) 2.82-3.09 (m, 4 H) 3.12-3.25 (m, 3 H) 2.95-3.05 (m, 1 H) 3.30 (s, 3 H) 3.37 (s, 3 H) 3.34-3.43 (m, 2 H) 3.48-3.63 (m, 3 H) 3.68-3.74 (m, 2 H) 3.90 (d, J = 6.1 Hz, 1 H) 3.95 (s, 3 H) 4.30 (q, J = 6.35 Hz, 2 H) 4.48 (d, J = 7.08 Hz, 1 H) 4.63 (t, J = 4.39 Hz, 1 H) 4.89-4.97 (m, 1 H) 5.01 (d, J = 4.40 Hz, 1 H) 6.87 (dd, J = 7.57, 4.88 Hz, 1 H) 7.59 (dd, J = 7.57, 1.71 Hz, 1 H) 8.08 (dd, J = 4.88, 1.71 Hz, 1 H) |
| 186 | 149 | [structure with piperidine, gem-dimethyl, 2-methoxyphenyl] | 949 FAB MASS | (400 MHz): 0.88 (d, J = 7.08 Hz, 3 H) 1.00 (d, J = 6.59 Hz, 3 H) 1.07 (s, 3 H) 1.10 (d, J = 6.59 Hz, 6 H) 1.19 (d, J = 5.86 Hz, 3 H) 1.23 (d, J = 7.08 Hz, 3 H) 1.28-1.35 (m, 3 H) 1.36 (s, 3 H) 1.50 (s, 6 H) 1.57-1.70 (m, 4 H) 1.86-1.92 (m, 1 H) 1.96 (dd, J = 14.9, 5.13 Hz, 1 H) 2.08 (d, J = 14.9 Hz, 1 H) 2.08-2.20 (m, 2 H) 2.29 (s, 6 H) 2.38-2.47 (m, 1 H) 2.57 (q, J = 6.59 Hz, 3 H) 2.60-2.80 (m, 3 H) 2.83-2.94 (m, 3 H) 2.98-3.04 (m, 1 H) 3.11-3.22 (m, 3 H) 3.27 (s, 3 H) 3.29-3.44 (m, 5 H) 3.56-3.62 (m, 1 H) 3.67-3.72 (m, 1 H) 3.86 (s, 3 H) 3.89 (d, J = 6.35 Hz, 1 H) 4.12 (q, J = 6.35 Hz, 1 H) 4.44 (d, J = 7.08 Hz, 1 H) 4.50 (d, J = 7.1 Hz, 1 H) 4.62 (t, J = 4.64 Hz, 1 H) 4.97 (d, J = 10.5 Hz, 1 H) 5.01 (d, J = 5.13 Hz, 1 H) 6.89 (d, J = 8.06 Hz, 1 H) 6.91 (t, J = 7.57 Hz, 1 H) 7.19-7.27 (m, 1 H) |

In Examples 107 to 121, by using the compound obtained in Example 3, (3) and corresponding amine reagents, the compounds shown in Table 5 were synthesized in the same manner as that of Example 3, (4).

In Example 122 to 186, by using the compound obtained in Example 3, (3) and corresponding amine reagents, the compounds shown in Table 5 were synthesized in the same manner as that of Example 13, (2). In Examples 171 and 172, the compounds were synthesized by separation of positional isomers.

Example 187

A preparation method of the compound represented by the formula (H) is shown below.

[Formula 24]

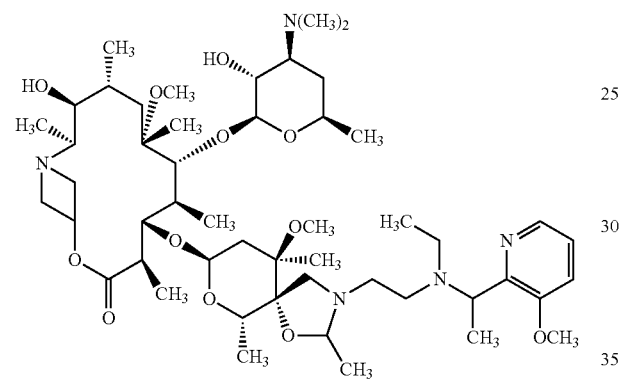

Formula (H)

Example 187

By using the compound obtained in Example 3, (3) (40 mg), and the compound obtained in Reference Example 22 (25.5 mg) as starting materials, the compound obtained in Example 41 and the compound represented by the formula (H) (3 mg) were obtained in the same manner as that of Example 13, (2).

MS (ESI) m/z=950.6 [M+H]$^+$ $^1$H-NMR (600 MHz, CDCl$_3$) δ (ppm): 0.85-0.91 (m, 3H), 0.98-1.05 (m, 6H), 1.06-1.28 (m, 19H), 1.39 (s, 7H), 1.55-1.69 (m, 1H), 1.88-1.96 (m, 1H), 2.10-2.17 (m, 2H), 2.30 (s, 6H), 2.41-2.93 (m, 1H), 3.00-3.05 (m, 1H), 3.13-3.25 (m, 4H), 3.26-3.52 (m, 9H), 3.56-3.63 (m, 1H), 3.67-3.75 (m, 1H), 3.79-3.90 (m, 5H), 3.97-4.20 (m, 1H), 4.34-4.42 (m, 1H), 4.45-4.55 (m, 2H), 4.61-4.66 (m, 1H), 5.00-5.07 (m, 1H), 7.10-7.15 (m, 2H), 8.13-8.18 (m, 1H)

Examples 188 to 216

Preparation methods of the compounds represented by the formula (G) having R defined in Tables 6-1 to 6-4 are shown below.

TABLE 6-1

| Example | Example of starting material | R | ESI MS (M + H) | $^1$H-NMR, CDCl$_3$, δ (ppm) |
|---|---|---|---|---|
| 188 | 101 | (structure) | 951 | (400 MHz): 0.88 (d, J = 7.1 Hz, 3 H) 0.92 (d, J = 6.8 Hz, 3 H) 0.97-1.06 (m, 6 H) 1.08-1.14 (m, 9 H) 1.15 (d, J = 6.3 Hz, 3 H) 1.39 (s, 3 H) 1.53-1.73 (m, 2 H) 2.02 (dd, J = 15.1, 5.1 Hz, 1 H) 2.04-220 (m, 3 H) 2.30 (s, 6 H) 2.42-2.77 (m, 10 H) 2.83-2.97 (m, 4 H) 3.00-3.07 (m, 1 H) 3.12-3.27 (m, 3 H) 3.30 (s, 3 H) 3.31-3.35 (m, 1 H) 3.38 (s, 3 H) 3.39-3.44 (m, 1 H) 3.45-3.54 (m, 1 H) 3.56-3.64 (m, 1 H) 3.70 (d, J = 9.8 Hz, 1 H) 3.81 (s, 3 H) 3.93 (d, J = 5.9 Hz, 1 H) 4.15 (q, J = 6.3 Hz, 1 H) 4.30-4.40 (m, 1 H) 4.50 (d, J = 7.3 Hz, 1 H) 4.64 (t, J = 4.6 Hz, 1 H) 4.92-5.02 (m, 1 H) 5.05 (d, J = 4.6 Hz, 1 H) 6.85 (d, J = 8.3 Hz, 1 H) 6.93 (t, J = 7.3 Hz, 1 H) 7.15-7.22 (m, 1 H) 7.37-7.46 (m, 1 H) |

TABLE 6-1-continued

| Example | Example of starting material | R | ESI MS (M + H) | ¹H-NMR, CDCl₃, δ (ppm) |
|---|---|---|---|---|
| 189 | 110 | (azetidine with N-CH₂-N(Et)-CH(Me)-(2-methoxyphenyl)) | 949 | (400 MHz): 0.88 (d, J = 7.33 Hz, 3 H) 0.98 (t, J = 6.83 Hz, 3 H) 1.01 (d, J = 6.84 Hz, 3 H) 1.03 (s, 3 H) 1.06 (d, J = 6.34 Hz, 3 H) 1.11 (d, J = 7.57 Hz, 3 H) 1.17-1.37 (m, 2 H) 1.21 (d, J = 6.10 Hz, 3 H) 1.24 (d, J = 7.33 Hz, 3 H) 1.26 (d, J = 7.32 Hz, 3 H) 1.37 (s, 3 H) 1.59-1.73 (m, 1 H) 1.94 (dd, J = 14.9, 5.37 Hz, 1 H) 2.03-2.17 (m, 3 H) 2.32 (s, 6 H) 2.42-2.67 (m, 7 H) 2.77-2.93 (m, 5 H) 2.95-3.05 (m, 2 H) 3.12-3.51 (m, 8 H) 3.27 (s, 3 H) 3.36 (s, 3 H) 3.56-3.63 (m, 1 H) 3.69 (dd, J = 9.52, 1.95 Hz, 1 H) 3.81 (s, 3 H) 3.89 (d, J = 6.35 Hz, 1 H) 4.12 (q, J = 6.35 Hz, 1 H) 4.28 (q, J = 6.84 Hz, 1 H) 4.46 (d, J = 7.08 Hz, 1 H) 4.63 (t, J = 4.64 Hz, 1 H) 4.90-5.05 (m, 1 H) 5.01 (d, J = 5.01 Hz, 1 H) 6.86 (dd, J = 8.30, 0.97 Hz, 1 H) 6.94 (t, J = 7.32 Hz, 1 H) 7.16-7.23 (m, 1 H) 7.34-7.39 (m, 1 H) |
| 190 | 118 | (azetidine with N-C(Me)₂-N(Et)-(2-methoxyphenyl)) | 949 | (400 MHz): 0.88 (d, J = 7.08 Hz, 3 H) 0.98-1.06 (m, 9 H) 1.04 (s, 3 H) 1.10 (d, J = 7.57 Hz, 3 H) 1.17-1.37 (m, 8 H) 1.37 (s, 3 H) 1.43 (s, 6 H) 1.50-1.80 (m, 1 H) 1.93 (dd, J = 14.90, 5.38 Hz, 1 H) 2.01-2.21 (m, 3 H) 2.32 (s, 6 H) 2.42-2.53 (m, 1 H) 2.58 (q, J = 6.60 Hz, 1 H) 2.77-2.93 (m, 6 H) 2.98-3.05 (m, 1 H) 3.10-3.51 (m, 10 H) 3.27 (s, 3 H) 3.36 (s, 3 H) 3.56-3.72 (m, 3 H) 3.79 (s, 3 H) 3.86-3.91 (m, 1 H) 4.12 (q, J = 6.34 Hz, 1 H) 4.46 (d, J = 7.32 Hz, 1 H) 4.63 (t, J = 4.64 Hz, 1 H) 4.89-5.04 (m, 1 H) 5.00 (d, J = 4.88 Hz, 1 H) 6.85-6.93 (m, 2 H) 7.17-7.24 (m, 1 H) 7.41 (dd, J = 7.82, 1.71 Hz, 1 H) |
| 191 | 180 | (N(Me)-CH(CH₂OH)-CH₂-N(Et)-CH(Me)-(2-methoxyphenyl)) | 967 FAB MASS | (400 MHz): 0.88 (d, J = 7.08 Hz, 3 H) 1.02 (d, J = 6.84 Hz, 3 H) 1.09 (s, 3 H) 1.12 (d, J = 7.57 Hz, 3 H) 1.14 (s, 3 H) 1.50 (d, J = 8.06 Hz, 3 H) 1.16 (d, J = 6.10 Hz, 3 H) 1.21-1.30 (m, 9 H) 1.34-1.40 (m, 3 H) 1.55-1.63 (m, 1 H) 2.00 (dd, J = 14.9, 5.13 Hz, 1 H) 2.08 (s, 3 H) 2.10-2.30 (m, 2 H) 2.28 (s, 6 H) 2.40-2.50 (m, 1 H) 2.55-2.74 (m, 6 H) 2.86-3.05 (m, 6 H) 3.13-3.25 (m, 3 H) 3.28 (s, 3 H) 3.34 (s, 3 H) 3.39-3.50 (m, 2 H) 3.58-3.63 (m, 1 H) 3.70 (d, J = 9.80 Hz, 1 H) 3.81 (s, 3 H) 3.89 (d, J = 6.35 Hz, 1 H) 4.15-4.22 (m, 1 H) 4.45-4.53 (m, 1 H) 5.03 (d, J = 4.88 Hz, 1 H) 6.91 (d, J = 8.55 Hz, 1 H) 6.95 (t, J = 7.32 Hz, 1 H) 7.23-7.32 (m, 2 H) |
| 192 | 124 | (N(Me)-CH₂CH₂-N(Me)-CH(Me)-(N-methylindol-4-yl)) | 946.7 | (600 MHz): 0.88 (d, J = 7.34 Hz, 3 H) 1.02 (d, J = 6.88 Hz, 3 H) 1.09-1.15 (m, 6 H) 1.17-1.27 (m, 10 H) 1.34-1.40 (m, 4 H) 1.45 (d, J = 6.88 Hz, 3 H) 1.61-1.65 (m, 1 H) 1.98-2.19 (m, 6 H) 2.27-2.32 (m, 9 H) 2.42-2.49 (m, 1 H) 2.54-2.61 (m, 3 H) 2.80 (d, J = 14.67 Hz, 1 H) 2.84-2.93 (m, 3 H) 3.00-3.05 (m, 1 H) 3.13-3.31 (m, 6 H) 3.29 (s, 3 H) 3.36-3.49 (m, 5 H) 3.58-3.63 (m, 1 H) 3.68-3.73 (m, 1 H) 3.78 (s, 3 H) 3.90-3.97 (m, 2 H) 4.11-4.18 (m, 1 H) 4.48 (d, J = 7.34 Hz, 1 H) 4.63 (t, J = 4.58 Hz, 1 H) 5.05 (t, J = 5.27 Hz, 1 H) 6.62-6.65 (m, 1 H) 7.01-7.04 (m, 1 H) 7.12-7.22 (m, 3 H) |
| 193 | 125 | (N(Me)-CH₂CH₂-N(Me)-CH(Me)-(biphenyl)) | 969.7 | (600 MHz): 0.89 (d, J = 5.96 Hz, 3 H) 1.02 (d, J = 6.42 Hz, 3 H) 1.08-1.32 (m, 19 H) 1.33-1.42 (m, 4 H) 1.61-1.69 (m, 1 H) 1.98-2.17 (m, 10 H) 2.26-2.34 (m, 6 H) 2.36-2.51 (m, 4 H) 2.55-2.62 (m, 1 H) 2.75-2.93 (m, 5 H) 3.00-3.05 (m, 1 H) 3.14-3.25 (m, 3 H) 3.27-3.31 (m, 3 H) 3.36-3.50 (m, 5 H) 3.54-3.63 (m, 2 H) 3.68-3.74 (m, 1 H) 3.90-3.94 (m, 1 H) 4.11-4.19 (m, 1 H) 4.48 (d, J = 6.88 Hz, 1 H) 4.61-4.66 (m, 1 H) 5.03-5.09 (m, 1 H) 7.14-7.18 (m, 1 H) 7.21-7.28 (m, 3 H) 7.30-7.42 (m, 4 H) 7.63-7.68 (m, 1 H) |

TABLE 6-1-continued

| Example | Example of starting material | R | ESI MS (M + H) | ¹H-NMR, CDCl₃, δ (ppm) |
|---|---|---|---|---|
| 194 | 126 | (structure) | 970.7 | (600 MHz): 0.86-0.91 (m, 3 H) 1.00-1.04 (m, 3 H) 1.09-1.32 (m, 19 H) 1.34-1.41 (m, 4 H) 1.61-1.68 (m, 1 H) 1.96-2.19 (m, 10 H) 2.30 (s, 6 H) 2.33-2.50 (m, 3 H) 2.56-2.62 (m, 1 H) 2.75-2.82 (m, 1 H) 2.82-2.94 (m, 3 H) 3.00-3.06 (m, 1 H) 3.13-3.52 (m, 14 H) 3.58-3.63 (m, 1 H) 3.68-3.74 (m, 1 H) 3.89-3.94 (m, 1 H) 4.12-4.19 (m, 1 H) 4.46-4.50 (m, 1 H) 4.62-4.66 (m, 1 H) 5.04-5.09 (m, 1 H) 7.13-7.18 (m, 1 H) 7.27-7.31 (m, 1 H) 7.33-7.41 (m, 2 H) 7.59-7.63 (m, 1 H) 7.66-7.72 (m, 1 H) 8.52-8.57 (m, 1 H) 8.58-8.63 (m, 1 H) |
| 195 | 127 | (structure) | 970.7 | (600 MHz): 0.86-0.91 (m, 3 H) 1.02 (d, J = 5.96 Hz, 3 H) 1.09-1.17 (m, 6 H) 1.19-1.29 (m, 10 H) 1.29-1.41 (m, 7 H) 1.57-1.67 (m, 1 H) 1.96-2.17 (m, 12 H) 2.31 (s, 6 H) 2.37-2.52 (m, 3 H) 2.56-2.63 (m, 1 H) 2.71-2.93 (m, 4 H) 3.00-3.05 (m, 1 H) 3.14-3.25 (m, 3 H) 3.27-3.31 (m, 3 H) 3.34-3.49 (m, 5 H) 3.58-3.64 (m, 1 H) 3.68-3.74 (m, 2 H) 3.89-3.94 (m, 1 H) 4.10-4.19 (m, 1 H) 4.46-4.50 (m, 1 H) 4.61-4.66 (m, 1 H) 5.04-5.08 (m, 1 H) 7.23-7.32 (m, 3 H) 7.32-7.39 (m, 2 H) 7.66-7.76 (m, 2 H) 8.65-8.70 (m, 1 H) |
| 196 | 131 | (structure) | 944.8 | (600 MHz): 0.86-0.97 (m, 3 H) 0.98-1.31 (m, 19 H) 1.32-1.49 (m, 7 H) 1.59-1.66 (m, 1 H) 1.83-2.15 (m, 4 H) 2.18-2.77 (m, 18 H) 2.81-2.93 (m, 4 H) 3.01-3.10 (m, 1 H) 3.14-3.50 (m, 11 H) 3.64-3.72 (m, 2 H) 3.83-3.92 (m, 1 H) 3.97-4.10 (m, 1 H) 4.20-4.33 (m, 1 H) 4.41-4.52 (m, 1 H) 4.60-4.72 (m, 1 H) 4.99-5.08 (m, 1 H) 7.37-7.44 (m, 1 H) 7.53-7.67 (m, 2 H) 7.96-8.03 (m, 1 H) 8.67-8.80 (m, 1 H) 8.85-8.95 (m, 1 H) |

TABLE 6-2

| Example | Example of starting material | R | ESI MS (M + H) | ¹H-NMR, CDCl₃, δ (ppm) |
|---|---|---|---|---|
| 197 | 135 | (structure) | 944.7 | (600 MHz): 0.88 (d, J = 7.34 Hz, 3 H) 0.98-1.04 (m, 3 H) 1.06-1.28 (m, 16 H) 1.32-1.39 (m, 4 H) 1.44-1.49 (m, 3 H) 1.53-1.66 (m, 1 H) 1.97-2.17 (m, 7 H) 2.19-2.64 (m, 15 H) 2.76-2.94 (m, 4 H) 2.99-3.05 (m, 1 H) 3.09-3.25 (m, 3 H) 3.25-3.30 (m, 3 H) 3.34-3.38 (m, 3 H) 3.38-3.48 (m, 2 H) 3.54-3.62 (m, 1 H) 3.67-3.73 (m, 1 H) 3.78-3.87 (m, 1 H) 3.87-3.93 (m, 1 H) 4.09-4.19 (m, 1 H) 4.43-4.50 (m, 1 H) 4.58-4.66 (m, 1 H) 5.02-5.07 (m, 1 H) 7.50-7.55 (m, 1 H) 7.64-7.70 (m, 1 H) 7.75-7.81 (m, 1 H) 8.04-8.10 (m, 2 H) 8.90-8.94 (m, 1 H) |
| 198 | 129 | (structure) | 960.8 | (600 MHz): 0.89 (d, J = 6.88 Hz, 3 H) 0.95-1.28 (m, 19 H) 1.33-1.40 (m, 4 H) 1.48 (s, 6 H) 1.61-1.68 (m, 1 H) 1.90-2.08 (m, 6 H) 2.11-2.16 (m, 1 H) 2.25 (s, 3 H) 2.31 (s, 6 H) 2.40-2.49 (m, 2 H) 2.55-2.63 (m, 1 H) 2.67-2.74 (m, 1 H) 2.83-2.92 (m, 4 H) 3.00-3.05 (m, 1 H) 3.13-3.25 (m, 4 H) 3.26 (s, 3 H) 3.35-3.45 (m, 6 H) 3.58-3.63 (m, 1 H) 3.66-3.71 (m, 1 H) 3.76 (s, 3 H) 3.87-3.91 (m, 1 H) 4.06-4.12 (m, 1 H) 4.46 (d, J = 7.34 Hz, 1 H) 4.62-4.65 (m, 1 H) 5.01 (d, J = 5.04 Hz, 1 H) 6.92-6.97 (m, 1 H) 7.00-7.05 (m, 2 H) 7.09-7.20 (m, 2 H) |

TABLE 6-2-continued

| Example | Example of starting material | R | ESI MS (M + H) | ¹H-NMR, CDCl₃, δ (ppm) |
|---|---|---|---|---|
| 199 | 143 | (structure) | 925.6 | (600 MHz): 0.87 (d, J = 7.34 Hz, 3 H) 1.00 (d, J = 6.42 Hz, 3 H) 1.10 (d, J = 7.79 Hz, 3 H) 1.13-1.27 (m, 13 H) 1.30-1.40 (m, 7 H) 1.61-1.65 (m, 1 H) 1.96-2.17 (m, 4 H) 2.17-2.31 (m, 12 H) 2.32-2.62 (m, 6 H) 2.79-2.93 (m, 4 H) 2.98-3.04 (m, 1 H) 3.11-3.23 (m, 3 H) 3.27-3.30 (m, 3 H) 3.35-3.38 (m, 3 H) 3.38-3.50 (m, 2 H) 3.55-3.61 (m, 1 H) 3.66-3.73 (m, 1 H) 3.87-3.95 (m, 2 H) 3.99 (s, 3 H) 4.13-4.19 (m, 1 H) 4.44-4.50 (m, 1 H) 4.60-4.64 (m, 1 H) 5.01-5.07 (m, 1 H) 8.53 (s, 1 H) 8.66 (s, 1 H) |
| 200 | 151 | (structure) | 946.7 | (600 MHz): 0.87 (d, J = 6.88 Hz, 3 H) 1.00 (d, J = 6.42 Hz, 3 H) 1.03-1.28 (m, 16 H) 1.32-1.36 (m, 1 H) 1.37 (s, 3 H) 1.40-1.45 (m, 3 H) 1.59-1.64 (m, 1 H) 1.86-2.18 (m, 4 H) 2 99-2.33 (m, 12 H) 2.37-2.63 (m, 6 H) 2.65-2.72 (m, 1 H) 2.81-2.93 (m, 3 H) 2.96-3.04 (m, 1 H) 3.10-3.20 (m, 3 H) 3.22-3.27 (m, 3 H) 3.37 (s, 3 H) 3.38-3.42 (m, 2 H) 3.55-3.62 (m, 1 H) 3.65-3.72 (m, 1 H) 3.84-3.90 (m, 1 H) 4.05-4.11 (m, 1 H) 4.11-4.18 (m, 3 H) 4.40-4.47 (m, 1 H) 4.48-4.58 (m, 1 H) 4.59-4.66 (m, 1 H) 4.93-4.99 (m, 1 H) 4.99-5.06 (m, 1 H) 6.36-6.43 (m, 1 H) 6.87-6.95 (m, 1 H) 6.96-7.02 (m, 1 H) 7.12-7.22 (m, 1 H) 7.43-7.51 (m, 1 H) |
| 201 | 156 | (structure) | 953.7 | (600 MHz): 0.86-0.91 (m, 3 H) 0.99-1.04 (m, 3 H) 1.05-1.14 (m, 9 H) 1.18-1.27 (m, 7 H) 1.33-1.40 (m, 4 H) 1.43-1.48 (m, 6 H) 1.62-1.68 (m, 1 H) 1.94-1.99 (m, 1 H) 2.04-2.18 (m, 5 H) 2.21 (s, 3 H) 2.31 (s, 6 H) 2.33 (s, 3 H) 2.40-2.50 (m, 4 H) 2.54-2.60 (m, 1 H) 2.85-2.93 (m, 4 H) 3.00-3.05 (m, 1 H) 3.12-3.24 (m, 4 H) 3.28 (s, 3 H) 3.35-3.48 (m, 6 H) 3.57-3.62 (m, 1 H) 3.67-3.71 (m, 1 H) 3.90 (d, J = 6.42 Hz, 1 H) 4.10-4.18 (m, 1 H) 4.47 (d, J = 7.34 Hz, 1 H) 4.61-4.65 (m, 1 H) 5.00-5.04 (m, 1 H) 7.00-7.05 (m, 1 H) 7.13-.18 (m, 1 H) 7.19-7.23 (m, 2 H) |
| 202 | 163 | (structure) | 949.7 | (600 MHz): 0.88 (d, J = 6.88 Hz, 3 H) 1.01 (d, J = 6.42 Hz, 3 H) 1.05-1.17 (m, 9 H) 1.17-1.28 (m, 7 H) 1.32-1.43 (m, 10 H) 1.57-1.66 (m, 1 H) 1.70-1.92 (m, 2 H) 1.94-2.00 (m, 1 H) 2.02-2.18 (m, 4 H) 2.29 (s, 6 H) 2.32 (s, 3 H) 2.36-2.48 (m, 1 H) 2.53-2.61 (m, 1 H) 2.79-2.94 (m, 6 H) 2.98-3.05 (m, 1 H) 3.11-3.23 (m, 3 H) 3.25-3.30 (m, 3 H) 3.33-3.38 (m, 3 H) 3.37-3.53 (m, 4 H) 3.55-3.62 (m, 1 H) 3.70 (d, J = 9.63 Hz, 1 H) 3.78 (s, 3 H) 3.90 (d, J = 5.50 Hz, 1 H) 4.10-4.19 (m, 1 H) 4.47 (d, J = 5.50 Hz, 1 H) 4.59-4.65 (m, 1 H) 5.02 (d, J = 5.04 Hz, 1 H) 6.84-6.93 (m, 2 H) 7.19 (t, J = 7.79 Hz, 1 H) 7.53-7.58 (m, 1 H) |
| 203 | 167 | (structure) | 963.9 | (600 MHz): 0.87 (d, J = 6.88 Hz, 3 H) 1.00 (d, J = 6.88 Hz, 3 H) 1.06-1.17 (m, 9 H) 1.17-1.27 (m, 7 H) 1.35 (d, J = 14.67 Hz, 1 H) 1.37-1.44 (m, 9 H) 1.44-1.52 (m, 1 H) 1.60-1.67 (m, 1 H) 1.84-2.02 (m, 3 H) 2.04-2.20 (m, 8 H) 2.29 (br s, 6 H) 2.33-2.41 (m, 2 H) 2.42-2.49 (m, 1 H) 2.54-2.61 (m, 1 H) 2.61-2.75 (m, 1 H) 2.82-2.96 (m, 5 H) 2.97-3.04 (m, 1 H) 3.11-3.24 (m, 3 H) 3.26-3.31 (m, 3 H) 3.34-3.38 (m, 3 H) 3.38-3.42 (m, 1 H) 3.42-3.49 (m, 1 H) 3.55-3.62 (m, 1 H) 3.67-3.72 (m, 1 H) 3.77 (s, 3 H) 3.87-3.94 (m, 1 H) 4.16 (q, J = 5.96 Hz, 1 H) 4.48 (d, J = 6.88 Hz, 1 H) 4.62 (t, J = 4.58 Hz, 1 H) 5.03 (d, J = 5.50 Hz, 1 H) 6.82-6.90 (m, 2 H) 7.14-7.21 (m, 1 H) 7.44-7.52 (m, 1 H) |

TABLE 6-2-continued

| Example | Example of starting material | R | ESI MS (M + H) | ¹H-NMR, CDCl₃, δ (ppm) |
|---|---|---|---|---|
| 204 | 171 | (structure) | 960.8 | (600 MHz): 0.69 (s, 3 H) 0.90 (d, J = 7.34 Hz, 3 H) 1.02 (d, J = 6.88 Hz, 3 H) 1.08 (d, J = 5.96 Hz, 3 H) 1.16 (d, J = 7.79 Hz, 3 H) 1.19-1.30 (m, 7 H) 1.36-1.43 (m, 4 H) 1.64-1.70 (m, 1 H) 1.75 (s, 3 H) 1.82 (s, 3 H) 1.88-1.93 (m, 1 H) 2.00-2.05 (m, 1 H) 2.10 (s, 3 H) 2.12-2.18 (m, 1 H) 2.29 (s, 6 H) 2.45-2.52 (m, 1 H) 2.60-266 (m, 1 H) 2.78-2.85 (m, 1 H) 2.88-3.06 (m, 3 H) 3.15-3.28 (m, 3 H) 3.31 (s, 3 H) 3.32 (s, 3 H) 3.33-3.45 (m, 2 H) 3.54-3.75 (m, 4 H) 3.81 (s, 3 H) 3.95-4.01 (m, 2 H) 4.11-4.18 (m, 1 H) 4.37-4.43 (m, 1 H) 4.52 (d, J = 6.88 Hz, 1 H) 4.61-4.66 (m, 1 H) 4.98-5.02 (m, 1 H) 6.81 (br s, 1 H) 6.94-6.98 (m, 2 H) 7.27-7.30 (m, 1 H) 7.46-7.51 (m, 1 H) 7.53 (br s, 1 H) |

TABLE 6-3

| Example | Example of starting material | R | ESI MS (M + H) | ¹H-NMR, CDCl₃, δ (ppm) |
|---|---|---|---|---|
| 205 | 172 | (structure) | 960.8 | (600 MHz): 0.87-0.92 (m, 6 H) 1.01 (d, J = 6.88 Hz, 3 H) 1.08 (d, J = 6.42 Hz, 3 H) 1.16 (d, J = 7.34 Hz, 3 H) 1.21-1.30 (m, 7 H) 1.37-1.43 (m, 4 H) 1.49 (s, 6 H) 1.68-1.73 (m, 1 H) 1.79-1.85 (m, 1 H) 2.09-2.18 (m, 2 H) 2.27 (s, 3 H) 2.32 (s, 6 H) 2.42-2.54 (m, 1 H) 2.60-2.66 (m, 1 H) 2.78-2.85 (m, 1 H) 2.90-3.00 (m, 2 H) 3.01-3.07 (m, 1 H) 3.14-3.28 (m, 3 H) 3.32 (s, 3 H) 3.32 (s, 3 H) 3.40-3.52 (m, 4 H) 3.57-3.62 (m, 1 H) 3.72-3.76 (m, 1 H) 3.80-3.84 (m, 4 H) 3.92 (d, J = 14.67 Hz, 1 H) 4.18 (d, J = 14.67 Hz, 1 H) 4.47 (d, J = 7.34 Hz, 1 H) 4.57-4.65 (m, 2 H) 4.95 (d, J = 4.58 Hz, 1 H) 6.87-6.91 (m, 2 H) 6.99 (s, 1 H) 7.15-7.20 (m, 1 H) 7.42 (s, 1 H) 7.84-7.88 (m, 1 H) |
| 206 | 101 | (structure) | 937 FAB MASS | (400 MHz): 0.89 (d, J = 7.6 Hz, 3 H) 0.92 (d, J = 7.1 Hz, 3 H) 1.02 (d, J = 6.8 Hz, 3 H) 1.12 (d, J = 7.6 Hz, 3 H) 1.15 (s, 3 H) 1.17 (d, J = 6.3 Hz, 3 H) 1.20-1.36 (m, 11 H) 1.38 (s, 3 H) 1.47-1.72 (m, 4 H) 1.98-2.07 (m, 2 H) 2.08-2.19 (m, 2 H) 2.23 (s, 3 H) 2.27-2.38 (m, 7 H) 2.42-2.69 (m, 7 H) 2.83-2.95 (m, 4 H) 3.00-3.06 (m, 1 H) 3.12-3.26 (m, 3 H) 3.30 (s, 3 H) 3.31-3.35 (m, 1 H) 3.37 (s, 3 H) 3.38-3.45 (m, 1 H) 3.46-3.54 (m, 1 H) 3.56-3.64 (m, 1 H) 3.67-3.73 (m, 1 H) 3.81 (s, 3 H) 3.92 (d, J = 6.1 Hz, 1 H) 4.05-4.14 (m, 1 H) 4.16 (q, J = 5.9 Hz, 1 H) 4.50 (d, J = 7.1 Hz, 1 H) 4.63 (t, J = 4.6 Hz, 1 H) 4.93-5.00 (m, 1 H) 5.05 (d, J = 4.2 Hz, 1 H) 6.86 (d, J = 8.3 Hz, 1 H) 6.93 (t, J = 7.6 Hz, 1 H) 7.15-7.23 (m, 1 H) 7.38-7.45 (m, 1 H) |
| 207 | 180 | (structure) | 953 FAB MASS | (400 MHz): 0.87 (d, J = 7.08 Hz, 3 H) 1.02 (d, J = 6.84 Hz, 3 H) 1.11 (s, 3 H) 1.12 (d, J = 7.57 Hz, 3 H) 1.16 (d, J = 6.10 Hz, 3 H) 1.23-1.27 (m, 6 H) 1.35 (d, J = 7.08 Hz, 3 H) 1.38 (s, 3 H) 1.59-1.65 (m, 1 H) 1.97 (dd, J = 14.9, 5.37 Hz, 1 H) 2.08 (d, J = 14.9 Hz, 1 H) 2.15 (s, 3 H) 2.27 (s, 3 H) 2.29 (s, 6 H) 2.31-2.47 (m, 2 H) 2.58 (dd, J = 13.7, 6.35 Hz, 1 H) 2.77-2.98 (m, 6 H) 3.03 (br s, 1 H) 3.14-3.23 (m, 3 H) 3.28 (s, 3 H) 3.37 (s, 3 H) 3.39-3.49 (m, 3 H) 3.56-3.65 (m, 2 H) 3.70 (dd, J = 9.77, 1.71 Hz, 1 H) 3.82 (s, 3 H) 3.90 (d, J = 6.34 Hz, 1 H) 4.15-4.24 (m, 1 H) 4.47 (d, J = 7.08 Hz, 1 H) 4.63 (t, J = 4.64 Hz, 1 H) 4.95 (br s, 1 H) 5.02 (d, J = 4.88 Hz, 1 H) 6.90 (d, J = 8.06 Hz, 1 H) 6.93 (t, J = 6.84 Hz, 1 H) 7.23-7.28 (m, 2 H) |

TABLE 6-3-continued

| Example | Example of starting material | R | ESI MS (M + H) | ¹H-NMR, CDCl₃, δ (ppm) |
|---|---|---|---|---|
| 208 | 118 | [azetidine-N(Me)-C(Me)(Me)-(2-methoxyphenyl)] | 935 | (400 MHz): 0.88 (d, J = 7.08 Hz, 3 H) 1.01 (d, J = 6.59 Hz, 3 H) 1.04 (s, 3 H) 1.06 (d, J = 6.35 Hz, 3 H) 1.10 (d, J = 7.57 Hz, 3 H) 1.17-1.37 (m, 8 H) 1.37 (s, 3 H) 1.40 (s, 6 H) 1.58-1.81 (m, 1 H) 1.94 (dd, J = 14.9, 5.37 Hz, 1 H) 2.03-2.22 (m, 3 H) 2.19 (s, 3 H) 2.32 (s, 6 H) 2.42-2.52 (m, 1 H) 2.57 (4, J = 6.84 Hz, 1 H) 2.81-2.93 (m, 4 H) 2.97-3.05 (m, 1 H) 3.11-3.63 (m, 11 H) 3.27 (s, 3 H) 3.35 (s, 3 H) 3.69 (d, J = 9.77 Hz, 1 H) 3.81 (s, 3 H) 3.89 (d, J = 6.35 Hz, 1 H) 4.12 (q, J = 6.35 Hz, 1 H) 4.46 (d, J = 7.08 Hz, 1 H) 4.62 (t, J = 4.40 Hz, 1 H) 4.93-5.04 (m, 2 H) 6.87-6.95 (m, 2 H) 7.18-7.24 (m, 1 H) 7.51 (dd, J = 7.82, 1.47 Hz, 1 H) |
| 209 | 110 | [azetidine-CH₂-N(Me)-CH(Me)-(2-methoxyphenyl)] | 935 | (400 MHz): 0.88 (d, J = 7.08 Hz, 3 H) 1.01 (d, J = 6.83 Hz, 3 H) 1.03 (s, 3 H) 1.05 (d, J = 6.35 Hz, 3 H) 1.10 (d, J = 7.57 Hz, 3 H) 1.17-1.37 (m, 2 H) 1.21 (d, J = 6.10 Hz, 3 H) 1.24 (d, J = 7.08 Hz, 3 H) 1.28 (d, J = 6.83 Hz, 3 H) 1.37 (s, 3 H) 1.57-1.73 (m, 1 H) 1.95 (dd, J = 14.9, 5.37 Hz, 1 H) 2.04-2.20 (m, 3 H) 2.16 (s, 3 H) 2.31 (s, 6 H) 2.40-2.51 (m, 2 H) 2.54-2.72 (m, 3 H) 2.79-2.93 (m, 5 H) 2.97-3.05 (m, 2 H) 3.11-3.63 (m, 9 H) 3.27 (s, 3 H) 3.36 (s, 3 H) 3.69 (d, J = 9.77 Hz, 1 H) 3.82 (s, 3 H) 3.89 (d, J = 6.10 Hz, 1 H) 4.06 (q, J = 7.08 Hz, 1 H) 4.12 (q, J = 6.35 Hz, 1 H) 4.46 (d, J = 7.33 Hz, 1 H) 4.63 (t, J = 4.40 Hz, 1 H) 4.98 (d, J = 10.5 Hz, 1 H) 5.01 (d, J = 4.88 Hz, 1 H) 6.87 (d, J = 8.30 Hz, 1 H) 6.95 (t, J = 7.57 Hz, 1 H) 7.18-7.24 (m, 1 H) 7.35 (dd, J = 7.57, 1.47 Hz, 1 H) |
| 210 | 186 | [piperidine-N(Me)-C(Me)(Me)-(2-methoxyphenyl)] | 963 | (400 MHz): 0.89 (d, J = 7.08 Hz, 3 H) 1.01 (d, J = 6.59 Hz, 3 H) 1.09 (s, 3 H) 1.10 (d, J = 7.81 Hz, 6 H) 1.12 (d, J = 7.81 Hz, 3 H) 1.20 (d, J = 6.10 Hz, 3 H) 1.25 (d, J = 6.84 Hz, 3 H) 1.50 (s, 6 H) 1.54-1.87 (m, 4 H) 1.91 (br d, J = 14.2 Hz, 1 H) 1.98 (dd, J = 14.9, 5.37 Hz, 1 H) 2.08 (d, J = 14.9 Hz, 1 H) 2.10-2.23 (m, 2 H) 2.29 (s, 3 H) 2.30 (s, 6 H) 2.39-2.48 (m, 1 H) 2.54-2.65 (m, 2 H) 2.69 (d, J = 14.6 Hz, 1 H) 2.79-2.93 (m, 5 H) 2.99-3.04 (m, 1 H) 3.11-3.22 (m, 4 H) 3.28 (s, 3 H) 3.30-3.46 (m, 5 H) 3.57-3.62 (m, 1 H) 3.67-3.71 (m, 1 H) 3.80 (s, 3 H) 3.90 (d, J = 6.35 Hz, 1 H) 4.13 (q, J = 6.10 Hz, 1 H) 4.46 (d, J = 7.33 Hz, 1 H) 4.62 (t, J = 4.64 Hz, 1 H) 4.90-5.01 (m, 1 H) 5.02 (d, J = 4.88 Hz, 1 H) 6.84-6.92 (m, 2 H) 6.84 (t, J = 6.84 Hz, 1 H) 7.53 (d, J = 8.55 Hz, 1 H) |
| 211 | 138 | [N(Me)-CH₂CH₂-N(Me)-C(Me)(Me)-phenyl] | 907 FAB MASS | (400 MHz): 0.90 (d, J = 7.08 Hz, 3 H) 1.02 (d, J = 6.84 Hz, 3 H) 1.12 (d, J = 7.57 Hz, 3 H) 1.15 (s, 3 H) 1.21 (d, J = 6.35 Hz, 3 H) 1.23 (d, J = 6.10 Hz, 3 H) 1.28 (d, J = 7.08 Hz, 3 H) 1.35 (s, 6 H) 1.40 (s, 3 H) 1.52-1.68 (m, 2 H) 2.03 (dd, J = 14.9, 5.13 Hz, 1 H) 2.10 (d, J = 14.9 Hz, 1 H) 2.11-2.20 (m, 1 H) 2.28 (s, 6 H) 2.30 (s, 6 H) 2.33-2.55 (m 2 H) 2.59 (q, J = 6.59 Hz, 1 H) 2.79 (d, J = 14.6 Hz, 1 H) 2.82-2.93 (m, 3 H) 3.00-3.06 (m, 1 H) 3.13-3.22 (m, 3 H) 3.23 (dd, J = 10.3, 7.08 Hz, 1 H) 3.31 (s, 3 H) 3.31-3.38 (m, 1 H) 3.40 (s, 3 H) 3.40-3.51 (m, 2 H) 3.57-3.64 (m, 1 H) 3.69-3.75 (m, 1 H) 3.92 (d, J = 6.35 Hz, 1 H) 4.17 (q, J = 6.10 Hz, 1 H) 4.49 (d, J = 7.32 Hz, 1 H) 4.64 (t, J = 4.40 Hz, 1 H) 4.99 (d, J = 102 Hz, 1 H) 5.08 (d, J = 4.40 Hz, 1 H) 7.16-7.21 (m, 1 H) 7.24-7.31 (m, 2 H) 7.52-7.57 (m, 2 H) |

TABLE 6-4

| Example | Example of starting material | R | ESI MS (M + H) | $^1$H-NMR, CDCl$_3$, δ (ppm) |
|---|---|---|---|---|
| 212 | 97 | (structure with nitrile, N-Me, chiral methyl, 2-methoxyphenyl) | 962 FAB MASS | (400 MHz): 0.88 (d, J = 7.08 Hz, 3 H) 1.01 (d, J = 6.59 Hz, 3 H) 1.10 (s, 3 H) 1.12 (d, J = 6.35 Hz, 3 H) 1.14 (d, J = 6.35 Hz, 3 H) 1.23 (d, J = 6.59 Hz, 3 H) 1.25 (d, J = 7.08 Hz, 3 H) 1.34 (d, J = 6.84 Hz, 3 H) 1.38 (s, 3 H) 1.62-1.67 (m, 1 H) ) 1.95-2.17 (m, 4 H) 2.21 (s, 3 H) 2.30 (s, 6 H) 2.42-2.63 (m, 8 H) 2.71-2.96 (m, 6 H) 2.99-3.05 (m, 1 H) 3.13-3.24 (m, 3 H) 3.28 (s, 3 H) 3.32-3.48 (m, 3 H) 3.37 (s, 3 H) 3.59 (dd, J = 8.55, 4.64 Hz, 1 H) 3.70 (d, J = 8.79 Hz, 1 H) 3.82 (s, 3 H) 3.91 (d, J = 6.10 Hz, 1 H) 4.11-4.17 (m, 1 H) 4.33-4.40 (m, 1 H) 4.48 (d, J = 7.32 Hz, 1 H) 4.63 (t, J = 4.64 Hz, 1 H) 4.93-4.50 (m, 1 H) 5.03 (d, J = 4.88 Hz, 1 H) 6.87 (d, J = 8.30 Hz, 1 H) 6.93 (t, J = 7.33 Hz, 1 H) 7.23 (t, J = 7.57 Hz, 1 H) 7.32 (d, J = 7.32 Hz, 1 H) |
| 213 | 97 | (structure with propyl, N-Me, chiral methyl, 2-methoxyphenyl) | 951 FAB MASS | (400 MHz): 0.82 (t, J = 7.32 Hz, 3 H) 0.88 (d, J = 7.32 Hz, 3 H) 1.01 (d, J = 6.84 Hz, 3 H) 1.11 (d, J = 5.62 Hz, 3 H) 1.12 (s, 3 H) 1.15 (d, J = 6.35 Hz, 3 H) 1.22-1.28 (m, 6 H) 1.29 (d, J = 6.84 Hz, 3 H) 1.38 (s, 3 H) 1.41-1.52 (m, 2 H) 1.61-1.67 (m, 1 H) 1.97-2.19 (m, 5 H) 2.23 (s, 3 H) 2.29 (s, 6 H) 2.30-2.38 (m, 1 H) 2.42-2.61 (m, 6 H) 2.80-2.93 (m, 3 H) 2.99-3.05 (m, 1 H) 3.13-3.25 (m, 3 H) 3.30 (s, 3 H) 3.31-3.49 (m, 2 H) 3.37 (s, 3 H) 3.56-3.62 (m, 1 H) 3.70 (d, J = 10.0 Hz, 1 H) 3.79 (s, 3 H) 3.92 (d, J = 6.10 Hz, 1 H) 4.15 (dd, J = 11.96, 5.62 Hz, 1 H) 4.35 (dd, J = 13.43, 6.59 Hz, 1 H) 4.48 (d, J = 7.08 Hz, 1 H) 4.63 (t, J = 4.64 Hz, 1 H) 4.95-5.02 (m, 1 H) 5.04 (d, J = 4.64 Hz, 1 H) 6.84 (d, J = 8.06 Hz, 1 H) 6.92 (t, J = 7.57 Hz, 1 H) 7.18 (t, J = 6.59 Hz, 1 H) 7.37 (d, J = 6.10 Hz, 1 H) |
| 214 | 121 | (structure with N-Me, gem-dimethyl, 2-hydroxyphenyl) | 923 FAB MASS | (400 MHz): 0.88 (d, J = 7.3 Hz, 3 H) 1.02 (d, J = 6.8 Hz, 3 H) 1.07-1.29 (m, 16 H) 1.32-1.40 (m, 4 H) 1.43 (s, 6 H) 1.61-1.72 (m, 1 H) 2.00 (dd, J = 14.6, 4.9 Hz, 1 H) 2.03-2.09 (m, 1 H) 2.10-2.16 (m, 1 H) 2.17 (s, 3 H) 2.18-2.28 (m, 1 H) 2.32 (s, 3 H) 2.33 (s, 6 H) 2.41-2.52 (m, 1 H) 2.54-2.78 (m, 3 H) 2.79-2.95 (m, 5 H) 2.98-3.06 (m, 1 H) 3.12-3.26 (m, 3 H) 3.29 (s, 3 H) 3.31-3.49 (m, 6 H) 3.56-3.64 (m, 1 H) 3.67-3.73 (m, 1 H) 3.90 (d, J = 6.1 Hz, 1 H) 4.16 (q, J = 6.3 Hz, 1 H) 4.47 (d, J = 7.1 Hz, 1 H) 4.63 (t, J = 4.6 Hz, 1 H) 4.92-5.00 (m, 1 H) 5.04 (d, J = 4.2 Hz, 1 H) 6.72-6.82 (m, 2 H) 7.02-7.16 (m, 2 H) |
| 215 | | (structure with S-linker, N-Me, gem-dimethyl, 2-methoxyphenyl) | 939 FAB MASS | (400 MHz): 0.87 (d, J = 7.32 Hz, 3 H) 1.01 (d, J = 6.59 Hz, 3 H) 1.08 (s, 3 H) 1.10 (d, J = 7.81 Hz, 3 H) 1.12 (d, J = 6.35 Hz, 3 H) 1.18 (d, J = 6.10 Hz, 3 H) 1.20-1.26 (m, 5 H) 1.33-1.35 (m, 1 H) 1.37 (s, 3 H) 1.43 (s, 6 H) 1.60-1.66 (m, 1 H) 1.95-2.18 (m, 3 H) 2.04 (s, 3 H) 2.24 (s, 3 H) 2.27 (s, 6 H) 2.41-2.48 (m, 2 H) 2.54-2.63 (m, 2 H) 2.56 (s, 3 H) 2.82-2.92 (m, 3 H) 2.96 (d, J = 12.0 Hz, 1 H) 3.03 (d, J = 3.42 Hz, 1 H) 3.13-3.22 (m, 3 H) 3.28 (s, 3 H) 3.34 (s, 3 H) 3.39-3.43 (m, 2 H) 3.45-3.53 (m, 1 H), 3.59 (dd, J = 8.06, 3.66 Hz, 1 H) 3.68 (dd, J = 8.06, 1.46 Hz, 1 H) 3.78 (s, 3 H) 3.85 (d, J = 3.42 Hz, 1 H) 4.12 (q, J = 7.08 Hz, 1 H) 4.30 (dd, J = 12.7, 6.35 Hz, 1 H) 4.46 (d, J = 7.08 Hz, 1 H) 4.63 (t, J = 4.64 Hz, 1 H) 5.00 (d, J = 4.88 Hz, 1 H) 6.84-6.91 (m, 2 H) 7.17 (dt, J = 8.06, 1.71 Hz, 1 H) 7.55 (dd, J = 7.57, 1.71 Hz) |

TABLE 6-4-continued

| Example | Example of starting material | R | ESI MS (M + H) | $^1$H-NMR, CDCl$_3$, δ (ppm) |
|---|---|---|---|---|
| 216 | | (structure: Me-N(Me)-CH$_2$CH$_2$-N(Me)-C(Me)(Me)-[2-(N(Me)$_2$)-phenyl]) | 950.8 | (600 MHz): 0.92 (d, J = 7.34 Hz, 3 H) 1.05 (d, J = 6.42 Hz, 3 H) 1.16 (d, J = 7.34 Hz, 3 H) 1.18 (s, 3 H) 1.22 (d, J = 6.42 Hz, 3 H) 1.24-1.33 (m, 7 H) 1.40 (d, J = 14.21 Hz, 1 H) 1.43 (s, 3 H) 1.56 (d, J = 6.42 Hz, 6 H) 1.65-1.71 (m, 1 H) 2.01-2.08 (m, 1 H) 2.08-2.22 (m, 3 H) 2.26 (s, 3 H) 2.27 (s, 3 H) 2.34 (s, 6 H) 2.45-2.75 (m, 6 H) 2.62 (s, 6 H) 2.83-2.98 (m, 4 H) 3.03-3.09 (m, 1 H) 3.17-3.29 (m, 3 H) 3.34 (s, 3 H) 3.42 (s, 3 H) 3.42-3.47 (m, 1 H) 3.47-3.55 (m, 1 H) 3.60-3.66 (m, 1 H) 3.72-3.78 (m, 1 H) 3.96 (d, J = 6.42 Hz, 1 H) 4.21 (q, J = 6.42 Hz, 1 H) 4.53 (d, J = 7.34 Hz, 1 H) 4.67 (t, J = 4.81 Hz, 1 H) 5.08 (d, J = 5.04 Hz, 1 H) 7.11 (t, J = 7.11 Hz, 1 H) 7.20-7.25 (m, 1 H) 7.33 (d, J = 6.42 Hz, 1 H) 7.77 (d, J = 8.25 Hz, 1 H) |

In Examples 188 to 191, by using the exemplary compounds shown in the columns of "Example of starting material" in Table 6, the compounds shown in Table 6 were synthesized in the same manner as that of Example 104.

In Examples 192 to 211, by using the exemplary compounds shown in the columns of "Example of starting material" in Table 6, the compounds shown in Table 6 were synthesized in the same manner as that of Example 103.

Example 212

The compound obtained in Example 97 (30 mg) was dissolved in ethanol (1 ml), acrylonitrile (0.07 ml) was added to the solution, and the resulting mixture was stirred at 70° C. for 13 hours. The reaction mixture was concentrated under reduced pressure, and the resulting residue was purified by preparative thin layer chromatography (chloroform:methanol:28% aqueous ammonia=10:1:0.1) to obtain the compound shown in Table 6 (25 mg).

Example 213

The compound obtained in Example 97 (40 mg) was dissolved in chloroform (1 ml), propionaldehyde (0.02 ml), and sodium triacetoxyborohydride (14 mg) were added to the solution, and the resulting mixture was stirred overnight at room temperature. Saturated aqueous sodium hydrogencarbonate and ethyl acetate were added to the reaction mixture, the layers were separated, and then the organic layer was dried over anhydrous magnesium sulfate, and filtered. The filtrate was concentrated under reduced pressure, and the resulting residue was purified by preparative thin layer chromatography (chloroform:methanol:28% aqueous ammonia=20:1:0.1) to obtain the compound shown in Table 6 (39 mg).

Example 214

The compound obtained in Example 121 (45.2 mg) was dissolved in methanol (2 ml), 10% palladium-carbon (8 mg) was added to the solution under an argon atmosphere, and the resulting mixture was stirred at room temperature for 1.5 hours under a hydrogen atmosphere of 1 atm. 10% Palladium-carbon (20 mg) was added to the reaction mixture, and the resulting mixture was further stirred at room temperature for 1.5 hours under a hydrogen atmosphere of 1 atm. The reaction mixture was filtered through Celite, then the filtrate was concentrated under reduced pressure, and the resulting residue was purified by preparative thin layer chromatography (chloroform:methanol:28% aqueous ammonia=12:1:0.1) to obtain the compound shown in Table 6 (36.6 mg).

Example 215

The compound obtained in Example 3, (3) (47 mg) and the compound obtained in Reference Example 151 (38 mg) were dissolved in ethanol (2 ml), cesium carbonate (44 mg) was added to the solution, and the resulting mixture was stirred at 60° C. for 4 hours. Saturated aqueous sodium hydrogencarbonate and ethyl acetate were added to the reaction mixture, the layers were separated, and then the organic layer was dried over anhydrous magnesium sulfate, and filtered. The filtrate was concentrated under reduced pressure, and the resulting residue was purified by preparative thin layer chromatography (chloroform:methanol:28% aqueous ammonia=20:1:0.1) to obtain the compound shown in Table 6 (31 mg).

Example 216

By using the compound obtained in Example 3, (3) (10.5 mg) and the compound obtained in Reference Example 152 (8.8 mg) as starting materials, the compound shown in Table 6 (7.6 mg) was obtained in the same manners as those of Example 13, (2), and Example 103.

Example 217

A preparation method of the compound represented by the formula (J) is shown below.

[Formula 25]

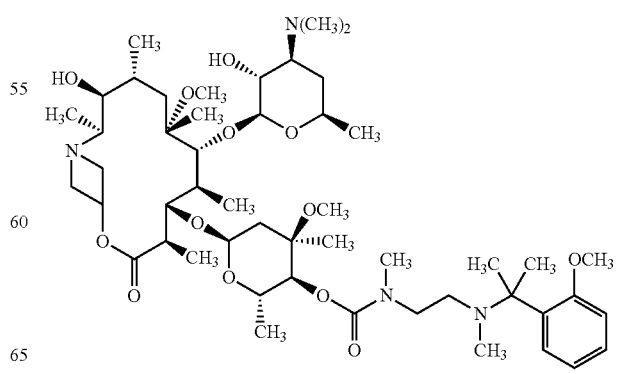

Formula (J)

Example 217

(1) The compound obtained in Example 2, (3) (90.0 mg) and the compound obtained in Reference Example 50 (84.1 mg) were dissolved in dimethylformamide (0.1 ml), and the solution was heated at 65° C. for 19 hours. The reaction mixture was concentrated under reduced pressure, and the resulting residue was purified by preparative thin layer chromatography (chloroform:methanol:28% aqueous ammonia=19:1:0.1) to obtain a carbamate compound (36.8 mg).

(2) By using the compound obtained in (1) mentioned above (43.1 mg) as a starting material, the compound represented by the formula (J) (21.8 mg) was obtained in the same manner as that of Example 1, (3).
MS (FAB) m/z=951 [M+H]$^+$
$^1$H-NMR (400 MHz, CDCl$_3$) δ (ppm): (400 MHz): 0.89 (d, J=7.1 Hz, 3H), 1.02 (d, J=6.6 Hz, 3H), 1.08-1.30 (m, 16H), 1.31-1.40 (m, 10H), 1.60-1.70 (m, 1H), 2.08-2.19 (m, 1H), 2.28 (s, 6H), 2.30 (s, 3H), 2.37-2.65 (m, 5H), 2.67-2.88 (m, 3H), 2.90-2.98 (m, 3H), 3.00-3.07 (m, 1H), 3.12-3.38 (m, 10H), 3.39-3.49 (m, 1H), 3.56-3.64 (m, 1H), 3.65-3.93 (m, 7H), 4.34-4.46 (m, 1H), 4.52-4.75 (m, 3H), 4.90-5.05 (m, 2H), 6.83-6.94 (m, 2H), 7.15-7.22 (m, 1H), 7.44-7.57 (m, 1H)

Examples 218 to 222

Preparation methods of the compounds represented by the formula (K) having R defined in Table 7 are shown below.

[Formula 26]

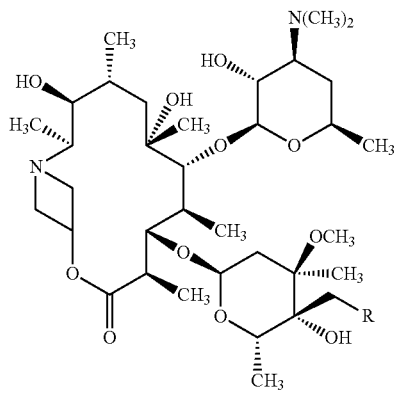

Formula (K)

TABLE 7

| Example | Reference Example | R | ESI MS (M + H) | $^1$H-NMR, CDCl$_3$, δ (ppm) |
|---|---|---|---|---|
| 218 | 50 | (structure) | 923.6 | (600 MHz): 0.93 (br s, 3 H) 1.05-1.15 (m, 9 H) 1.18-1.33 (m, 13 H) 1.39-1.46 (m, 7 H) 1.62-1.78 (m, 2 H) 1.94-2.07 (m, 4 H) 2.19 (s, 3 H) 2.26 (s, 3 H) 2.29 (s, 6 H) 2.37-2.68 (m, 6 H) 2.76-2.85 (m, 2 H) 3.15-3.49 (m, 11 H) 3.70-3.82 (m, 4 H) 4.09-4.16 (m, 1 H) 4.32-4.42 (m, 2 H) 4.70-4.75 (m, 1 H) 5.03-5.07 (m, 1 H) 6.84-6.92 (m, 2 H) 7.14-7.21 (m, 1 H) 7.58-7.63 (m, 1 H) |
| 219 | 67 | (structure) | 923.7 | (600 MHz): 0.89-0.98 (m, 6 H) 1.05-1.15 (m, 9 H) 1.17-1.34 (m, 10 H) 1.39-1.50 (m, 10 H) 1.60-1.80 (m, 2 H) 1.96-2.06 (m, 3 H) 2.10-2.22 (m, 6 H) 2.29 (s, 6 H) 2.38-2.50 (m, 2 H) 2.51-2.59 (m, 1 H) 2.63-2.71 (m, 1 H) 2.76-2.84 (m, 1 H) 3.09-3.15 (m, 1 H) 3.17-3.43 (m, 9 H) 3.48-3.55 (m, 1 H) 3.73-3.82 (m, 4 H) 4.23-4.29 (m, 1 H) 4.31-4.36 (m, 1 H) 4.42 (d, J = 7.34 Hz, 1 H) 4.71-4.75 (m, 1 H) 5.03-5.07 (m, 1 H) 6.85-6.92 (m, 2 H) 7.18-7.22 (m, 1 H) 7.41-7.44 (m, 1 H) |
| 220 | 74 | (structure) | 939.7 | (600 MHz): 0.92-0.98 (m, 3 H) 1.05-1.13 (m, 12 H) 1.18 (dd, J = 8.02, 6.19 Hz, 7 H) 1.30 (d, J = 6.88 Hz, 3 H) 1.35 (d, J = 6.88 Hz, 3 H) 1.43 (br s, 3 H) 1.59-1.79 (m, 2 H) 1.90-2.05 (m, 4 H) 2.28 (s, 6 H) 2.36-2.58 (m, 7 H) 2.64-2.83 (m, 6 H) 3.19-3.24 (m, 3 H) 3.26 (s, 3 H) 3.42-3.54 (m, 3 H) 3.59-3.63 (m, 1 H) 3.68-3.71 (m, 1 H) 3.82 (s, 3 H) 4.27-4.32 (m, 1 H) 4.34-4.38 (m, 2 H) 4.45 (q, J = 6.88 Hz, 1 H) 4.71-4.74 (m, 1 H) 5.01 (d, J = 4.58 Hz, 1 H) 6.87-6.96 (m, 2 H) 7.22-7.29 (m, 2 H) |
| 221 | 64 | (structure) | 924.7 | (600 MHz): 0.91-0.98 (m, 3 H) 1.05-1.15 (m, 9 H) 1.21-1.33 (m, 10 H) 1.39-1.45 (m, 9 H) 1.61-1.80 (m, 2 H) 1.95-2.09 (m, 4 H) 2.18-2.22 (m, 4 H) 2.26 (s, 3 H) 2.29 (s, 6 H) 2.33-2.68 (m, 6 H) 2.75-2.87 (m, 3 H) 3.17-3.52 (m, 10 H) 3.70-3.77 (m, 1 H) 3.93 (s, 3 H) 4.09-4.20 (m, 1 H) 4.31-4.43 (m, 2 H) 4.69-4.76 (m, 1 H) 5.03-5.08 (m, 1 H) 6.78-6.86 (m, 1 H) 7.91-8.04 (m, 2 H) |
| 222 | 46 | (structure) | 937.7 | (600 MHz): 0.90-0.96 (m, 3 H) 1.00 (t, J = 7.11 Hz, 3 H) 1.05-1.12 (m, 9 H) 1.18-1.33 (m, 10 H) 1.39-1.47 (m, 10 H) 1.61-1.77 (m, 2 H) 1.93-2.07 (m, 4 H) 2.27 (s, 3 H) 2.30 (s, 6 H) 2.41-2.69 (m, 7 H) 2.76-2.85 (m, 2 H) 3.28 (s, 10 H) 3.42-3.49 (m, 2 H) 3.71-3.75 (m, 1 H) 3.79 (s, 3 H) 4.11-4.16 (m, 1 H) 4.32-4.36 (m, 1 H) 4.39 (d, J = 7.34 Hz, 1 H) 4.70-4.75 (m, 1 H) 5.04 (d, J = 5.04 Hz, 1 H) 6.85-6.91 (m, 2 H) 7.15-7.20 (m, 1 H) 7.50-7.53 (m, 1 H) |

In Examples 218 to 222, by using the compound obtained in Example 13, (1) and corresponding amine reagents, the compounds shown in Table 7 were synthesized in the same manner as that of Example 13, (2).

Example 223

A preparation method of the compound represented by the formula (L) is shown below.

[Formula 27]

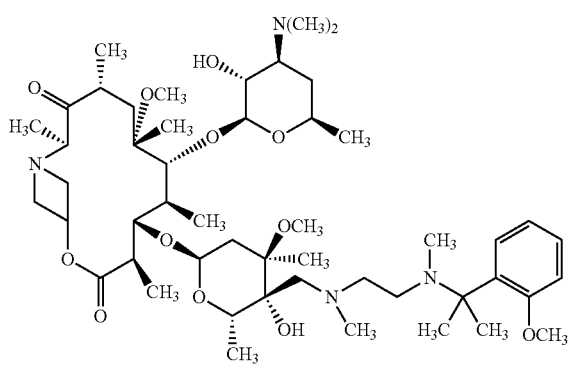

Formula (L)

Example 223

(1) By using the compound obtained in Example 3, (3) (300 mg) as a starting material, a 2'-O-acetyl compound (327 mg) was obtained in the same manner as that of Example 4, (1).
(2) N-Chlorosuccinimide (343 mg) was dissolved in chloroform (5 ml), and the solution was cooled to −20° C. Dodecyl methyl sulfide (795 μl) was added to the solution, the resulting mixture was stirred at the same temperature for 15 minutes, then a solution of the compound obtained in (1) mentioned above (324 mg) in chloroform (5 ml) was added to the reaction mixture, and the resulting mixture was stirred at the same temperature for 15 minutes. Triethylamine (716 μl) was added to the reaction mixture, the resulting mixture was stirred at the same temperature for 45 minutes, then saturated aqueous sodium hydrogencarbonate was added to the reaction mixture, the resulting mixture was warmed to room temperature, chloroform was added to the mixture, and the layers were separated. The organic layer was dried over anhydrous magnesium sulfate, and filtered, then the filtrate was concentrated under reduced pressure, and the resulting residue was purified by silica gel column chromatography (chloroform:methanol:28% aqueous ammonia=40:1:0.1 to 10:1:0.1) to obtain a 9-ketone compound (225 mg).
(3) The compound obtained in (2) mentioned above (225 mg) was dissolved in methanol, and the solution was stirred at room temperature for 16 hours, and under reflux by heating for 6.5 hours. The reaction mixture was concentrated under reduced pressure, and the resulting residue was purified by silica gel column chromatography (chloroform:methanol: 28% aqueous ammonia=40:1:0.1 to 10:1:0.1) to obtain a deprotected compound (147 mg).
(4) By using the compound obtained in (3) mentioned above (103 mg), and the compound obtained in Reference Example 50 (104 mg) as starting materials, the compound represented by the formula (L) (65.9 mg) was obtained in the same manner as that of Example 13, (2).

MS (ESI) m/z 935.7 [M+H]$^+$ $^1$H-NMR (600 MHz, CDCl$_3$) δ (ppm): 1.08-1.19 (m, 21H), 1.20-1.22 (m, 1H), 1.22 (d, J=5.96 Hz, 3H), 1.38 (s, 3H), 1.42 (d, J=4.13 Hz, 3H), 1.53-1.67 (m, 2H), 1.92-1.97 (m, 1H), 2.00-2.08 (m, 3H), 2.17 (s, 3H), 2.18-2.23 (m, 1H), 2.25 (s, 3H), 2.30 (s., 6H), 2.34-2.91 (m, 8H), 3.17 (s, 3H), 3.20-3.25 (m, 2H), 3.27 (s, 3H), 3.40-3.45 (m, 1H), 3.45-3.51 (m, 1H), 3.54-3.59 (m, 1H), 3.69 (d, J=9.63 Hz, 1H), 3.73 (d, J=7.79 Hz, 1H), 3.76-3.78 (m, 1H), 3.79 (s, 3H), 3.80-3.85 (m, 1H), 4.12 (q, J=6.42 Hz, 1H), 4.39 (d, J=6.88 Hz, 1H), 4.76 (t, J=3.44 Hz, 1H), 4.94 (d, J=5.04 Hz, 1H), 6.85-6.89 (m, 2H), 7.14-7.19 (m, 1H), 7.61 (d, J=7.34 Hz, 1H)

Example 224

A preparation method of the compound represented by the formula (M) is shown below.

[Formula 28]

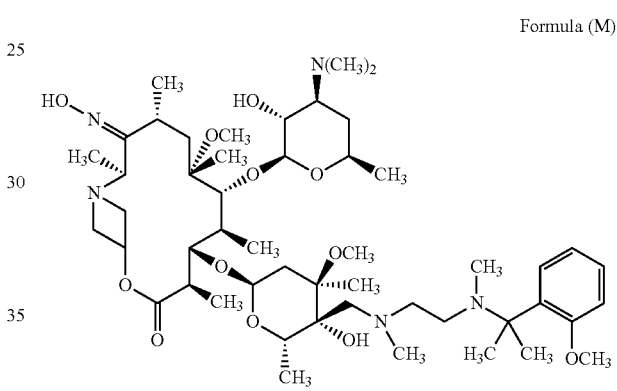

Formula (M)

Example 224

By using the compound obtained in Example 223 (36 mg) as a starting material, the compound represented by the formula (M) (2.2 mg) was obtained in the same manner as that of Example 6.

MS (ESI) m/z 950.8 [M+H]$^+$ $^1$H-NMR (600 MHz, CDCl$_3$) δ (ppm): 1.07-1.28 (m, 26H), 1.36-1.44 (m, 6H), 1.63-1.67 (m, 1H), 1.91-2.07 (m, 4H), 2.18 (s, 3H), 2.25 (s, 3H), 2.30 (s, 6H), 2.36-3.19 (m, 10H), 3.20-3.74 (m, 11H), 3.27 (s, 3H), 3.79 (s, 3H), 4.09-4.16 (m, 1H), 4.36-4.43 (m, 1H), 4.74-4.79 (m, 1H), 4.91-4.97 (m, 1H), 6.84-6.89 (m, 2H), 7.14-7.19 (m, 1H), 7.61 (d, J=7.79 Hz, 1H)

Test Example 1

In Vitro Antibacterial Activity

In vitro antibacterial activities of the compounds of the present invention against various test bacteria were measured according to the microbroth dilution method (CLSI method). The exemplary compounds shown in Table 9 and the comparative agent 1, clarithromycin, were used as test substances. The test bacteria used are shown in Table 8. The results are shown as MIC values (minimum inhibitory concentration, μg/ml) in Table 9.

TABLE 8

| Test bacteria | Symbols of bacteria |
| --- | --- |
| H. influenzae ATCC 43095 | A |
| H. influenzae Rd | B |
| S. pneumoniae ATCC 49619 | C |
| S. pneumoniae ATCC 700904 | D |

TABLE 9

| Compound | A | B | C | D |
| --- | --- | --- | --- | --- |
| Comparative agent 1 | 4 | 8 | 0.03 | >128 |
| Example 1 | 0.5 | 1 | 0.12 | >128 |
| Example 2 | 4 | 8 | 0.06 | 0.25 |
| Example 3 | 4 | 4 | 0.03 | 0.12 |
| Example 5 | 4 | 8 | 0.03 | 0.5 |
| Example 12 | 8 | 8 | 0.03 | 0.25 |
| Example 70 | 4 | 4 | 0.12 | 0.25 |
| Example 71 | 2 | 2 | 0.03 | 0.12 |
| Example 84 | 4 | 4 | 0.016 | 0.06 |
| Example 107 | 4 | 4 | 0.03 | 0.06 |
| Example 132 | 4 | 8 | 0.06 | 1 |
| Example 133 | 8 | 16 | 0.12 | 0.5 |
| Example 162 | 2 | 2 | 0.03 | 0.12 |
| Example 195 | 4 | 8 | 0.03 | 0.06 |
| Example 204 | 16 | 16 | 0.03 | 1 |
| Example 221 | 8 | 8 | 0.06 | 1 |

INDUSTRIAL APPLICABILITY

The compounds of the present invention have potent antibacterial activity against various microorganisms, and even against *Haemophilus influenzae*, erythromycin resistant pneumococci and the like, against which sufficient antibacterial activity cannot be obtained with conventional macrolide antibiotics, and therefore, they can be used as medicaments for prophylactic and/or therapeutic treatment of various microbial infectious diseases.

What is claimed is:

1. A 10a-azalide compound represented by the formula (I):

(I)

wherein, in the formula, $R^2$ and $R^3$ combine together to represent an oxo group, or one of them is a hydrogen atom, and the other is:
a hydroxyl group,
a protected hydroxyl group,
a group represented by the formula —$X^{031}$—$R^{031}$, or a group represented by the formula (II):

(II)

wherein $X^{031}$ is:
a group represented by the formula —O—,
a group represented by the formula —OCO—, or
a group represented by the formula —OCON($R^{20}$)—,
$R^{031}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A,
the group A is a group consisting of a hydroxyl group, a halogen atom, an amino group, a carboxyl group, a cyano group, a $C_{1-6}$ alkyl group (this $C_{1-6}$ alkyl group may be substituted with amino group, or a $C_{1-6}$ alkylamino group), a $C_{1-6}$ alkylamino group, a $C_{1-6}$ haloalkyl group, a $C_{1-6}$ alkoxy group, a $C_{1-6}$ alkylthio group, a $C_{2-7}$ alkoxycarbonyl group, nitro group, a saturated heterocyclic group, a $C_{7-12}$ aralkyloxy group, and a $C_{1-11}$ acyl group,
one of $R^{32}$ and $R^{33}$ is a hydrogen atom, and the other is:
a hydrogen atom,
a hydroxyl group,
a protected hydroxyl group,
an amino group,
a protected amino group,
a group represented by the formula —$X^{331}$—$R^{331}$,
a group represented by the formula —$X^{331}$—$A^{331}$—$X^{332}$—$R^{331}$,
a group represented by the formula —$X^{331}$—$A^{331}$—$X^{332}$—$A^{332}$—$X^{333}$—$R^{331}$, or
a group represented by the formula —$X^{331}$—$A^{331}$—$X^{332}$—$A^{332}$—$X^{333}$—$A^{333}$—$X^{334}$—$R^{331}$,
wherein $X^{331}$ is:
a group represented by the formula —O—,
a group represented by the formula —OCO—,
a group represented by the formula —OCON($R^{20}$)—,
a group represented by the formula —N($R^{20}$)—,
a group represented by the formula —N($R^{20}$)CO—, or a group represented by the formula —OCSN($R^{20}$)—, and $R^{331}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or one of $R^{32}$ and $R^{33}$ is a hydroxyl group, and the other is:
a group represented by the formula —$X^{335}$—$R^{332}$,
a group represented by the formula —$X^{335}$—$A^{334}$—$X^{336}$—$R^{332}$, or
a group represented by the formula —$X^{335}$—$A^{334}$—$X^{336}$—$A^{335}$—$X^{337}$—$R^{332}$,
wherein $X^{335}$ is:
a single bond,
a group represented by the formula —$CH_2N(R^{20})$—,
a group represented by the formula —$CH_2N(R^{20})CO$—,
a group represented by the formula —$CH_2N(R^{20})CO_2$—,
a group represented by the formula —$CH_2N(R^{20})CON(R^{21})$—,
a group represented by the formula —$CH_2$—$A^{336}$—,
a group represented by the formula —$CH_2O$—, or
a group represented by the formula —$CH_2S(O)_p$—,
$A^{336}$ is:
a divalent nitrogen-containing heterocyclic group which may be substituted with a hydroxyl group or a $C_{1-6}$ alkoxy group,
$R^{332}$ is:
a $C_{1-6}$ alkyl group which may be substituted with 1 to 3 groups selected from the group consisting of "an amino group, a hydroxyl group, an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, and
p is an integer of 0 to 2, or $R^{32}$ and $R^{33}$ combine together to represent oxo group, an oxime group,
a protected oxime group,
a group represented by the formula 3:

[Formula 3]

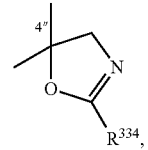

a group represented by the formula 4:

[Formula 4]

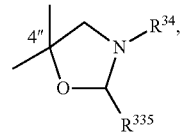

or a group represented by the formula 5:

[Formula 5]

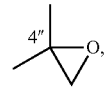

wherein $R^{334}$ is:
a group represented by the formula —OH, or by the formula —SH,
$R^{335}$ is a hydrogen atom, or a $C_{1-6}$ alkyl group,
$R^{34}$ is:
a group represented by the formula —$R^{336}$,
a group represented by the formula —$A^{337}$—$X^{338}$—$R^{336}$, or
a group represented by the formula —$A^{337}$—$X^{338}$—$A^{338}$—$X^{339}$—$R^{336}$, and
$R^{336}$ is:
a $C_{1-6}$ alkyl group which may be substituted with 1 to 3 groups selected from the group consisting of "an amino group, hydroxyl group, an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, $R^4$ is:
a hydrogen atom,
a group represented by the formula —$R^{041}$,
a group represented by the formula —$CH_2$—CH(OH)—$CH_2$—$NHR^{041}$, or
a group represented by the formula —$CH_2$—CH(OH)—$CH_2$—NH—$A^{041}$—$X^{042}$—$R^{041}$,
  wherein $A^{041}$ is:
  a divalent $C_{1-10}$ aliphatic hydrocarbon group, or
  a divalent heterocyclic group, and
  $R^{041}$ is:
  a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  an aryl group which may be substituted with 1 to 3 groups selected from the group A,
  a heterocyclic group which may be substituted with 1 to 3 groups selected from the group A, or
  a biaryl group which may be substituted with 1 to 3 groups selected from the group A, or $R^4$ may combine with $R^6$ to form a cyclic carbonate [—$CON(R^{22})$—], one of $R^5$ and $R^6$ is hydrogen atom, and the other is:
a hydrogen atom,
a hydroxyl group,
a protected hydroxyl group,
an amino group,
a protected amino group,
a group represented by the formula —$X^{051}$—$R^{051}$, or
a group represented by the formula —$X^{051}$—$A^{051}$—$X^{052}$—$R^{051}$,
  wherein $X^{051}$ is:
  a group represented by the formula —O—,
  a group represented by the formula —$OCON(R^{22})$—,
  a group represented by the formula —$N(R^{22})$—, or
  a group represented by the formula —$N(R^{22})CO$—, and
  $R^{051}$ is:
  a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  an aryl group which may be substituted with 1 to 3 groups selected from the group A,
  a heterocyclic group which may be substituted with 1 to 3 groups selected from the group A, or
  a biaryl group which may be substituted with 1 to 3 groups selected from the group A, or $R^5$ and $R^6$ combine together to represent
an oxo group,
an oxime group,
a protected oxime group,
a group represented by the formula =N—$X^{053}$—$R^{052}$, or,
a group represented by the formula =N—$X^{053}$—$A^{052}$—$X^{054}$—$R^{052}$,
  wherein $X^{053}$ is:
  a group represented by the formula —O—, or
  a group represented by the formula —CO—, and
  $R^{052}$ is:
  a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
  an aryl group which may be substituted with 1 to 3 groups selected from the group A,
  a heterocyclic group which may be substituted with 1 to 3 groups selected from the group A, or
  a biaryl group which may be substituted with 1 to 3 groups selected from the group A, $R^7$ is:
a hydrogen atom, or
a protective group of hydroxyl group, $R^8$ and $R^9$, which are the same or different, represent
a hydrogen atom,
a $C_{1-6}$ alkyl group, or
a protective group of an amino group, $X^{332}, X^{333}, X^{334}, X^{336}, X^{337}, X^{338}, X^{339}, X^{042}, X^{052}$, and $X^{054}$ mentioned above, which are the same or different, represent a single bond,
a group represented by the formula —O—,
a group represented by the formula —OCO—,
a group represented by the formula —OCO$_2$—,
a group represented by the formula —OCON(R$^{25}$)—,
a group represented by the formula —S(O)$_r$—,
a group represented by the formula —SO$_2$N(R$^{25}$)—,
a group represented by the formula —OCS—,
a group represented by the formula —CO—,
a group represented by the formula —CO$_2$—,
a group represented by the formula —CON(R$^{25}$)—,
a group represented by the formula —CH=N—,
a group represented by the formula —CH=N—O—,
a group represented by the formula —C(R$^{25}$)=N—,
a group represented by the formula —C(R$^{25}$)=N—O—,
a group represented by the formula —C(R$^{25}$)=N—N(R$^{26}$)—,
a group represented by the formula —CH=N—N(R$^{25}$)—,
a group represented by the formula —CS—,
a group represented by the formula —C(S)O—,
a group represented by the formula —CSN(R$^{25}$)—,
a group represented by the formula —O—N=C(R$^{25}$)—,
a group represented by the formula —N=CH—,
a group represented by the formula —N(R$^{25}$)—,
a group represented by the formula —N(R$^{25}$)CO—,
a group represented by the formula —N(R$^{25}$)CS—,
a group represented by the formula —N(R$^{25}$)SO$_2$—,
a group represented by the formula —N(R$^{25}$)CO$_2$—, or
a group represented by the formula —N(R$^{25}$)CON(R$^{26}$)—,
r is an integer of 0 to 2,
$A^{331}, A^{332}, A^{333}, A^{334}, A^{335}, A^{337}, A^{338}, A^{051}$, and $A^{052}$ mentioned above, which are the same or different, represent a divalent C$_{1-6}$ aliphatic hydrocarbon group which may be substituted with a hydroxyl group, a C$_{1-6}$ alkoxy group, an amino group, a C$_{1-6}$ alkylamino group, or a heterocyclic group,
an arylene group which may be substituted with a hydroxyl group or a C$_{1-6}$ alkoxy group, or
a divalent heterocyclic group which may be substituted with a hydroxyl group or a C$_{1-6}$ alkoxy group, and $R^{20}, R^{21}, R^{22}, R^{25}$, and $R^{26}$ mentioned above, which are the same or different, represent a hydrogen atom, or a C$_{1-6}$ alkyl group which may be substituted with 1 to 3 groups selected from the group A, or a salt thereof.

2. The 10a-azalide compound according to claim 1 or a salt thereof, wherein R$^2$ and R$^3$ combine together to represent an oxo group, or one of them is a hydrogen atom, and the other is:
a hydroxyl group,
a protected hydroxyl group,
a group represented by the formula —X$^{031}$—R$^{031}$, or a group represented by the formula (II):

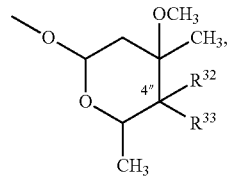

wherein X$^{031}$ is:
a group represented by the formula —O—,
a group represented by the formula —OCO—, or
a group represented by the formula —OCON(R$^{20}$)—,
R$^{031}$ is:
a C$_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
a C$_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
a C$_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
an aryl group which may be substituted with 1 to 3 groups selected from the group B,
a heterocyclic group which may be substituted with 1 to 3 groups selected from the group B, or
a biaryl group which may be substituted with 1 to 3 groups selected from the group B,
the group B is a group consisting of hydroxyl group, a halogen atom, an amino group, a carboxyl group, a cyano group, a C$_{1-6}$ alkyl group, a C$_{1-6}$ alkylamino group, a C$_{1-6}$ haloalkyl group, a C$_{1-6}$ alkoxy group, a C$_{2-7}$ alkoxycarbonyl group, a nitro group, a saturated heterocyclic group and a C$_{1-11}$ acyl group,
one of R$^{32}$ and R$^{33}$ is hydrogen atom, and the other is:
a hydrogen atom,
a hydroxyl group,
a protected hydroxyl group,
an amino group,
a protected amino group,
a group represented by the formula —X$^{331}$—R$^{331}$,
a group represented by the formula —X$^{331}$—A$^{331}$—X$^{332}$—R$^{331}$,
a group represented by the formula —X$^{331}$—A$^{331}$—X$^{332}$—A$^{332}$—X$^{333}$—R$^{331}$, or
a group represented by the formula —X$^{331}$—A$^{331}$—X$^{332}$—A$^{332}$—X$^{333}$—A$^{333}$—X$^{334}$—R$^{331}$,
wherein X$^{331}$ is:
a group represented by the formula —O—,
a group represented by the formula —OCO—,
a group represented by the formula —OCON(R$^{20}$)—,
a group represented by the formula —N(R$^{20}$)—,
a group represented by the formula —N(R$^{20}$)CO—, or
a group represented by the formula —OCSN(R$^{20}$)—,
and
R$^{331}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, or one of $R^{32}$ and $R^{33}$ is a hydroxyl group, and the other is:

a group represented by the formula —$X^{335}$—$R^{332}$ a group represented by the formula —$X^{335}$—$A^{334}$—$X^{336}$—$R^{332}$, or a group represented by the formula —$X^{335}$—$A^{334}$—$X^{336}$—$A^{335}$—$X^{337}$—$R^{332}$, wherein $X^{335}$ is:

a single bond, a group represented by the formula —$CH_2N(R^{20})$—, a group represented by the formula —$CH_2N(R^{20})CO$—, a group represented by the formula —$CH_2N(R^{20})CO_2$—, a group represented by the formula —$CH_2N(R^{20})CON(R^{21})$—, a group represented by the formula —$CH_2O$—, or a group represented by the formula —$CH_2S(O)_p$—, $R^{332}$ is:

a $C_{1-6}$ alkyl group which may be substituted with 1 to 3 groups selected from the group consisting of "an amino group, hydroxyl group, an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, and p is an integer of 0 to 2, or $R^{32}$ and $R^{33}$ combine together to represent an oxo group, an oxime group, a protected oxime group, a group represented by the formula 7:

[Formula 7]

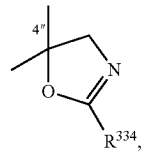

or a group represented by the formula 8:

[Formula 8]

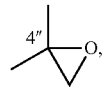

wherein $R^{334}$ is:

a group represented by the formula —OH, or by the formula —SH, $R^4$ is:

a hydrogen atom, a group represented by the formula —$R^{041}$, a group represented by the formula —$CH_2$—$CH(OH)$—$CH_2$—$NHR^{041}$, or a group represented by the formula —$CH_2$—$CH(OH)$—$CH_2$—NH—$A^{041}$—$X^{042}$—$R^{041}$ wherein $A^{041}$ is:

a divalent $C_{1-10}$ aliphatic hydrocarbon group, or a divalent heterocyclic group, and $R^{041}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)", an aryl group which may be substituted with 1 to 3 groups selected from the group B, a heterocyclic group which may be substituted with 1 to 3 groups selected from the group B, or a biaryl group which may be substituted with 1 to 3 groups selected from the group B, or $R^4$ may combine with $R^6$ to form a cyclic carbonate [—$CON(R^{22})$—], one of $R^5$ and $R^6$ is a hydrogen atom, and the other is:

a hydrogen atom, a hydroxyl group,
a protected hydroxyl group,
an amino group,
a protected amino group,
a group represented by the formula —$X^{051}$—$R^{051}$, or
a group represented by the formula —$X^{051}$—$A^{051}$—$X^{052}$—$R^{051}$,
  wherein $X^{051}$ is:
  a group represented by the formula —O—,
  a group represented by the formula —OCON($R^{22}$)—,
  a group represented by the formula —N($R^{22}$)—, or
  a group represented by the formula —N($R^{22}$)CO—, and
  $R^{051}$ is:
  a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
  a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
  a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
  an aryl group which may be substituted with 1 to 3 groups selected from the group B,
  a heterocyclic group which may be substituted with 1 to 3 groups selected from the group B, or
  a biaryl group which may be substituted with 1 to 3 groups selected from the group B, or
$R^5$ and $R^6$ combine together to represent
an oxo group,
an oxime group,
a protected oxime group,
a group represented by the formula =N—$X^{053}$—$R^{052}$, or
a group represented by the formula =N—$X^{053}$—$A^{052}$—$X^{054}$—$R^{052}$,
  wherein $X^{053}$ is:
  a group represented by the formula —O—, or
  a group represented by the formula —CO—, and
  $R^{052}$ is:
  a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
  a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
  a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group B)",
  an aryl group which may be substituted with 1 to 3 groups selected from the group B,
  a heterocyclic group which may be substituted with 1 to 3 groups selected from the group B, or
  a biaryl group which may be substituted with 1 to 3 groups selected from the group B,
$X^{332}$, $X^{333}$, $X^{334}$, $X^{336}$, $X^{337}$, $X^{042}$, $X^{052}$, and $X^{054}$ mentioned above, which are the same or different, represent
a single bond,
a group represented by the formula —O—,
a group represented by the formula —OCO—,
a group represented by the formula —OCO$_2$—,
a group represented by the formula —OCON($R^{25}$)—,
a group represented by the formula —S(O)$_r$—,
a group represented by the formula —SO$_2$N($R^{25}$)—,
a group represented by the formula —OCS—,
a group represented by the formula —CO—,
a group represented by the formula —CO$_2$—,
a group represented by the formula —CON($R^{25}$)—,
a group represented by the formula —CH=N—,
a group represented by the formula —CH=N—O—,
a group represented by the formula —C($R^{25}$)=N—,
a group represented by the formula —C($R^{25}$)=N—O—,
a group represented by the formula —C($R^{25}$)=N—N($R^{26}$)—,
a group represented by the formula —CH=N—N($R^{25}$)—,
a group represented by the formula —CS—,
a group represented by the formula —C(S)O—,
a group represented by the formula —CSN($R^{25}$)—,
a group represented by the formula —O—N=C($R^{25}$)—,
a group represented by the formula —N=CH—,
a group represented by the formula —N($R^{25}$)—,
a group represented by the formula —N($R^{25}$)CO—,
a group represented by the formula —N($R^{25}$)CS—,
a group represented by the formula —N($R^{25}$)SO$_2$—,
a group represented by the formula —N($R^{25}$)CO$_2$—, or
a group represented by the formula —N($R^{25}$)CON($R^{26}$)—, and
r is an integer of 0 to 2,
$A^{331}$, $A^{332}$, $A^{333}$, $A^{334}$, $A^{335}$, $A^{051}$, and $A^{052}$ mentioned above, which are the same or different, represent
a divalent $C_{1-10}$ aliphatic hydrocarbon group which may be substituted with hydroxyl group, a $C_{1-6}$ alkoxy group, or a heterocyclic group,
an arylene group which may be substituted with hydroxyl group or a $C_{1-6}$ alkoxy group, or
a divalent heterocyclic group which may be substituted with hydroxyl group or a $C_{1-6}$ alkoxy group, and
$R^{20}$, $R^{21}$, $R^{22}$, $R^{25}$, and $R^{26}$ mentioned above, which are the same or different, represent
a hydrogen atom, or a $C_{1-6}$ alkyl group which may be substituted with 1 to 3 groups selected from the group B.

3. The 10a-azalide compound according to claim 2 or a salt thereof, wherein one of $R^2$ and $R^3$ is a hydrogen atom, and the other is:
a group represented by the formula (II),
$R^4$ is a hydrogen atom, or a methyl group
one of $R^5$ and $R^6$ is a hydrogen atom, and the other is:
a hydroxyl group, or an amino group, or
$R^5$ and $R^6$ combine together to represent
an oxo group, or an oxime group,
$R^7$ is a hydrogen atom, and
$R^8$ and $R^9$ are methyl groups.

4. The 10a-azalide compound according to claim 3 or a salt thereof, wherein one of $R^{32}$ and $R^{33}$ is a hydroxyl group, and the other is:
a group represented by the formula —CH$_2$N($R^{20}$)—$R^{332}$, a group represented by the formula —CH$_2$N(R$^{20}$)-A$^{334}$—X$^{336}$—R$^{332}$, or a group represented by the formula —CH$_2$N(R$^{20}$)-A$^{334}$—X$^{336}$—A$^{335}$—X$^{337}$—R$^{332}$.

5. The 10a-azalide compound according to claim 3 or a salt thereof, wherein one of R$^{32}$ and R$^{33}$ is a hydroxyl group, and the other is:

a group represented by the formula —CH$_2$N(R$^{20}$)-A$^{334}$—X$^{336}$—R$^{332}$.

6. The 10a-azalide compound according to claim 5 or a salt thereof, wherein A$^{334}$ is a C$_{2-6}$ alkylene group, and X$^{336}$ is:

a group represented by the formula —N(R$^{25}$)—.

7. The 10a-azalide compound according to claim 3 or a salt thereof, wherein one of R$^{32}$ and R$^{33}$ is a hydrogen atom, and the other is:

a group represented by the formula —OCON(R$^{20}$)—R$^{331}$, a group represented by the formula —OCON(R$^{20}$)-A$^{331}$—X$^{332}$—R$^{331}$, or a group represented by the formula —OCON(R$^2$)-A$^{331}$—X$^{332}$—A$^{332}$—X$^{333}$—R$^{331}$.

8. The 10a-azalide compound according to claim 3 or a salt thereof, wherein one of R$^{32}$ and R$^{33}$ is a hydrogen atom, and the other is:

a group represented by the formula) —OCON(R$^{20}$)-A$^{331}$—X$^{332}$—R$^{331}$.

9. The 10a-azalide compound according to claim 8 or a salt thereof, wherein A$^{331}$ is a C$_{2-6}$ alkylene group, X$^{332}$ is:

a group represented by the formula —N(R$^{25}$)—.

10. A medicament composition containing a substance selected from the group consisting of the 10a-azalide compound according to claim 1, and a physiologically acceptable salt thereof as an active ingredient.

11. The medicament composition according to claim 10, for treatment of a bacterial infectious disease.

12. A medicament composition containing a substance selected from the group consisting of the 10a-azalide compound according to claim 2, and a physiologically acceptable salt thereof as an active ingredient.

13. The medicament composition according to claim 12, for treatment of a microbial infectious disease.

14. A medicament composition containing a substance selected from the group consisting of the 10a-azalide compound according to claim 3, and a physiologically acceptable salt thereof as an active ingredient.

15. The medicament composition according to claim 14, for treatment of a microbial infectious disease.

16. A medicament composition containing a substance selected from the group consisting of the 10a-azalide compound according to claim 4, and a physiologically acceptable salt thereof as an active ingredient.

17. The medicament composition according to claim 16, for treatment of a microbial infectious disease.

18. A medicament composition containing a substance selected from the group consisting of the 10a-azalide compound according to claim 5, and a physiologically acceptable salt thereof as an active ingredient.

19. The medicament composition according to claim 18, for treatment of a microbial infectious disease.

20. A medicament composition containing a substance selected from the group consisting of the 10a-azalide compound according to claim 6, and a physiologically acceptable salt thereof as an active ingredient.

21. The medicament composition according to claim 20, for treatment of a microbial infectious disease.

22. A medicament composition containing a substance selected from the group consisting of the 10a-azalide compound according to claim 7, and a physiologically acceptable salt thereof as an active ingredient.

23. The medicament composition according to claim 22, for treatment of a microbial infectious disease.

24. A medicament composition containing a substance selected from the group consisting of the 10a-azalide compound according to claim 8, and a physiologically acceptable salt thereof as an active ingredient.

25. The medicament composition according to claim 24, for treatment of a microbial infectious disease.

26. A medicament composition containing a substance selected from the group consisting of the 10a-azalide compound according to claim 9, and a physiologically acceptable salt thereof as an active ingredient.

27. The medicament composition according to claim 26, for treatment of a microbial infectious disease.

28. A method of treatment of a microbial infection, comprising administering an effective amount of the medicament according to claim 1 to a mammal to treat the microbial infection.

29. A method of treatment of a bacterial infection, comprising administering an effective amount of the medicament according to claim 1 to a mammal to treat the bacterial infection.

30. The medicament composition according to claim 10, for treatment of a microbial infectious disease.

* * * * *

UNITED STATES PATENT AND TRADEMARK OFFICE
CERTIFICATE OF CORRECTION

PATENT NO. : 8,299,035 B2
APPLICATION NO. : 12/992335
DATED : October 30, 2012
INVENTOR(S) : T. Sugimoto et al.

It is certified that error appears in the above-identified patent and that said Letters Patent is hereby corrected as shown below:

In the Claims:

Column 209, line 40 (claim 7, line 20) of the printed patent, "—OCON($R^2$)" should be -- —OCON($R^{20}$) --.

Signed and Sealed this
Fourth Day of June, 2013

Teresa Stanek Rea
*Acting Director of the United States Patent and Trademark Office*